US012766185B2

(12) United States Patent
Butler

(10) Patent No.: US 12,766,185 B2
(45) Date of Patent: Oct. 20, 2026

(54) METHODS FOR USE OF AN ANGIOCRINE FACTOR IN TREATING A PATIENT EXPOSED TO A MYELOABLATIVE INSULT

(71) Applicant: Hackensack Meridian Health Center for Discovery and Innovation, Nutley, NJ (US)

(72) Inventor: Jason M. Butler, Nutley, NJ (US)

(73) Assignee: Hackensack Meridian Health Center for Discovery and Innovation, Nutley, NJ (US)

( * ) Notice: Subject to any disclaimer, the term of this patent is extended or adjusted under 35 U.S.C. 154(b) by 1133 days.

(21) Appl. No.: 17/780,933

(22) PCT Filed: Nov. 25, 2020

(86) PCT No.: PCT/US2020/062397
§ 371 (c)(1),
(2) Date: May 27, 2022

(87) PCT Pub. No.: WO2021/108689
PCT Pub. Date: Jun. 3, 2021

(65) Prior Publication Data
US 2023/0226150 A1 Jul. 20, 2023

Related U.S. Application Data

(60) Provisional application No. 62/980,108, filed on Feb. 21, 2020, provisional application No. 62/941,190, filed on Nov. 27, 2019.

(51) Int. Cl.
*A61K 38/18* (2006.01)
*A61K 35/28* (2015.01)
*A61P 7/06* (2006.01)

(52) U.S. Cl.
CPC .............. *A61K 38/18* (2013.01); *A61K 35/28* (2013.01); *A61P 7/06* (2018.01)

(58) Field of Classification Search
CPC ................................ A61K 38/18; A61K 35/28
See application file for complete search history.

(56) References Cited

U.S. PATENT DOCUMENTS

| | | | |
|---|---|---|---|
| 2005/0066266 | A9 | 3/2005 | Hastings et al. |
| 2018/0110832 | A1 | 4/2018 | Morrison et al. |
| 2019/0231823 | A1 | 8/2019 | Butler et al. |

FOREIGN PATENT DOCUMENTS

| | | | |
|---|---|---|---|
| CN | 102559725 | A * | 7/2012 |
| WO | 2010/052580 | A2 | 5/2010 |
| WO | 2016/004068 | A1 | 1/2016 |
| WO | 2016/172026 | A1 | 10/2016 |

OTHER PUBLICATIONS

Dutka et al., Heart Fail. Rev., 2021, vol. 27(4):1395-1411.*
Zittoun et al., N. Engl. J. Med., 1995, vol. 332:217-223.*
Menon, MB, et al., p38 MAP Kinase and MAPKAP Kinases MK2/3 Cooperatively Phosphorylate Epithelial Keratins. J. Biol. Chem. (2010) 285: 33242-33251.
Merrifield, R.B., (1963) Solid Phase Peptide Synthesis. I. The Synthesis of a Tetrapeptide. J. Am. Chem. Soc. 85: 2149-2154.
Mirantes, C., et al. Pro-inflammatory cytokines: emerging players regulating HSC function in normal and diseased hematopoiesis. Experimental cell research (2014) 329, 248-254.
Mittal, M., et al., Reactive oxygen species in 1035 inflammation and tissue injury. Antioxid Redox Signal (2014) 20, 1126-1167.
Mori, Y. et al., "Prospective isolation of human erythroid lineage-committed progenitors," Proc. Natl Acad. Sci. USA (2015) 112 (31): 9638-43.
Morrison SJ and Weissman IL. The long-term repopulating subset of hematopoietic stem cells is deterministic and isolatable by phenotype. Immunity. Nov. 1994; 1(8):661-73.
Morrison, S. J. & Scadden, D. T. The bone marrow niche for haematopoietic stem cells. Nature (2014) 505, 327-334.
Mossadegh-Keller, N. et al. M-CSF instructs myeloid lineage fate in single haematopoietic stem cells. Nature (2013) 497, 239-243.
Munshi, A. and Ramesh, R. Mitogen-activated protein kinases and their role in radiation response. Genes Cancer (2013) 4, 401-408.
Murakami, M., and Simons, M., Regulation of Vascular Integrity. J. Mol. Med. (Berl) (2009) 87 (6): 571-82.
Murakami, M.and Simons, M., Fibroblast growth factor regulation of neovascularization, Curr. Opin. Hematol. (2008) 15: 215-220.
Najar, M. et al., "Mesenchymal stromal cells and immunomodulation: A gathering of regulatory immune cells", Cytotherapy, vol. 18(2): 160-171, (2016).
Nakagawa, M. M., et al., (2018). Constitutive Activation of NF-?B Pathway in Hematopoietic Stem Cells Causes Loss of Quiescence and Deregulated Transcription Factor Networks. Frontiers in Cell and Developmental Biology, 6, 143.
Nakamura-Ishizu, A., et al., The analysis, roles and regulation of quiescence in hematopoietic stem cells. Development (2014) 141: 4656-4666.
Ogonek, J. et al., "Immune reconstitution after allogeneic hematopoietic stem cell transplantation" Front. Immunol. (2016) 7: 507.
Oikonomidi, S., et al. Matrix metalloproteinases in respiratory diseases: from pathogenesis to potential clinical implications. Curr Med Chem. 2009; 16(10): 1214-1228.

(Continued)

*Primary Examiner* — Xiaozhen Xie
(74) *Attorney, Agent, or Firm* — Bochner PLLC; Beverly W. Lubit

(57) ABSTRACT

The described invention identifies endothelial cells within the perivascular niche as a crucial component in driving bone marrow (BM) inflammation and HSC dysfunction. We demonstrate that crosstalk between ERK-MAPK and NF-κB signaling pathways within the endothelium plays a key role in modulating the outcomes of chronic inflammation. Sustained activation of the MAPK pathway selectively within the endothelium of adult mice leads to inflammation-induced HSC dysfunction including loss of engraftment ability and a myeloid-biased output. HSC defects caused by endothelial MAPK activation are completely resolved upon simultaneous inhibition of endothelial NF-κB signaling. The described invention identifies Stem Cell Growth Factor alpha (SCGF) as a niche-derived factor that suppresses BM inflammation and enhances hematopoietic recovery following myelosuppressive injury.

13 Claims, 62 Drawing Sheets

Specification includes a Sequence Listing.

(56) References Cited

OTHER PUBLICATIONS

Orford, KW and Scadden, DT, Deconstructing stem cell self-renewal: genetic insights into cell-cycle regulation. Nature Rev. Genet. (2008) 9: 115-128.
Parcellier, A. et al., HSP27 Is a Ubiquitin-Binding Protein Involved in I-kappaBalpha Proteasomal Degradation. (2003) Mol Cell Biol, 23(16): 5790-5802.
Pardee, AB, A restriction point for control of normal animal cell proliferation. Proc. Natl Acad. Sci. USA (1974) 71: 1286-90.
Payne, S., et al., Endothelial-Specific Cre Mouse Models. Arterioscler Thromb Vasc Biol (2018) 38, 2550-2561.
Pepper, MS, Transforming growth factor-beta: vasculogenesis, angiogenesis, and vessel wall integrity. Cytokine Growth Factor Rev. (1997) 8: 21-43.
Pietras, E. M. et al. Chronic interleukin-1 exposure drives haematopoietic stem cells towards precocious myeloid differentiation at the expense of self-renewal. Nature Cell Biology (2016) 18, 607-618.
Pietras, E. M. Inflammation: a key regulator of hematopoietic stem cell fate in health and disease. Blood (2017) 130, 1693-1698.
Pietras, EM. et al., Cell cycle regulation in hematopoietic stem cells. J. Cell Biol. (2011) 195: 709-720.
Pinho, S., Frenette, P.S. Haematopoietic stem cell activity and interactions with the niche. Nat Rev Mol Cell Biol 20, 303-320 (2019).
Pober, JS and Sessa, WC, Evolving functions of endothelial cells in inflammation. Nat. Rev. Immunol. (2007) 7: 803-815.
Poulos, M. G. et al. Endothelial Jagged-1 is Necessary for Homeostatic and Regenerative Hematopoiesis. Cell reports (2013) 4, 1022-1034.
Poulos, M. G. et al. Endothelial-specific inhibition of NF-kappaB enhances functional haematopoiesis. Nat Commun (2016) 7, 13829.
Poulos, M.G. et al. "Endothelial transplantation rejuvenates aged hematopoietic stem cell function." J. Clin. Invest. (2017) 127: 4164-78.
Rabinovitch, A. et al. Roles of cytokines in the pathogenesis and therapy of type 1 diabetes. Cell Biochem Biophys. (2007) 48 (2-3): 159-63.
Rafii, S., Butler, J. M. & Ding, B. S. Angiocrine functions of organ-specific endothelial cells. Nature (2016) 529, 316-325.
Ramalingam, P. et al., "Regulation of the hematopoietic stem cell llifecycle by the endothelial niche," Curr. Opin. Hematol. (2017) 24(4): 289-99.
Riley, et al., "Hematologic Aspects of Myeloablative Therapy and Bone Marrow Transplantation." Journal of Clinical Laboratory Analysis (2005)19:47-79.
Rossi, D. et al. The biology of chemokines and their receptors. Annu Rev Immunol. (2000) 18: 217-242.
Roth Flach, R. J. et al. Endothelial protein kinase MAP4K4 promotes vascular inflammation and atherosclerosis. Nat Commun (2015) 6, 8995.
Roux, PP, and Blennis, J., Erk and p38 MAPK-Activated Protein Kinases: a Family of Protein Kinases with Diverse Biological Functions. Microbiol. & Molec. Biol. Revs. (2004) 68 (2): 320-344.
Sanchez, A. et al. Map3k8 controls granulocyte colony-stimulating factor production and neutrophil precursor proliferation in lipopolysaccharide-induced emergency granulopoiesis. Sci Rep (2017) 7, 5010.
Schepers, K., Campbell, T. B. & Passegue, E. Normal and leukemic stem cell niches: insights and therapeutic opportunities. Cell stem cell (2015) 16, 254-267.
Schrum, S. et al. Synthesis of the CC-chemokines MIP-1alpha, MIP-1beta, and RANTES is associated with a type 1 immune response. J Immunol. (1996) 157: 3598-3604.
Simionescu, N. et al., Open junctions in the endothelium of the postcapillary venules of the diaphragm, J. Cell Biol. (1978) 79: 27-44.
Simons, M., Angiogenesis Where Do We Stand Now?. Circulation (2005) 111: 1556-66.
Sisken, JE and Morasca, L., Intrapopulation kinetics of the mitotic cycle. J. Cell Biol. (1965) 25: 179-189.
Sivan, U, et al. 2019 Role of angiocrine signals in bone development, homeostasis and disease. Open Biol. 9: 190144.
Sorensen, I., et al.,. DLL1-mediated Notch activation regulates endothelial identity in mouse fetal arteries. Blood (2009) 113, 5680-5688.
Srinivasan, L. et al. PI3 kinase signals BCR-dependent mature B cell survival. Cell 139, 573-586, (2009).
Suda, T. et al., Single-cell origin of mouse hemopoietic colonies expressing multiple lineages in variable combinations . . . Proc. Nat. Acad. Sci. USA (1983) 80: 6689-93.
Sun, SC., The noncanonical NF-κB pathway. (2012) Immunol. Rev. 246: 125-140.
Taddei, A., et al., Endothelial adherens junctions control tight junctions by VE-cadherin-mediated upregulation of claudin-5. Nat. Cell Biol. (2008) 10: 923-34.
Takubo, K. et al. Regulation of the HIF-1alpha level is essential for hematopoietic stem cells. Cell Stem Cell (2010) 7, 391-402.
Tang, Y., et al., The contribution of the Tie2+ lineage to primitive and definitive hematopoietic cells. Genesis (2010) 48, 563-567.
Taub, D.D. et al. Recombinant human interferon-inducible protein 10 is a chemoattractant for human monocytes and T lymphocytes and promotes T cell adhesion to endothelial cells . . . J Exp Med. (1993) 177:1809-1814.
Tonks, NK, Protein tyrosine phosphatases: from genes, to function, to disease, Nat. Rev. Mol. Cell Biol. (2006) 7: 833-846.
Vandoorne, K. et al. Imaging the Vascular Bone Marrow Niche During Inflammatory Stress. Circ Res 123, 415-427 (2018).
Wagers, A. J. The stem cell niche in regenerative medicine. Cell stem cell 10, 362-369 (2012).
Wang, JCY and Dick, JE, Cancer stem cells: lessons from leukemia. Trends Cell Biol. (2005) 15: 494-501.
Wang, L. et al. Notch-dependent repression of miR-155 in the bone marrow niche regulates hematopoiesis in an NF-kappaB-dependent manner. Cell stem cell (2014) 15, 51-65.
Wang, Y., et al., Inhibition of p38 MAPK attenuates ionizing radiation-induced hematopoietic cell senescence and residual bone marrow injury. Radiat Res (2011) 176, 743-752.
Wei, Q. and Frenette, P. S. Niches for Hematopoietic Stem Cells and Their Progeny. Immunity (2018) 48, 632-648.
Weis, SM and Chesh, DA, Pathophysiological consequences of VEGF-induced vascular permeability. Nature (2005) 437: 497-504.
Weiskopf, K. et al., "Myeloid cell origins, differentiation, and clinical implications," Microbiol. Spectr. (2016) 4(5): 10.1128/microbiolspec. MCHD-0031-2016.
Wessel, A. W. & Hanson, E. P., A method for the quantitative analysis of stimulation-induced nuclear translocation of the p65 subunit of NF-kappaB from patient-derived dermal fibroblasts. Methods Mol Biol 1280, 413-426 (2015).
Winkler, I. G. et al. Vascular niche E-selectin regulates hematopoietic stem cell dormancy, self renewal and chemoresistance. Nature medicine (2012) 18, 1651-1657.
Wu, C. and Ghosh, S. Differential phosphorylation of the signal-responsive domain of I kappa B alpha and I kappa B beta by I kappa B kinases. J Biol Chem 278, 31980-31987 (2003).
Wu, DJ et al, High expression of WNT7A predicts poor prognosis and promote tumor metastasis in pancreatic ductal adenocarcinoma . . . Sci Rep (2018) 8(1): 15792.
Xiao, L., et al., New paradigms in inflammatory signaling in vascular endothelial cells. Am. J Physiology. Heart and circulatory physiology (2014)306, H317-325.
Xu et al. Stem cell factor is selectively secreted by arterial endothelial cells in bone marrow. Jun. 2, 2018, vol. 9, article 2449 (pp. 1-13).
Yang, F., et al., IKK beta plays an essential role in the phosphorylation of RelA/p65 on serine 536 induced by lipopolysaccharide. J Immunol 170, 5630-5635 (2003).
Yin, T., & Li, L. (2006). The stem cell niches in bone. The Journal of Clinical Investigation, 116(5), 1195-1201.
Youn B-S. et al. Chemokines, chemokine receptors and hematopoiesis. Immunol Rev. (2000) vol. 177: 150-174.
Yu, VWC, and Scadden, DT, "Herterogeneity of the bone marrow niche," Curr. Opin. Hematol. (2016) 23(4): 331-38.

(56) References Cited

OTHER PUBLICATIONS

Yue, R., et al., Clec11a/osteolectin is an osteogenic growth factor that promotes the maintenance of the adult skeleton. Elife 5, 18782 (2016).
Zhang, H. et al. Sepsis Induces Hematopoietic Stem Cell Exhaustion and Myelosuppression through Distinct Contributions of TRIF and MYD88. Stem Cell Reports (2016) 6, 940-956.
Zhang, X., et al., 2005, Periosteal stem cells are essential for bone revitalization and repair. J. Musculoskelet. Neuronal. Interact. 5(4): 360-362.
Zhao, J. L. and Baltimore, D. Regulation of stress-induced hematopoiesis. Current Opinion Hematology (2015) 22, 286-292.
Zhou, B. O., et al., Leptin-receptor-expressing mesenchymal stromal cells represent the main source of bone formed by adult bone marrow. Cell stem cell (2014) 15, 154-168.
Carrelha, J. et al., "Hierarchically Related Lineage-Restricted Fates of Multipotent Hematopoietic Stem Cells", Experimental Hematology, vol. 64 Issue No. Supplement S57-S58, Aug. 2018.
Decision of Refusal of the Japan Patent Office in related Japanese Appl. No. 2022-532070, dated Oct. 17, 2024, 5 pages.
Alvarez, S. et al., GM-CSF and IL-3 activities in schistosomal liver granulomas are controlled by stroma associated heparan sulfate proteoglycans. J Leukoc Biol., vol. 59(3): 435-441, (1996).
Andrae, J. et al., Role of platelet-derived growth factors in physiology and medicine. Genes Dev. (2008) 22: 1276-1312.
Aoki, M. et al., Endothelial apoptosis induced by oxidative stress through activation of NF-kappaB: antiapoptotic effect of antioxidant agents on endothelial cells. Hypertension (2001) 38: 48-55.
Atilla, E., et al., A Review of Myeloablative vs Reduced Intensity/Non-Myeloablative Regimens in Allogeneic Hematopoietic Stem Cell Transplantations. Balkan Medical Journal, (2017) 34(1), 1-9.
Baker, R. G., et al., NF-kappaB, inflammation, and metabolic disease. Cell metabolism 13, 11-22 (2011).
Baldridge, M. T., et al., Inflammatory signals regulate hematopoietic stem cells. Trends in immunology, (2011) 32 (2), 57-65.
Barnes, PJ (2016) "Kinases as Novel Therapeutic Targets in Asthma and Chronic Obstructive Pulmonary Disease" Pharmacological Revs. 68: 788-815.
Barnes, PJ, (2016) "Kinases as novel therapeutic targets in asthma and chronic obstructive pulmonary disease," Pharmacol. Rev. 68: 788-815.
Bartels, K., et al., Hypoxia and inflammation are two sides of the same coin. Proc Natl Acad Sci USA (2013) 110, 18351-18352.
Baselet, B., et al. Pathological effects of ionizing radiation: endothelial activation and dysfunction. Cell Mol Life Sci (2019) 76, 699-728.
Benedito, R. et al. The notch ligands Dll4 and Jagged1 have opposing effects on angiogenesis. Cell 137, 1124-1135, (2009).
Betsholtz, C. Insight into the physiological functions of PDGF through genetic studies in mice, Cytokine Growth Factor Rev. (2004) 15: 215-228.
Bigarella, C. L., et al., Stem cells and the impact of ROS signaling. Development (2014) 141, 4206-4218.
Boehm, J. S. et al. Integrative genomic approaches identify IKBKE as a breast cancer oncogene. Cell 129, 1065-1079 (2007).
Boettcher, S. and Manz, M. G. Regulation of Inflammation- and Infection-Driven Hematopoiesis. Trends in Immunology (2017) 38(5), 345-357.
Boettcher, S. et al. Endothelial cells translate pathogen signals into G-CSF-driven emergency granulopoiesis. Blood (2014) 124, 1393-1403.
Bottero, V., et al., NF-kappaB and the regulation of hematopoiesis. Cell death and differentiation 13, 785-797 (2006).
Boulais, P. E., & Frenette, P. S. (2015). Making sense of hematopoietic stem cell niches. Blood, 125(17), 2621-2629.
Bowers, E. et al. Granulocyte-derived TNFalpha promotes vascular and hematopoietic regeneration in the bone marrow. Nature Medicine 24, 95-102, (2018).
Bowie, JU, et al. A Method to Identify Protein Sequences That Fold into Known Three-Dimensional Structure. Science 253:164 (1991).
Bradley, L.M. et al. Islet-Specific Th1, But Not Th2, Cells Secrete Multiple Chemokines and Promote Rapid Induction of Autoimmune Diabetes. J Immunol. (1999). 162:2511-2520.
Brown, G. D., et al., C-type lectins in immunity and homeostasis. Nature reviews. Immunology (2018) 18, 374-389.
Brown, K., et al., Control of I kappa B-alpha proteolysis by site-specific, signal-induced phosphorylation. Science 267, 1485-1488 (1995).
Brown, K., et al., Mutual regulation of the transcriptional activator NF-kappa B and its inhibitor, I kappa B-alpha. Proc Natl Acad Sci USA 90, 2532-2536 (1993).
Butler, J. M. et al. Endothelial cells are essential for the self-renewal and repopulation of Notch-dependent hematopoietic stem cells. Cell stem cell (2010) 6, 251-264.
Campisi, J. Senescent cells, tumor suppression, and organismal aging: good citizens, bad neighbors. Cell (2005) 120: 513-22).
Cargnello, M. and Roux, PP, Activation and Function of the MAPKs and Their Substrates, the MAPK-Activated Protein Kinases. Microbiol. Mol. Biol. Rev. (2011) 75(1): 50-83.
Carpino, LA and Han, GY, (1972), 9-Fluorenylmethoxycarbonyl amino-protecting group J. Org. Chem. 37:3403-3409.
Carson K. et al., Chapter 35—Reimmunization after stem cell transplantation, in Hematopoietic Stem Cell Transplantation in Clinical Practice (2009) United Kingdom: Churchill Livingstone/Elsevier.Sciences.
Challen, G.A., et al., Mouse Hematopoietic Stem Cell Identification And Analysis, Cytometry A., 2009, 75(1):14-24.
Cheung, TH and Rando, TA, Molecular regulation of stem cell quiescence. Nat. Rev. Mol. Cell Biol. (2013) 14: 329-340.
Comazzetto, S. et al. Restricted Hematopoietic Progenitors and Erythropoiesis Require SCF from Leptin Receptor+ Niche Cells in the Bone Marrow. Cell Stem Cell (2019) 24, 477-486.
Crane, GM, et al., "Adult haematopoietic stem cell niches," Nat. Rev. Immunol. (2017) 17(9): 573-90.
Crivellato, E., The role of angiogenic growth factors in organogenesis. (2011) Int. J. Dev. Biol. 55: 365-375.
Davis, L.A. et al., "Mesodermal fate decisions of a stem cell: the Wnt switch", Cell Mol Life Sci., vol. 65(17): 2568-2574, (2008).
Defalco, J. et al. Virus-assisted mapping of neural inputs to a feeding center in the hypothalamus. Science 291, 2608-2613 (2001).
Dejana, E., Endothelial cell-cell junctions: happy together, Nat. Rev. Mol. Cell Biol. (2004) 5: 261-270.
Desterke, et al., "Inflammation as a Keystone of Bone Marrow Stroma Alterations in Primary Myelofibrosis", Mediators of Inflammation, vol. 2015, Article ID 415024, 16 pages, 2015.
Ding, L. and Morrison, S. J. Haematopoietic stem cells and early lymphoid progenitors occupy distinct bone marrow niches. Nature (2013) 495, 231-235.
Ding, L., et al., Endothelial and perivascular cells maintain haematopoietic stem cells. Nature (2012) 481, 457-462.
Doan, P. L. et al. Epidermal growth factor regulates hematopoietic regeneration after radiation injury. Nature medicine (2013) 19, 295-304.
Dong, F. et al. Cadmium induces vascular permeability via activation of the p38 MAPK pathway. Biochem Biophys Res Commun (2014) 450, 447-452.
Dzierzak, E. et al., Of lineage and legacy: the development of mammalian hematopoietic stem cells, Nature Immunol., vol. 9(2): 129-136, (2008).
Eltzschig, H. K. and Carmeliet, P., Hypoxia and inflammation. N Engl J Med (2011) 364, 656-665.
Espin-Palazon, R., et al. Proinflammatory Signals as Fuel for the Fire of Hematopoietic Stem Cell Emergence. Trends in cell biology 28, 58-66 (2018).
Fiedler, U, and Augustin, HG, Angiopoietins: a link between angiogenesis and inflammation, Trends Immunol. (2006) 27: 552-58.
Fields, G.B. and Noble, R.L., Solid phase peptide synthesis utilizing 9-fluorenylmethoxycarbonyl amino acids. 1990, Int. J. Pept. Protein Res. 35:161-214.
Forde, A., et al., Temporal Cre-mediated recombination exclusively in endothelial cells using Tie2 regulatory elements. Genesis (2002) 33, 191¬-197.

(56) References Cited

OTHER PUBLICATIONS

Fundamental Immunology, 4th Ed., William E. Paul, ed. Lippincott-Raven Publishers, Philadelphia (1999) at 1051-1053.
Gareus, R. et al. Endothelial cell-specific NF-kappaB inhibition protects mice from atherosclerosis. Cell Metabolism (2008) 8, 372-383.
Butler, J.M., et al. Endothelial MAPK Activation Disrupts Hematopoiesis By Depleting Plasma SCGF, Blood, American Society of Hematology, vol. 132, Nov. 29, 2018, p. 1290, XP086592635.
Ramalingam, P., et al. Chronic activation of endothelial MAPK disrupts hematopoiesis via NFKB dependent inflammatory stress reversible by SCGF. Nat Commun 11, 666, Dec. 1, 2020 (Dec. 1, 2020), XP055866720.
Liu B., et al., Biglycan promotes the chemotherapy resistance of colon cancer by activating NF-kappa B signal transduction. Mol Cell Biochem 449, 285-294, May 14, 2018 (May 14, 2018) XP036628080.
Extended European Search Report dated Oct. 18, 2023, EP Appl. No. 20894750.7, 13 pages.
Geest, C. R. and Coffer, P. J. MAPK signaling pathways in the regulation of hematopoiesis. Journal of Leukocyte Biology (2009) 86, 237-250.
Gluzman, Y., SV40-transformed simian cells support the replication of early SV40 mutants. Cell, 23:175 (1981).
Gold, L. et al. Aptamer-based multiplexed proteomic technology for biomarker discovery. PloS One 5, e15004 (2010).
Greenbaum, A. et al. CXCL12 in Early Mesenchymal Progenitors is Required for Hematopoietic Stem Cell Maintenance. Nature (2013) 495, 227-230.
Griz, E. "Specification and function of hemogenic endothelium during embryogenesis," Cell Mol. Life Sci. (2016) 73: 1547-67.
Grzywacz, B. et al, Natural Killer Cell differentiation by myeloid progenitors, Blood (2011) 117 (13): 3548-58.
Guay, J. et al., Regulation of actin filament dynamics by p38 map kinase-mediated phosphorylation of heat shock protein 27. (1997) J. Cell Sci. 110: 357-68.
Guiot, J. et al. Blood Biomarkers in Idiopathic Pulmonary Fibrosis. Lung (2017) 195(3): 273-280.
Gurgis, FMS, et al., Mitogen-activated protein kinase-activated protein kinase 2 in neuroinflammation, heat shock protein 27 phosphorylation, and cell cycle: role and targeting. Molecular Pharmacol. (2014) 85: 345-56.
Gyurkocza, B. and Sandmaier, B.M. "Conditioning regimens for hematopoietic cell transplantation: one size does not fit all." Blood (2014) vol. 124,3: 344-53.
Halle, M. et al. Sustained inflammation due to nuclear factor-kappa B activation in irradiated human arteries. J. Am. Coll. Cardiol. (2010), 55: 1227-1236.
Hayden, MS and Ghosh, S NF-κB, the first quarter-century: remarkable progress and outstanding questions. (2012) Genes Dev. 26: 203-234.
Hayflick, L. and Moorhead, PS, The serial cultivation of human diploid cell strains. Expl Cell Res., (1961) 25: 585-621.
Hooper, A. T. et al. Engraftment and reconstitution of hematopoiesis is dependent on VEGFR2-mediated regeneration of sinusoidal endothelial cells. Cell stem cell (2009) 4, 263-274.
Hu, Y. & Smyth, G. K. Elda: extreme limiting dilution analysis for comparing depleted and enriched populations in stem cell and other assays. J Immunol Methods 347, 70-78, (2009).
Hynes, RO, Cell-matrix adhesion in vascular development. J. Thromb. Haemost. (2007) 5 (Suppl. 1): 32-40.
Inra, C. N. et al. A perisinusoidal niche for extramedullary haematopoiesis in the spleen. Nature (2015) 527, 466-471.
International Search Report and Written Opinion, PCT/US2020/62397, date of mailing Mar. 4, 2021, 18 pgs.
Ito, C. et al. Serum stem cell growth factor for monitoring hematopoietic recovery following stem cell transplantation. Bone Marrow Transplant (2003) 32, 391-398.
Janeways Immunobiology. 9th ed., GS, Garland Science, Taylor & Francis Group, 2017. pp. 232-233.
Jin, Z., et al., Essential Role of Endothelial MCPIP in Vascular Integrity and Post-Ischemic Remodeling Int. J. Mol. Sci. (2019) 20(1): 172.
Karhausen, J., et al., Inflammatory hypoxia: role of hypoxia-inducible factor. Cell Cycle (2005) 4, 256-258.
Kawamoto, H. and Minato, N. Myeloid cells. Intl J. Biochem. Cell Biol. (2004) 36 (8): 1374-1379.
Keller, C. C. et al. Suppression of a novel hematopoietic mediator in children with severe malarial anemia. Infect Immun (2009) 77, 3864-3871.
Kempe, S. et al., NF-κB controls the global pro-inflammatory response in endothelial cells: evidence for the regulation of a pro-atherogenic program. Nucleic Acids Res. (2005) 33: 5308-5319.
Kilani, B. et al. Comparison of endothelial promoter efficiency and specificity in mice reveals a subset of Pdgfb-positive hematopoietic cells. J Thromb Haemost (2019) 17, 827-840.
Kisseleva, T. et al. NF-kappaB regulation of endothelial cell function during LPS-induced toxemia and cancer. J Clin Invest 116, 2955-2963 (2006).
Kobayashi, H. et al. Angiocrine factors from Akt-activated endothelial cells balance self-renewal and differentiation of haematopoietic stem cells. Nature cell biology (2010) 12, 1046-1056.
Kopp, et al. "The Bone Marrow Vascular Niche: Home of HSC Differentiation and Mobilization." Physiology 20: 349-356, 2005.
Korhonen, H. et al. Anaphylactic shock depends on endothelial Gq/G11. J Exp Med (2009) 206, 411-420.
Korpela, E. and Liu, S. K. Endothelial perturbations and therapeutic strategies in normal tissue radiation damage. Radiation Oncology (2014) 9, 266.
Kovtonyuk, L. V., et al., Inflamm-Aging of Hematopoiesis, Hematopoietic Stem Cells, and the Bone Marrow Microenvironment. Frontiers in immunology 7, 502 (2016).
Kusumbe, A. P. et al. Age-dependent modulation of vascular niches for haematopoietic stem cells. Nature (2016) 532, 380-384.
Lane, S. W., et al. Modulating the stem cell niche for tissue regeneration. Nature Biotechnology 32, 795-803 (2014).
Langen, U. H. et al. Cell-matrix signals specify bone endothelial cells during developmental osteogenesis. Nature cell biology (2017) 19, 189-201.
Li, J. et al, "Isolation and transcriptome analyses of human erythroid progrenitors: BFU-E and CFU-E." Blood (2014) 124 (24): 3636-45.
Li, L. et al. P38/MAPK contributes to endothelial barrier dysfunction via MAP4 phosphorylation-dependent microtubule disassembly in inflammation-induced acute lung injury. Sci Rep (2015) 5, 8895.
Li, X. M., et al., Bone marrow sinusoidal endothelial cells undergo nonapoptotic cell death and are replaced by proliferating sinusoidal cells in situ to maintain the vascular niche following lethal irradiation. Exp Hematol (2008) 36, 1143-1156.
Li, Y, et al. Insulin-like growth factor 1 enhances the migratory capacity of mesenchymal stem cells. 2007 Biochem. Biophys. Res. Communic. 356(3): 780-784.
Li, Y. et al., Inflammatory signaling regulates embryonic hematopoietic stem and progenitor cell production. Genes Dev., vol. 28(23): 2597-2612, (2014).
Loberg, RD, et al., Enhanced Glycogen Synthase Kinase-3beta Activity Mediates Hypoxia-induced Apoptosis of Vascular Smooth Muscle Cells and Is Prevented by Glucose Transport and Metabolism*. J. Biol. Chem. 277 (44): 41667-673 (2002).
Loetscher P. et al. The Ligands of CXC Chemokine Receptor 3, I-TAC, Mig, and IP10, Are Natural Antagonists for CCR3. J. Biol. Chem. (2001). 276: 2986-2991.
Lombardi, V et al. The Role of Costimulatory Molecules in Allergic Disease and Asthma. (2010) Int. Arch. Allergy Immunol. 151: 179-89.
Ludin, A. et al. Reactive oxygen species regulate hematopoietic stem cell self-renewal, migration and development, as well as their bone marrow microenvironment. Antioxid Redox Signal (2014) 21, 1605-1619.
Lussana, F. & Rambaldi, A. Inflammation and myeloproliferative neoplasms. Journal of autoimmunity (2017) 85, 58-63.

(56) References Cited

OTHER PUBLICATIONS

Mackay C.R. Chemokines: immunology's high impact factors. Nat Immunol., vol. 2: 95-101, (2001).
Manz, MG, et al., "Prospective isolation of human clonogenic common myeloid progenitors." Proc. Natl Acad. Sci. USA (2002) 99 (18): 11872-77.
Matthay, K.K. et al., Role of Myeloablative Therapy in Improved Outcome for High Risk Neuroblastoma: Review of Recent Children's Cancer Group Results. Eur J Cancer, vol. 31A, No. 4, 572-575 (1995).
Mazumder, B., et al., Translation control: a multifaceted regulator of inflammatory response. J Immunol (2010) 184, 3311-3319.
Mcdermott, B. T., et al., Translational regulation contributes to the secretory response of chondrocytic cells following exposure to Interleukin-1beta. J Biol Chem (2019) 294(35) 13027-13039.

* cited by examiner

FIG. 1H
Limiting Dilution Analysis
Whole Bone Marrow
| | Cell Dose | LTMR/recipient |
|---|---|---|
| Control | 50,000 | 3/10 |
| | 100,000 | 5/10 |
| | 250,000 | 10/10 |
| *CDH5-MAPK* | 50,000 | 1/10 |
| | 100,000 | 4/10 |
| | 250,00 | 7/10 |
FIG. 1I
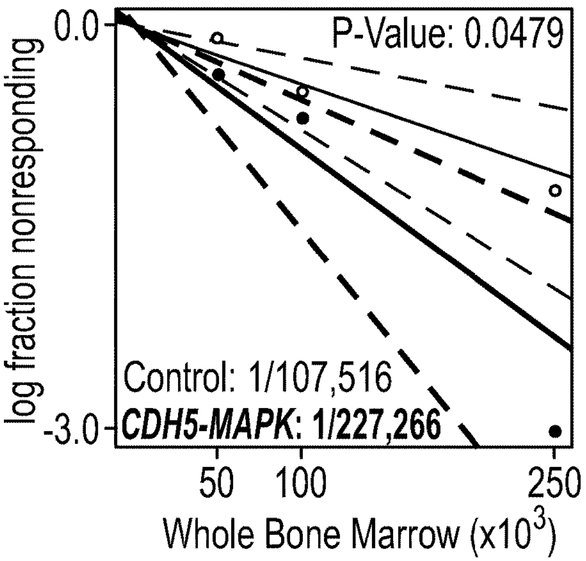
FIG. 1J
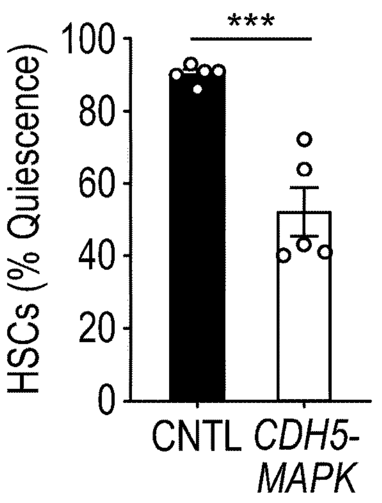
FIG. 1K
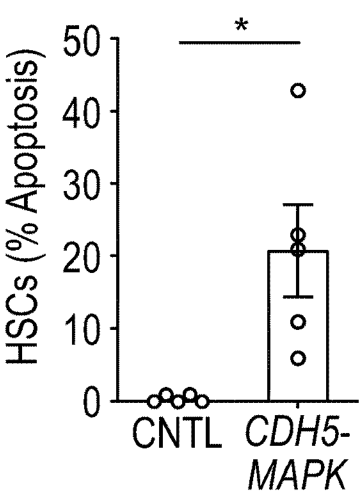

Pathway Analysis
- inflammatory response
- inflammation of organ
- inflammation of absolute anatomical region FIG. 4D
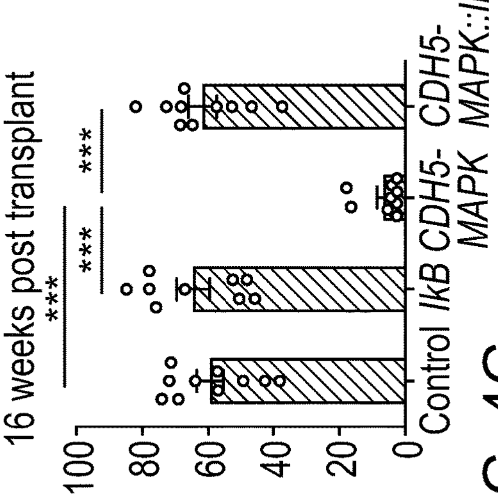
FIG. 4E
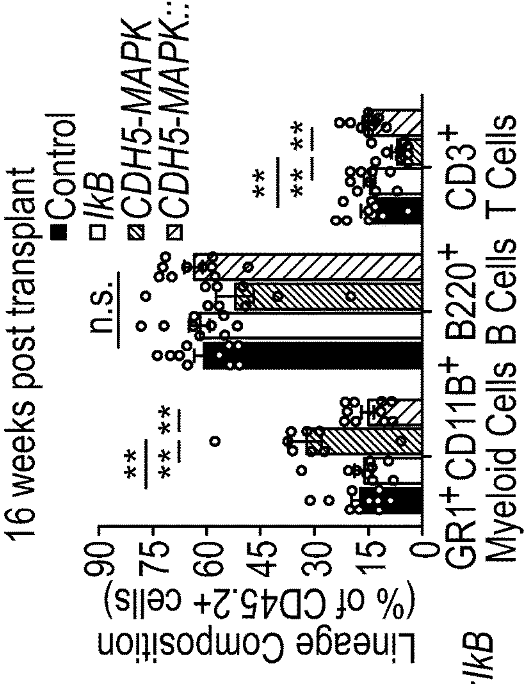
FIG. 4F
Limiting Dilution Analysis
Whole Bone Marrow
| | Cell Dose | LTMR/ recipient |
|---|---|---|
| Control | 50,000 | 2/10 |
| | 100,000 | 4/10 |
| | 250,000 | 10/10 |
| *IkB* | 50,000 | 7/10 |
| | 100,000 | 9/10 |
| | 250,000 | 10/10 |
| *CDH5-MAPK* | 50,000 | 0/10 |
| | 100,000 | 2/10 |
| | 250,000 | 6/10 |
| *CDH5-MAPK::IkB* | 50,000 | 4/10 |
| | 100,000 | 7/10 |
| | 250,000 | 10/10 |
FIG. 4G
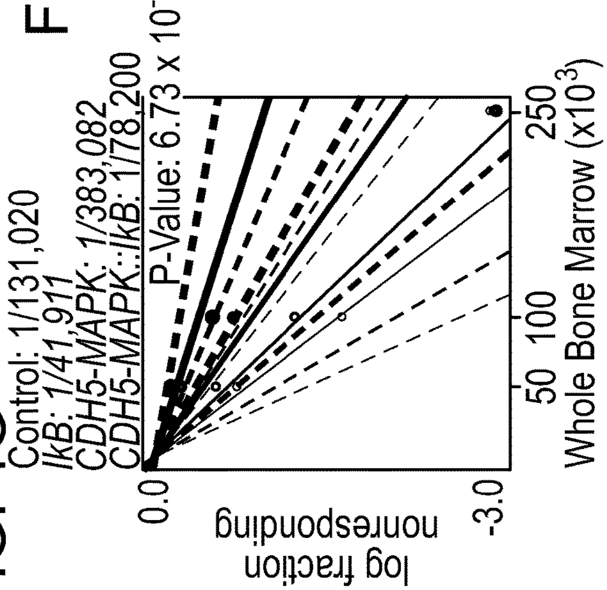
FIG. 4H
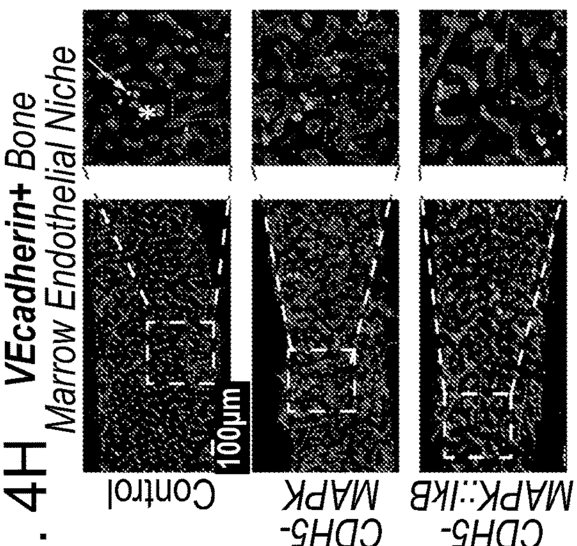

Cells per femur
MPP (x10²)
CLP (x10²)
CMP (x10³)
GMP (x10³)
MEP (x10³)

Cells per femur (x10⁵)
sIgM-B220+
Prepro B
Pro B
Pre B

Lineage Composition (% of Bone Marrow CD45+)
CD11b+Gr1+
B220+
CD3+
Control
IkB
CDH5-MAPK
CDH5-MAPK::IkB Peripheral blood counts
RBCs per μL (x10⁶)
WBCs per μL (x10³)
Platelets per μL (x10⁵)

Kisseleva T, et al. 2006 JCI PMID: 17053836
Poulos M, et al. 2016. Nature Communications PMID: 28000664

SUPP. FIG. 1A
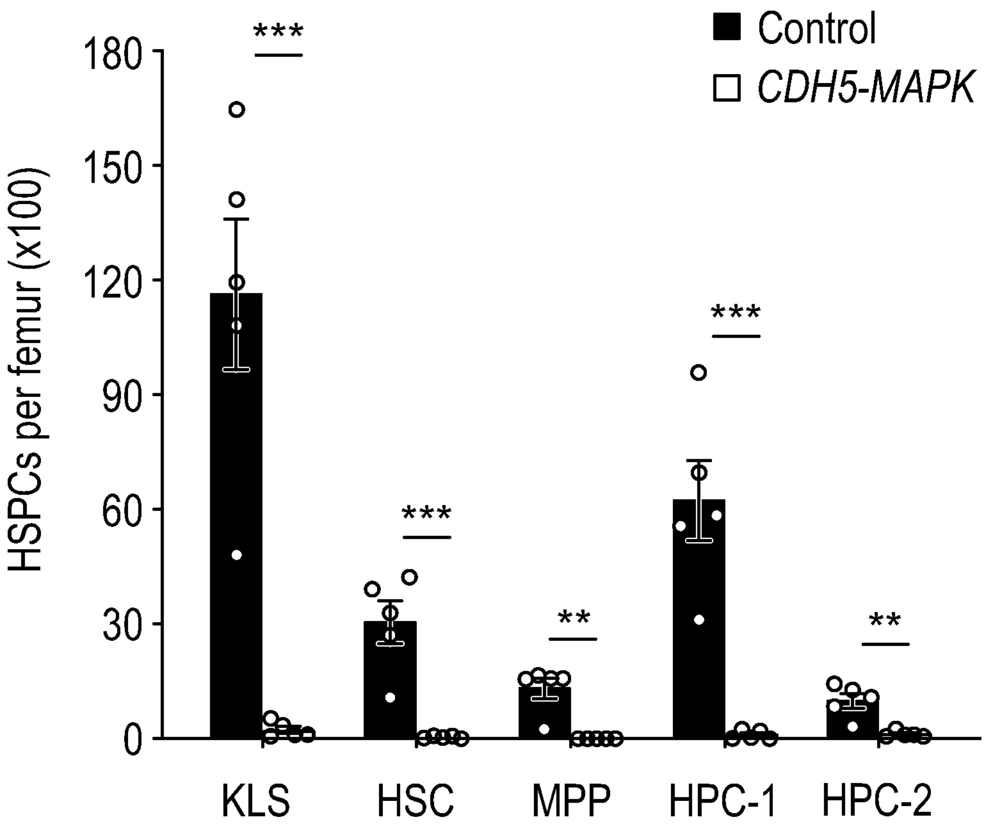

SUPP. FIG. 1B
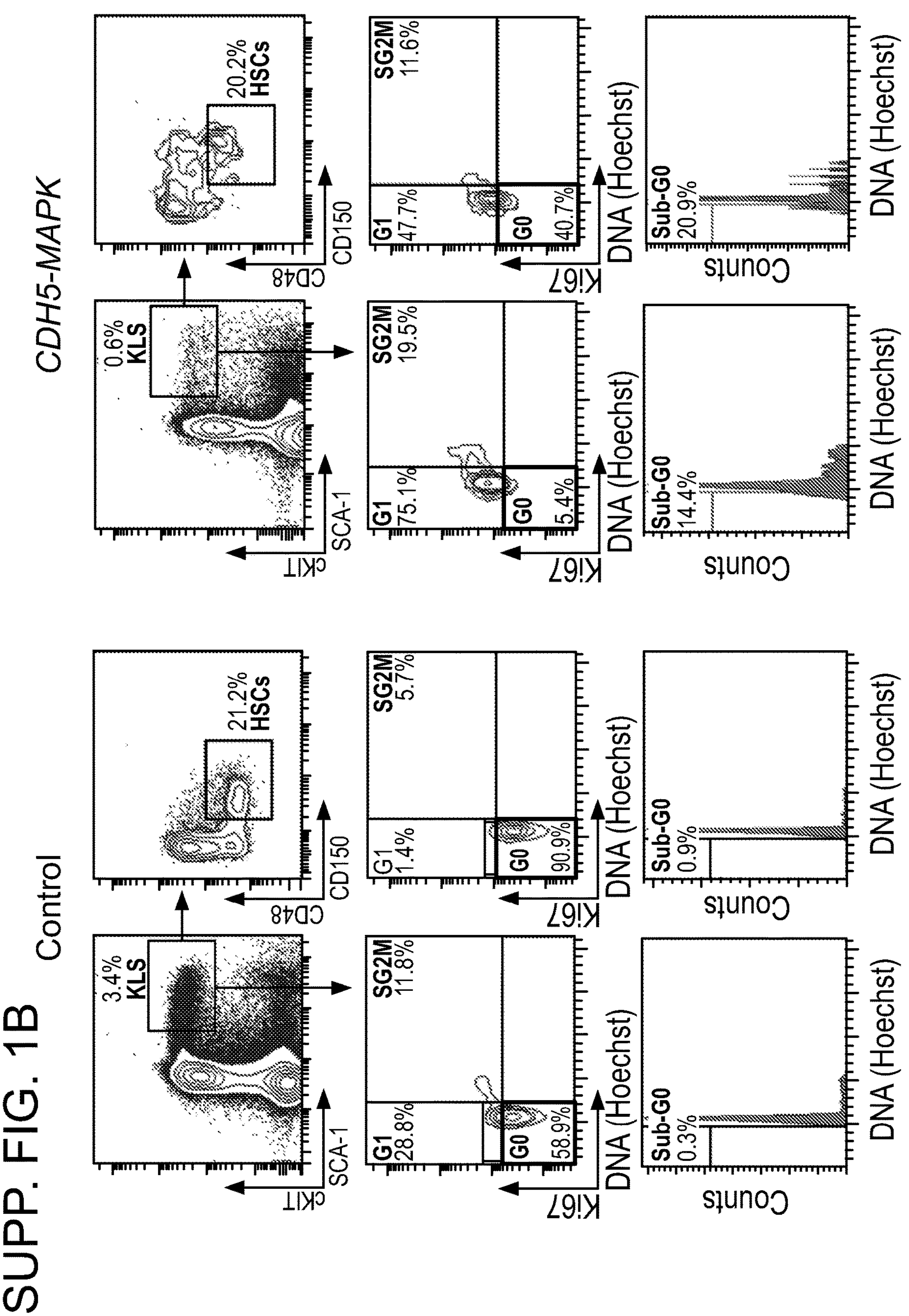

SUPP. FIG. 1C
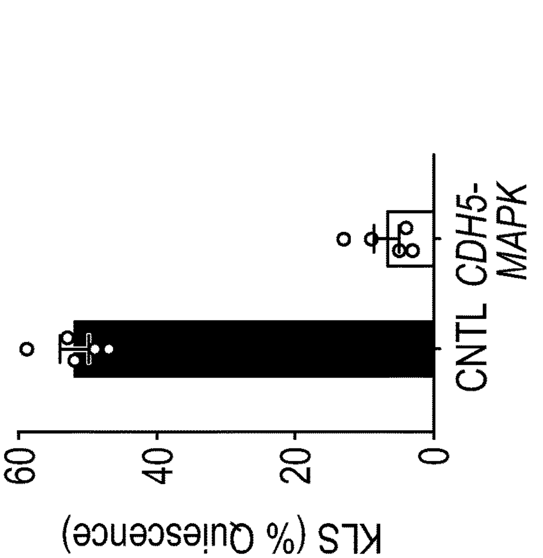
SUPP. FIG. 1D
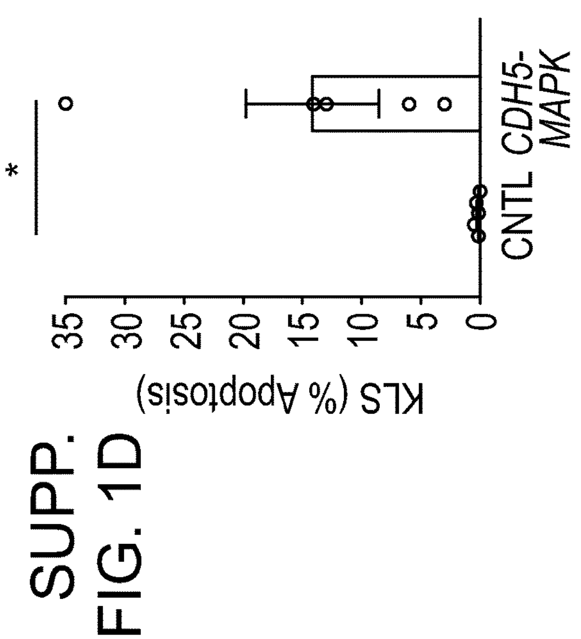
SUPP. FIG. 1E
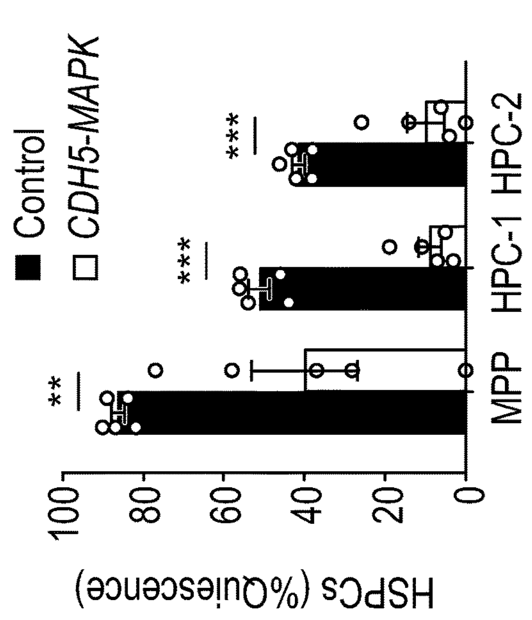
SUPP. FIG. 1F
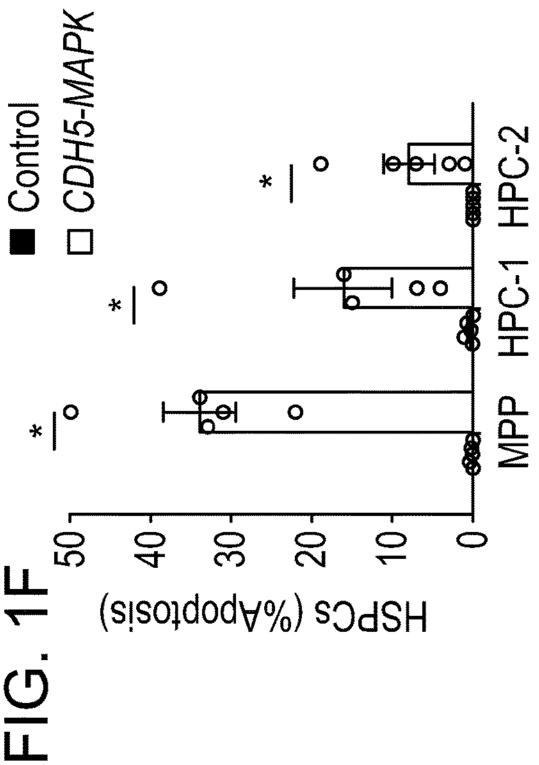

SUPP. FIG. 2A
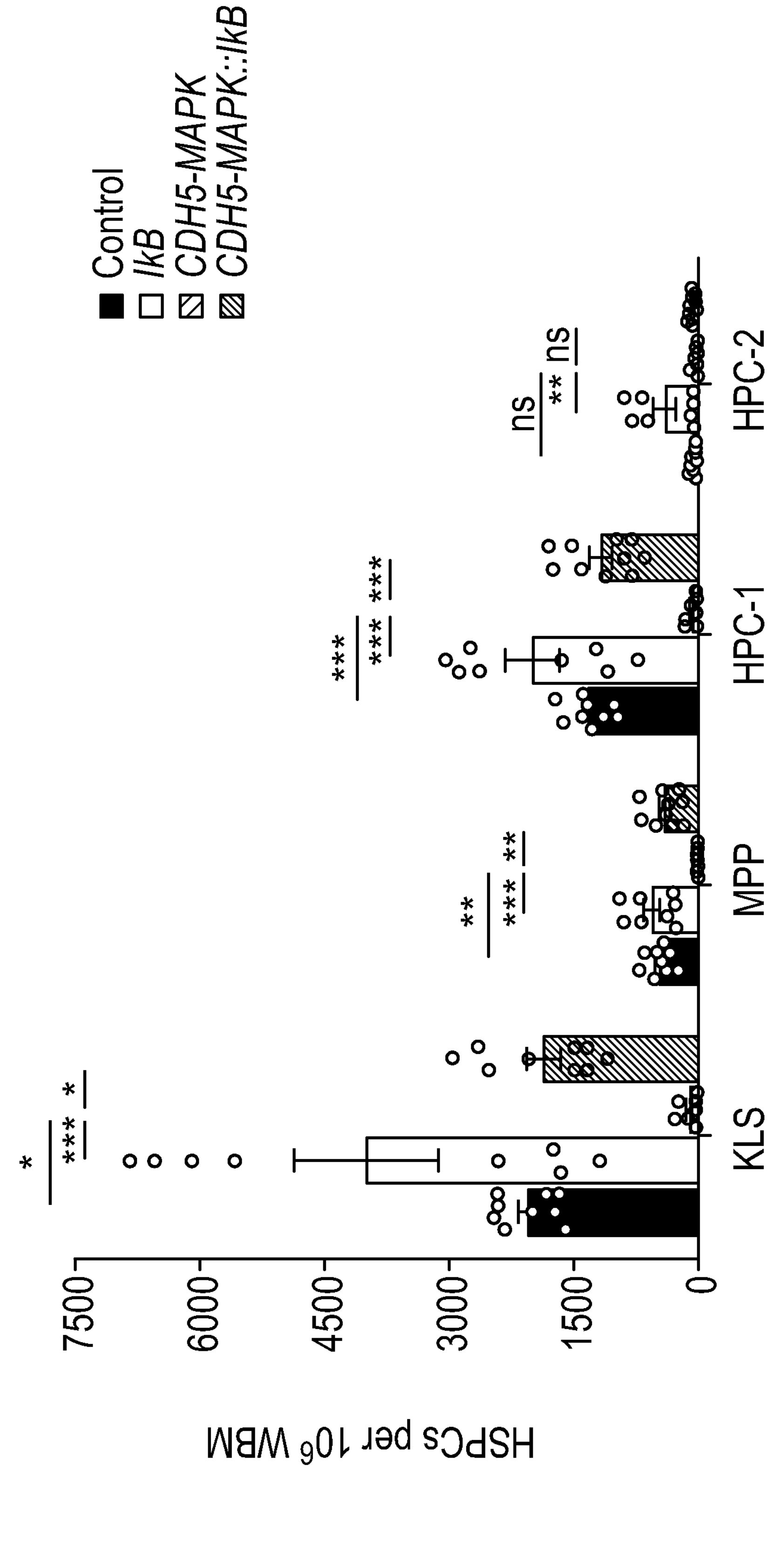

SUPP. FIG. 2B
Gating strategy for lineage composition
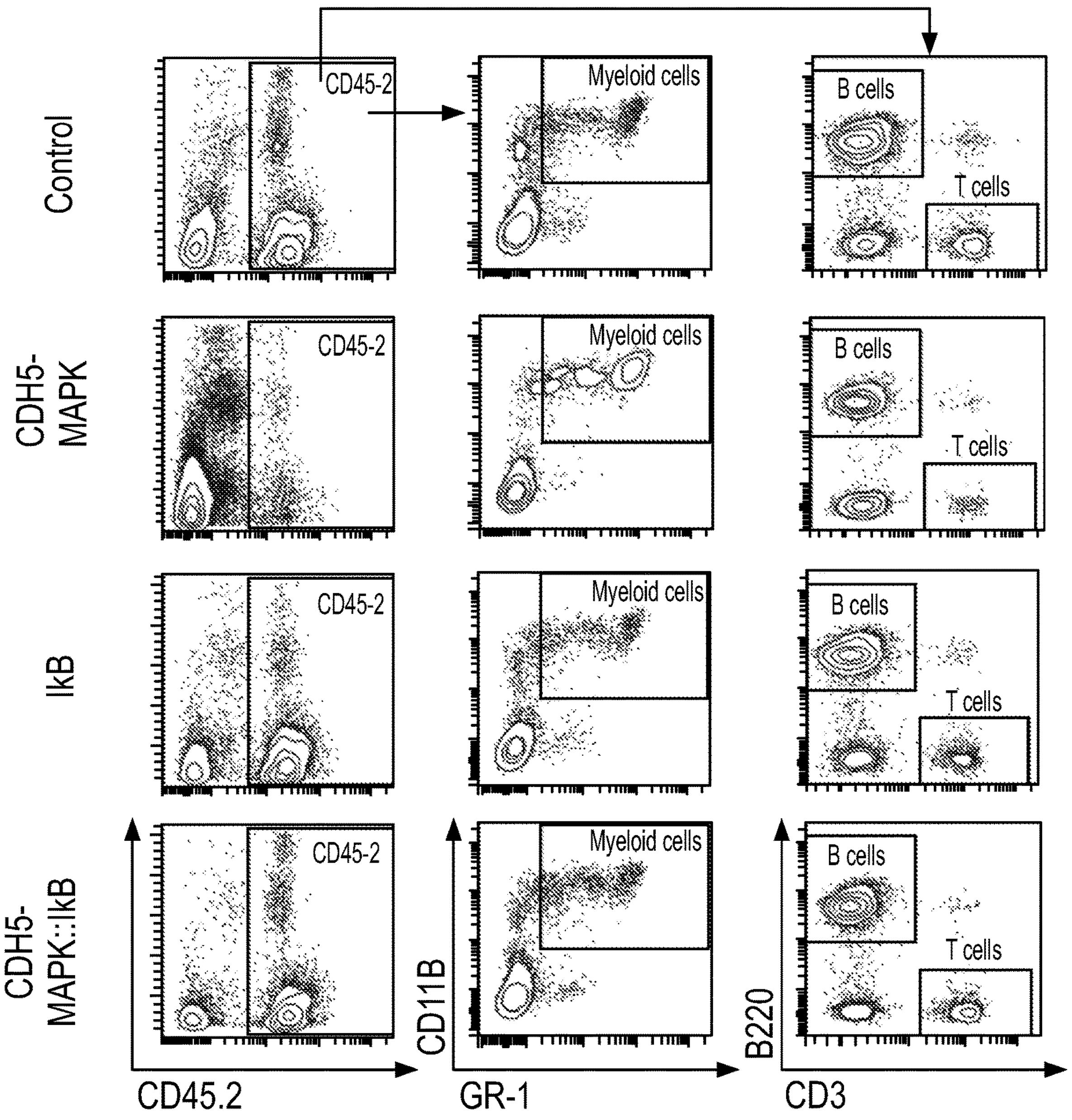

SUPP. FIG. 2C
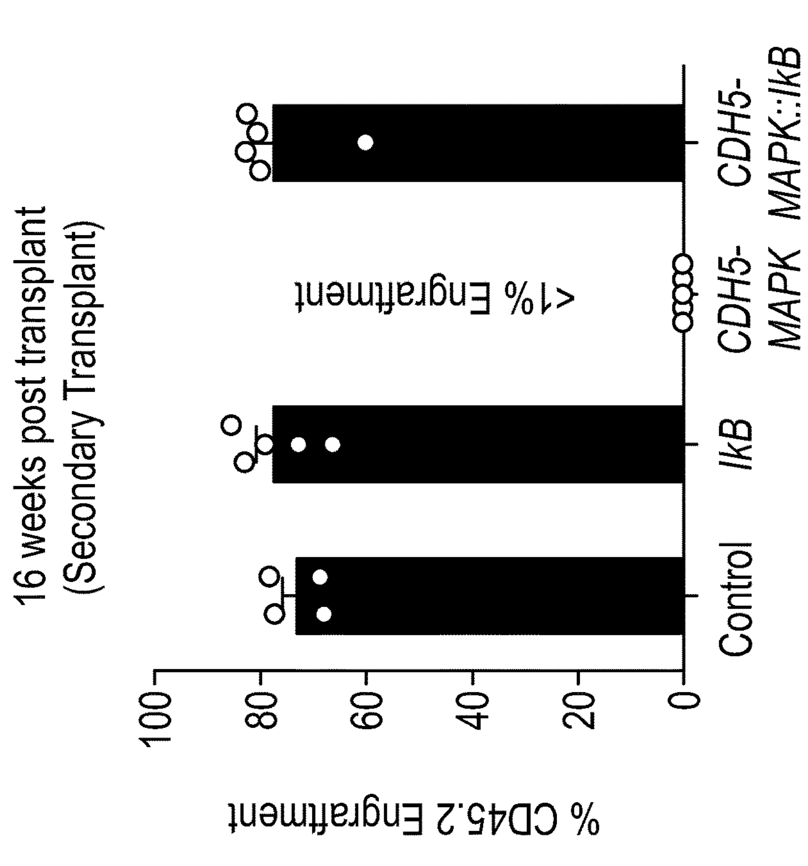
SUPP. FIG. 2D
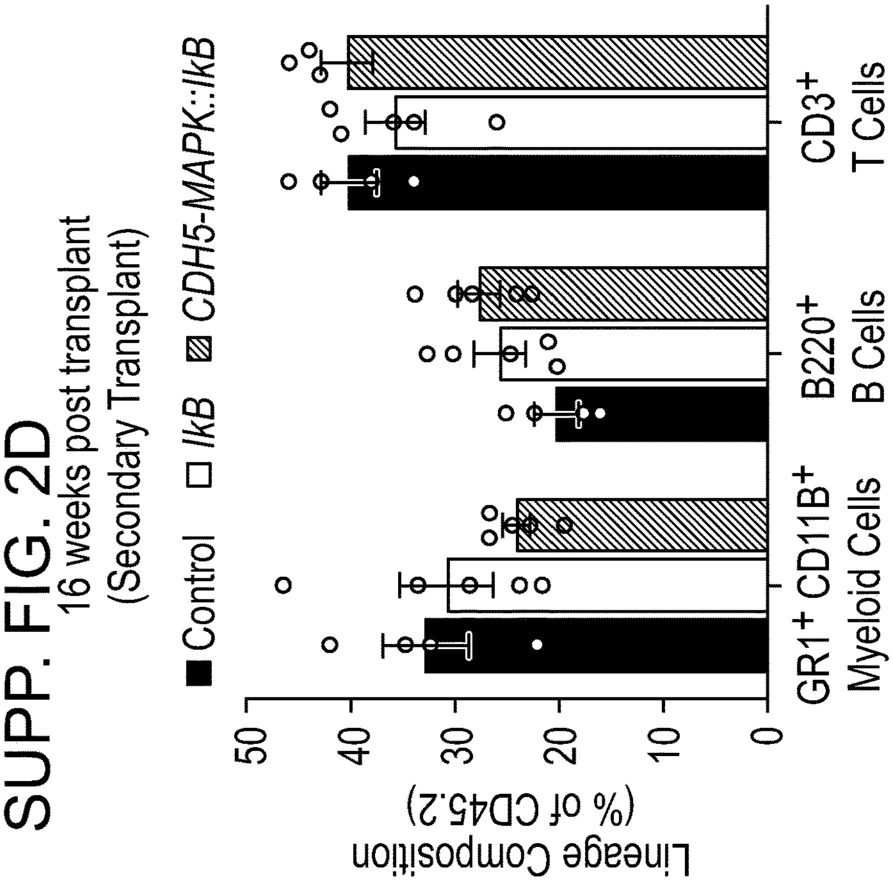

SUPP. FIG. 2E
Gating Strategy for hematopoietic progenitor subsets
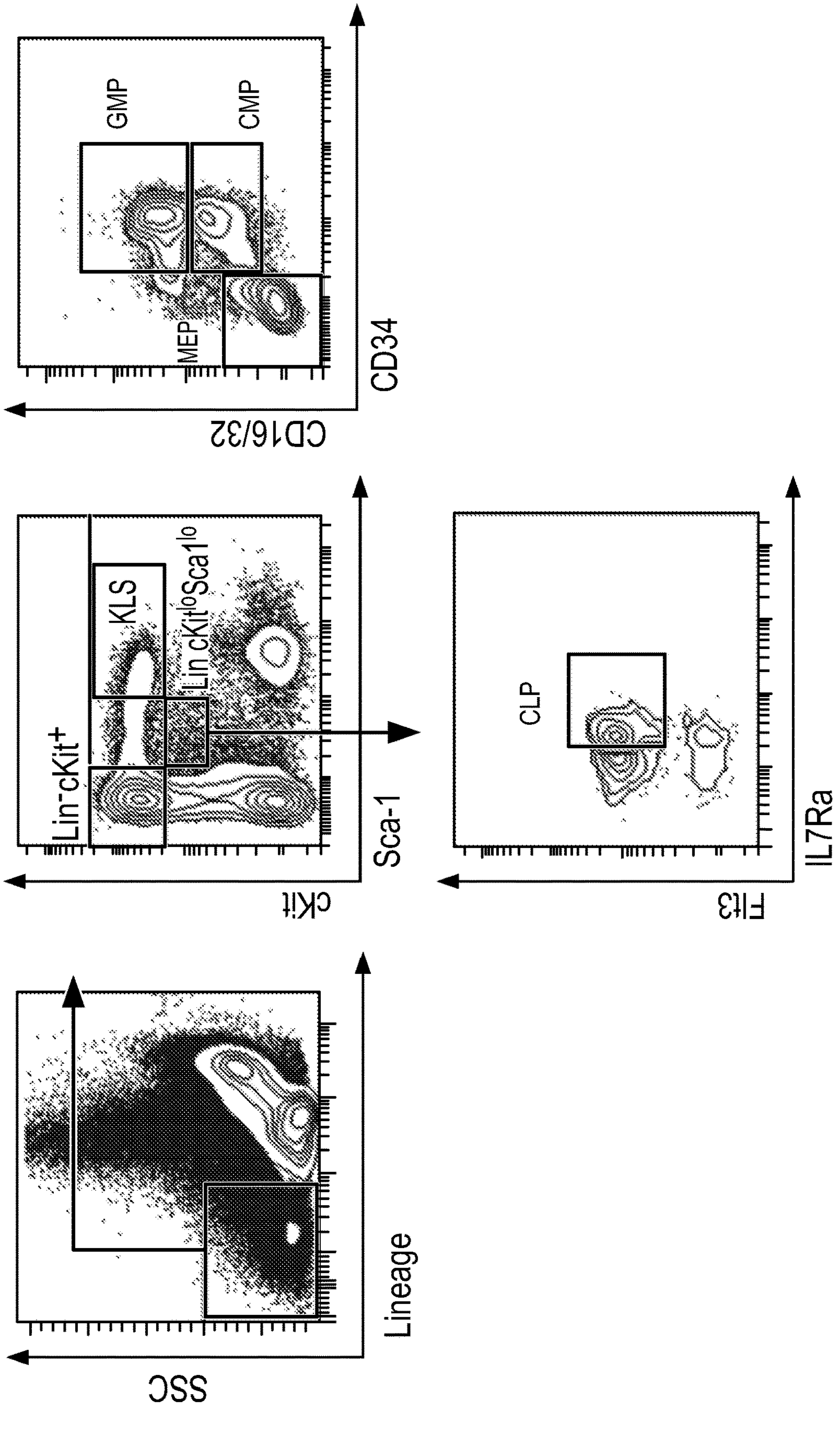

SUPP. FIG. 2F
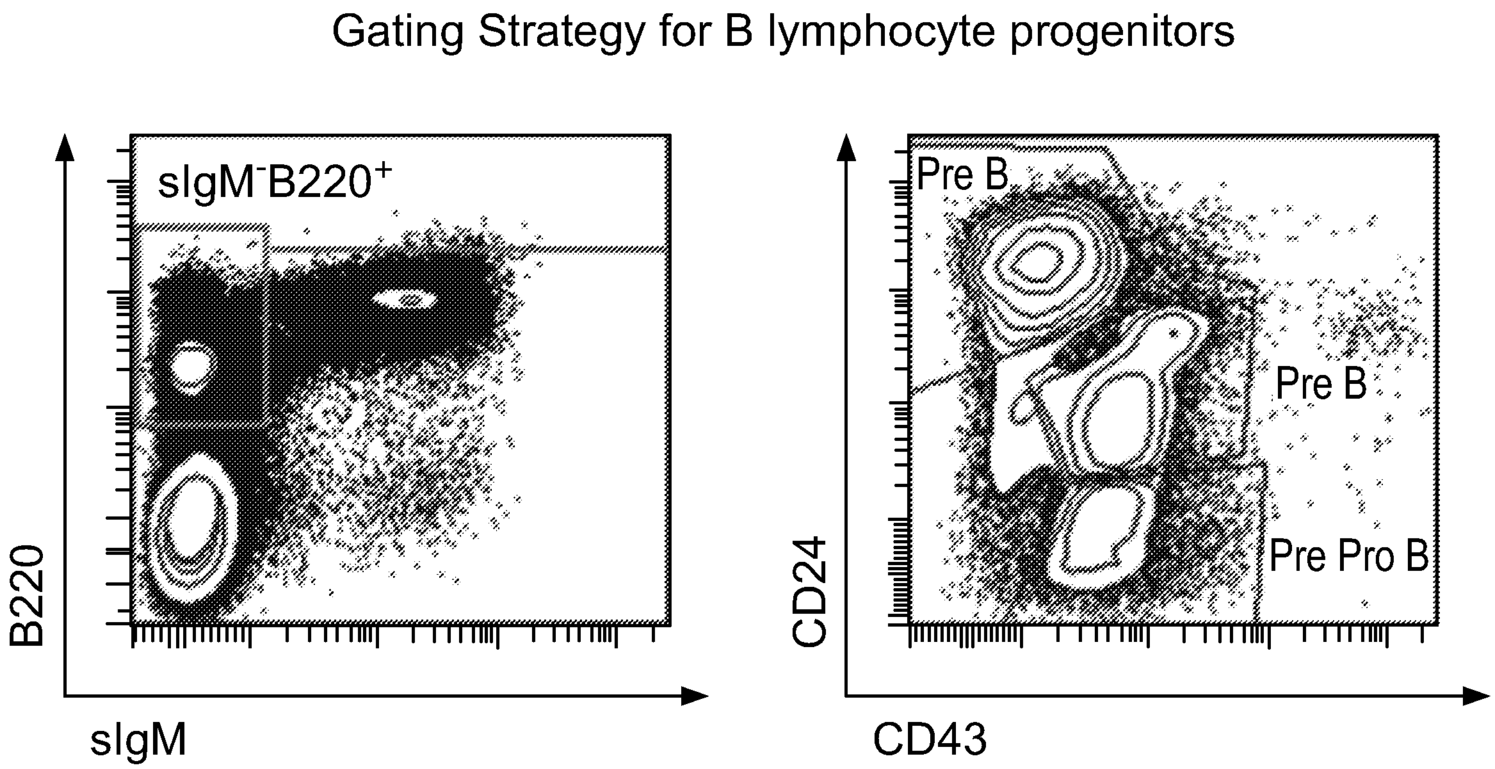

SUPP. FIG. 3A
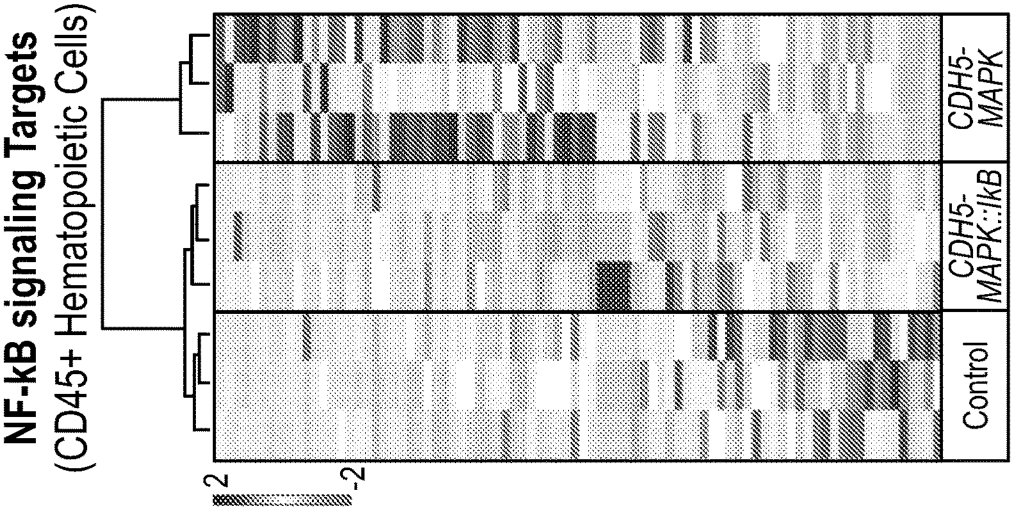
SUPP. FIG. 3B
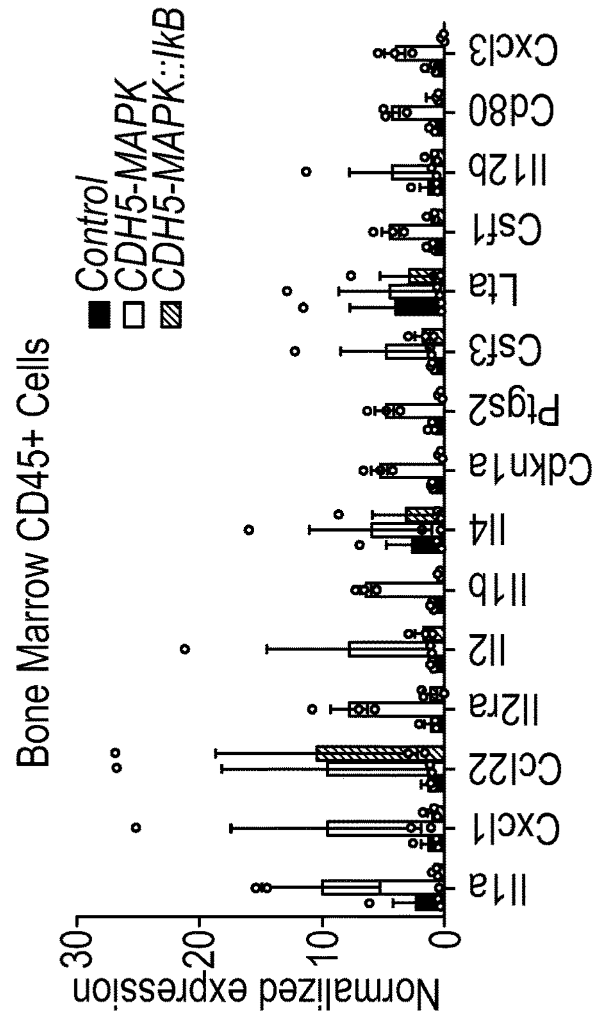

SUPP. FIG. 3C
NF-kB signaling Targets
(Bone Marrow Stromal Cells)
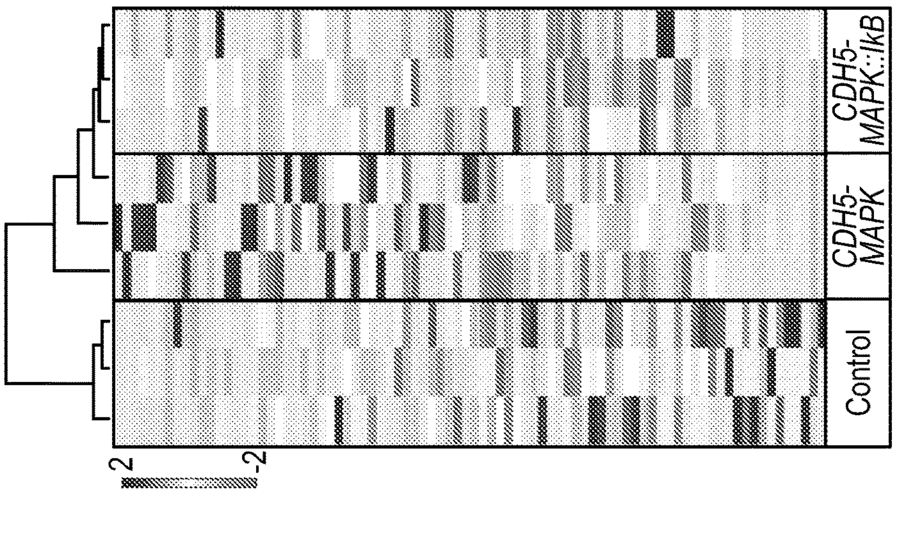
SUPP. FIG. 3D
Bone Marrow Stromal Cells
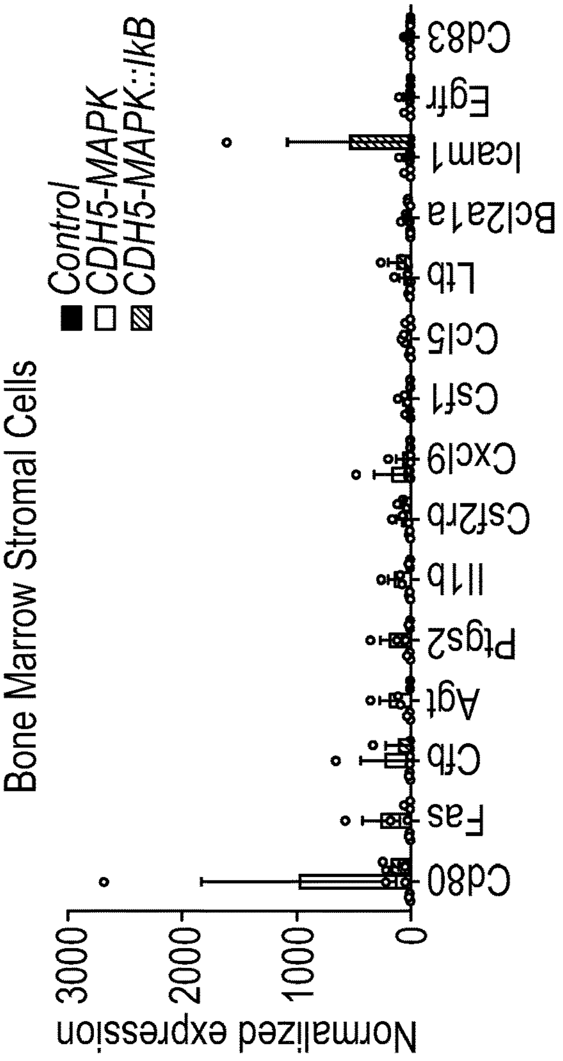

SUPP. FIG. 3E
NF-kB Signaling Targets
(Whole Bone Marrow Microenvironment)
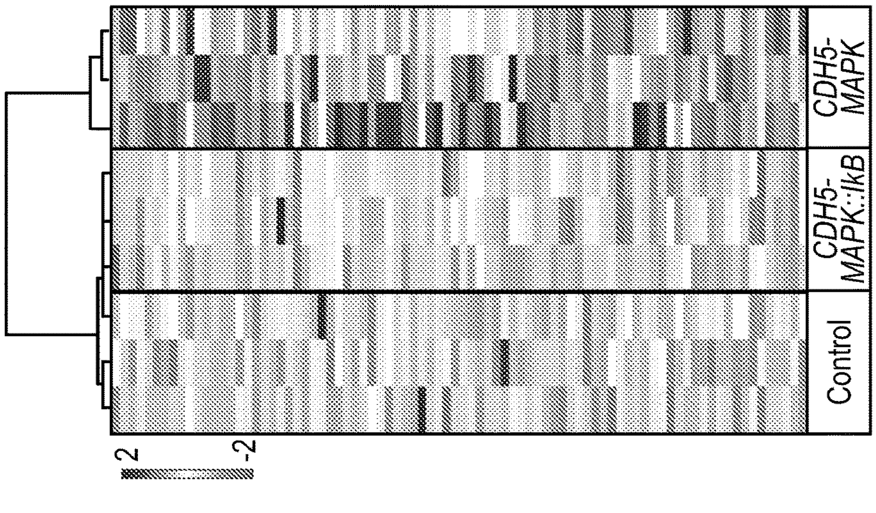
SUPP. FIG. 3F
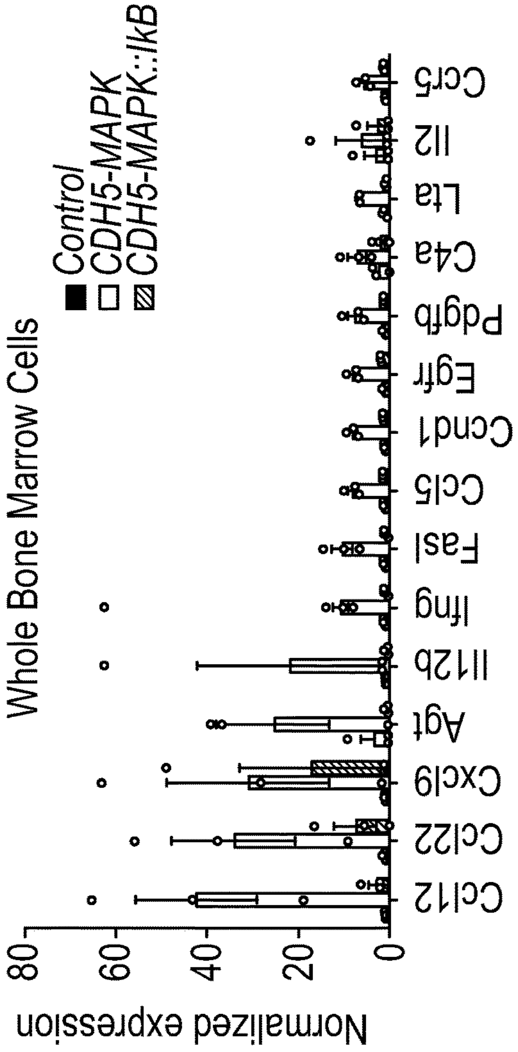

SUPP. FIG. 4A
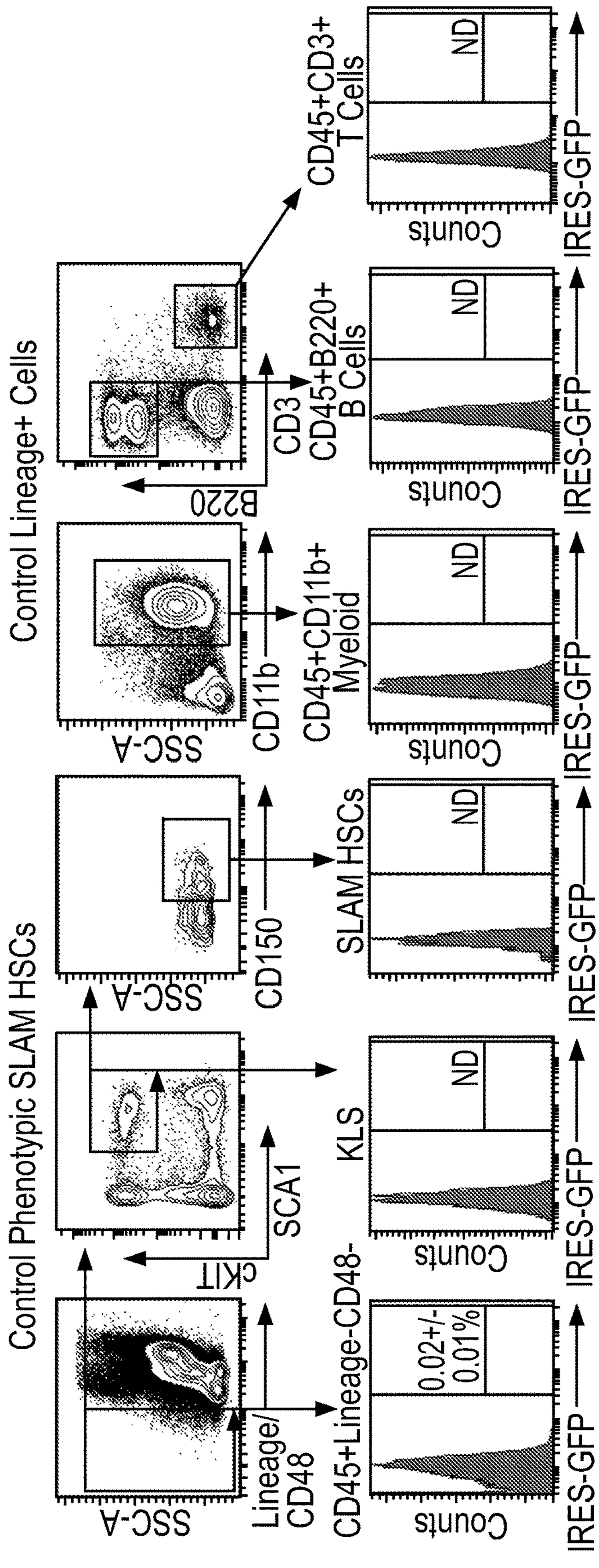

SUPP. FIG. 4B
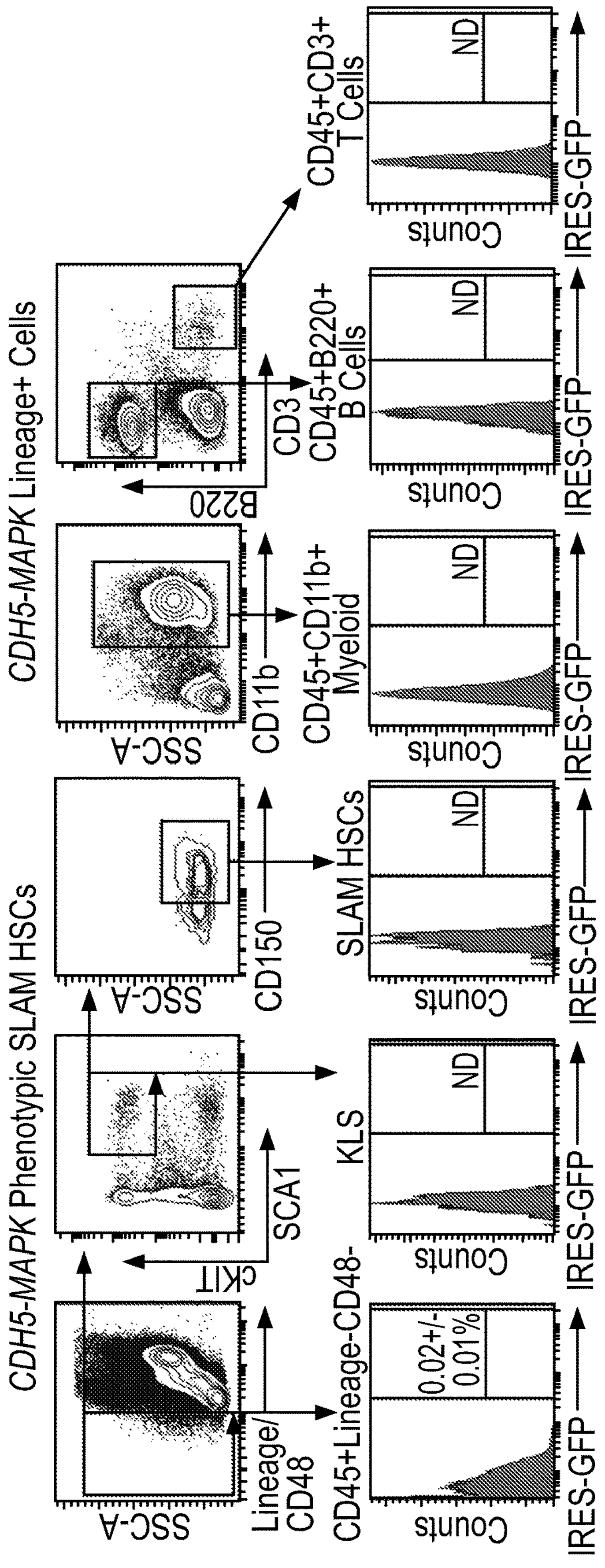

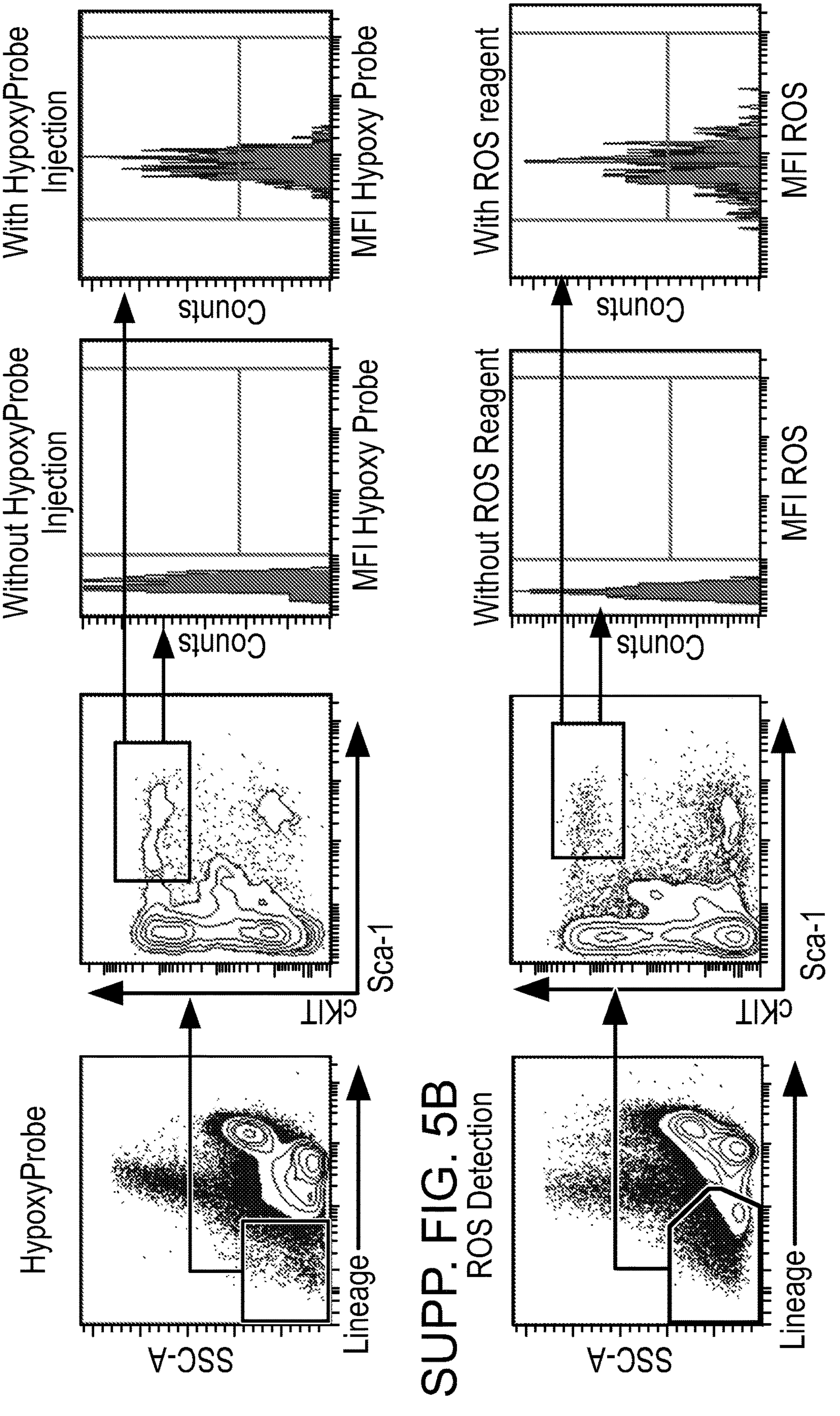
SUPP. FIG. 5A
SUPP. FIG. 5B

SUPP. FIG. 6A
*In Vivo* Sorted BMECs and Stroma
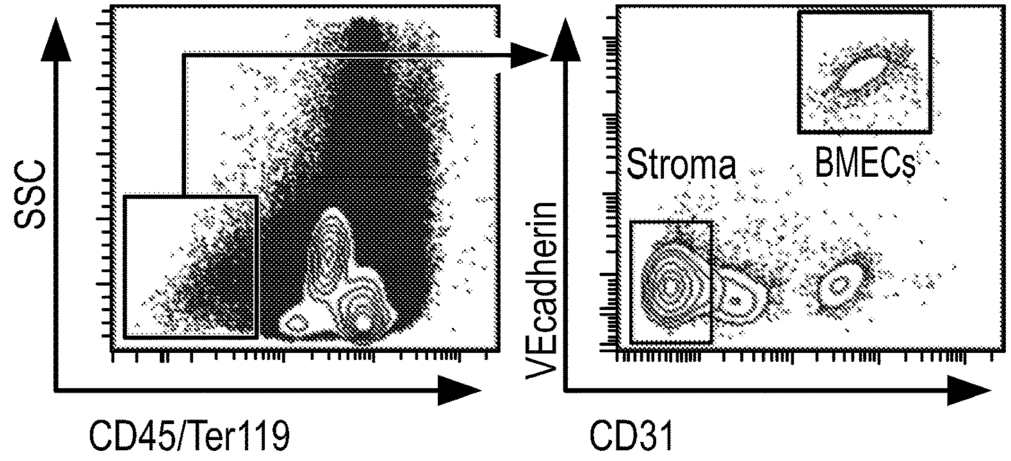
SUPP. FIG. 6B
*In Vivo* Sorted Lepr+ Cells
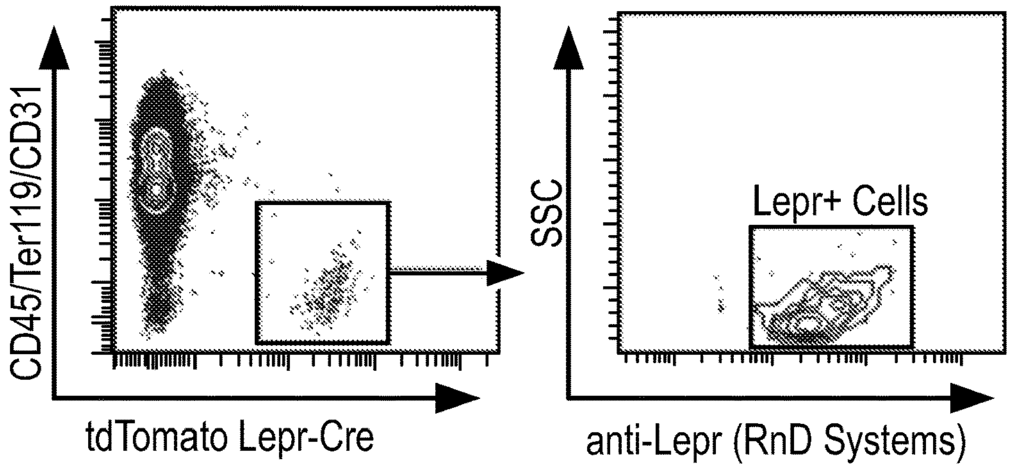
SUPP. FIG. 6C
*In Vivo* Sorted Osteoblasts
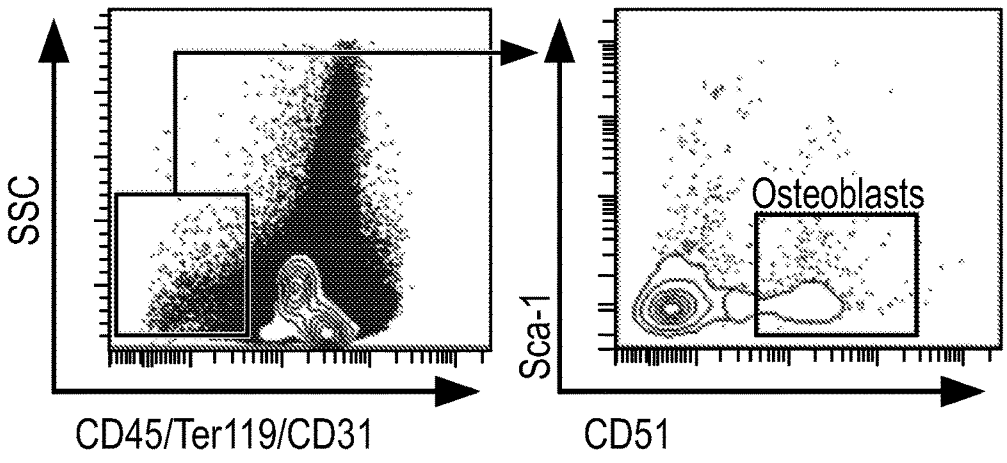

SUPP. FIG. 6D
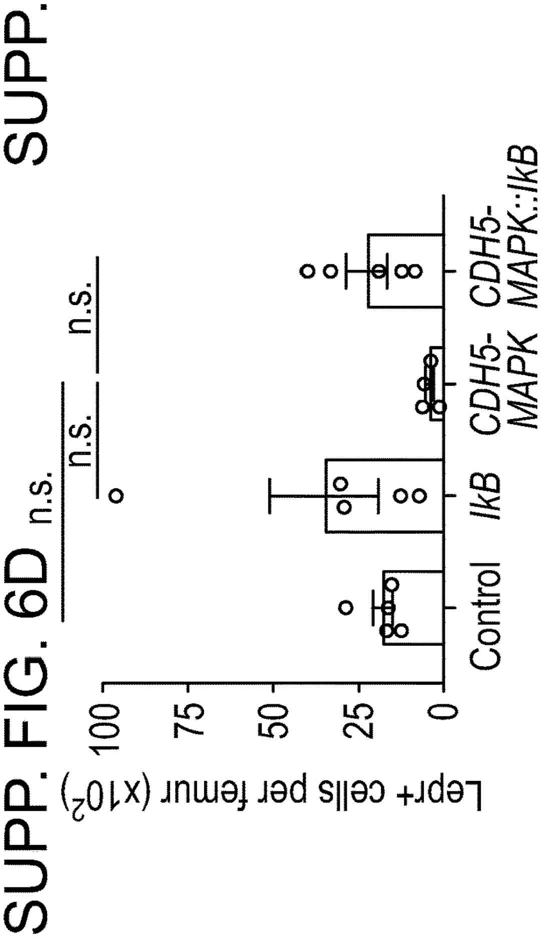
SUPP. FIG. 6E
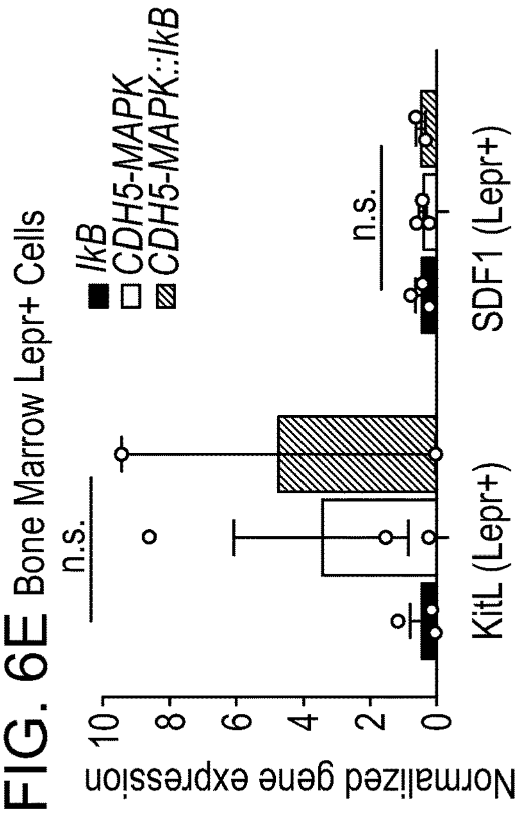
SUPP. FIG. 6F
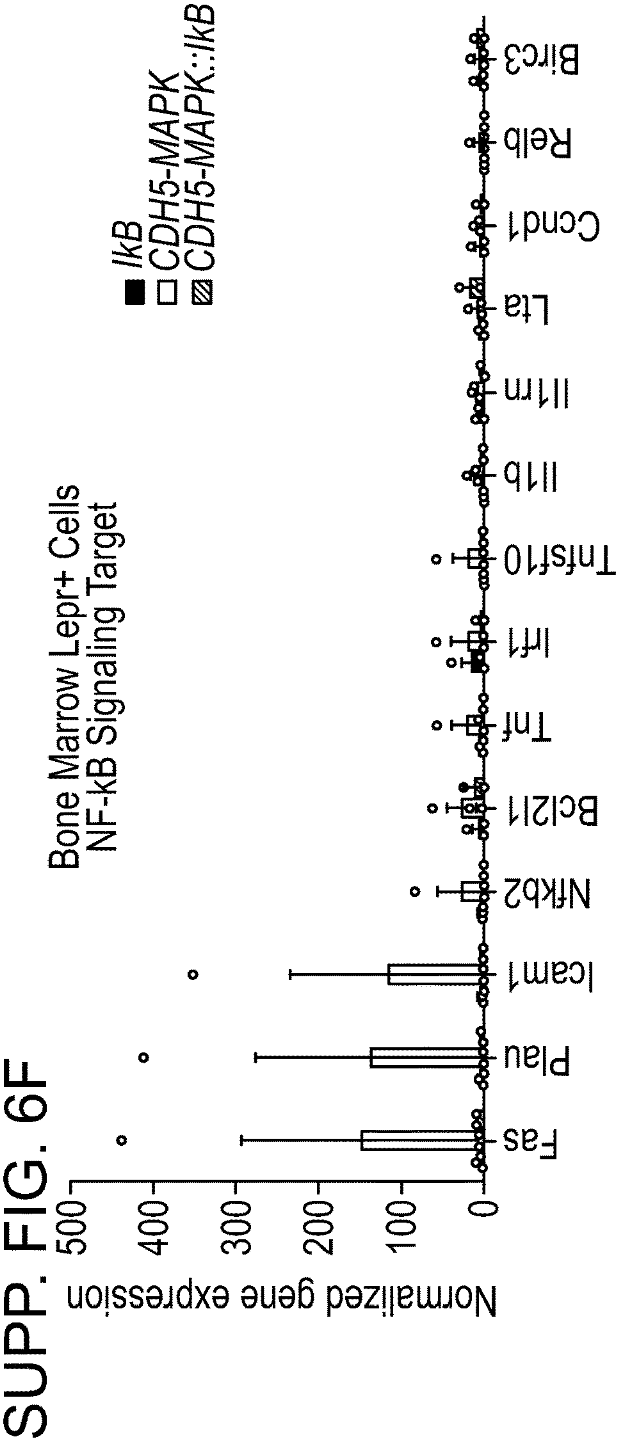

SUPP. FIG. 6G
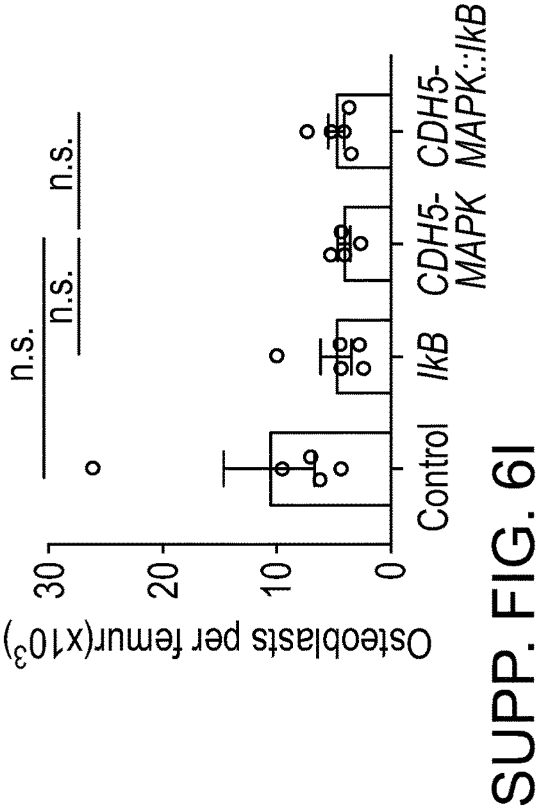
SUPP. FIG. 6H
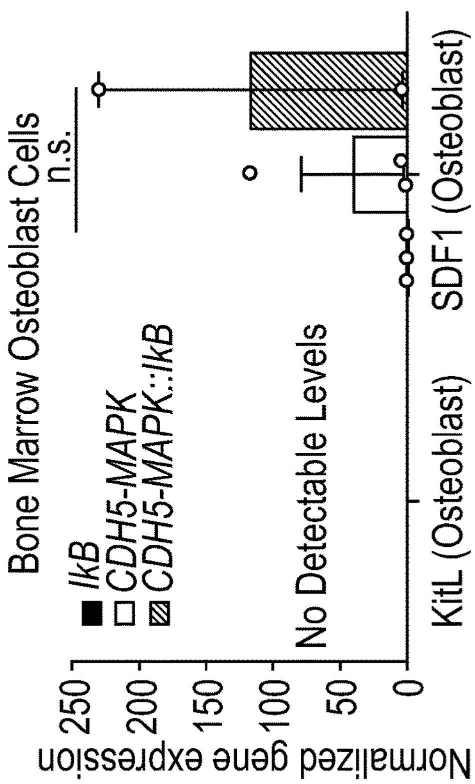
SUPP. FIG. 6I
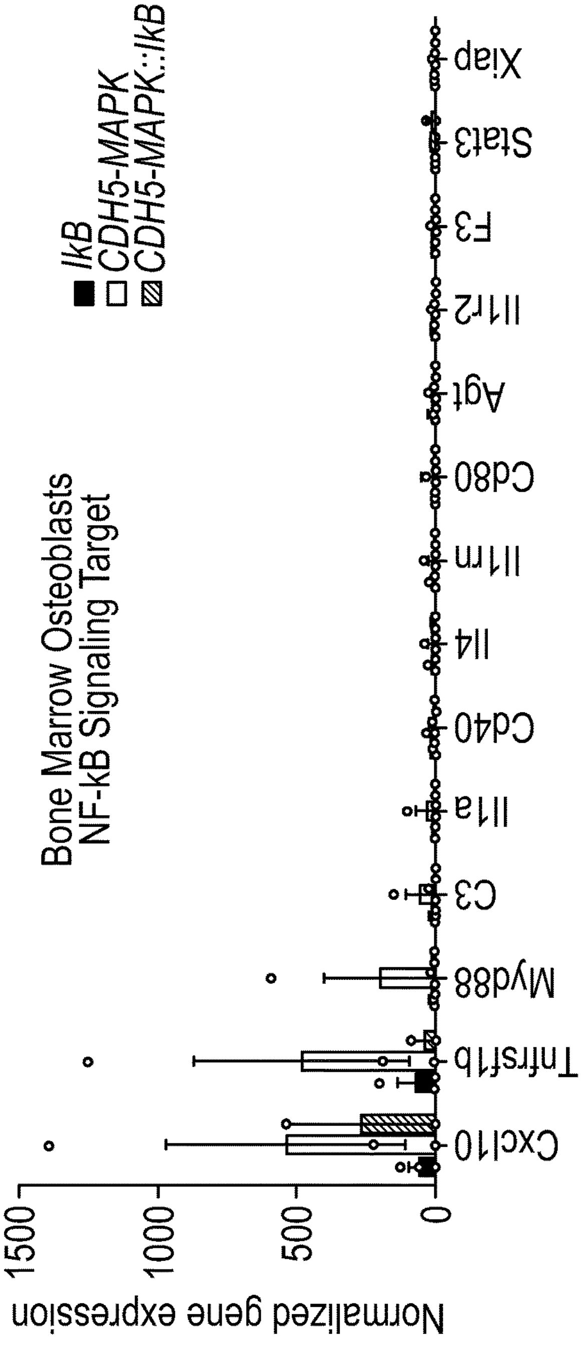

SUPP. FIG. 7B
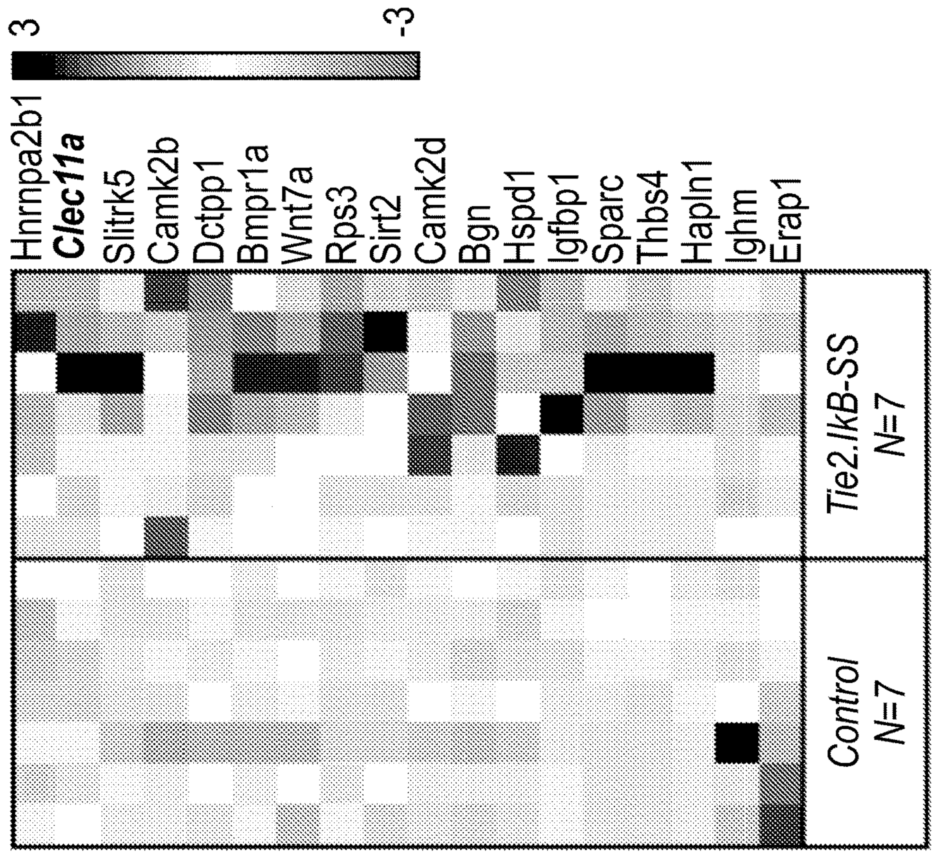
SUPP. FIG. 7A
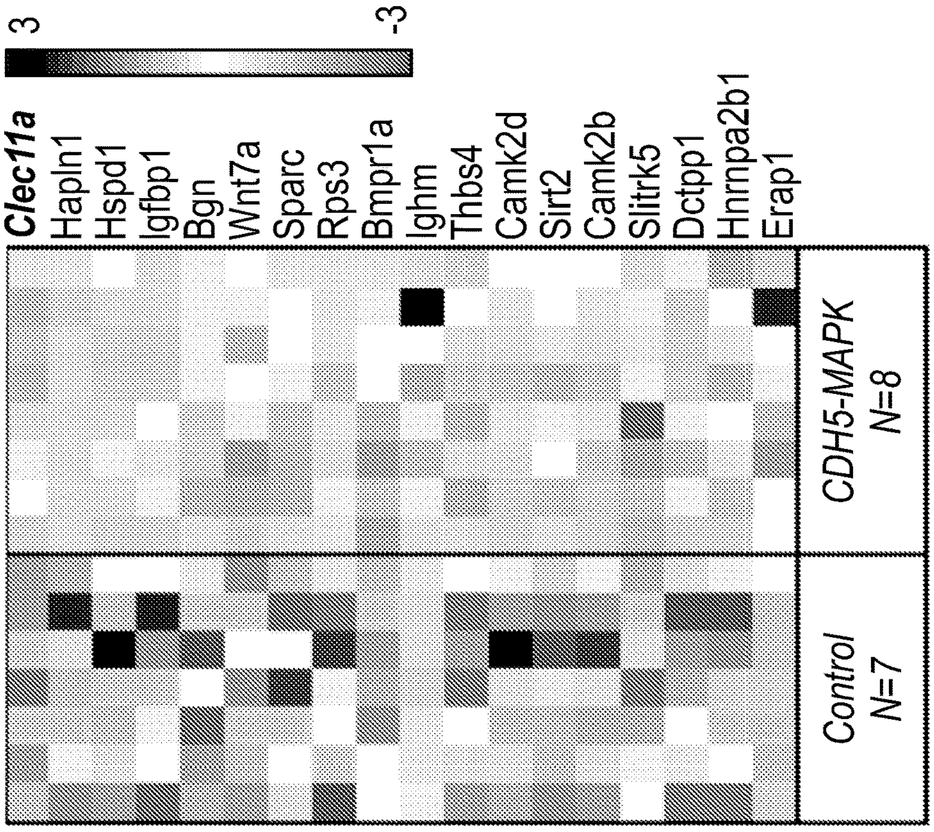

SUPP. FIG. 7C
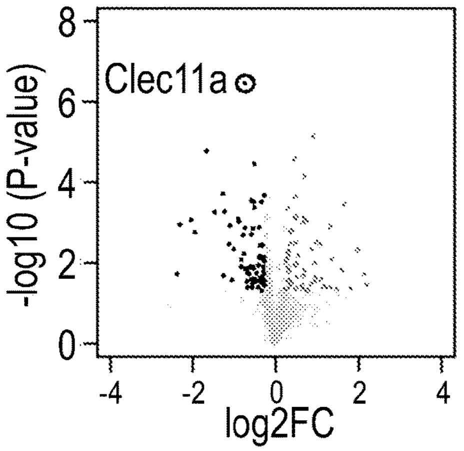
SUPP. FIG. 7D
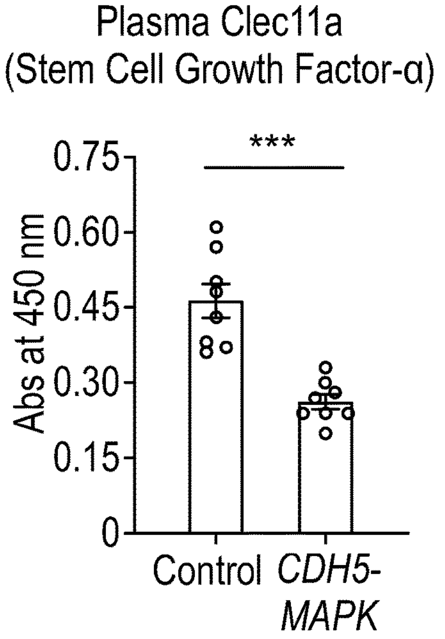
SUPP. FIG. 7E
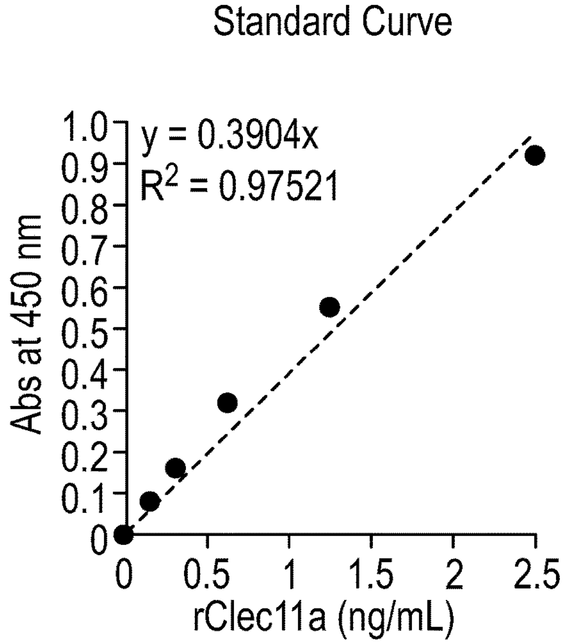
SUPP. FIG. 7F
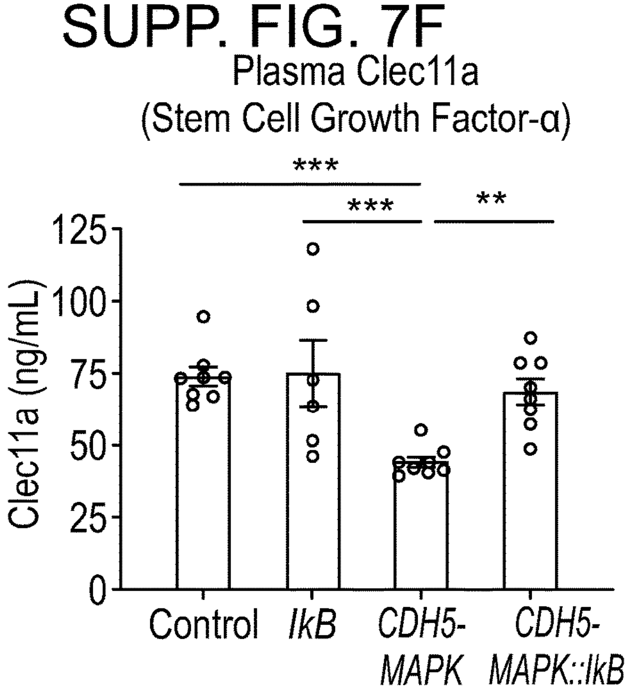

SUPP. FIG. 8A
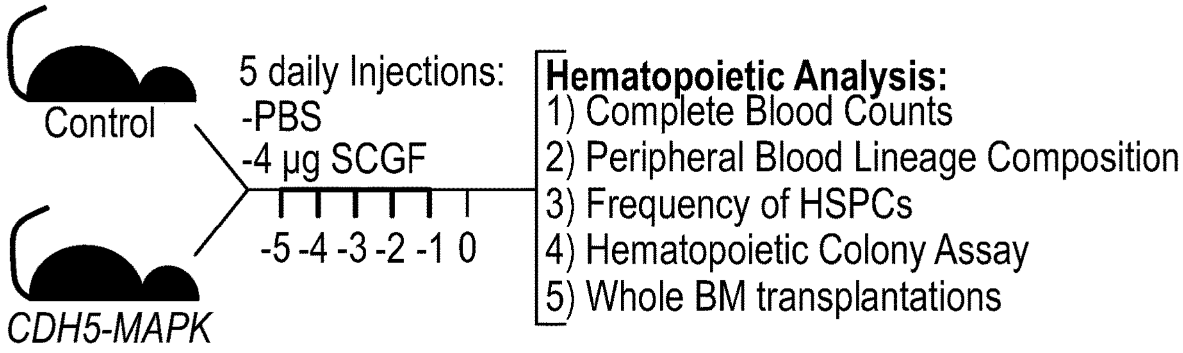
SUPP. FIG. 8B
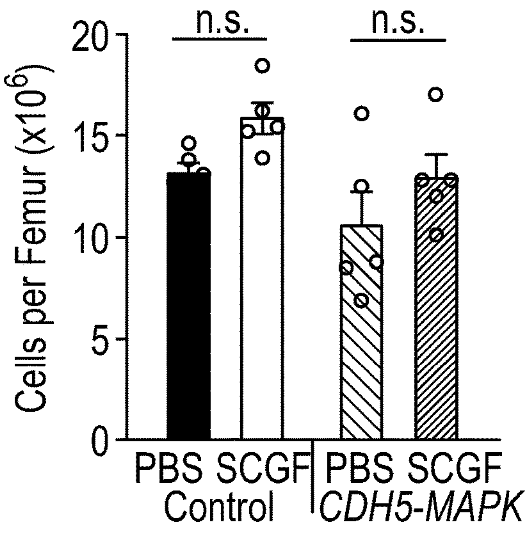
SUPP. FIG. 8C
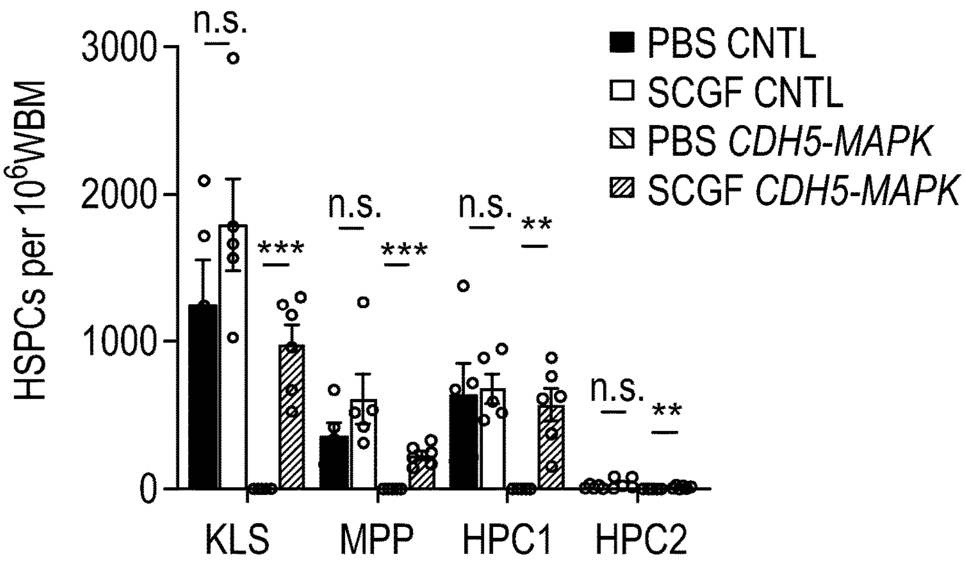

SUPP. FIG. 8D
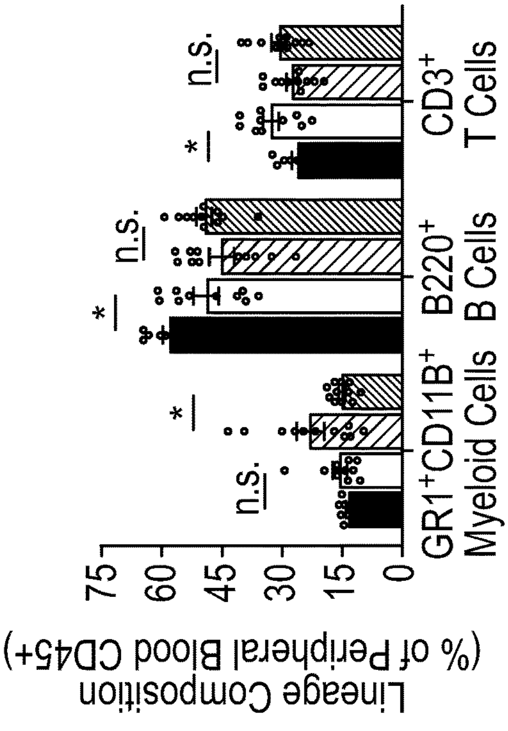
SUPP. FIG. 8E
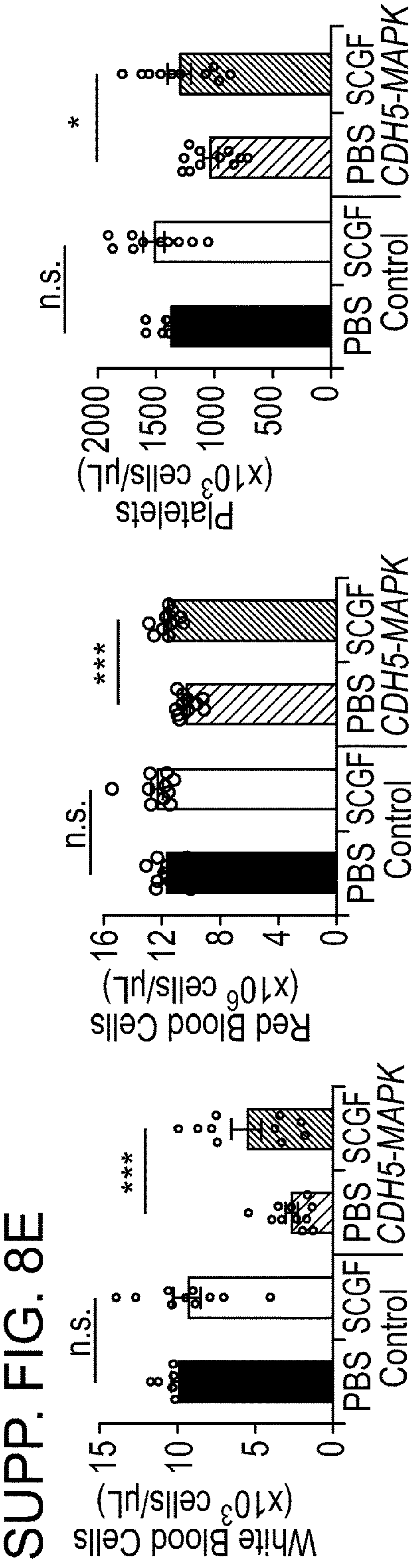

SUPP. FIG. 9A
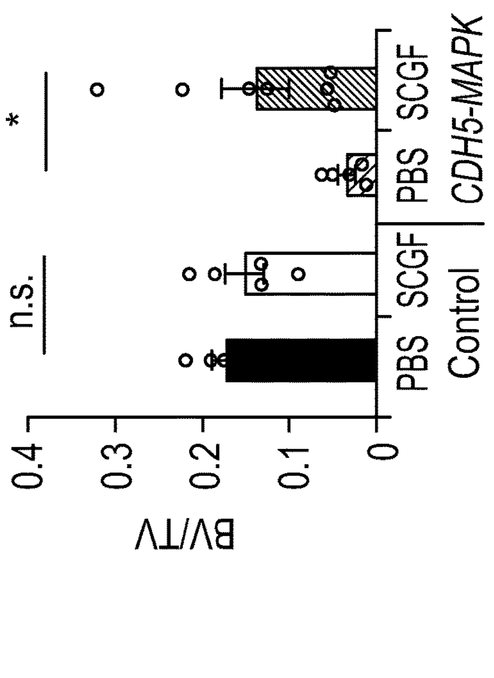
SUPP. FIG. 9B
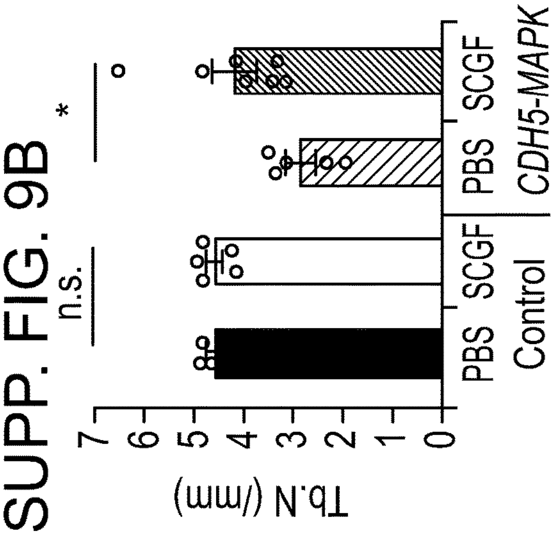
SUPP. FIG. 9C
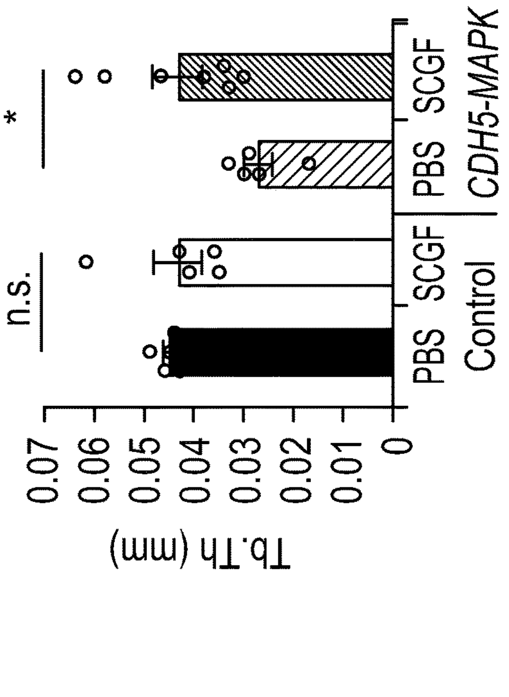
SUPP. FIG. 9D
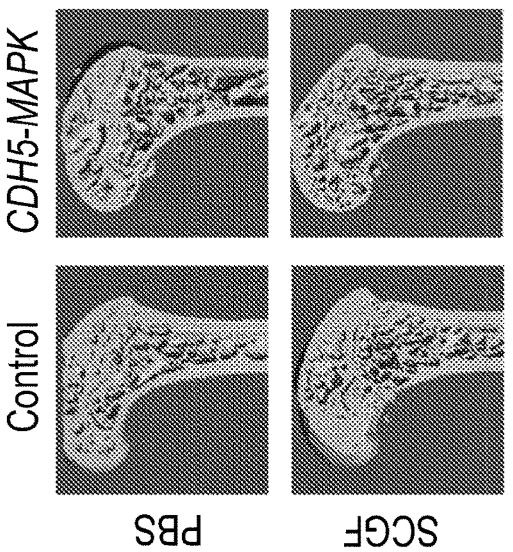

SUPP. FIG. 9E
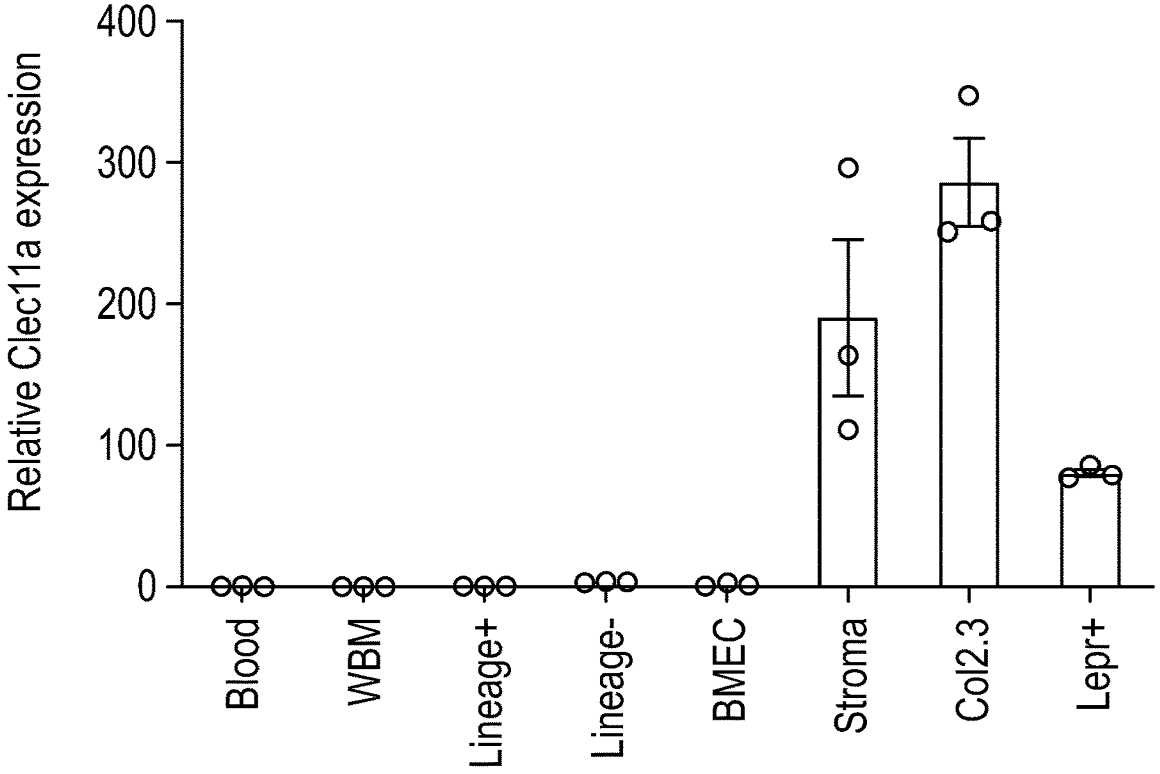
SUPP. FIG. 9F
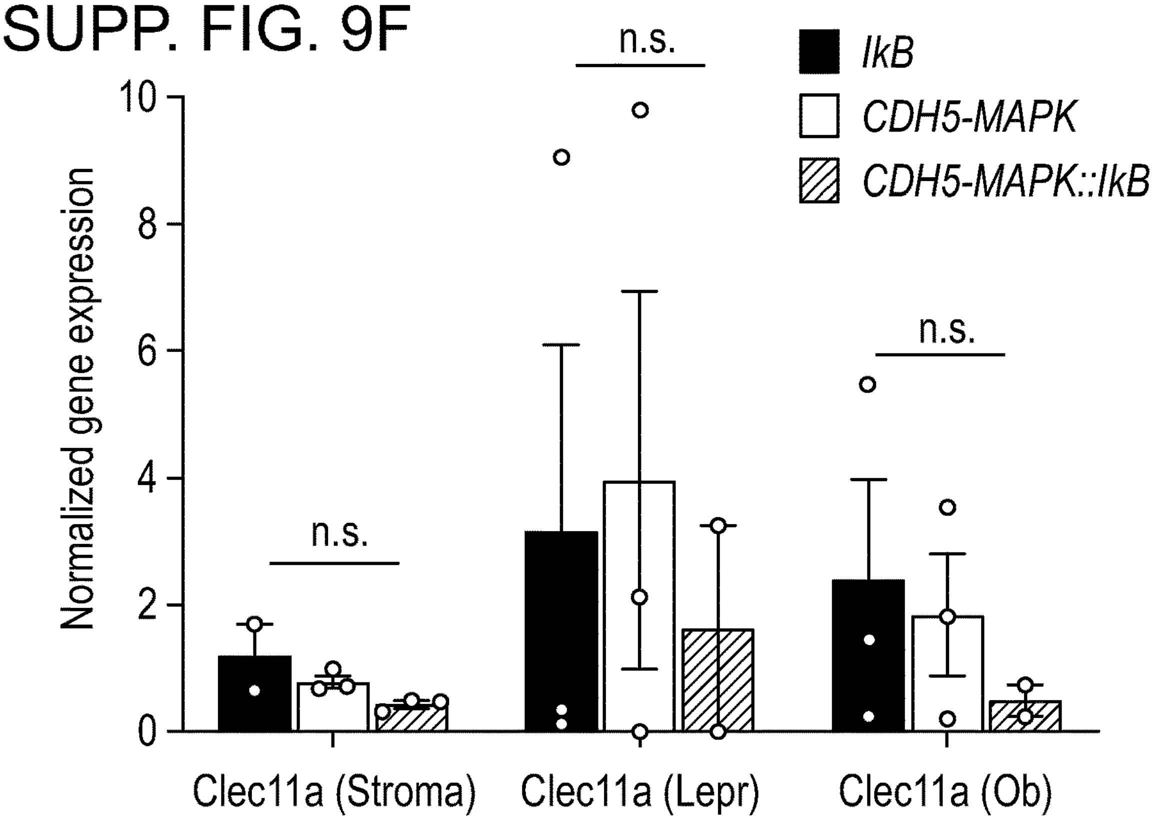

SUPP. FIG. 10A
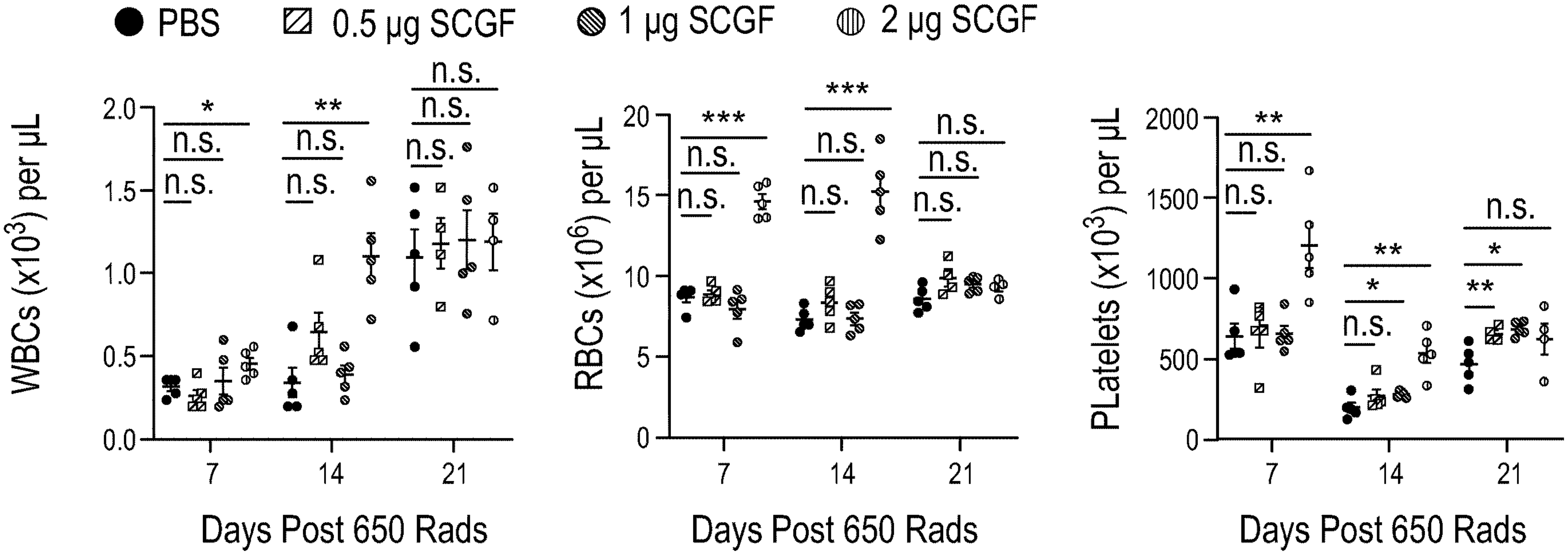
SUPP. FIG. 10B
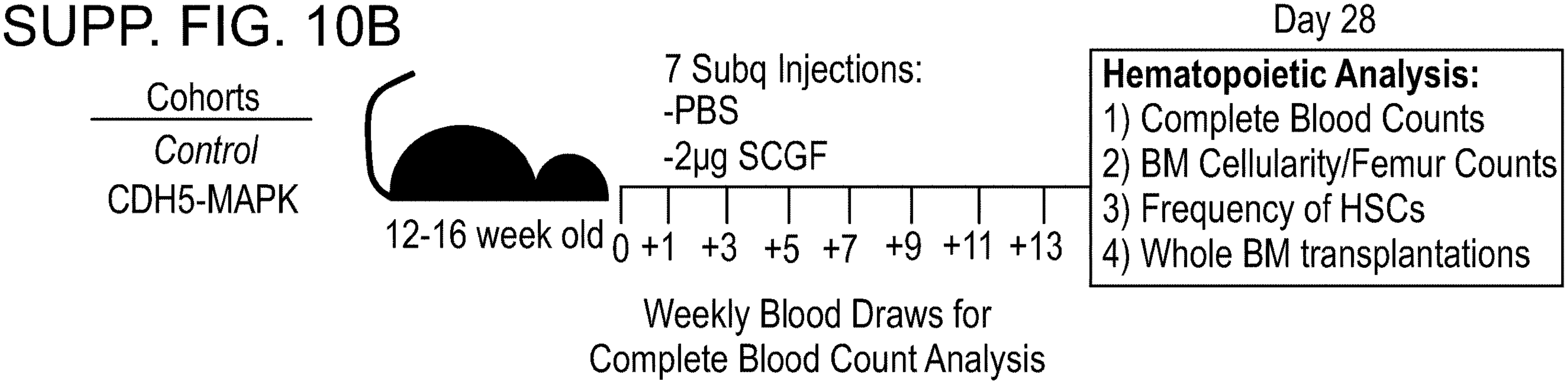

SEQUENCE LISTING

```
<160> NUMBER OF SEQ ID NOS: 17

<210> SEQ ID NO 1
```

<211> LENGTH: 17
<212> TYPE: PRT
<213> ORGANISM: Unknown
<220> FEATURE:
<223> OTHER INFORMATION: Description of Unknown:
      nuclear localization sequence
<220> FEATURE:
<221> NAME/KEY: MOD_RES
<222> LOCATION: (3)..(12)
<223> OTHER INFORMATION: Any amino acid

<400> SEQUENCE: 1

```
Lys Lys Xaa Xaa Xaa Xaa Xaa Xaa Xaa Xaa Xaa Xaa Lys Arg Arg Lys
1               5                   10                  15

Lys
```

<210> SEQ ID NO 2
<211> LENGTH: 7
<212> TYPE: PRT
<213> ORGANISM: Unknown
<220> FEATURE:
<223> OTHER INFORMATION: Description of Unknown:
      nuclear localization sequence

<400> SEQUENCE: 2

```
Leu Leu Lys Arg Arg Lys Lys
1               5
```

<210> SEQ ID NO 3
<211> LENGTH: 1970
<212> TYPE: DNA
<213> ORGANISM: Mus musculus

<400> SEQUENCE: 3

```
aagagaagct gaggagatca aaagttgaga cagagcagat caggagggaa ggcagaagag     60

aaagcctggc agaaagaagg tccaaggggc ttgtgagctg cccaccagac tgggacactt    120

gctaggtcta tacagcagtc ctacccctgg cattctgacc tctctactat ttgggtgctg    180

ggaagcccag ctggatgcag gcagcctggc tcttgggggc cctagtggtc cctcagcttt    240

tgagttttgg tcatggagcc cgaggtcctg ggagggagtg ggagggaggc tggggaggtg    300

ccctggagga ggagagagag cgggagtcac agatgttgaa gaatctccag gaggccctag    360

ggctgcccac tggggtggga aatgaggata atcttgctga aaaccctgaa gacaaagagg    420

tctgggagac cacagagact caaggggaag aagaggaaga ggaaatcacc acagcacctt    480

cttctagtcc caaccctttc cccagccctt ctcccacacc agaggacact gtcacttaca    540

tcttgggccg cttggccagc ctcgatgcag gcctacacca attgcacgtc cgtctgcacg    600

ttttggacac ccgtgtggtt gagctgaccc aggggctgcg gcagctgcgg gatgctgcga    660

gtgacacccg cgactcagtg caagccctga aggaggtcca ggaccgtgct gagcaggagc    720

acggccgctt ggagggctgc ctgaagggcc tgcgccttgg ccacaagtgc ttcctgctct    780

cgcgagactt cgagacccag gcggcggcgc aggcgcggtg caaggcgcga ggtgggagct    840

tagcacagcc tgcggaccgc cagcaaatgg atgcgctaag ccggtactta cgcgccgctc    900

tcgcccccta caactggccg gtgtggctgg gagtgcacga tcggcgctcc gaggggctct    960

acctttcga gaacggccag cgcgtgtctt tcttcgcctg gcaccgcgca ttcagcctgg    1020

agtccggcgc ccagcctagt gcggcaacac atccactcag cccggatcag cccaatggcg   1080

gcgtcctgga gaactgcgtg gcccaggcct cagacgacgg ttcttggtgg gaccatgact   1140

gtgagcggcg cctctacttc gtctgcgagt tccccttcta gagaaccggt ctctgcccag   1200
```

gagctctagt gcacattttg caccgtacac cgcgcaccct attgttaggg gcctgggagt 1260
cgctcagaga ttaagcgtga ccatgaatac attttaatca gaagaggttt tttattttag 1320
atactggcac ccagactgat tggggccagg tgtgctcctg agattgcttc caagatgcat 1380
tatcagccca gggattttaa aggcaaaccc cacaagattg catgtagcct gcttacatgt 1440
aggccggagc ataaaaattt aacatatatg tcttgaagtt gtcctagtca tcctttgagc 1500
agaggaagca agattagtta caaaaacaga aatcgcagtt agtcttacaa ctaaatttgc 1560
taggacagca aattttacaa ggccaatcaa tttcagaata gtcttcaata tctgggagaa 1620
tgaggaagta gatggactgt tagtgtacag cccacacaag ctaggggctt tcgtctgagg 1680
catattttgc tttggttttt caagcagtga gtctaaactt ttaaatgtaa tattaaccac 1740
catacgtaca atgtgcattc cgcaccctga actccacccc gtgcatcttc cactctgcac 1800
tctatagtgc accctgcatc ttgagccctc cttgggccag aactgccgcc aatcccggct 1860
ggtcccccag ccccagactt ctccatgtcc ccacctgtct ttgaaacttc aaggtctcaa 1920
ataggcccag tgccaataaa tccttttaaa atataaaaaa aaaaaaaaaa 1970

<210> SEQ ID NO 4
<211> LENGTH: 328
<212> TYPE: PRT
<213> ORGANISM: Mus musculus

<400> SEQUENCE: 4

Met Gln Ala Ala Trp Leu Leu Gly Ala Leu Val Val Pro Gln Leu Leu
1 5 10 15

Ser Phe Gly His Gly Ala Arg Gly Pro Gly Arg Glu Trp Glu Gly Gly
20 25 30

Trp Gly Gly Ala Leu Glu Glu Glu Arg Glu Arg Glu Ser Gln Met Leu
35 40 45

Lys Asn Leu Gln Glu Ala Leu Gly Leu Pro Thr Gly Val Gly Asn Glu
50 55 60

Asp Asn Leu Ala Glu Asn Pro Glu Asp Lys Glu Val Trp Glu Thr Thr
65 70 75 80

Glu Thr Gln Gly Glu Glu Glu Glu Glu Glu Ile Thr Thr Ala Pro Ser
85 90 95

Ser Ser Pro Asn Pro Phe Pro Ser Pro Ser Pro Thr Pro Glu Asp Thr
100 105 110

Val Thr Tyr Ile Leu Gly Arg Leu Ala Ser Leu Asp Ala Gly Leu His
115 120 125

Gln Leu His Val Arg Leu His Val Leu Asp Thr Arg Val Val Glu Leu
130 135 140

Thr Gln Gly Leu Arg Gln Leu Arg Asp Ala Ala Ser Asp Thr Arg Asp
145 150 155 160

Ser Val Gln Ala Leu Lys Glu Val Gln Asp Arg Ala Glu Gln Glu His
165 170 175

Gly Arg Leu Glu Gly Cys Leu Lys Gly Leu Arg Leu Gly His Lys Cys
180 185 190

Phe Leu Leu Ser Arg Asp Phe Glu Thr Gln Ala Ala Ala Gln Ala Arg
195 200 205

Cys Lys Ala Arg Gly Gly Ser Leu Ala Gln Pro Ala Asp Arg Gln Gln
210 215 220

Met Asp Ala Leu Ser Arg Tyr Leu Arg Ala Ala Leu Ala Pro Tyr Asn
225 230 235 240

```
Trp Pro Val Trp Leu Gly Val His Asp Arg Arg Ser Glu Gly Leu Tyr
                245                 250                 255

Leu Phe Glu Asn Gly Gln Arg Val Ser Phe Phe Ala Trp His Arg Ala
            260                 265                 270

Phe Ser Leu Glu Ser Gly Ala Gln Pro Ser Ala Ala Thr His Pro Leu
        275                 280                 285

Ser Pro Asp Gln Pro Asn Gly Gly Val Leu Glu Asn Cys Val Ala Gln
    290                 295                 300

Ala Ser Asp Asp Gly Ser Trp Trp Asp His Asp Cys Glu Arg Arg Leu
305                 310                 315                 320

Tyr Phe Val Cys Glu Phe Pro Phe
                325
```

<210> SEQ ID NO 5
<211> LENGTH: 1375
<212> TYPE: DNA
<213> ORGANISM: Homo sapiens

<400> SEQUENCE: 5

```
agagacgagg agaggaacag gaagagagaa gctgggagaa tcgggaacct gggggctagt     60

gacctgcaca cagggcaggg gcactcggca gttcccagag gccacccctc ccaccccaga    120

catccagaca tctggaactt tgggtgccaa gagtccagct taatgcaggc agcctggctt    180

ttgggggctt tggtggtccc ccagctcttg ggctttggcc atggggctcg gggagcagag    240

agggagtggg agggaggctg gggaggtgcc caggaggagg agcgggagag ggaggccctg    300

atgctgaagc atctgcagga agccctagga ctgcctgctg ggaggggggga tgagaatcct    360

gccggaactg ttgagggaaa agaggactgg gagatggagg aggaccaggg ggaggaagag    420

gaggaggaag caacgccaac cccatcctcc ggccccagcc cctctcccac ccctgaggac    480

atcgtcactt acatcctggg ccgcctggcc ggcctggacg caggcctgca ccagctgcac    540

gtccgtctgc acgcgttgga cacccgcgtg gtcgagctga cccaggggct gcggcagctg    600

cggaacgcgg caggcgacac ccgcgatgcc gtgcaagccc tgcaggaggc gcagggtcgc    660

gccgagcgcg agcacggccg cttggagggc tgcctgaagg ggctgcgcct gggccacaag    720

tgcttcctgc tctcgcgcga cttcgaagct caggcggcgg cgcaggcgcg gtgcacggcg    780

cggggcggga gcctggcgca gccggcagac cgccagcaga tggaggcgct cactcggtac    840

ctgcgcgcgg cgctcgctcc ctacaactgg cccgtgtggc tgggcgtgca cgatcggcgc    900

gccgagggcc tctacctctt cgaaaacggc cagcgcgtgt ccttcttcgc ctggcatcgc    960

tcaccccgcc ccgagctcgg cgcccagccc agcgcctcgc cgcatccgct cagcccggac   1020

cagcccaacg gtggcacgct cgagaactgc gtggcgcagg cctctgacga cggctcctgg   1080

tgggaccacg actgccagcg gcgtctctac tacgtctgcg agttcccctt ctagcggggc   1140

cggtaccccg cctccctgcc catcccacca cccggccttt ccctgcgccg tgcccaccct   1200

cctccggaat ctcccttccc ttcctggcca cgaatggcag cgtcctcccc gacccccagt   1260

ctgggcgctt ctgggagggc tcttgcggtg ccggcactcc tccttgttag tgtctttcct   1320

tgaaggggcg ggcaccaggc taggtccggt gccaataaat ccttgtggaa tctga        1375
```

<210> SEQ ID NO 6
<211> LENGTH: 323
<212> TYPE: PRT
<213> ORGANISM: Homo sapiens

<400> SEQUENCE: 6

Met Gln Ala Ala Trp Leu Leu Gly Ala Leu Val Val Pro Gln Leu Leu
1               5                   10                  15

Gly Phe Gly His Gly Ala Arg Gly Ala Glu Arg Glu Trp Glu Gly Gly
            20                  25                  30

Trp Gly Gly Ala Gln Glu Glu Glu Arg Glu Arg Glu Ala Leu Met Leu
        35                  40                  45

Lys His Leu Gln Glu Ala Leu Gly Leu Pro Ala Gly Arg Gly Asp Glu
    50                  55                  60

Asn Pro Ala Gly Thr Val Glu Gly Lys Glu Asp Trp Glu Met Glu Glu
65                  70                  75                  80

Asp Gln Gly Glu Glu Glu Glu Glu Glu Ala Thr Pro Thr Pro Ser Ser
                85                  90                  95

Gly Pro Ser Pro Ser Pro Thr Pro Glu Asp Ile Val Thr Tyr Ile Leu
            100                 105                 110

Gly Arg Leu Ala Gly Leu Asp Ala Gly Leu His Gln Leu His Val Arg
        115                 120                 125

Leu His Ala Leu Asp Thr Arg Val Val Glu Leu Thr Gln Gly Leu Arg
    130                 135                 140

Gln Leu Arg Asn Ala Ala Gly Asp Thr Arg Asp Ala Val Gln Ala Leu
145                 150                 155                 160

Gln Glu Ala Gln Gly Arg Ala Glu Arg Glu His Gly Arg Leu Glu Gly
                165                 170                 175

Cys Leu Lys Gly Leu Arg Leu Gly His Lys Cys Phe Leu Leu Ser Arg
            180                 185                 190

Asp Phe Glu Ala Gln Ala Ala Ala Gln Ala Arg Cys Thr Ala Arg Gly
        195                 200                 205

Gly Ser Leu Ala Gln Pro Ala Asp Arg Gln Gln Met Glu Ala Leu Thr
    210                 215                 220

Arg Tyr Leu Arg Ala Ala Leu Ala Pro Tyr Asn Trp Pro Val Trp Leu
225                 230                 235                 240

Gly Val His Asp Arg Arg Ala Glu Gly Leu Tyr Leu Phe Glu Asn Gly
                245                 250                 255

Gln Arg Val Ser Phe Phe Ala Trp His Arg Ser Pro Arg Pro Glu Leu
            260                 265                 270

Gly Ala Gln Pro Ser Ala Ser Pro His Pro Leu Ser Pro Asp Gln Pro
        275                 280                 285

Asn Gly Gly Thr Leu Glu Asn Cys Val Ala Gln Ala Ser Asp Asp Gly
    290                 295                 300

Ser Trp Trp Asp His Asp Cys Gln Arg Arg Leu Tyr Tyr Val Cys Glu
305                 310                 315                 320

Phe Pro Phe

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
aggtcctggg agggagtg 18

<210> SEQ ID NO 8

<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 8
gggcctcctg gagattctt 19

<210> SEQ ID NO 9
<211> LENGTH: 24
<212> TYPE: DNA
<213> ORGANISM: Unknown
<220> FEATURE:
<223> OTHER INFORMATION: Description of Unknown:
target sequence

<400> SEQUENCE: 9
cagggtccac ctacataaat gcca 24

<210> SEQ ID NO 10
<211> LENGTH: 26
<212> TYPE: DNA
<213> ORGANISM: Unknown
<220> FEATURE:
<223> OTHER INFORMATION: Description of Unknown:
target sequence

<400> SEQUENCE: 10
ccttcttcac atcgtgtgac catgac 26

<210> SEQ ID NO 11
<211> LENGTH: 28
<212> TYPE: DNA
<213> ORGANISM: Unknown
<220> FEATURE:
<223> OTHER INFORMATION: Description of Unknown:
target sequence

<400> SEQUENCE: 11
gagagactgg atttggaatc aaatgcac 28

<210> SEQ ID NO 12
<211> LENGTH: 25
<212> TYPE: DNA
<213> ORGANISM: Unknown
<220> FEATURE:
<223> OTHER INFORMATION: Description of Unknown:
target sequence

<400> SEQUENCE: 12
ctcataggca agcacattcc ctgtg 25

<210> SEQ ID NO 13
<211> LENGTH: 26
<212> TYPE: DNA
<213> ORGANISM: Unknown
<220> FEATURE:
<223> OTHER INFORMATION: Description of Unknown:
target sequence

<400> SEQUENCE: 13
atggccaatt tactgaccgt acacca 26

<210> SEQ ID NO 14
<211> LENGTH: 26

-continued

```
<212> TYPE: DNA
<213> ORGANISM: Unknown
<220> FEATURE:
<223> OTHER INFORMATION: Description of Unknown:
      target sequence

<400> SEQUENCE: 14

acgatgaagc atgtttagct ggccca                                    26


<210> SEQ ID NO 15
<211> LENGTH: 25
<212> TYPE: DNA
<213> ORGANISM: Unknown
<220> FEATURE:
<223> OTHER INFORMATION: Description of Unknown:
      target sequence

<400> SEQUENCE: 15

tggcaccaca ccttctacaa tgagc                                     25


<210> SEQ ID NO 16
<211> LENGTH: 23
<212> TYPE: DNA
<213> ORGANISM: Unknown
<220> FEATURE:
<223> OTHER INFORMATION: Description of Unknown:
      target sequence

<400> SEQUENCE: 16

agacctggct ttcctcaact tcc                                       23


<210> SEQ ID NO 17
<211> LENGTH: 23
<212> TYPE: DNA
<213> ORGANISM: Unknown
<220> FEATURE:
<223> OTHER INFORMATION: Description of Unknown:
      target sequence

<400> SEQUENCE: 17

cagcacccaa ggacaccaaa agc                                       23
```

METHODS FOR USE OF AN ANGIOCRINE FACTOR IN TREATING A PATIENT EXPOSED TO A MYELOABLATIVE INSULT

CROSS-REFERENCE TO RELATED APPLICATIONS

This application is a 35 U.S.C. § 371 national stage filing of International Application No. PCT/US2020/062397, filed on Nov. 25, 2020, which in turn claims the benefit of priority to U.S. Provisional Application No. 62/941,190 (filed Nov. 27, 2019), entitled "Endothelial MPAK Activation Disrupts Hematopoiesis by Inducing NF-kB-dependent Inflammatory Stress" and U.S. Provisional Application No. 62/980,108 (filed Feb. 21, 2020), entitled "Methods for Use of a Pharmaceutical Composition Comprising an Angiocrine Factor in Treating a Patient Exposed to a Myeloablative Insult". The contents of each of the foregoing applications are incorporated by reference herein in their entirety.

STATEMENT OF GOVERNMENT FUNDING

This invention was made with Government support under contracts HL133021 and 1R01CA204308 awarded by the National Institutes of Health. The Government has certain rights in this invention.

SEQUENCE LISTING

The instant application contains a Sequence Listing which has been submitted electronically in ASCII format and is hereby incorporated by reference in its entirety. Said ASCII copy, created on Nov. 25, 2020, is named 128533-02520_SL.txt and is 13,431 bytes in size.

FIELD OF THE INVENTION

The described invention relates to hematopoietic recovery following myelosuppressive injury.

BACKGROUND OF THE INVENTION

Hematopoiesis

Multipotent self-renewing hematopoietic stem cells (HSCs) regenerate the adult blood system after transplantation. The term "hematopoiesis" as used herein refers to the process by which the cellular constituents of blood are continually replenished throughout the lifetime of an organism by differentiating from hematopoietic stem cells (HSCs) to mature, functional cell types of the blood lineages. The hematopoietic lineage is divided into two main branches: the myeloid arm and the lymphoid arm. The Common Myeloid Progenitor (CMP) gives rise to the myeloid arm, which can give rise to all myeloid cells. The Common Lymphoid Progenitor (CLP) gives rise to the lymphoid arm, which can give rise to all lymphoid cells.

The hematopoietic stem cell (HSC) is a multipotent stem cell that resides in the bone marrow and has the ability to form all the cells of the blood and immune system. It has the ability to self-replicate and differentiate into progeny of multiple lineages. Human HSC activity resides in CD34Thy-1− populations. [Weiskopf, K. et al., "Myeloid cell origins, differentiation, and clinical implications," Microbiol. Spectr. (2016) 4(5): 10.1128/microbiolspec.MCHD-0031-2016]. The CD90+CD45RA− population contains the true long-term HSC in humans, while the CD90−CD45RA− population represents an intermediate downstream multipotent progenitor (MPP). [Id]. The lin-CD34+CD38+ population of human bone marrow has limited ability to self-renew and exhibits a high proportion of myeloid-biased differentiation [Id., citing Manz, M G, et al, "Prospective isolation of human clonogenic common myeloid progenitors." Proc. Natl Acad. Sci. USA (2002) 99 (18): 11872-77]. Expression of CD45RA and IL-3Rσ further subdivided this population, yielding three distinct subpopulations: IL-3RαloCD45RA−, IL-3RαloCD45RA+, and IL-3Rα-CD45RA− cells. In vitro, the IL-3RαloCD45RA− population gave rise to the full range of the myeloid lineage, including mixed colonies, suggesting this population represented the human common myeloid progenitor (CMP) [Id., citing Manz, M G, et al, "Prospective isolation of human clonogenic common myeloid progenitors." Proc. Natl Acad. Sci. USA (2002) 99 (18): 11872-77]. On the other hand, the IL-3RαloCD45RA+ population only gave rise to cells of the granulocyte and macrophage lineages, and the IL-3Rα-CD45RA− population predominantly gave rise to cells of the erythroid and megakaryocyte lineage; thereby indicating these populations represented the granulocyte/macrophage lineage-restricted progenitor (GMP) and the megakaryocyte/erythrocyte lineage-restricted progenitor (MEP), respectively [Id., citing Manz, M G, et al, "Prospective isolation of human clonogenic common myeloid progenitors." Proc. Natl Acad. Sci. USA (2002) 99 (18): 11872-77].

Within the human MEP population, fractionation studies helped define the unipotent human erythrocyte progenitor (EP) as $CD71^{intermediate(int)/+}$CD105+, and when sorted to purity, gave rise exclusively to erythrocytes in vitro with no megakaryocyte potential [Id., citing Mori, Y. et al., "Prospective isolation of human erythroid lineage-committed progenitors," Proc. Natl Acad. Sci. USA (2015) 112 (31): 9638-43]. Additionally, an erythrocyte-biased MEP (E-MEP) was identified as CD71+CD105− that was an intermediate between the MEP and the EP [Id]. Downstream stages of human erythropoiesis have also been isolated to purity, including the primitive erythroid progenitor cells (burst-forming unit-erythroid or BFU-E) and later-stage colony-forming-unit-erythroid (CFU-E). These populations were principally distinguished as IL-3R−CD34+CD36− and IL-3R−CD34~CD36+, respectively [Id., citing Li, J. et al, "Isolation and transcriptome analyses of human erythroid progrenitors: BFU-E and CFU-E." Blood (2014) 124 (24): 3636-45].

Stem Cell Niches

Effective functioning of the body's tissues and organs depends upon innate regenerative processes that maintain proper cell numbers (homeostasis) and replace damaged cells after injury (repair). In many, though not all tissues, regenerative potential is determined by the presence and functionality of a dedicated population of stem and progenitor cells, which respond to exogenous cues to produce replacement cells when needed. (Wagers, A. J. The stem cell niche in regenerative medicine. Cell stem cell 10, 362-369, doi:10.1016/j.stem.2012.02.018 (2012)). These cells exist in a specialized environment, termed a "stem cell niche", which provides spatial, temporal, and structural boundaries sufficient to protect these cells from damage or loss while maintaining communication with their surrounding to ensure appropriate responsiveness to phsiolgical cues for cell replacement and repair. (Wagers, A. J. The stem cell niche in regenerative medicine. Cell stem cell 10, 362-369, doi:10.1016/j.stem.2012.02.018 (2012)).

Stem cell niches have been identified and characterized in many tissues, including the germline, bone marrow, digestive and respiratory systems, skeletal muscle, skin, hair follicle, mammary gland, and central and peripheral nervous systems. (Wagers, A. J. The stem cell niche in regenerative medicine. Cell stem cell 10, 362-369, doi:10.1016/j.stem.2012.02.018 (2012)).

Stem cell niche environments are composed of cellular and environmental components that are critical to their function and maintenance. Cell-cell interactions provide structural support, regulate adhesive interactions, and produce soluble signals that control stem cell function. Environmental components include physical forces such as pressure, structure, and chemical signals, and temperature, as well as physiological parameters, such as interaction with the extracellular matrix (ECM). (Id.).

Heterologous cell-cell interactions in stem cell niches exhibit complex, bidirectional signaling that is dependent on tight regulation and often cell-to-cell contact. Stem cell niches contain tissue specific and generic cell populations, each of which have specialized roles. (Lane, S. W., Williams, D. A. & Watt, F. M. Modulating the stem cell niche for tissue regeneration. Nature biotechnology 32, 795-803, doi:10.1038/nbt.2978 (2014)).

The hematopoietic microenvironment localized in the marrow space in adult bone and comprises a range of different cell types that distinctly define the hematopoietic stem cell (HSC) niche, including osteoblastic, vascular, and neural cells, megakaryocytes, macrophages and immune cells. Secreted and membrane-bound factors, including Wnt, SCF, Notch and chemokines directly bind surface receptors on stem cells to regulate cell fate, self-renewal and polarity. (Lane, S. W., Williams, D. A. & Watt, F. M. Modulating the stem cell niche for tissue regeneration. Nature biotechnology 32, 795-803, doi:10.1038/nbt.2978 (2014)).

The close association of many stem cell types with the vasculature and nervous system allows for modulation of stem cell responses by metabolic cues and circadian rhythms, and provides a conduit through which inflammatory and immune cells, as well as humoral factors, can be delivered to the niche. (Wagers, A. J. The stem cell niche in regenerative medicine. Cell stem cell 10, 362-369, doi: 10.1016/j.stem.2012.02.018 (2012)). Immunological cells provide dynamic regulation of niches during inflammation and tissue damage, which is tightly regulated through the presence of "immune privilege" (referring to the observation that tissue grafts placed in certain anatomical sites, including the brain and eye, can survive for extended periods of time) and evasion from this privilege. (Lane, S. W., Williams, D. A. & Watt, F. M. Modulating the stem cell niche for tissue regeneration. Nature biotechnology 32, 795-803, doi: 10.1038/nbt.2978 (2014)).

Extracellular matrix (ECM) proteins and stem cell interactions with the ECM provide retention cues, as well as mechanical signals, based in part on substrate rigidity, which allow stem cells to respond to external physical forces. ECM proteins are critical for orientation and structural maintenance of the niche and provide instructive signals through ligand interaction with integrins expressed on stem cells. (Lane, S. W., Williams, D. A. & Watt, F. M. Modulating the stem cell niche for tissue regeneration. Nature biotechnology 32, 795-803, doi:10.1038/nbt.2978 (2014)). In addition, the ECM can sequester or concentrate growth factors, chemokines, and other stem cell regulatory molecules by binding both locally and systematically produced factors within the niche. (Wagers, A. J. The stem cell niche in regenerative medicine. Cell stem cell 10, 362-369, doi: 10.1016/j.stem.2012.02.018 (2012)).

Physical parameters, such as topography, rigidity/elasticity, shear forces, temperature, oxygen tension, and blood flow direct stem cell maintenance and differentiation. Further, many stem cell niches have altered environmental characteristics and require tight metabolic regulation to maintain the long-term quiescence and self-renewal of stem cell populations. (Lane, S. W., Williams, D. A. & Watt, F. M. Modulating the stem cell niche for tissue regeneration. Nature biotechnology 32, 795-803, doi:10.1038/nbt.2978 (2014)).

While the specific components that constitute a particular stem cell niche may vary in different tissues under distinct physiological contexts, in all cases, the signals provided by these cellular and acellular components appear to be integrated by stem cells to inform their fate decisions, including choices between quiescence or proliferation, self-renewal or differentiation, migration or retention, and cell death or survival. (Wagers, A. J. The stem cell niche in regenerative medicine. Cell stem cell 10, 362-369, doi:10.1016/j.stem.2012.02.018 (2012)).

Hematopoietic Stem Cell Niches

The hematopoietic system supplies the human body with >100 billion mature blood cells every day that carry out functions such as oxygen transport, immunity, and tissue remodeling. The haematopoietic system consists of various populations of highly specialized cells that have unique functions, such as oxygen transport and immune defense. It is estimated that an adult human generates ~$4\text{-}5\times10^{11}$ haematopoietic cells per day. The continuous production of many blood cell types requires a highly regulated, yet highly responsive, system. Within the mammalian haematopoietic organization, rare haematopoietic stem cells (HSCs) sit at the top of the hierarchy. (Pinho, S., Frenette, P.S. Haematopoietic stem cell activity and interactions with the niche. *Nat Rev Mol Cell Biol* 20, 303-320 (2019) doi:10.1038/s41580-019-0103-9).

HSC Niche Development

During development, HSCs traffic between niches in order to establish hematopoiesis. Primitive hematopoiesis takes place in the yolk sac approximately on embryonic day 7.0 (E7.0) when immature precursors give rise to erythrocytes that will supply oxygen to the developing embryo. The presence of the first definitive HSC known to be able to fully reconstitute the hematopoietic system upon transplantation is found in the aorta-gonad-mesonephros in mice and humans. However, some studies have suggested that yolk sac cells from E9.0 to E10.0 can mature into definitive HSCs when transplanted into a newborn rather than an adult mouse. In addition, the placenta represents a significant reservoir of HSCs during development. Once the vasculature is developed, HSCs migrate to the fetal liver on or near E12.0 where they expand and differentiate. Fetal liver HSCs are actively cycling in contrast to their bone marrow counterparts and can also out-compete adult bone marrow HSCs when transplanted into irradiated recipients. During HSC expansion in the fetal liver, chondrocytes and osteoblasts are produced within mesenchymal condensations to create cartilage and bone. Skeletal remodeling is associated with bone vascularization, which allows homing of HSCs and colonization of the fetal bone marrow by E17.5. This process is mediated through CXCL12 production by bone marrow stromal cells, which attract HSCs expressing CXCR4 and specific adhesion molecules expressed on bone marrow endothelium. (Boulais, P. E., & Frenette, P. S. (2015). Making sense of hematopoietic stem cell niches. *Blood,* 125(17), 2621-2629. doi:10.1182/blood-2014-09-570192).

HSC Niche and the Bone Marrow Microenvironment

In adult bones, HSCs are essentially kept in the G0 phase of the cell cycle in a stage of metabolic dormancy or quiescence, which preserves their function by limiting damage associated with cell replication. However, quiescent HSCs can quickly respond to a broad range of niche or systemic signals by entering the cell cycle and proliferating. These instructive cues are therefore essential for tailoring HSC differentiation and adjusting blood production to the needs of the organism. HSCs can also leave the BM niche upon receiving mobilization signals and enter the bloodstream to ensure immune surveillance of peripheral tissues and engraft distant BM sites. Thus, HSCs critically depend on short- and long-range instructive cues from the BM niche for many aspects of their biology, including cell cycle and trafficking activity, due to the dynamic regulation of the switch between quiescence/proliferation and anchoring/mobilization.

Resident Niche Cells. The HSC stem cell niche contains a variety of cell types, each with a distinct function, such as osteoblastic, vascular, and neural cells, megakaryocytes, macrophages and immune cells each have important roles and can be considered to define distinct HSC niches. It further comprises other specicialied niches, for example, the osteoblastic and perivascular niches. Research is conflicting whether these two niches have distinct, specialized roles or whether there is coordinated regulation of HSCs and therefore functional overlap. For example, NG2+$^{peri}$-arteriolar cells regulate quiescence within long-term HSCs, and this quiescence appears essential for HSC function. Other cells, such as endosteal macrophages, retain HSCs within the niche, and loss of these cells causes mobilization of HSCs out of their supportive microenvironment. (Lane, S. W., Williams, D. A. & Watt, F. M. Modulating the stem cell niche for tissue regeneration. Nature biotechnology 32, 795-803, doi:10.1038/nbt.2978 (2014)).

Direct cell contact. Direct cell contact can be mediated by a range of receptors, such as cell-cell adhesion molecules and receptors with membrane bound ligands. For example, in bone marrow, Notch ligands expressed by sinusoidal cells are essential for HSC self-renewal during recovery from myeloablative injury. (Lane, S. W., Williams, D. A. & Watt, F. M. Modulating the stem cell niche for tissue regeneration. Nature biotechnology 32, 795-803, doi:10.1038/nbt.2978 (2014)).

Secreted Factors. Indirect communication between stem cells and niche cells is mediated by secreted factors. Mobilization of HSCs from their niche, for example, by using cytokines such as granulocyte colony-stimulating factor (G-CSF) or granulocyte-macrophage colony-stimulating factor (GM-CSF), is widely used to support treatment of hematological malignancy, bone marrow failure and rare genetic disorders. These factors act in a variety of ways, including promoting expansion of HSCs and release of HSC-niche adhesion. (Lane, S. W., Williams, D. A. & Watt, F. M. Modulating the stem cell niche for tissue regeneration. Nature biotechnology 32, 795-803, doi:10.1038/nbt.2978 (2014)). Specifically, Secreted factors like stem cell factor (SCF), transforming growth factor beta-1 (TGF-b1), platelet factor 4 (PF4 or CXCL4), angiopoietin 1 (ANGPT1), and thrombopoietin (TPO) are all critical enforcers of HSC quiescence. Alongside the essential chemokine stromal-derived factor 1 (SDF1a or CXCL12) and its C-X-C chemokine receptor type 4 (CXCR4), adhesion molecules such as vascular cell adhesion protein 1 (VCAM-1), various selectins, and extracellular matrix (ECM) proteins like fibronectin or hyaluronic acid are all essential regulators of HSC homing and anchoring in the niche.

The decision to remain at a quiescent state or to enter into an actively proliferating state is controlled by number of factors through both cell intrinsic and extrinsic mechanisms. In response to extrinsic soluble factors; inflammatory cytokines such as interferon (IFN)-α and IFN-γ; growth factors such as granulocyte colony stimulating factor (GCSF), stem cell factor (SCF), and thrombopoietin (TPO); cytokines such as transforming growth factor (TGF)-β and tumor necrosis factor (TNF)-α; and chemokines such as the stromal cell derived factor (SDF)-1, HSCs can either enter dormancy or the cell cycle. Intrinsic factors that regulate HSC quiescence include: cell cycle inhibitors such as p21 and p57; transcription factors (TFs) such as Gfi1, Egr1, FOXOs, and PBX1; and ubiquitin ligases such as c-Cb1, Itch, Fbxw7, and A20. A harmony between intrinsic and extrinsic factors is essential for proper maintenance of HSCs in the bone marrow niche. (Nakagawa, M. M., Chen, H., & Rathinam, C. V. (2018). Constitutive Activation of NF-κB Pathway in Hematopoietic Stem Cells Causes Loss of Quiescence and Deregulated Transcription Factor Networks. *Frontiers in cell and developmental biology,* 6, 143).

Bone Microenvironment. The bone marrow can be subdivided into a hematopoietic cell compartment and the stroma, which is mainly composed of fibroblasts, adipocytes, nerves, and the bone marrow's vascular system. (Kopp, et. al. "The Bone Marrow Vascular Niche: Home of HSC Differentiation and Mobilization." PHYSIOLOGY 20: 349-356, 2005; 10.1152/physiol.00025.2005).

Arterial vessels enter the marrow through foramina nutricia and then divide into several arterioles. Small arterioles and capillaries from these vessels span throughout the bone marrow and supply sinusoids, which are interconnected by intersinusoidal capillaries. The sinusoids are radially distributed around the draining central sinus, which measures ~100 m in diameter. The bone marrow sinusoids are unique and are not to be compared with regular veins. The sinusoidal wall consists of a single layer of endothelial cells and is devoid of supporting cells. The endothelial cells have no connective tissue covering, but are rather in direct contact with the parenchymal cells. The surrounding hematopoietic marrow is the major cellular moiety that supports reconstruction and remodeling of the sinusoidal microcirculation.

The rapid induction of marrow hypocellularity with cytotoxic agents or radiation is followed by a marked dilatation and collapse of the sinusoids and the central sinus. The lack of a regular vessel wall in sinusoids is reflected by a high level of permeability. The bone marrow microenvironment houses HSCs and hematopoietic progenitor cells (HPCs), where the bone microanatomic environment composed of neighboring stromal cells supports and instructs the stem cells. It has been postulated that the stromal environment itself might determine the quality of hematopoiesis. (Kopp, et. al. "The Bone Marrow Vascular Niche: Home of HSC Differentiation and Mobilization." PHYSIOLOGY 20: 349-356, 2005; 10.1152/physiol.00025.2005).

HSCs and HPCs are not randomly distributed in the bone marrow but rather are localized close to the endosteum of the bone and around blood vessels. In addition, the embryonic marrow shows the first hematopoietic colonies next to the endosteum. Researchers have identified a gradient of cell development in the bone marrow with undifferentiated cells being located along the endosteum and differentiation and maturation being associated with centripetal movement toward the highly vascularized bone marrow cavity. (Kopp, et. al. "The Bone Marrow Vascular Niche: Home of HSC Differentiation and Mobilization." PHYSIOLOGY 20: 349-356, 2005; 10.1152/physiol.00025.2005).

The bone marrow microenvironment houses not only the HSC niche, but also the osteoblastic or endosteal niche, and the vascular niche of each is defined by the role they play in the localization of stem cells. The osteoblastic niche in the bone marrow provides signals for the maintenance of repopulating cells in an undifferentiated state. These spatial differences in hematopoietic tissues do not reflect or translate into the properties of the harbored stem cells themselves. Further research showed that stromal structures like the bone marrow sinusoidal vessels could serve as alternative cellular scaffolds upon which hematopoietic cells could reside and mature.

To delineate the bone marrow sinusoidal and arteriole network as a separate anatomic and functional entity from the endosteal zone, the name "vascular niche" is employed. Ultrastructural studies have demonstrated that differentiated rather than immature hematopoietic cells have a close association with the bone marrow microvasculature in the vascular niche. Further, nearly all mature megakaryocytes were found to be located adjacent to the thin-walled sinusoids, and whole megakaryocytes where shown to be able to transmigrate through intact endothelial cells. This observation is not limited to thrombopoiesis but can be applied to erythroid and B-lymphoid progenitors, as these lineages have also been reported to reside in defined niches within the marrow. These findings point to progenitor-stromal cell interactions as being critical determinants in the maturation process, further reinforcing the idea of stem cell niches as microanatomic structures that are both permissive and instructive for stem cell maintenance and differentiation. Further, bone marrow endothelial cells (BMECs) were found to have adhesive properties, interactions with angiogeneic and chemokinetic factors, and contribution to supporting HSC self-renewal and differentiation thereby demonstrating the interdependence of the bone marrow parenchyma and the vascular niche. (Crane, G M, et al., "Adult haematopoietic stem cell niches," Nat. Rev. Immunol. (2017) 17(9): 573-90; Ramalingam, P. et al., "Regulation of the hematopoietic stem cell llifecycle by the endothelial niche," Curr. Opin. Hematol. (2017) 24(4): 289-99; Yu, V W, and Scadden, D T, "Herterogeneity of the bone marrow niche," Curr. Opin. Hematol. (2016) 23(4): 331-38; Kopp, et. al. "The Bone Marrow Vascular Niche: Home of HSC Differentiation and Mobilization." PHYSIOLOGY 20: 349-356, 2005; 10. 1152/physiol.00025.2005).

Angiocrine Factors

There are numerous angiocrine growth factors that play multiple roles in bone tissue cell signaling in the bone microenvironmnent. Table 2 below describes such angiocrine factors and their crosstalk with tissue cells in bone. (Sivan U, De Angelis J, Kusumbe A P. 2019 Role of angiocrine signals in bone development, homeostasis and disease. Open Biol. 9: 190144).

| Angiocrine Factor | Source | Target Cell | Function |
|---|---|---|---|
| OPG | endothelial cell | osteoclasts | inhibit osteo-clastogenesis |
| SEMA-III | endothelial cells | osteoclasts | bone remodeling |
| IL-33 | CD105+ endothelial cells | osteoblasts | osteogenesis, haematopoiesis |
| BMP-2 | endothelial cells | chondrocytes | endochondral bone formation, fracture repair |
| matrix metallo-proteinases: | type H endothelial cells | chondrocytes | cartilage resorption, directional |

-continued

| Angiocrine Factor | Source | Target Cell | Function |
|---|---|---|---|
| Mmp2, Mmp9, Mmp14 | | | bone elongation |
| Timp1, Timp2, Timp3, Timp4 | type H endothelial cells | chondrocytes | bone resorption and remodelling |
| SCF | type H, arterial and sinuspoidal endothelial cells | HSCs | HSC maintenance |
| nidogen-1 | sinusoidal and perivascular stromal cells | pro-B cells | pro-B cell maintenance |
| IL-7 | endothelial cells and perivascular stromal cells | pro-B cells | pro-B cell maintenance |
| CXCL12 | endothelial cells and mesenchymal stem cells | HSCs | HSC maintenance |
| tenascin-C | endothelial cells | HSCs | HSC survival |
| FGF-2 | endothelial cells | HSPCs | HSPC expansion |
| Jag-1 | endothelial cells | HSCs | HSC regeneration, lymphoma cell proliferation |
| NOS2 | endothelial cells | osteoblast | negative regulation of osteoblast differentiation |
| PDGF | endothelial cells | osteo-progenitor | osteoprogenitor proliferation and survival |
| TGF | endothelial cells | osteo-progenitor | osteoprogenitor survival |
| FGF1 | endothelial cells | osteoblast and osteo-progenitor | osteoprogenitor survival |
| Noggin | endothelial cells | osteoblast and osteo-progenitor | bone growth, mineralization and chondrocyte maturation |
| BMP-4 | endothelial cells | HSPC | expansion of HSPC |
| angiopotein-1 | endothelial cells | HSPC | protection of HSPC |
| VCAM-1 | endothelial cells | osteoclasts, leucocytes and fibroblasts | leucocytes trafficking, protection of DTCs |
| E-selectin | endothelial cells | osteoclasts, leucocytes | trafficking leucocytes, cancer metastasis |
| von Willebrand factor | endothelial cells | disseminated tumour cells | protection of DTCs |
| thrombo-spondin-1 | endothelial cells | disseminated tumour cells | quiescence of DTCs |
| IGFBP2 | endothelial cells | HSPC | expansion of HSPCs |
| ICAM-1 | endothelial cells | leucocytes and fibroblasts | leucocytes trafficking |

The link between hematopoietic and endothelial cells was found to be the hemangioblast, a common precursor for endothelial cells and hematopoietic cells. There is a strong interdependence of HSCs/HPCs and endothelial cells embryologically, which extends to the adult. (Kopp, et. al. "The Bone Marrow Vascular Niche: Home of HSC Differentiation and Mobilization." PHYSIOLOGY 20: 349-356, 2005; 10.1152/physiol.00025.2005).

Bone marrow endothelial cells (BMECs) are key to a mechanistic understanding of the blood cell-producing capability of the bone marrow (i.e., hematopoiesis). Studies on other endothelial cell types like human umbilical vein endothelial cells (HUVECs) showed that transendothelial trafficking was dependent on the expression of surface receptors or adhesion molecules, which were inducible by inflammatory cytokines. Therefore, it was thought that the release of mature blood cells as well as HSC/HPC mobilization and homing were likely to be regulated by similar mechanisms. BMECs were found to support the proliferation and differentiation of hematopoietic progenitors in vitro via production of various cytokines and also possibly via physical contact. Coculturing megakaryocytes and BMECs resulted in survival prolongation of BMECs, probably because megakaryocytes secrete the endothelial cell survival factor VEGF-A. (Kopp, et. al. "The Bone Marrow Vascular Niche: Home of HSC Differentiation and Mobilization." PHYSIOLOGY 20: 349-356, 2005; 10.1152/physiol.00025.2005).

The sufficiency of the vasculature of the bone marrow microenvironment is also key to hematopoiesis. Indeed, a function of the vascular niche interaction with BMECs is to provide a cellular platform conducive to HSC support, however the molecular mechanism by which the proper structural integrity of endothelial cells leads to this development is still unclear. (Kopp, et. al. "The Bone Marrow Vascular Niche: Home of HSC Differentiation and Mobilization." PHYSIOLOGY 20: 349-356, 2005; 10.1152/physiol.00025.2005).

Vascular Integrity

The integrity of blood vessels is critical to vascular homeostasis. Murakami, M., and Simons, M. J. Mol. Med. (Berl) (2009) 87 (6): 571-82). Maintenance of the vasculature is an active biological process that requires continuous, basal cellular signaling. Failure of this system results in serious consequences, such as hemorrhage, edema, inflammation, and tissue ischemia.

As currently understood, the steps in new vessel formation include endothelial cell proliferation and migration followed by assembly into a new vascular structure, lumen formation and, finally, maturation of the newly formed endothelial tube. Id. The latter part, tube stabilization and restoration of the barrier function, is crucial for newly formed vessels' maturation. Id. This stabilization stage requires activation of distinct cellular signaling pathways which are different from the signaling pathways that initiate vascular cell proliferation and migration. Moreover, not only newly formed vessels, but also existing vessels need to be actively maintained in order to maintain their integrity and tissue homeostasis. Id. Experience with various therapeutic angiogenic approaches has demonstrated that it is not simply sufficient to induce new vessel growth to achieve a functionally meaningful improvement in perfusion, but that prevention of vessel regression and promotion of vessel maturation are equally important (Id., citing Simons, M., Circulation (2005) 111: 1556-66).

Studies in various animal models as well as mouse and human genetic studies have identified a number of factors that play critical roles in active maintenance of blood vessel integrity during the embryonic vessel development or in the adult vasculature. These factors work coordinately over many steps of vascular stabilization and maintenance in an orchestrated manner. During the process of vascular formation, after nascent vessels are assembled, endothelial cells develop cell-cell junctions to establish an effective barrier, a process in which Ang1-Tie2 and FGF systems play pivotal roles (Id., citing Fiedler, U, Augustin, HG, Trends Immunol. (2006) 27: 552-58; Murakami, M., Simons, M.; Curr. Opin. Hematol. (2008) 15: 215-220). Concomitantly, while mesenchymal progenitor cells differentiate into pericytes or smooth muscle cells through the action of TGF-β, PDGF-BB derived from endothelial tip cells promotes pericyte recruitment and proliferation (Id., citing Pepper, MS, Cytokine Growth Factor Rev. (1997) 8: 21-43); Betsholtz, C. Cytokine Growth Factor Rev. (2004) 15: 215-228; Andrrae, J. et al., Genes Dev. (2008) 22: 1276-1312). Throughout this process, integrins mediate extracellular matrix (ECM)-cell signaling that further directs vessel stabilization (Id., citing Hynes, R O, J. Thromb. Haemost. (2007) 5 (Suppl. 1): 32-40).

Vascular integrity is tightly regulated by a number of factors that ensure proper functions of various components of the blood vessel wall. One of the early hallmarks of deteriorating vascular integrity is increased permeability which is predominantly controlled by endothelial junction stability. Selective regulation of vascular permeability is achieved by regulation of the size and state of paracellular gaps and control of the transcellular transport. The normal vasculature demonstrates a certain level of basal permeability that varies from bed to bed. Early studies have revealed constitutively open junctions in a subset of vascular beds (Id., citing Simionescu, N. etal., J. Cell Biol. (1978) 79: 27-44). Under normal conditions, about 30% of endothelial cell-cell junctions in postcapillary venules, where active permeability regulation occurs, are open and permeable to ~60 Å molecules. (Id.) Upon stimulation with either histamine or 5-HT (5-hydroxytriptamine), cellular junctions in postcapillary venules selectively open up and allow passage of larger molecules; however, outflow through venular junctions is limited and restricted to the perivascular spaces ((Id., citing Simionescu, N. etal., J. Cell Biol. (1978) 79: 27-44), which suggests the existence of an external barrier in the perivascular tissue. (Id.)

Increased endothelial permeability, elicited by physiological and pathological stimuli, is usually reversible and does not permanently deteriorate vascular integrity. Interference with endothelial junctional components can, however, leads to severe impairment of vascular integrity. In this scenario, junctional disruption is usually accompanied by eventual endothelial detachment from the vessel wall followed by thrombus formation. Although the sequence of events in this process is not well understood, it is possible that duration of permeability-inducing stimuli may influence the outcome. (Id.) Unlike transient increase of vascular permeability, which endothelial cells can quickly restore the barrier function by reestablishing VE-cadherin-based junctions, prolonged stimuli may leads to a more profound effect such as accumulation of reactive oxygen species (ROS). Excessive amounts of ROS, known to exert a number of adverse effects on endothelial function, may mediate such a scenario. In fact ROS can irreversibly inactivate protein tyrosine phosphatases (PTPs) by oxidizing a Cys residue in the active site, thereby affecting tyrosine phosphorylation-dependent signaling events (Id., citing Tonks, NK, Nat. Rev. Mol. CVell Biol. (2006) 7: 833-846).

Endothelial junctions—In endothelial cells, among the three types of intercellular junctions, namely adherens-, tight- and gap junction, adherens and tight junction contribute to the structural integrity of the endothelium (Id., citing Dejana, E., Nat. Rev. Mol. Cell Biol. (2004) 5: 261-270). Although it is difficult to precisely delineate the functional difference of these two types of junctions, it has been shown that assembly of tight junctions is dependent on prior formation of adherens junctions, and it is generally considered that adherens junctions are primarily important for the control of endothelial permeability, whereas tight junctions are implicated in blocking the movement of lipids and integral membrane proteins between the apical and basolateral surfaces of the cell (molecular fence) (Id., citing Dejana, E., Nature Rev. Mol. Cell Biol. (2004) 5:261-270; Taddei, A., et al., Nat. Cell Biol. (2008) 10: 923-34).

Each type of junction possesses a distinct set of proteins. Cadherins are a family of transmembrane proteins that constitute adherens junctions and mediate cell-cell contacts in a calcium-dependent manner through trans-homophilic interactions. In endothelial cells, VE-cadherin localizes at sites of cellular contacts, regulating the formation of adherens junctions and connecting the site of the junction to the actin cytoskeleton.

Stability of VE-cadherin at adherens junctions, which is controlled by binding to catenins, especially to p120-catenin, is critical to the maintenance of endothelial permeability and integrity. Src family kinases have been known to play an important role in VEGF-induced increase in endothelial permeability, and VE-cadherin phosphorylation via Src triggers disruption of cell-cell contacts, leading to VE-cadherin internalization (Id., citing Weis, S M, Chesh, D A, Nature (2005) 437: 497-504). This process is thought to be important for the establishment of endothelial motility and the angiogenic phenotype of "activated" endothelial cells. Thus, endothelial junctions are dynamic structures that actively assemble and disassemble even in the quiescent monolayer, suggesting that the balance of action controlling net VE-cadherin dynamics determines the endothelial behavior.

Inflammation and Niches

Inflammatory signals play key roles during diverse processes including embryonic specification of the hematopoietic stem cell (HSC) during development, emergency granulopoiesis during infections, and hematopoietic regeneration following transplantation. [4-8]

Although every stem cell niche is dynamic and exhibits cell turnover, it is useful to distinguish between niche cells that are 'permanent residents' (such as endothelial cells, nerve cells and connective tissue fibroblasts) and cells that occupy the niche in a transient fashion. (such as immune cells and cells that respond to tissue damage, for example, to protect against pathogens or to promote healing). In contrast to resident niche cells, many cells of the innate and adaptive immune system migrate into and out of tissues. The function of immune cells can be modulated to promote stem cell function. (Lane, S. W., Williams, D. A. & Watt, F. M. Modulating the stem cell niche for tissue regeneration. Nature biotechnology 32, 795-803, doi:10.1038/nbt.2978 (2014)).

Proinflammatory mediators that regulate HSC development include toll-like receptors (TLR), cytokines, and eicosanoids, each of which activates the immune system to fight insult. Tissue disruption due to injury or pathogenic agents leads to the release of proinflammatory cytokines that result in classical inflammation. Briefly, myeloid cells (such as macrophages and neutrophils) are armed with toll-like receptors (TLRs) and nucleotide-binding oligomerization domain (NOD)-like receptors (NLRs), which on recognition of damage-asociated molecular patterns (DAMPs) and pathogen-associated molecular patterns (PAMPs), induce the proliferation of proinflammatory cytokines and eicosanoids. TLRs promote the induction of gene expression and the intracellular accumulation of major proinflammatory cytokines interleukin (IL)-1β and IL-18 via the master inflammation/immune transcription factor nuclear factor kappa B (NF-κB). Subsequently, recognition of PAMPs/DAMPs in the cytosolid compartment by NLRs promote caspase-1 mediated proteolytic cleavage and release of proinflammatory cytokines and cytosolic phospholipase A2-mediated eicosanoid biosynthesis. Proinflammatory cytokines and eicosanoids then activate immune cells to eliminate the cause of infection and restore healthy tissue. (Espin-Palazon, R., Weijts, B., Mulero, V. & Traver, D. Proinflammatory Signals as Fuel for the Fire of Hematopoietic Stem Cell Emergence. Trends in cell biology 28, 58-66, doi:10.1016/j.tcb.2017.08.003 (2018).

HSCs are believed to sense immune or tissue insults by both cell intrinsic and extrinsic mechanisms. HSCs respond dynamically to locally produced cytokines (niche/microenviroment) and distally (injury or infection) produced cytokines, including pro-inflammatory cytokines, chemokines and PAMPS. HSCs and hematopoietic stem and progenitor cells (HSPCs) indirectly (through proinflammatory cytokines or DAMPs) or directly (through PAMPs) sense the immune or tissue insult. Typically, HSCs respond to proinflammatory signals by skewing normal hematopoiesis towards myelopoiesis, often at the expense of lymphopoiesis and erthythropoiesis, which is thought to occur to replenish the number of myeloid cells as the existing cells have been recruited to the site of infection. (Espin-Palazon, R., Weijts, B., Mulero, V. & Traver, D. Proinflammatory Signals as Fuel for the Fire of Hematopoietic Stem Cell Emergence. Trends in cell biology 28, 58-66, doi:10.1016/j.tcb.2017.08.003 (2018).

Similar to differentiated immune cells, HSCs recognize insult through their expression of TLRs. Ligation of TLR signals in HSCs leads to proliferation and differentiation. A cell extrinsic mode of recognition of a tissue or immune insult by HSCs involves signaling through receptors for pro-inflammatory cytokines. (Nakagawa, M. M., Chen, H., & Rathinam, C. V. (2018). Constitutive Activation of NF-κB Pathway in Hematopoietic Stem Cells Causes Loss of Quiescence and Deregulated Transcription Factor Networks. Frontiers in cell and developmental biology, 6, 143).

A spectrum of pro-inflammatory cytokines and chemokines, including IL1, IL6, IL8, TNF, CC-Chemokine ligand 2 (CCL2), IFN-α and IFN-γ has been shown to influence HSCs. Indeed, the stimulation of agonists for TLR2, TLR7, and TLR8 in vitro has been shown to induce cytokine production, e.g., IL-1b, IL-6, IL-8, TNF-α, and GM-CSF, as well as cell differentiation of the myeloid lineage. The exposure of human CD34+ HSPCs to IFN-γ has been shown to produce drastic transcriptional changes in genes involved in pro-apoptotic processes, immune responses, and myeloid proliferation that results in an increased number of viable cells. While some transcriptional changes are specific to HSPCs, others, e.g., cell growth and signal transduction, generally occur in stromal cells incubated with IFN-γ. In contrast, studies have shown that in vitro stimulation with IFN-γ and TNF severely compromised the ability of HSPCs to undergo multi-lineage reconstitution in xenografted mice. (Kovtonyuk, L. V., Fritsch, K., Feng, X., Manz, M. G. & Takizawa, H. Inflamm-Aging of Hematopoiesis, Hematopoietic Stem Cells, and the Bone Marrow Microenvironment. Frontiers in immunology 7, 502, doi:10.3389/fimmu.2016.00502 (2016)). Membrane-anchored TNF-α has been found to enhance the engraftment of purified HSCs in allogeneic and syngeneic recipients. (Espin-Palazon, R., Weijts, B., Mulero, V. & Traver, D. Proinflammatory Signals as Fuel for the Fire of Hematopoietic Stem Cell Emergence. Trends in cell biology 28, 58-66, doi:10.1016/j.tcb.2017.08.003 (2018).

Prolonged exposure of HSCs to pro-inflammatory cytokines causes diminished self-renewal and quiescence. In this regard, NF-κB can be viewed as a gatekeeper on the inflammatory control of HSCs because the pro-inflammatory cytokines produced and secreted by HSCs are dependent on NF-κB function. Briefly, NF-κB proteins act as transcription factors and are regarded as the master regulators of innate and adaptive immunity. There are five key members of this family in mammals: Rel A (p65), Rel B, c-Rel, p50/p105 (also known as NF-κB1) and p100/52 (also known as NF-κB2). NF-κB signals are activated in response to various upstream stimuli. In the absence of any activating signals, inhibitor of NF-κB (IκB) proteins form complexes with inactive NF-κB proteins and remain in the cytoplasm. Following an activating signal, the IκB kinase (IKK) complex, which is composed of two kinases; IKK1 (IKKα), IKK2 (IKKβ) and a regulatory subunit NEMO (IKKγ), phosphorylates IκB, which leads to ubiquitylation and subsequent degradation of IκB. This results in the release of NF-κB complexes from the cytoplasm to the nucleus, where they activate expression of target genes. Therefore, the IKK complex plays a major role in the entire cascade of NF-κB signals as decontrolled activation of the IKK complex can lead to detrimental downstream consequences. IKK complex phosphorylates IκB proteins at two amino (N)-terminal regulatory serine residues. In the majority of the canonical NF-κB signaling pathways, IKK2 is necessary and sufficient to phosphorylate IκB and activate NF-κB. (Nakagawa, M. M., Chen, H., & Rathinam, C. V. (2018). Constitutive Activation of NF-κB Pathway in Hematopoietic Stem Cells Causes Loss of Quiescence and Deregulated Transcription Factor Networks. *Frontiers in cell and developmental biology,* 6, 143).

In the context of NF-κB in the HSC niche, NF-κB is the major downstream effector of signals transduced by both TLRs and pro-inflammatory cytokines. Uncontrolled NF-κB activity results in increased expression of pro-inflammatory cytokines, including TNF, IL1, IL6, and IFN-γ. Defects in the negative regulatory circuits of NF-κB signaling cause loss of quiescence and pre-mature depletion of HSCs. While these studies highlight the importance of NF-κB pathways in HSC quiescence, the downstream consequences of NF-κB signals and the precise mechanisms through which NF-κB controls HSCs remain largely unknown. Constitutive activation of NF-κB has been documented in different types of human diseases, including myeloid neoplasms; for example, NF-κB has been shown to be constitutively active in leukemic stem cells (LSCs). (Nakagawa, M. M., Chen, H., & Rathinam, C. V. (2018). Constitutive Activation of NF-κB Pathway in Hematopoietic Stem Cells Causes Loss of Quiescence and Deregulated Transcription Factor Networks. *Frontiers in cell and developmental biology,* 6, 143).

The activation of quiescent ECs to generate the pro-inflammatory response is typically driven by transcription factor nuclear factor κB (NF-κB), which not only activates the transcription of the pro-inflammatory genes including TNF-α, interleukin-1(IL-1), E-selectin, vascular cell adhesion molecule 1(VCAM-1), and intercellular adhesion molecule 1(ICAM-1), but also renders ECs more susceptible to apoptosis (Jin, Z., et al., Int. J. Mol. Sci. (2019) 20(1): 172; citing Pober, J S, Sessa, WC, Nat. Rev. Immunol. (2007) 7: 803-815; Aoki, M. et al., Hypertension (2001) 38: 48-55; Kempe, S. etal., Nucleic Acids Res. (2005) 33: 5308-5319).

The role of proinflammatory immunomodulators is not limited to adult HSC function. Studies have found that proinflammatory pathways, such as the prototypical proinflammatory transcription factor NF-κB, are linked to the formation of the hematopoietic system during embryogenesis in both vertebrates and invertebrates. Other immunomodulators also have an effect on HSC specification (identity), emergence and maintenance during hemopoetic system formation. For example, IL-3, a cytokine that regulates the function, proliferation, and differentiation of immune cells, has been found to promote survival of HSCs in the murine arota-gonad-mesonephors (AGM) region, which is the site of HSC specification, by acting downstream of Runx1, an essential transcription factor in HSC specification. In another example, IL-1, a regulator of inflammation, plays an active role in HSC development by enhancing HSC expansion. Prostaglandin E2 (PGE2), a major regulator of inflammation, has also been shown to be a potent inducer for HSC emergence or expansion by controlling Wnt autonomously in HSCs at the level of beta-catenin degradation through cAMP/PKA mediated stabilizing phosphorylation events. (Espin-Palazon, R., Weijts, B., Mulero, V. & Traver, D. Proinflammatory Signals as Fuel for the Fire of Hematopoietic Stem Cell Emergence. Trends in cell biology 28, 58-66, doi:10.1016/j.tcb.2017.08.003 (2018)).

HSC fate decisions have been linked to proinflammatory cytokines TNFα, IFNγ, and IL-1β where in addition to TLR4 signalling, these cytokines are each a key determinant of HSC specification. TNFα acts through TNF receptor 2 (TNFR2) to specify HSCs from hemogenic endothelial cells (HEs), a specialized subset of developing vascular endodthelium that acquires hematopoieatic potential and can give ries to multilineage hematopoietic stem and progenitor cells during a narrow developmental window in e.g., the extra-embryonic yolk sac and embryonic aorta-gonad-mesonephros. Griz, E. "Specification and function of hemogenic endothelium during embryogenesis," Cell Mol. Life Sci. (2016) 73: 1547-67). Action of TNFR2 is required for the expression of jag1a, a Notch ligand essential for HSC specification in the dorsal aorta. Expression of Jag1 signals to the Notch1a receptor on adjacent hemogenic endothelium cells (i.e., specialized endothelial cells from which HSPCs originate) to help establish the HSC fate. Proinflammatory transcription factor NF-κB has been found to be active in nascent HSCs. TNFR2, NF-κB member p65 and TLR4 are all upgregulated in HSCs. Moreover, TLR4, IL-1β and TNFα is required for HSC specification by acting upstream of NF-κB and Notch. It was demonstrated that HSCs, but not endothelial cells, rapidly respond to IFNs. IFN-α4 and IFN-γ are also needed for HSC specification across vertebrates through IFNαR1 and IFNγR1, respectively. Unlike TNF-α and TLR4 signaling, IFN-γ acts downstream of Notch signaling and blood flow by activating Stat3. IFN-γ signaling acts autonomously in the HE. (Espin-Palazon, R., Weijts, B., Mulero, V. & Traver, D. Proinflammatory Signals as Fuel for the Fire of Hematopoietic Stem Cell Emergence. Trends in cell biology 28, 58-66, doi:10.1016/j.tcb.2017.08.003 (2018)).

Cellular sources of proinflammatory cytokines during hematopoietic system formation are not well known. (Espin-Palazon, R., Weijts, B., Mulero, V. & Traver, D. Proinflammatory Signals as Fuel for the Fire of Hematopoietic Stem Cell Emergence. Trends in cell biology 28, 58-66, doi: 10.1016/j.tcb.2017.08.003 (2018)). Such cytokines are known to have an influence on HSC differentiation. In steady state, platelet-biased HSCs are at the top of the hematopoietic hierarchy and are able to generate myeloid-biased and lymphoid-biased HSCs. Myeloid-biased HSCs can generate both balanced- and lymphoid-biased HSCs, whereas lymphoid-biased HSCs do not generate their myeloid-biased counterparts. Platelet-biased HSCs have the potential to repopulate platelet populations faster than other HSC subsets. Myeloid-biased HSCs preferentially give rise to myeloid lineage cells through myeloid committed progenitors. Balanced HSCs make equal contributions to both myeloid and lymphoid lineages. Lymphoid-biased HSCs predominantly generate lymphoid over myeloid lineage cells through lymphoid-committed progenitors. Inflammation specifically chronic inflammation enhances myeloid lineage production, including myeloid progenitors and mature myeloid cells, leading to myeloid bias in hematopoiesis. (Kovtonyuk, L. V., Fritsch, K., Feng, X., Manz, M. G. & Takizawa, H. Inflamm-Aging of Hematopoiesis, Hematopoietic Stem Cells, and the Bone Marrow Microenvironment. Frontiers in immunology 7, 502, doi:10.3389/fimmu.2016.00502 (2016)).

Therefore, while inflammation is a key driver of hematopoesis, sustained inflammation has been proposed as a key driver of aging-associated hematopoietic defects, including loss of HSC self-renewal ability, myeloid-biased differentiation and a predisposition towards leukemias (Kovtonyuk, L. V., et al. Inflamm-Aging of Hematopoiesis, Hematopoietic Stem Cells, and the Bone Marrow Microenvironment. Frontiers in immunology (2016) 7, 502, doi:10.3389/fimmu.2016.0050); Pietras, E. M. et al. Chronic interleukin-1 exposure drives haematopoietic stem cells towards precocious myeloid differentiation at the expense of self-renewal. Nature cell biology (2016) 18, 607¬-618, doi:10.1038/ncb3346; Lussana, F. & Rambaldi, A. Inflammation and myeloproliferative neoplasms. Journal of autoimmunity (2017) 85, 58-63, doi:10.1016/j.jaut.2017.06.010; Pietras, E. M. Inflammation: a key regulator of hematopoietic stem cell fate in health and disease. Blood (2017) 130, 1693-1698, doi:10.1182/blood-2017-06-780882).

Growing evidence indicates that the crosstalk between hematopoietic cells and the niche initiates and sustains chronic inflammation within the bone marrow (BM), although their precise contributions in this process remain unclear. (Kovtonyuk, L. V., et al. Inflamm-Aging of Hematopoiesis, Hematopoietic Stem Cells, and the Bone Marrow Microenvironment. Frontiers in immunology (2016) 7, 502, doi:10.3389/fimmu.2016.0050); Pietras, E. M. et al. Chronic interleukin-1 exposure drives haematopoietic stem cells towards precocious myeloid differentiation at the expense of self-renewal. Nature cell biology (2016) 18, 607 ¬-618, doi:10.1038/ncb3346; Lussana, F. & Rambaldi, A. Inflammation and myeloproliferative neoplasms. Journal of autoimmunity (2017) 85, 58-63, doi:10.1016/j.jaut.2017.06.010; Pietras, E. M. Inflammation: a key regulator of hematopoietic stem cell fate in health and disease. Blood (2017) 130, 1693-1698, doi:10.1182/blood-2017-06-780882).

Within the BM microenvironment, endothelial cells (ECs) have been established as an integral component of the HSC-supportive perivascular niche, as illustrated by their expression of a diverse array of HSC-regulatory paracrine factors (Hooper, A. T. et al. Engraftment and reconstitution of hematopoiesis is dependent on VEGFR2-¬mediated regeneration of sinusoidal endothelial cells. Cell stem cell (2009) 4, 263-274, doi:10.1016/j.stem.2009.01.006; Butler, J. M. et al. Endothelial cells are essential for the self-renewal and repopulation of Notch, dependent hematopoietic stem cells. Cell stem cell (2010) 6, 251-264, doi:10.1016/j.stem.2010.02.001; Kobayashi, H. et al. Angiocrine factors from Akt-activated endothelial cells balance self-renewal and differentiation of haematopoietic stem cells. Nature cell biology (2010) 12, 1046-1056, doi:10.1038/ncb2108; Winkler, I. G. et al. Vascular niche E-selectin regulates hematopoietic stem cell dormancy, self renewal and chemoresistance. Nature medicine (2012) 18, 1651-1657, doi:10.1038/nm.2969; Ding, L., et al., Endothelial and perivascular cells maintain haematopoietic stem cells. Nature (2012) 481, 457-462, doi:10.1038/nature10783; Poulos, M. G. et al. Endothelial jagged-1 is necessary for homeostatic and regenerative 947 hematopoiesis. Cell reports (2013) 4, 1022-1034, doi:10.1016/j.celrep.2013.07.048; Greenbaum, A. et al. CXCL12 in early mesenchymal progenitors is required for haematopoietic stem-cell maintenance. Nature (2013) 495, 227-230, doi:10.1038/nature11926; Doan, P. L. et al. Epidermal growth factor regulates hematopoietic regeneration after radiation injury. Nature medicine (2013) 19, 295-304, doi:10.1038/nm.3070; Poulos, M. G. et al. Endothelial-specific inhibition of NF-kappaB enhances functional haematopoiesis. Nat Commun (2016) 7, 13829, doi:10.1038/ncomms13829; Kusumbe, A. P. et al. Age-dependent modulation of vascular niches for haematopoietic stem cells. Nature (2016) 532, 380-384, doi:10.1038/nature17638; Morrison, S. J. & Scadden, D. T. The bone marrow niche for haematopoietic stem cells. Nature (2014) 505, 327-334, doi:10.1038/nature12984; Rafii, S., Butler, J. M. & Ding, B. S. Angiocrine functions of organ-specific endothelial cells. Nature (2016) 529, 316-325, doi:10.1038/nature17040). Modulation of signaling pathways within the endothelium has also been shown to directly impact niche activity, thereby regulating HSC self-renewal and lineage commitment decisions (Kobayashi, H. et al. Angiocrine factors from Akt-activated endothelial cells balance self-renewal and differentiation of haematopoietic stem cells. Nature cell biology (2010) 12, 1046-1056, doi:10.1038/ncb2108 (2010); Poulos, M. G. et al. Endothelial-specific inhibition of NF-kappaB enhances functional haematopoiesis. Nat Commun (2016) 7, 13829, doi:10.1038/ncomms13829; Kusumbe, A. P. et al. Age-dependent modulation of vascular niches for haematopoietic stem cells. Nature (2016) 532, 380-384, doi:10.1038/nature17638). In addition to serving as tissue-specific niche cells, endothelium is a key determinant in chronic inflammation (Rafii, S., Butler, J. M. & Ding, B. S. Angiocrine functions of organ-specific endothelial cells. Nature (2016) 529, 316-325, doi:10.1038/nature17040; Pober, J. S. & Sessa, W. C. Evolving functions of endothelial cells in inflammation. Nature reviews. Immunology (2007) 7, 803-815, doi:10.1038/nri2171) and has emerged as an important source of niche-derived inflammatory signals within the BM, including IL-1 and G-CSF, which drive myelopoiesis during response to acute demands (Pietras, E. M. et al. Chronic interleukin-1 exposure drives haematopoietic stem cells towards precocious myeloid differentiation at the expense of self-renewal. Nature cell biology (2016) 18, 607 ¬-618, doi:10.1038/ncb3346; Boettcher, S. et al. Endothelial cells translate pathogen signals into G-CSF-driven emergency granulopoiesis. Blood (2014) 124, 1393-1403, doi:10.1182/blood-2014-04-570762). Sustained endothelial inflammation has been implicated in the initiation of myeloproliferative diseases through the expression of G-CSF and TNFα (Wang, L. et al. Notch-dependent repression of miR-155 in the bone marrow niche regulates hematopoiesis in an NF-kappaB-dependent manner. Cell stem cell (2014) 15, 51-65, doi:10.1016/j.stem.2014.04.021. However, signaling pathways mediating chronic endothelial inflammation within the BM microenvironment that impact niche activity and HSC function remain poorly understood.

NF-κB and MAPK are the principal signaling pathways regulating chronic inflammatory responses within endothelial cells (Pober, J. S. & Sessa, W. C. Evolving functions of endothelial cells in inflammation. Nature reviews. Immunology (2007) 7, 803-815, doi:10.1038/nri2171). However, their role in modulating inflammation within the BM endothelial niche and the concomitant impact on HSC function remains unexplored. Prior research has shown that suppression of NF-κB signaling within the endothelium enhances steady state hematopoiesis as well as regeneration following myelosuppression, in part by decreasing pro-inflammatory cytokines (Poulos, M. G. et al. Endothelial-specific inhibition of NF-kappaB enhances functional haematopoiesis. Nat Commun (2016) 7, 13829, doi:10.1038/ncomms13829). Recent reports suggest that endothelial MAPK plays essential roles during inflammatory processes including LPS-induced granulopoiesis and chronic vascular inflammation associated atherosclerosis(Sanchez, A. et al. Map3k8 controls granulocyte colony-stimulating factor production and neutrophil precursor proliferation in lipopolysaccharide-induced emergency granulopoiesis. Sci Rep (2017) 7, 5010, doi:10.1038/s41598-017-04538-3; Roth Flach, R. J. et al. Endothelial protein kinase MAP4K4 promotes vascular inflammation and atherosclerosis. Nat Commun (2015) 6, 8995, doi:10.1038/ncomms9995). Utilizing an ex vivo niche model system, it has been demonstrated that endothelial MAPK activation drives myeloid-biased differentiation of co-cultured HSCs at the expense of their self-renewal, features that are suggestive of an inflammatory stress (Kobayashi, H. et al. Angiocrine factors from Akt-activated endothelial cells balance self-renewal and differentiation of haematopoietic stem cells. Nature cell biology (2010) 12, 1046-1056, doi:10.1038/ncb2108).

Myoablative Therapy

In patients that require reconstitution of their hematopoetic system, preparative or conditioning regimens are administered as part of the procedure to achieve 2 goals: provide sufficient immunoablation to prevent host rejection and provide tumor cytoreduction/disease eradication. There are variations of conditioning regimens as the intensity can vary based on disease-related factors such as diagnosis and remission status, as well as patient-related factors including age, donor availability, and presence of comorbid conditions. Conditioning regimens have been classified as high-dose (myeloablative), reduced-intensity, and nonmyeloablative therapy. (Gyurkocza, Boglarka, and Brenda M Sandmaier. "Conditioning regimens for hematopoietic cell transplantation: one size does not fit all." *Blood* (2014) vol. 124,3: 344-53). Myeoablative therapy (MBT) refers to the treatment of a patient with high-dose chemotherapy (HDC) or HDC with total body radiation (TBI) to eradicate the immune and hematopoietic systems as well as all malignant cells within the body. Typically, patients who receive MBT have done so in preparation for bone marrow transplantation, stem cell transplantation, or hematopoietic cell transplantation (referred to herein as "stem cell rescue" or "SCR"); however, as seen in Table 3 below, MBT can also be used as a treatment type for various types of malignancies in which SCR has not been shown to be beneficial. (Riley, et al., "Hematologic Aspects of Myeloablative Therapy and Bone Marrow Transplantation." Journal of Clinical Laboratory Analysis (2005)19:47-79).

TABLE 3

Indications for Myeoblative Therapy/Stem Cell Rescue

| Type of disease | Specific diseases |
|---|---|
| Primary and secondary | Aplastic anemia |
| | Amegakaryocytosis/congenital thrombocytopenia |

TABLE 3-continued

Indications for Myeoblative Therapy/Stem Cell Rescue

| Type of disease | Specific diseases |
|---|---|
| bone marrow failure | Fanconi anemia |
| | Paroxysmal nocturnal hemoglobinuria (PNH) |
| Hematopoietic malignancies | Acute leukemias |
| | Chronic leukemia |
| | Myelodysplastic syndromes |
| | Myeloproliferative disorders |
| | Non-Hodgkin lymphoma |
| | Plasma cell diseases |
| | Histiocytic disorders |
| Solid tumors | Breast cancer |
| | Renal cell carcinoma |
| | Neuroblastoma |
| | Ewing sarcoma |
| | Testicular carcinoma |
| Congenital hematopoietic and immunodeficiency states | Immunodeficiencies (severe combined immunodeficiency, etc.) |
| | Granulocyte deficiencies (chronic granulomatous disease, etc.) |
| | Hemoglobulinopathies (beta-thalassemia major, sickle cell disease) |
| Inherited metabolic disorders | Mucopolysaccharidoses |
| | Hurler's syndrome |
| Type of disease | Specific diseases |
| | Hunter's syndrome |
| | Niemann-Pick disease |
| | Mucolipidosis II |
| Other inherited diseases | Osteopetrosis |
| | Glanzmann thromboasthenia |
| | Lesch-Nyhan syndrome |
| | Cartilage-hair hypoplasia |

Generally, MBT regimens consist of HDC with alkylating agents (single agent types or multiple), and are delivered with or without TBJ. Such regimens are expected to ablate marrow hematopoiesis, thereby not allowing autologous hematologic recovery. (Gyurkocza, Boglarka, and Brenda M Sandmaier. "Conditioning regimens for hematopoietic cell transplantation: one size does not fit all." *Blood* (2014) vol. 124,3: 344-53). Examples of specific MBT regimens can be seen in Table 4 below, reproduced in part from Atilla, E., Ataca Atilla, P., & Demirer, T. A Review of Myeloablative vs Reduced Intensity/Non-Myeloablative Regimens in Allogeneic Hematopoietic Stem Cell Transplantations. *Balkan medical journal*, (2017) 34(1), 1-9.

TABLE 4

Myeloablative Therapy Treatments and Dosages

| Myeloablative Therapy | Total Dosage (Days) |
|---|---|
| Cv/TBI | |
| Cy (mg/kg) | 120 (−6, −5) |
| Total body irridation (GY) | 12-14 (−3 to −1) |
| Bu/Cv | |
| Bu (mg/kg) | 16 (−7 to −4) |
| Cy (mg/kg) | 120 (−3 to −2) |
| BACT | |
| BCNU ($mg/m^2$) | 200 (−6) |
| ARA-C ($mg/m^2$) | 800 (−5 to −2) |
| Cy (mg/kg) | 50 (−5 to −2) |
| 6-Thioguanine ($mg/m^2$) | 800 (−5 to −2) |
| BEAM | |
| BCNU ($mg/m^2$) | 300 (−6) |
| Etoposide ($mg/m^2$) | 800 (−5 to −2) |
| ARA-C ($mg/m^2$) | 800 (−5 to −2) |
| Melphalan ($mg/m^2$) | 140 (−1) |

TABLE 4-continued

| Myeloablative Therapy Treatments and Dosages | |
|---|---|
| Myeloablative Therapy | Total Dosage (Days) |
| TBI/VP | |
| Total body irridation (Gy) | 12-13.2 (−7 to −4) |
| Etoposide (mg/kg) | 60 (−3) |
| AC/TBI | |
| ARA-C (g/m$^2$) | 36 (−9 to −4) |
| Total body irridation (Gy) | 12 (−3 to −1) |
| Mel/TBI | |
| Melphalan (mg/m$^2$) | 110-140 |
| Total body irridation (Gy) | 10-14 |
| Cv/VP/TBI | |
| Cy (mg/kg) | 120 (−6, −5) |
| Etoposide (mg/kg) | 30-60 (−4) |
| Total body irridation (Gy) | 12-13.8 (−3 to −1) |
| TBI/TT/Cv | |
| Total body irridation (Gy) | 13.8 (−9 to −6) |
| Thiotepa (mg/kg) | 10 (−5, −4) |
| Cy (mg/kg) | 120 (−3, −2) |
| Bu/Cy/Mel | |
| Bu (mg/kg) | 16 (−7 to −4) |
| Cy (mg/kg) | 120 (−3, −2) |
| Mel (mg/m$^2$) | 140 (−1) |

ATG: anti-thymocyte globulin,
Bu: busulfan,
Cy: cyclophosphamide,
Mel: melphalan,
TBI: total body irridation,
TTP: thiotepa,
VP: etoposide Total Body Irradation (TBI). TBI and high-dose TBI are widely used as part of the conditioning regimen due to its immunosuppressive properties, its effectiveness against most leukemias and lymphomas, and its ability to penetrate to sanctuary sites. The majority of regimens combined 12- to 16-Gy TBI, usually fractionated (meaning when the total dose of radiation is divided into several, smaller doses over a period of several days), with other chemotherapeutic agents, most commonly, cyclophosphamide, based on its antineoplastic and immunomodulatory properties. In general, higher doses of TBI, although reducing the relapse risk, resulted in increased, often fatal, gastrointestinal, hepatic, and pulmonary toxicities, secondary malignancies, and impaired growth and development in children. In addition to the delivered dose, other factors, such as dose rate, fractionation, interval between fractions, and the source of radiation (such as cobalt-60 vs linear accelerator) could also impact both the antineoplastic and toxic effects of TBJ. Fractionation resulted in decreased organ toxicity but also sustained antineoplastic effects, due to a higher proportion of intact repair mechanisms retained in normal tissues as opposed to leukemic cells. Hyperfractionation (multiple fractions per day) with lung shielding resulted in a decreased incidence of interstitial pneumonitis of 4%, down from 50% observed with single-fraction TBI without lung shielding. The majority of TBI schedules in use today are either fractionated or hyperfractionated. In addition to cyclophosphamide, various agents, such as cytarabine (AraC), etoposide, melphalan, and busulfan, have been combined with high-dose TBI as conditioning regimens. (Gyurkocza, Boglarka, and Brenda M Sandmaier. "Conditioning regimens for hematopoietic cell transplantation: one size does not fit all." *Blood* (2014) vol. 124,3: 344-53).

The administration of high-dose TBI is associated with immediate and delayed toxicities, although it is not always possible to distinguish which component of the conditioning regimen is responsible for any given toxicity. Nausea, vomiting, transient acute parotiditis, xerostomia, mucositis, and diarrhea are commonly observed acute complications. Interstitial pneumonitis, idiopathic pulmonary fibrosis, and reduced lung pulmonary function can also be related to high-dose TBI. In addition, renal damage can occur and can be delayed (i.e., up to ~2 years) after high-dose TBI. The occurrence of sinusoidal obstruction syndrome (SOS; formerly known as veno-occlusive disease of the liver) is more common in chemotherapy-based regimens described en infra. Long-term side effects of high-dose TBI include infertility, cataract formation, hyperthyroidism and thyroiditis, and secondary malignancies. (Gyurkocza, Boglarka, and Brenda M Sandmaier. "Conditioning regimens for hematopoietic cell transplantation: one size does not fit all." *Blood* (2014) vol. 124,3: 344-53).

High Dose Chemotherapy (HDC). The main component of HDC is the delivery of alkylating agents due to their favorable toxicity profile (marrow toxicity as dose-limiting toxicity) and their effect on nondividing tumor or malignant cells. Other agents that can be used include anthracyclines and taxanes. To avoid short- and long-term toxicities associated with high-dose TBI, especially in patients who received previous radiation therapy, high-dose chemotherapy-based regimens have been developed both in the autologous and allogeneic settings where TBI is replaced with additional chemotherapeutic agents. Alkalyating agents are often delivered with immunosuppressives; the treatment can include busulfan, cyclophosphamide, or fludarabine, melphalan, theiotepa, etoposide, and treosulfan, and the like, and combinations of such therapeutics. (Gyurkocza, Boglarka, and Brenda M Sandmaier. "Conditioning regimens for hematopoietic cell transplantation: one size does not fit all." *Blood* (2014) vol. 124,3: 344-53).

Morphological effects of MBT. The morphologic features of the bone marrow in a patient receiving MBT are determined by the overlapping processes of cell death and hematopoietic reconstitution. Aggressive chemotherapy alone or with TBI results in the obliteration of nearly all of the hematopoietic and immune cells over a period of several days. At the end of this period, the bone marrow is profoundly hypocellular, with an intact stroma containing a homogenous, periodic acid Schiff (PAS)-positive proteinaceous transudate resembling fibrinoid necrosis. A few residual plasma cells and macrophages are usually present, and vascular congestion, areas of nonspecific hemorrhage, small noncaseating granulomas, stromal edema, eosinophilia, mildreticulin fibrosis, sinus ectasia, osteocyte necrosis, and other anomalies may be found. A period of weeks is required for the restoration of normal levels of red blood cells, platelets, and granulocytes after MBT, with or without stem cell rescue, while complete functional reconstitution of the hematopoietic system takes place over a period of years. Further, in spite of the relatively rapid restoration of peripheral blood cell counts following myeloablative chemotherapy or bone marrow transplantation, there is a continuing severe cellular and humoral immunodeficiency for months to years. (Gyurkocza, Boglarka, and Brenda M Sandmaier. "Conditioning regimens for hematopoietic cell transplantation: one size does not fit all." *Blood* vol. 124,3 (2014): 344-53).

The myeloablative and conditioning regimens that purge malignant progenitors from the bone marrow may also remove or damage nonmalignant hematopoietic and stromal progenitor cells, resulting in a diminished capacity for transplanted and native stem cell renewal. This deficit is not always apparent from examination of a post transplant peripheral smear or marrow biopsy. A severe prolonged deficiency of erythroid and megakaryocyte marrow progenitors may persist for many years after bone marrow transplantation, even though peripheral blood cell counts and marrow cellularity may reach pre-transplant levels. Colony forming units-fibroblasts (CFU-f), the precursor stromal compartment for cells of the osteogenic lineage, are critical to hematopoietic cell survival, proliferation, and differentiation. CFU-f reconstitution may take as long as 12 years to reach pretransplant numbers and is solely of host origin.

Stem Cell Rescue (SCR) Therapy

Stem cell rescue (or rescue transplant) is a method of replacing blood-forming stem cells that were destroyed by treatment with high doses of anticancer drugs or radiation therapy. It is usually done using the patient's own stem cells that were saved before treatment. The stem cells help the bone marrow recover and make healthy blood cells. Stem cell rescue may also allow more chemotherapy or radiation therapy to be given so that more cancer cells are killed.

Typically following MBT, patients will receive an infusion of hematopoietic stem cells isolated from either bone marrow or peripheral blood with the intent of curing a systemic malignancy, inherited metabolic disease, or potentially fatal disease of the hematopoietic or immune systems. The rationale for bone marrow transplantation in patients with bone marrow failure, malignancies, and congenital hematopoietic and immunodeficiency states is to supply normal stem cells for marrow repopulation after obliteration of the diseased marrow. Regeneration of new bone marrow ("bone marrow reconstitution") occurs during recovery from myeloablative therapy, either from stem cell progenitors or, less often, from residual host progenitors. (Riley, et al., "Hematologic Aspects of Myeloablative Therapy and Bone Marrow Transplantation." Journal of Clinical Laboratory Analysis (2005) 19:47-79).

Morphologic Features of Stem Cell Rescue. The immediate post-chemotherapy or post-transplant period is usually followed by 1 to 2 weeks of marked marrow aplasia (meaning incomplete, retarded or defective development). Fat cell regeneration provides the first morphologic evidence of bone marrow regeneration, followed at day 6 to day 14 by the appearance of minute clusters of immature, monotypic hematopoietic cells that gradually mature and enlarge. These colonies are comprised of cells of a single hematopoietic lineage ("monophyletic"), usually myeloid or erythroid, and presumably arise from committed stem cells in the bone marrow transplant patient. The regenerating colonies tend to be paratrabecular in patients receiving bone marrow transplant only and interstitial following stem cell transplantation. Very early post-transplant hematopoiesis is usually polyclonal but may be monoclonal. Early erythropoietic islands are usually dominated by large basophilic normoblasts that may exhibit dyserythropoietic features. As hematopoietic reconstitution continues, the distribution of hematopoietic cells in the bone marrow is often atypical, such that clusters of myeloid precursors are abnormally localized in the intratrabecular areas and erythroid precursors occur near the endosteum. Megakaryocytes are normally the last to engraft. They are usually localized in the central part of the intertrabecular areas, and may appear in clusters, rather than in their normal scattered distribution. Macrophages, pseudo-Gaucher cells, and sheets of regenerating promyelocytes may also appear. (Riley, et al., "Hematologic Aspects of Myeloablative Therapy and Bone Marrow Transplantation." Journal of Clinical Laboratory Analysis (2005)19:47-79).

The gradual return to normal bone marrow cellularity is accompanied by resolution of the edema, reticulin fibrosis (meaning incrased reticulin staining), and fibrinoid necrosis (meaning a type of necrosis that occurs in the wall of a small artery or arteriole that is pink in color, and resembles fibrin (thus, fibrinoid); it represents actual death or necrosis of the cell wall). The marrow should be approximately 50% normocellular by the third posttransplantation week and normocellular by 8 to 12 weeks. The time course of the progression from early hematopoiesis to normal marrow cellularity is extremely variable; some patients may achieve normal cellularity in as little as 14 days, while others require several months. However, 28 days is typical.The kinetics of engraftment depend on the source of donor cells (e.g., peripheral blood stem cells, cord blood, bone marrow), the dose of infused CD34+ cells, the type and dose of exogenous hematopoietic growth factors (i.e., G-CSF, rhGM-CSF, erythropoietin), and HLA crossmatching. The rate of marrow recovery is affected by the homing efficiency and clonogenic potential of the transplanted cells and whether the infused cells were expanded in vitro prior to infusion. (Riley, et al., "Hematologic Aspects of Myeloablative Therapy and Bone Marrow Transplantation." Journal of Clinical Laboratory Analysis (2005)19:47-79).

In the peripheral blood, granulocyte colony stimulating factor (G-CSF) and granulocyte-macrophage colony stimulating factor (GM-CSF) cause an increase in the total white blood cell count and the absolute number of neutrophils, monocytes, and eosinophils. Their effects on the bone marrow include eosinophilic hyperplasia and increases in cellularity and the myeloid:erythroid (M:E) ratio. In addition, prominently granulated and/or vacuolated neutrophils and neutrophilic precursors appear in both the peripheral blood and bone marrow. (Riley, et al., "Hematologic Aspects of Myeloablative Therapy and Bone Marrow Transplantation." Journal of Clinical Laboratory Analysis (2005) 19:47-79).

MBT and SCR Hematologic Consequences

Stem cell rescue via bone marrow transplantation is often compared to solid organ transplantation, but it is unique in several ways. Because bone marrow is a liquid "organ," the problems of compatible organ size, biliary and ureteral obstruction, and other surgical problems are not encountered. Since bone marrow is rapidly replenished by normal individuals, cadaver organs are not required, and the living donor sustains no permanent organ insufficiency. Patients can even supply their own bone marrow for later transfusion (autologous SCR). However, transplant recipients receiving a marrow donation from another individual (allogeneic SCR) face the problem of graft rejection, as well as rejection of the host by the graft, known as graft-vs.-host-disease (GVHD). In addition, bone marrow transplant recipients are profoundly immunosuppressed until bone marrow reconstitution occurs, and they are extremely susceptible to opportunistic infections and other problems during this period. Therefore, SCR via bone marrow transplantation is a very expensive undertaking with a significant morbidity and mortality rate. Consequently, the indications for this procedure are limited and potential recipients undergo a thorough, and potentially lengthy, screening process. (Riley, et al., "Hematologic Aspects of Myeloablative Therapy and Bone Marrow Transplantation." Journal of Clinical Laboratory Analysis (2005) 19:47-79). The below table briefly outlines adverse hematologic consequences of MBT and/or SCR.

TABLE 5

| Adverse hematologic consequences of myeloabalative therapy and/or stem cell rescue | |
|---|---|
| Problem | Diagnostic features |
| Engraftment failure and delayed engraftment | Marked marrow hypocellularity<br>Diffuse histiocytic proliferation<br>Careful review of bone marrow aspirate, biopsy, and clot section supplemental by flow cytometry and/or immunoperoxidase staining |
| Residual bone marrow disease | |
| Minimal residual disease | Advanced diagnostic technique with detection limit of at least $10^{-3}$ cells |
| Hematogones | Flow Cytometric immunophenotypic analysis |
| Graft-versus-host disease | Proliferation of macrophages, myelofibrosis, bone marrow hypoplasia |
| Myelofibrosis | Reticulin fibrosis, usually in patients with CML |
| Therapy-related acute leukemia (t-AML) | Morphology, immunophenotypic analysis, molecular analysis, EBV analysis |
| Post-transplant lymphoproliferative disorders (PTLD) | Cytopenias with bone marrow hypocellularity, stromal damage, edema, perivascular plasmacytosis, necrobiosis of neutrophilic granulocytes, and cellular debris |
| Toxic myelopathy | |

Engraftment Failure, Acute Graft Rejection, and Delayed Engraftment

Many factors may cause poor outcome after SCR via bone marrow transplantation ("graft failure") or the loss of recently engrafted marrow tissue ("graft rejection"). Generally, failure of initial engraftment (primary graft failure) is due to genetic differences between the donor and recipient, damaged stem cells or an insufficient numbers of stem cells, inadequate immunosuppression or pretransplant conditioning, alloimmunization due to previous multiple blood transfusions, excessive T-cell depletion of the engrafted material, an abnormal microenvironment in the bone marrow of the host, an abnormal donor marrow, drug toxicity, or viral infections. Failure of the graft after engraftment (secondary graft failure) occurs as a result of drugtoxicity, infections, fibrosis, or cell-mediated immune reactions. (Riley, et al., "Hematologic Aspects of Myeloablative Therapy and Bone Marrow Transplantation." Journal of Clinical Laboratory Analysis (2005) 19:47-79).

Immunologically-mediated bone marrow acute graft rejection is particularly common in three situations:1) multiply-transfused patients with aplastic anemia, 2) patients receiving bone marrow from an major histocompatability mismatched donor, and 3) patients receiving T-cell depleted bone marrow. The incidence of acute rejection is only about 1% in patients receiving an immunologically unmanipulated, HLA-matched graft from a sibling, but increases to 8-15% in patient sreceiving T-cell depleted-phenotypically matched grafts.

Graft rejection is primarily caused by host T lymphocytes that survive the pretransplant conditioning regimen, proliferate in the allografted bone marrow, then suppress the growth of donor cells, and initiate cell-mediated responses against donor targets. Slightly different mechanisms of rejection may be involved in different patient populations, since suppressor T lymphocytes (CD3+CD8+CD57+) predominate in HLA-matched siblings undergoing allograft rejection, while cytotoxic T lymphocytes (CD3+CD8+CD57−) are found in rejecting marrow transplant patients receiving an HLA-matched allograft from an unrelated donor. (Riley, et al., "Hematologic Aspects of Myeloablative Therapy and Bone Marrow Transplantation." Journal of Clinical Laboratory Analysis (2005)19:47-79).

Severe thrombocytopenia after primary post-transplant recovery of platelets ("secondary failure of platelet recovery" or "SFPR") is associated with serious complications, a poor clinical outcome, or even death. Thrombocytopenia occurs in as many as 20% of patients undergoing allogeneic transplantation, but has a much lower incidence (8%) in autologous transplantation. Cytomegalovirus infection has been implicated as a significant risk factor for the development of SFPR by several groups of investigators. (Riley, et al., "Hematologic Aspects of Myeloablative Therapy and Bone Marrow Transplantation." Journal of Clinical Laboratory Analysis (2005) 19:47-79).

Morphologically, bone marrow aspirate smears from patients with engraftment failure or delayed engraftment are markedly hypocellular, with a predominance of stromal cells, while core biopsies and clot sections often show diffuse proliferation of histiocytes (stationary phagocytic cells present in onnective tissue). (Riley, et al., "Hematologic Aspects of Myeloablative Therapy and Bone Marrow Transplantation." Journal of Clinical Laboratory Analysis (2005) 19:47-79).

Clinically, early graft failure (>50 days post transplantation) is manifested by host T lymphocytosis (CD3+, CD8+, DR+),while late graft failure (>50 days post transplantation) is associated with a syndrome of delayed granulopoietic regeneration, fever of unknown origin, and abdominal symptomatology. Graft rejection is often heralded by progressive lymphocytosis (high lymphocyte count) and a sudden drop in the absolute neutrophil count. The prognosis for continued successful engraftment is poor once lymphocytosis occurs, although the infusion of donor lymphocytes has been successful in a few patients. Preventive therapy in high-risk patients is directed at the inclusion of increased total body irradiation, total lymphoid irradiation, or immunosuppressive agents into the preconditioning regimen. (Riley, et al., "Hematologic Aspects of Myeloablative Therapy and Bone Marrow Transplantation." Journal of Clinical Laboratory Analysis (2005) 19:47-79).

Minimal Residual Disease (MRD)

MRD is the persistence of leukemic cells in the bone marrow after remission induction therapy (meaning initial treatment with anticancer drugs) below the limit of detection by conventional morphologic assessment. It is believed that these residual leukemic cells are the possible source of disease relapse in many patients who achieve "complete" morphologic remission from various forms of leukemia, thereby leading to residual or relapse bone marrow disease. The clinically relevant level of sensitivity for MRD detection has not been established, nor has it been documented that additional therapy to eradicate very small numbers of residual cells improves survival for patients in clinical and morphologic remission. (Riley, et al., "Hematologic Aspects of Myeloablative Therapy and Bone Marrow Transplantation." Journal of Clinical Laboratory Analysis (2005) 19:47-79).

Graft-Versus-Dost Disease (GVHD)

GVHD is a major cause of morbidity and mortality following allogeneic bone marrow transplantation. It occurs in approximately 50% of cases with histocompatible marrow transfusions, and in nearly all cases of bone marrow transplantation with an HLA-mismatched marrow. When moderate to severe, GVHD has a significant mortality rate (40-80%). Although GVHD is a complex immunologic phenomenon that is poorly understood, it is usually a T-cell mediated process occurring in an environment of lymphocyte subset imbalance, alloantigen presentation, and abnormal production or increased responsiveness to cytokines. Both acute and chronic forms of GVHD are recognized.

Acute GVHD (aGVHD) follows lymphocyte reactivity to disparities of "minor" histocompatibility antigens in the skin, gastrointestinal tract, and liver. An increased likelihood of GVHD is associated with HLA disparity between donor and host, the older age of donor and host, allosensitization of the donor, sex mismatch between donor and recipient, increased intensity of the preparative regimen, and donor T cell dose. Clinical symptomatology varies from mild skin rashes, gastrointestinal (GI) disturbances (nausea, vomiting, diarrhea), and impaired liver function tests, to life-threatening disease, with skin destruction, liver failure, bloody diarrhea, and severe immunosuppression. Approximately 5-10% of marrow-transfused patients die of GVHD. (Riley, et al., "Hematologic Aspects of Myeloablative Therapy and Bone Marrow Transplantation." Journal of Clinical Laboratory Analysis (2005)19:47-79).

Chronic GVHD (cGVHD) may follow the acute process or develop de novo. It occurs in 25-65% of bone marrow transplant recipients. The platelet count is a predictor of survival; platelet counts <100,000/mL are associated with an overall mortality of >50%. cGVHD is believed to represent an immunodysregulatory state characterized by autoimmune phenomena, and the clinical picture resembles autoimmune disease, with involvement of the skin, GI tract, and liver. Circulating autoantibodies are present, and deposits of complement and immunoglobulins have been identified at the dermal-epidermal junction. Risk factors for cGVHD include prior aGVHD, older donor or recipient age, HLA mismatch, use of an unrelated donor, viral infection, splenectomy, donor lymphocyte infusion (DLI), and use of peripheral blood stem cells to treat cGVHD. (Riley, et al., "Hematologic Aspects of Myeloablative Therapy and Bone Marrow Transplantation." Journal of Clinical Laboratory Analysis (2005) 19:47-79).

Myelofibrosis

Mild transient reticulin fibrosis is not uncommon after chemotherapy, but severe collagen fibrosis is more typical of chronic myelogenous leukemia. Bone marrow fibrosis is marked by an increase in increased reticulin fiber density, and, in severe cases, an increased number of CD61+ megakaryopoiesis, increased CD68+ macrophages, a decreased number of erythroid precursors, and an elevated platelet count. There is usually an initial regression of myelofibrosis after transplantation, but it often recurs in areas of regenerating hematopoiesis, and is associated with the presence of atypical dwarf megakaryocytes, severe acute GVHD, and a significant delay in the time to achieve transfusion independence. (Riley, et al., "Hematologic Aspects of Myeloablative Therapy and Bone Marrow Transplantation." Journal of Clinical Laboratory Analysis (2005) 19:47-79).

Therapy-Related Acute Leukemia

Therapy-related acute myeloid leukemia (t-AML) is a form of secondary leukemia arising from cytotoxic chemotherapy and/or radiation therapy. The incidence of t-AML following high-dose chemotherapy for a prior malignancy is progressively increasing and t-AMLs are among the most common second malignancies in both pediatric and adult populations. Polymorphism or homozygous gene deletions of glutathione S-transferases P1, M1, and T1 may play a role in the increased incidence of t-AML due to insufficient detoxification of the chemotherapeutic drugs. Patients treated for Hodgkin's lymphoma, non-Hodgkin's lymphoma (NHL), myeloma, polycythemia vera, breast cancer, ovarian carcinoma, testicular carcinoma, or de novo acute lymphoblastic leukemia (ALL) are at the greatest risk of developing t-AML, and more than 50% of patients with secondary AML have breast cancer, NHL, and Hodgkin's lymphoma. In contrast to t-AML, the incidence of therapy-related ALL is rare, with limited indications of the use of previous drugs, such as those used in MBT, as being indicative. (Riley, et al., "Hematologic Aspects of Myeloablative Therapy and Bone Marrow Transplantation." Journal of Clinical Laboratory Analysis (2005) 19:47-79).

Post Transplant Lymphoproliferative Disorders (PTLDs)

PTLDs are lymphoid neoplasms that develop as a consequence of immunosuppressive therapy in patients receiving bone marrow or solid organ transplants. The spectrum of post transplant lymphoproliferative disease ranges from benign to malignant monoclonal or polyclonal lymphoid proliferations, and it occurs in about 2% of solid organ transplant recipients, approximately 1% of autologous bone marrow transplant recipients, and up to 20% of patients with multiple risk factors, including receipt of an HLA-mismatched allogeneic marrow transplant and immunosuppressive therapy for GVHD, such as anti-CD3 monoclonal OKT3, cyclosporine A, and FK506. Epstein-Barr virus, either primary or reactivated, is strongly associated with development of PTLD. Impaired immune surveillance, chronic antigenic stimulation from the allograft, and the oncogenic effects of immunosuppressive therapy are additional factors that lead to PTLDs. In contrast to the typical extranodal involvement of solid organ transplant recipients with PTLD, bone marrow allograft recipients with PTLD often have widespread disease involving both nodal and extranodal sites. (Riley, et al., "Hematologic Aspects of Myeloablative Therapy and Bone Marrow Transplantation." Journal of Clinical Laboratory Analysis (2005) 19:47-79).

Toxic Myelopathy

Toxic myelopathy is a rare bone marrow lesion caused by toxic damage to the stromal and mesenchymal components of the bone marrow. Persistent cytopenia is the clinical hallmark of toxic myelopathy; the bone marrow is hypocellular with prominent stromal damage, including edema, perivascular plasmacytosis, necrobiosis of neutrophilic granulocytes, and cellular debris. Toxic myelopathy occurs <1% of patients receiving chemotherapy or radiotherapy. (Riley, et al., "Hematologic Aspects of Myeloablative Therapy and Bone Marrow Transplantation." Journal of Clinical Laboratory Analysis (2005) 19:47-79).

Many, if not all, of these conditions arise from incomplete removal of the disease/malignant cells through insufficient MBT therapy, improper stem cell rescue, use of immunosuppressives as typically required after MBT, or damage in the bone marrow environment. The prevention of successful SCR and/or associated conditions may be linked to the hematopoiesis system in the patient receiving MBT. It has been hypothesized that chronic inflammation within tissue specific microenvironments impairs the ability of supportive niche cells to appropriately nurture their cognate stem cells thereby preventing SCR and hematopoiesis reconstitution. (Wagers, A. J. The stem cell niche in regenerative medicine. Cell stem cell (2012)10, 362-369, doi:10.1016/j.stem.2012.02.018; Lane, S. W., Williams, D. A. & Watt, F. M. Modulating the stem cell niche for tissue regeneration. Nature biotechnology (2014) 32, 795-803, doi:10.1038/nbt.2978; Schepers, K., Campbell, T. B. & Passegue, E. Normal and leukemic stem cell niches: insights and therapeutic opportunities. Cell stem cell (2015) 16, 254-267, doi:10.1016/j.stem.2015.02.014911).

Recovery from Myelosuppression.

Immune reconstitution follows a general pattern developing from immature to mature immune functions. (Carson K. et al., Chapter 35—Reimmunization after stem cell transplantation," in Hematopoietic Stem Cell Transplantation in Clinical Practice (2009); (Butler, J. M. et al. Endothelial cells are essential for the self-renewal and repopulation of Notch, dependent hematopoietic stem cells. Cell stem cell (2010) 6, 251-264, doi:10.1016/j.stem.2010.02.001; Kobayashi, H. et al. Angiocrine factors from Akt-activated endothelial cells balance self-renewal and differentiation of haematopoietic stem cells. Nature cell biology (2010) 12, 1046-1056, doi:10.1038/ncb2108; Winkler, I. G. et al. Vascular niche E-selectin regulates hematopoietic stem cell dormancy, self renewal and chemoresistance. Nature medicine (2012) 18, 1651-1657, doi:10.1038/nm.2969; Ding, L., et al., Endothelial and perivascular cells maintain haematopoietic stem cells. Nature (2012) 481, 457-462, doi: 10.1038/nature10783; Poulos, M. G. et al. Endothelial jagged-1 is necessary for homeostatic and regenerative 947 hematopoiesis. Cell reports (2013) 4, 1022-1034, doi: 10.1016/j.celrep.2013.07.048; Greenbaum, A. et al. CXCL12 in early mesenchymal progenitors is required for haematopoietic stem-cell maintenance. Nature (2013) 495, 227-230, doi:10.1038/nature11926; Doan, P. L. et al. Epidermal growth factor regulates hematopoietic regeneration after radiation injury. Nature medicine (2013) 19, 295-304, doi:10.1038/nm.3070) Immune reactivity during the first month post graft is extremely low. Id. Innate immunity is the first to regain function. Ogonek, J. et al., "Immune reconstitution after allogeneic hematopoietic stem cell transplantation" Front. Immunol. (2016) 7: 507. doi: 10.3389/fimmu.2016.00507). The reappearance of hematopoietic lineages follows a reproducible order, with monocytoid cells emerging first in the peripheral blood, followed by granulocytes and then NK cells. The recovery of NK cells significantly precedes T cells and B cells, with respect to both cell number and functional maturation (Grzywacz, B. et al, Natural Killer Cell differentiation by myeloid progenitors, Blood (2011) 117 (13): 3548-58). Cytotoxic and phagocytic functions recover by day 100, but the more specialized functions of T- and B-lymphocytes may remain impaired for a year or even longer. After a period of time, the various components of the immune systems of most healthy marrow recipients begin to work synchronously, whereas the immune systems of patients with chronic graft-versus-host disease (GvHD) remain suppressed. Delayed and incomplete immune reconstitution renders the patient susceptible to infections which are associated with high morbidity and mortality after allo-HCT.

It has long been known that hematopoietic regeneration and revascularization of the bone marrow cavity after radiation exposure are temporallyrelated, and that there is no hematopoietic regeneration without vascular reconstitution of the bone marrow. It is now recognized that hematopoietic regeneration after myelosuppression with cytotoxic agents or whole-body irradiation is interdependent on the bone marrow sinusoidal network and hematopoietic cells as well as on megakaryocyte maturation.(Kopp, et. al. "The Bone Marrow Vascular Niche: Home of HSC Differentiation and Mobilization." PHYSIOLOGY 20: 349-356, 2005; 10.1152/physiol.00025.2005).

Myelosuppression leads not only to apoptosis of cycling hematopoietic cells, but also to the destruction of the bone marrow vasculature. Because the intricate network of sinusoids lack a regular vessel wall, they are especially affected by ionizing radiation and they display ultrastructural signs of necrosis, marked dilation, and overt breakdown with plasma and blood cell leakage. Bone marrow sinusoids seem to be supported by their neighboring hematopoietic cells themselves; losing this support means losing stability, leading to hemorrhage within the bone marrow cavity after radiation or myelosuppressive chemotherapy. In the process of hematopoietic regeneration, the sinusoids are reconstructed. The processes hematopoiesis and angiogenesis thereforeare closely linked. (Kopp, et. al. "The Bone Marrow Vascular Niche: Home of HSC Differentiation and Mobilization." PHYSIOLOGY 20: 349-356, 2005; 10.1152/physiol.00025.2005).

The vasculature provides a protective niche for HSCs following chemotherapy, promoting bone and haematopoietic regeneration. Long-term, quiescent HSCs are associated with both sinusoids and arteries. The vascular niche is essential to regenerate the HSC population after irradiation. Transplantation of bone marrow ECs following irradiation enhances haematopoiesis and protects radiosensitive tissue. Irradiated mice transplanted with bone marrow EC culture conditioned media showed increased survival, indicating that angiocrine factors can enhance survival but not compensate for a complete loss of HSCs. Endothelial-specific deletion of the Notch ligand JAG-1 leads to an impairment in HSC regeneration and increase lethality following irradiation. In addition to Notch signalling, ECs upregulate Fgf-2, Bmp4, Igfbp2 and Angiopoetin-1 to expand the haemopoietic stem progenitor cells (HSPCs), indicating these angiocrine factors may be useful to protect HSC following irradiation. (Sivan U, De Angelis J, Kusumbe A P. 2019 Role of angiocrine signals in bone development, homeostasis and disease. Open Biol. 9: 190144).

The described invention provides a method of treating a subject exposed to a myeloablative insult comprising administering to the subject a pharmaceutical composition comprising a therapeutic amount of an angiocrine factor. The method is effective to preserve vascular integrity, to increase bone marrow cellularity; to enhance long term engraftment potential; to effect multi-lineage reconstitution; to inhibit vascular inflammation, and to preserve HSC function.

SUMMARY OF THE INVENTION

According to one aspect, the described invention provides a method for reducing vascular inflammation within a hematopoietic bone marrow microenvironment comprising bone marrow endothelial cells (BMECs), hematopoietic stem cells (HSCs) and bone marrow stromal cells following a myelosuppressive insult, wherein reduced BMEC activity leads to defects in steady state hematopoiesis and HSC function comprising: administering to the subject a pharmaceutical composition comprising a recombinant or synthetic angiocrine factor and a pharmaceutically acceptable carrier, and enhancing hematopoietic recovery in the hematopoietic bone marrow microenvironment following the myelosuppressive insult by one or more of: reducing inflammation in the hematopoietic microenvironment of the bone marrow; preserving vascular integrity in the hematopoietic microenvironment of the bone marrow; increasing frequency and numbers of cell types in the hematopoietic compartment comprising one or more of hematopoietic stem cells (HSC), hematopoietic stem and progenitor cells (HSPCs), multipotent progenitor cells (MPPs), and hematopoietic progenitor cell subsets to effect multi-lineage reconstitution, wherein the vascular inflammation comprises one or more of increased vascular dilatation, decreased vascular integrity comprising increased bone marrow vascular leakiness, and increased levels of inflammatory mediators.

According to one embodiment of the method, the angiocrine factor is one or more recombinant or synthetic protein selected from the group consisting of Clec11a, Hapln1, Hspd1, Igfbp1, Bgn, Wnt7a, Sparc, RP53, Bmpr1a, Ighm, Thbs4, Camk2d, Sirt2, Camk2b, Slitrk5, Dctpp1, Hnrnpa2b, Erap1. According to another embodiment, the angiocrine factor is a recombinant or synthetic Clec11α (stem cell growth factor). According to another embodiment, the inflammation in the hematopoietic microenvironment of the bone marrow comprises vascular inflammation, inflammation of BM stromal cells, and inflammation of hematopoietic cells. According to another embodiment, the defects in HSC function include impaired HSC quiescence and increased HSC apoptosis. According to another embodiment, reducing vascular inflammation includes suppressing downstream NFkB signaling in the BMECs within the bone marrow; downregulating target NFkB genes in endothelial cells in the bone marrow or both. According to another embodiment, the myelosuppressive insult comprises exposure to radiation, chemotherapy or both. According to another embodiment, the radiation is sublethal radiation, total body irradiation, total lymphoid irradiation. According to another embodiment, the myelosuppressive insult comprises chemotherapy. According to another embodiment, the myelosuppressive insult is myeloablative. According to another embodiment, the bone marrow (BM) microenvironement comprises BMECs, BM stromal cells, BM Lepr+ cells, and BM osteoblasts. According to another embodiment, the BMECs are sinusoidal and arteriole BMECs. According to another embodiment, the immunophenotype of BMECs is CD45−Ter119−CD31+VEcadherin+. According to another embodiment, the immunophenotype of BM stromal cells is CD45−Ter119−CD31−VEcadherin−. According to another embodiment, the immunophenotype of BM Lepr+ cells within the BM stromal population is CD45-Ter119−CD31−Lepr+. According to another embodiment, the immunophenotype of murine HSCs comprises lin-Ter119−CD11b−GR1−B220−CD3−CD41−ckit+SCA1+CD48-CD150+. According to another embodiment, the immunophenotype of human HSCs comprises CD45RA−CD38−CD34+CD90+. According to another embodiment, reduced BMEC activity after the myeloablative insult leads to defects in steady state hematopoieisis and HSC function.

According to another aspect, the described invention provides a method for improving hematopoietic homing, engraftment, reconstitution and regeneration of bone marrow after a myelosuppressive insult in a subject in need thereof comprising administering to the subject a pharmaceutical composition comprising a recombinant or synthetic angiocrine factor and a pharmaceutically acceptable carrier; and; administering a stem cell co-therapy comprising transplantation of a therapeutic amount of multipotent, self-renewing hematopoietic stem cells (HSCs) effective to regenerate the blood system and promote hematopoietic reconstitution of the bone marrow, and; administering a vascular endothelial co-therapy comprising transplantation of a therapeutic amount of BM endothelial cells (BMECs) effective to regenerate the blood system and promote hematopoietic reconstitution of the bone marrow, and; reducing vascular inflammation within a hematopoietic bone marrow microenvironment comprising bone marrow endothelial cells (BMECs), hematopoietic stem cells (HSCs) and bone marrow stromal cells following the myelosuppressive insult, wherein reduced BMEC activity leads to defects in steady state hematopoiesis and HSC function, and enhancing hematopoietic recovery in the hematopoietic bone marrow microenvironment following the myelosuppressive insult by one or more of: reducing inflammation in the hematopoietic microenvironment of the bone marrow; preserving vascular integrity in the hematopoietic microenvironment of the bone marrow; increasing frequency and numbers of cell types in the hematopoietic compartment comprising one or more of hematopoietic stem cells (HSC), hematopoietic stem and progenitor cells (HSPCs), multipotent progenitor cells (MPPs), and hematopoietic progenitor cell subsets to effect multi-lineage reconstitution, wherein the vascular inflammation comprises one or more of increased vascular dilatation, decreased vascular integrity comprising increased bone marrow vascular leakiness, and increased levels of inflammatory mediators.

According to one embodiment of the method, the angiocrine factor is one or more recombinant or synthetic protein selected from the group consisting of Clec11a, Hapln1, Hspd1, Igfbp1, Bgn, Wnt7a, Sparc, RP53, Bmpr1a, Ighm, Thbs4, Camk2d, Sirt2, Camk2b, Slitrk5, Dctpp1, Hnrnpa2b, Erap1. According to another embodiment, the angiocrine factor is a recombinant or synthetic Clec11α (stem cell growth factor). According to another embodiment, the defects in HSC function include impaired HSC quiescence and increased HSC apoptosis.

According to another embodiment, the stem cell co-therapy comprises: isolating hematopoietic stem cells from a population of mononuclear cells isolated from a tissue source, enriching the isolated population of mononuclear cells for hematopoietic stem cells by positive or negative selection, and administering the enriched isolated population of hematopoietic stem cells to the subject.

According to another embodiment, the vascular endothelial cell co-therapy comprises isolating endothelial cells from human umbilical cord, enriching the isolated population for vascular endothelial cells by positive or negative selection, and administering the enriched isolated population of vascular endothelial cells to the subject.

According to another embodiment, the tissue source is autologous. According to another embodiment, the tissue source is allogeneic. According to another embodiment, reducing vascular inflammation includes suppressing downstream NFkB signaling in the BMECs within the bone marrow; downregulating target NFkB genes in endothelial cells in the bone marrow or both. According to another embodiment, the myelosuppressive insult comprises exposure to radiation, chemotherapy or both. According to another embodiment, the radiation is sublethal radiation, total body irradiation, total lymphoid irradiation. According to another embodiment, the myelosuppressive insult is chemotherapy. According to another embodiment, the myelosuppressive insult is myeloablative. According to another embodiment, the bone marrow (BM) microenvironment comprises BMECs, BM stromal cells, BM Lepr+ cells, and BM osteoblasts. According to another embodiment, the BMECs are sinusoidal and arteriole BMECs. According to another embodiment, the immunophenotype of BMECs is CD45−Ter119−CD31+VEcadherin+. According to another embodiment, the immunophenotype of BM stromal cells is CD45−Ter119−CD31−VEcadherin−.

According to another embodiment, the immunophenotype of BM Lepr+ cells within the BM stromal population is CD45−Ter119−CD31−Lepr+. According to another embodiment, the immunophenotype of murine HSCs comprises lin−Ter119−CD11b−GR1−B220−CD3−CD41−ckit+SCA1+ CD48−CD150+. According to another embodiment, the immunophenotype of human HSCs comprises CD45RA−CD38−CD34+CD90+. According to another embodiment, the method enhances long term stable engraftment of the bone marrow, reduced myeloid bias in the peripheral blood or both. According to another embodiment, the pharmaceutical composition is administered before, after, or contemporaneously with the administration of the stem cell co-therapy. According to another embodiment, the inflammation in the hematopoietic microenvironment of the bone marrow comprises vascular inflammation, inflammation of BM stromal cells, and inflammation of hematopoietic cells.

BRIEF DESCRIPTION OF THE DRAWINGS

FIG. 1A, FIG. 1B, FIG. 1C, FIG. 1D, FIG. 1E, FIG. 1F, FIG. 1G, FIG. 1H, FIG. 1I, FIG. 1K shows that CDH5-MAPK mice manifest HSC and hematopoietic defects. FIG. 1A: Total cells per femur (n=5 mice/cohort). FIG. 1B: Frequency of phenotypic HSCs per $10^6$ femur cells assessed by flow cytometry (n=5 mice/cohort). FIG. 1C: Representative contour plots demonstrating gating strategy for quantification of BM HSC and HSPC frequency by Flow cytometry. FIG. 1D: Frequency of phenotypic HSPCs per 106 femur cells assessed by flow cytometry (n=5 mice/cohort). FIG. 1E: Methylcellulose-based progenitor assay. Bar graphs indicate number of CFUs per 105 whole bone marrow (WBM) (n=3 mice/cohort). FIG. 1F and FIG. 1G show competitive repopulation assays assessing total CD45.2+ cell engraftment and CD45.2+ lineage distribution over 4 months (n=10 recipients/cohort; n=5 donors/cohort). For evaluating competitive repopulation, $5\times10^5$ donor WBM cells (CD45.2) were transplanted with $5\times10^5$ competitor WBM cells (CD45.1) into pre-conditioned CD45.1 recipient mice. FIG. 1H: is a table representing the number of recipients that were positive for long term, multi¬=lineage reconstitution (LTMR) following whole bone marrow limiting dilution transplantation assay (n=10 recipients/cohort per cell dose; n=5 donors/cohort). FIG. 1I: is a line graph displaying estimates of HSC frequency in the indicated genotypes with dashed lines representing 95% confidence intervals. Stem cell frequency and significance were determined using Extreme Limiting Dilution Analysis (ELDA). FIG. 1J shows cell cycle analysis of HSCs in the indicated genotypes by flow cytometry (n=5 mice/cohort). FIG. 1K shows quantification of HSC apoptosis in the indicated genotypes by flow cytometry (n=5 mice/cohort). Error bars represent sample mean±SEM. Statistical significance was determined using two-tailed unpaired Student's t-test, wherein * P<0.05;  P<0.01; and * P<0.001.

FIG. 2A shows representative immunofluorescence images of femurs intravitally-labeled with a vascular-specific CD144/VEcadherin antibody (red) demonstrating vascular dilatation in CDH5-MAPK mice. FIG. 2B shows quantification of Evan's Blue Dye (EBD) extravasation (n=5 mice/cohort). FIG. 2C shows representative images of femurs isolated from mice injected with EBD. FIG. 2D) depicts a microtiter plate demonstrating intensity of extracted EBD for each sample. Non-injected controls were used to determine baselines. FIG. 2E) is a heat map of 242 differentially expressed proteins in plasma of CDH5-MAPK mice identified by proteomic analysis (n=7 control and n=8 CDH5,MAPK mice). FIG. 2F) shows Ingenuity Pathway Analysis of differentially expressed proteins demonstrating that inflammatory responses are over-represented in CDH5-MAPK mice. FIG. 2G and FIG. 2H show an immunoblot analysis of bone marrow endothelial cells (BMECs) isolated from CDH5-MAPK mice and quantification, respectively, demonstrating that MEK1DD expression in BMECs results in an increase in ERK1/2 and p65 phosphorylation (n=3 biological replicates per genotype). FIG. 2I and FIG. 2J show representative immunofluorescence images and quantification demonstrating increased levels of nuclear p65 in BMECs derived from CDH5-MAPK mice as compared to controls. Control BMECstreated with TNFα (10 ng/mL for 15 minutes) were used as a positive control for the assay. Each dot within the bar graph represents nuclear p65 staining intensity per individual cell. Error bars represent sample mean±SEM. Statistical significance was determined using two-tailed unpaired Student's t-test. * P<0.05;  P<0.01; * P<0.001.

FIG. 3A and FIG. 3B) show ilmmunoblot analysis and quantification, respectively, demonstrating that expression of IkB-SS in BMECs isolated from CDH5-MAPK mice does not affect ERK1/2 or p65 phosphorylation. Black arrowhead represents endogenous IκBa whereas red arrowhead represents IkB¬SS transgene. FIG. 3C and FIG. 3D) show representative immunofluorescence images and quantification, respectively, demonstrating increased levels of nuclear p65 in BMECs derived from CDH5-MAPK mice as compared to controls. Note that expression of IkB-SS in BMECs isolated from CDH5-MAPK mice (CDH5-MAPK::IkB) decreases nuclear p65 levels. Each dot within the bar graph represents nuclear p65 staining intensity per individual cell. FIG. 3E and FIG. 3F) show a heatmap (FIG. 3E) and bar graph (FIG. 3F) demonstrating increased expression of NF-κB dependent inflammatory genes within BMECs of CDH5-MAPK mice. Crossing CDH5-MAPK with Tie2.IkB-SS mice (CDH5-MAPK::IkB) resulted in decreased expression of NF-κB dependent target genes. Expression of housekeeping gene Actb was used for normalization. Dendrograms represent unsupervised hierarchical clustering of the entire dataset. (n=3 mice/cohort). FIG. 3G) shows representative immunofluorescence images of femurs intravitally-labeled with a vascular-specific CD144/VEcadherin antibody (red) demonstrating that suppression of NF-κB signaling within endothelial cells of CDH5-MAPK mice resolves their vascular dilatation. Error bars represent sample mean±SEM. One-way ANOVA for multiple comparisons and Tukey's correction was performed to determine significance. * P<0.05;  P<0.01; 1233 * P<0.001.

FIG. 4A, FIG. 4B, FIG. 4C, FIG. 4D, FIG. 4E, FIG. 4F, FIG. 4G, FIG. 4H FIG. 4J show that Endothelial NF-κB inhibition restores HSC activity in CDH5-MAPK mice. FIG. 4A) shows total cells per femur (n=7-10 mice/cohort). FIG. 4B) shows Frequency of phenotypic HSCs per $10^6$ femur cells assessed by flow cytometry (n=7-10 mice/cohort). FIG. 4C) shows results of a methylcellulose-based progenitor assay. Bar graphs indicate number of CFUs per $10^5$ WBM (n=4 mice/cohort). FIG. 4D and FIG. 4E) show results of competitive repopulation assays assessing total CD45.2+ cell engraftment and CD45.2+ lineage distribution 4 months post-transplantation. For evaluating competitive repopulation, $5\times10^5$ donor WBM cells (CD45.2) were transplanted with $5\times10^5$ competitor WBM cells (CD45.1) into pre-conditioned CD45.1 recipient mice. (n=9-10 recipients/cohort; n=5 donors per cohort). FIG. 4F) is a table representing the number of recipients that were positive for long term, multi-lineage reconstitution (LTMR) following whole bone marrow limiting dilution transplantation assay (n=10 recipients/cohort per cell dose, n=5 donors per cohort). FIG. 4G) is a Log fraction plot of limiting dilution analysis, which indicates that CDH5-MAPK::IkB mice display an increase in frequency of HSCs capable of LTMR as compared to CDH5-MAPK mice. Dashed lines indicated 95% confidence intervals. Stem cell frequency and significance were determined using Extreme Limiting Dilution Analysis (ELDA). FIG. 4H and FIG. 4I) show representative whole mount immunofluorescence images of femurs and quantification of HSC distance from blood vessels of mice intravitally-labeled with a vascular-specific CD144/VEcadherin antibody (red) demonstrating that endothelial MAPK activation disrupts interactions of HSCs (white) with the vascular niche that are restored in CDH5-MAPK::IkB mice. CD48+ and Lineage+ cells (blue channel) are not shown for better visualization of HSC interactions with the vasculature. Yellow arrowhead denotes a typical HSC (defined as LineagenegCD48negCD150bright) located in close proximity to a sinusoidal vessel. Yellow asterisk denotes a megakaryocyte. Each dot within the bar graph represents the distance of an individual HSC from its nearest blood vessel (n=3 mice/cohort). FIG. 4J) shows the time-course of peripheral blood recovery following irradiation (650 Rads) (n=6-10 mice/cohort). The colors of significance asterisks represent comparisons of the indicated genotypes with CDH5-MAPK mice. Results demonstrate a myeloprotective effect in CDH5-MAPK::IkB mice, indistinguishable from Tie2.IkB-SS mice. Error bars represent sample mean±SEM. One-way ANOVA for multiple comparisons and Tukey's correction was performed to determine significance. * P<0.05;  P<0.01; * P<0.001. 1

FIG. 5A and FIG. 5B) show total cells per femur of the indicated hematopoietic progenitors estimated by Flow cytometry (n=4-5 mice/cohort). FIG. 5C) shows lineage composition of CD45+ cells within BM, (n=4-5 mice/cohort). FIG. 5D) shows steady state peripheral blood counts (n=4-6 mice/cohort). FIG. 5E) shows lineage composition of CD45+ cells within peripheral blood (n=5 mice/cohort) FIG. 5F) shows HSPC frequency in peripheral blood (n=5 mice/cohort). FIG. 5G) shows gross images of spleen from the indicated genotypes. FIG. 5H) shows spleen cellularity in the indicated genotypes (n=4-5 mice/cohort). FIG. 5I, FIG. 5K) show total cells per spleen of the indicated hematopoietic progenitors (n=4-5 mice/cohort). FIG. 5L) shows lineage composition of CD45+ cells within spleen (n=4-5 mice/cohort). Note that crossing CDH5-MAPK with Tie2.IkB-SS mice (CDH5-MAPK::IkB) restores the hematopoietic and HSPC attributes of CDH5-MAPK mice to control levels. Error bars represent sample mean±SEM. One-way ANOVA for multiple comparisons and Tukey's correction was performed to determine significance. * P<0.05;  P<0.01; * P<0.001. 1

FIG. 6A) is a schematic describing breeding strategy for generation of CDH5-MAPK mice. FIG. 6B) is a schematic describing Tamoxifen regimen before experimental analysis. Representative flow cytometry contour plots demonstrating GFP expression in whole bone marrow cells of CDH5-MAPK mice. Numbers indicate average frequency of cells in the indicated quadrants as percentage of total BM cells±SEM (n=4-5 mice/cohort). Note that GFP expression is detected exclusively in cells within the CD45− fraction of whole bone marrow cells and demonstrate surface expression of endothelial markers. FIG. 6C) shows that analysis of phospho-ERK1/2 expression by flow cytometry confirms in vivo activation of MAPK pathway in BMECs of CDH5-MAPK mice following Tamoxifen administration (n=3 mice/cohort). FIG. 6D) shows that GFP+ BMECs as compared to GFP-BMECs within CDH5-MAPK mice demonstrate increased phospho-ERK1/2 expression by flow cytometry, confirming the fidelity of GFP reporter for tracking cre-mediated recombination in vivo. (n=3 mice/cohort). FIG. 6E) shows that endothelial cells within the BM of CDH5,MAPK mice (defined as CD45−Ter119−CD31+VEcadherin+) demonstrate cre-mediated recombination, whereas stromal cells (defined as CD45−Ter119−CD31−VEcadherin−) do not (n=4 mice/cohort). FIG. 6F) is a schematic describing the Tie2.IkB-SS mouse model. FIG. 6G) shows an Agarose gel electrophoresis image of RT-PCR amplicons for the indicated genes using RNA isolated from FACS sorted endothelial cells and CD45+ hematopoietic cells in the indicated genotypes (n=3 mice/cohort). Note that IkB-SS transgene is expressed in endothelial cells and shows no detectable expression in hematopoietic cells. Also note the expression of cre transgene in endothelial cells of CDH5-MAPK mice and no detectable expression in hematopoietic cells. NTC denotes 'No Template Control'. Sort purity was confirmed using expression of Cdh5 (for endothelial cells) and Ptprc (for hematopoietic cells).

FIG. 7A) shows estimation of oxygenation status in BM HSPCs based on quantification of Hypoxyprobe by Flow cytometry (n=5 mice/cohort). FIG. 7B) shows quantification of ROS levels in HSPCs by Flow cytometry based quantification of CellROX orange (n=5 mice/cohort). Note that CDH5-MAPK HSPCs display increased hypoxia and ROS levels that are resolved by crossing with Tie2.IkB-SS mice. FIG. 7C) shows cell cycle analysis of HSPCs based on Ki67-Hoechst staining by Flow cytometry (n=5 mice/cohort). FIG. 7D) shows quantification of apoptosis in HSPCs by quantification of percentage of cells in Sub-G0/G1 phase by Flow cytometry (n=5 mice/cohort). HSPCs from CDH5-MAPK mice display a loss of quiescence and increased apoptosis that is resolved upon suppression of their endothelial NF-κB signaling. FIG. 7E, FIG. 7F, FIG. 7G, FIG. 7H) show quantification of Hypoxia, ROS levels, quiescence and apoptosis, respectively, in the indicated BM niche cells by Flow cytometry (n=4-5 mice/cohort). FIG. 7I and FIG. 7K) show estimation of BMECs and stromal cells per femur by Flow cytometry (n=4-5 mice/cohort). FIG. 7J and FIG. 7L) show expression of pro-HSC paracrine factors in FACS sorted BM niche cells by RT-qPCR (n=3 mice/cohort). Actb was used for normalization. FIG. 7M) shows identification of commonly upregulated NF-κB target genes from qPCR-array data in BM stromal cells, hematopoietic cells and ECs of CDH5-MAPK mice using Venny. FIG. 7N, FIG. 7O, FIG. 7P, FIG. 7Q) show RT-qPCR confirmation of I11b and Csf1 expression in the indicated cell types (n=3 mice/cohort). Actb was used for normalization. Notice that inhibition of endothelial NF-κB signaling significantly suppresses the expression of I11b and Csf1 within the whole bone marrow of CDH5-MAPK mice. Error bars represent sample mean±SEM. One-way ANOVA for multiple comparisons and Tukey's correction was performed to determine significance. * P<0.05;  P<0.01; * P<0.001.

FIG. 8A) shows frequency of phenotypic HSCs per $10^6$ WBM (n=9-10 mice/cohort). FIG. 8B) shows representative contour plots demonstrating that SCGF infusion restores phenotypic HSC defects observed in CDH5-MAPK mice. FIG. 8C) shows results of a methylcellulose-based progenitor assay (n=5 mice/cohort). FIG. 8D and FIG. 8E) show results of a competitive repopulation assay assessing total CD45.2+ cell engraftment and CD45.2+ lineage distribution 4 months post-transplantation (n=5 recipients/cohort; n=5 donors per cohort). For competitive repopulation assays, $5\times10^5$ donor WBM cells (CD45.2) were transplanted along with $5\times10^5$ competitor WBM cells (CD45.1) into pre-conditioned CD45.1 recipient mice. Note that donor cells derived from SCGF treated CDH5-MAPK mice displayed a significant increase in engraftment efficiency with the resolution of the myeloid bias and increase in lymphoid output. Also, note that SCGF does not significantly impact the hematopoietic function or phenotype of control mice. FIG. 8F and FIG. 8G) show a secondary transplantation assay wherein WBM cells from long-term engrafted primary recipients were isolated and transplanted into pre-conditioned CD45.1 recipient mice ($2\times10^6$ donor WBM cells per recipient). (n=5 recipients/cohort; n=5 donors per cohort). FIG. 8H) shows analysis of BM vascular leakiness by Evan's Blue Dye (EBD) extravasation reveals that SCGF infusion significantly reduces vascular leakiness of CDH5-MAPK mice (n=3-5 mice/cohort). FIG. 8I) shows representative immunofluorescence images of femurs intravitally-labeled with a vascular-specific VECAD antibody (red) demonstrating reversal of vascular dilatation in CDH5-MAPK mice treated with SCGF. FIG. 8J) shows normalized gene expression of NF-κB target genes within the BM microenvironment of indicated genotypes as compared to PBS treated control mice. B2m was used for normalization (n=3 mice/cohort). FIG. 8K and FIG. 8L) show representative immunofluorescence images and quantification demonstrating decreased levels of nuclear p65 in BMECs derived from CDH5-MAPK mice treated with SCGF. Error bars represent sample mean±SEM. Statistical significance was determined using two-tailed unpaired Student's t-test for pairwise comparison and One-way ANOVA for multiple comparisons. * P<0.05;  P<0.01; * P<0.001.

FIG. 9A and FIG. 9B) show results following 650 Rads of irradiation, 2 g of SCGF was infused on alternate days into control and CDH5,MAPK mice for a total of 7 injections starting at Day +1 and hematopoietic recovery was assessed for 28. SCGF infusion promoted a significant increase in white blood cell, neutrophil, red blood cell, and platelet recovery at indicated time points in a) control mice (n=6-7 mice/cohort) as well as b) CDH5,MAPK mice (n=7-8 mice/cohort). FIG. 9C and FIG. 9D) show representative immunofluorescence images of femurs intravitally-labeled with a vascular-specific CD144/VEcadherin antibody (red) at 28 days following irradiation demonstrating that SCGF infusion improved vascular recovery in both c) control mice as well as d) CDH5-MAPK mice. FIG. 9E) shows total cells per femur (n=4-7 mice/cohort). FIG. 9F) shows frequency of phenotypic HSCs per $10^6$ femur cells assessed by flow cytometry (n=4-7 mice/cohort). FIG. 9G and FIG. 9H) show competitive repopulation assays assessing total CD45.2+ cell engraftment and CD45.2+ lineage distribution of donor WBM cells. Donor cells were isolated 28 days post-irradiation from PBS/SCGF treated control and CDH5-MAPK mice. $2.5\times10^6$ donor WBM cells (CD45.2) were transplanted with $5\times10^5$ competitor WBM cells (CD45.1) into pre-conditioned CD45.1 recipient mice. (n=9-10 recipients/cohort; n=5 donors per cohort). FIG. 9I and FIG. 9J) show results of a secondary transplantation assay wherein WBM cells from long-term engrafted primary recipients were isolated and transplanted into pre-conditioned CD45.1 recipient mice. $2\times10^6$ donor WBM cells were transplanted per secondary recipient. (n=4-5 recipients/cohort; n=5 donors per cohort). Error bars represent sample mean±SEM. Statistical significance was determined using two-tailed unpaired Student's t-test. * P<0.05;  P<0.01; * P<0.001.

FIG. 12A, FIG. 12, FIG. 12C. FIG. 12A. In steady state, platelet-biased HSCs are at the top of the hematopoietic hierarchy and are able to generate myeloid-biased and lymphoid-biased HSCs. In turn, myeloid-biased HSCs can generate both balanced- and lymphoid-biased HSCs, whereas lymphoid-biased HSCs do not generate their myeloid-biased counterparts. Platelet-biased HSCs have the potential to repopulate platelet populations faster than other HSC subsets. Myeloid-biased HSCs preferentially give rise to myeloid lineage cells through myeloid committed progenitors. Balanced HSCs make equal contributions to both myeloid and lymphoid lineages. Lymphoid-biased HSCs predominantly generate lymphoid over myeloid lineage cells through lymphoid-committed progenitors. Dashed lines represent the potential of one HSC subset to generate another HSC subset. Solid lines represent differentiation potential. FIG. 12C. During the processes of aging, myeloid-biased HSCs increase and produce more myeloid than lymphoid cells. Red arrows indicate the dominant differentiation pathway. Dashed lines represent a potential pathway. Solid lines represent the differentiation potential shown previously. The thickness of the lines reflects the relative contributions to each lineage commitment. (Taken from Kovtonyuk, L. V., Fritsch, K., Feng, X., Manz, M. G. & Takizawa, H. Inflamm-Aging of Hematopoiesis, Hematopoietic Stem Cells, and the Bone Marrow Microenvironment. Frontiers in immunology 7, 502, doi:10.3389/fimmu.2016.00502 (2016)).

SUPP. FIG. 1A, SUPP. FIG. 1B, SUPP. FIG. 1C, SUPP. FIG. 1D, SUPP. FIG. 1E, SUPP. FIG. 1F show that CDH5, MAPK mice displayed a significant decline in the frequency and absolute numbers of immunophenotypically defined HSCs (defined as cKIT+LineageNeg CD41−SCA1+ CD150+CD48Neg), as well as hematopoietic stem and progenitor cells (HSPCs) including KLS cells (cKIT+LineageNeg SCA1+), multipotent progenitors (MPPs; cKIT+ LineageNeg SCA1+CD150 NegCD48Neg) and hematopoietic progenitor cell subsets (HPC-1 and HPC-2 defined as cKIT+LineageNeg SCA1+CD150 NegCD48+ and cKIT+ LineageNeg SCA1+CD150+CD48+, respectively), as compared to their littermate controls (SUPP. FIG. 1A).Cell cycle analysis demonstrated that HSCs and HSPCs from CDH5-MAPK mice displayed a loss of quiescence and increased apoptosis as compared to their littermate controls (SUPPL. FIG. 1B, SUPP. FIG. 1C, SUPP FIG. 1D, SUPP. FIG. 1E, SUPP FIG. 1F). Taken together, these data suggest that chronic activation of endothelial MAPK adversely impacts niche activity leading to defects in steady state hematopoiesis and HSC function.

SUPP. FIG. 2A, SUPP. FIG. 2B, SUPP. FIG. 2C, SUPP. FIG. 2D, SUPP. FIG. 2E, SUPP. FIG. 2F. Hematopoietic analysis of CDH5-MAPK::IkB mice demonstrated a restoration of BM cellularity and frequency of phenotypic HSCs and HSPCs (SUPP. FIG. 2A). HSC functionality assayed by competitive BM transplantations demonstrated a complete recovery of long-term engraftment potential and a reversal of myeloid-biased differentiation in CDH5-MAPK::IkB mice (SUPP. FIG. 2B). WBM cells derived from CDH5-MAPK::IkB mice were also able to maintain their serial repopulation 180 and multi-lineage reconstitution abilities during secondary transplantation assays (SUPP. FIG. 2C and SUPP. FIG. 2D). CDH5-MAPK mice displayed a decline in immunophenotypically defined BM multipotent progenitors (MPPs), common lymphoid progenitors (CLPs), common myeloid progenitors (CMPs), granulocyte/macrophage progenitors (GMPs), megakaryocyte/erythroid progenitors (MEPs), and B cell progenitor subsets (sIgM-B220+ B cells, Pre-Pro B cells, Pro B cells and Pre B cells) which was functionally reflected in their decreased peripheral blood counts.(SUPP. FIG. 2E and SUPP. FIG. 2F).

SUPP. FIG. 3A, SUPP. FIG. 3B, SUPP. FIG. 3C, SUPP. FIG. 3D, SUPP. FIG. 3E, SUPP. FIG. 3F. SUPP. FIG. 3. RT¬qPCR analysis revealed an overall upregulation of NF-kB target genes in hematopoietic cells (CD45+), stromal cells (CD45−Ter119−CD31−VEcadherin−) as well as in unfractionated whole bone marrow (WBM) cells of CDH5-MAPK mice (SUPP. FIG. 3A, SUPP. FIG. 3B, SUPP. FIG. 3C, SUPP. FIG. 3D, SUPP. FIG. 3E, SUPP. FIG. 3F), demonstrating that endothelial MAPK activation drives a generalized inflammatory response within the BM.

SUPP. FIG. 4A, SUPP. FIG. 4B. The fidelity of transgene expression in CDH5-MAPK mice was verified by using the endogenous Rosa26:eGFP reporter system to track cre mediated 248 recombination. GFP expression was strictly confined to endothelial cells within the bone marrow with no detectable expression in any of the hematopoietic subsets analyzed including HSCs as well as myeloid cells, B cells and T cells (SUPP. FIG. 4A and SUPP. FIG. 4B).

SUPP. FIG. 5A, SUPP. FIG. 5B. shows that HSPCs of CDH5-MAPK mice demonstrated a significant increase in hypoxia and ROS levels along with a loss of quiescence and increased apoptosis (SUPP. FIG. 5A and SUPP. FIG. 5B).

SUPP. FIG. 6A, SUPP. FIG. 6B, SUPP. FIG. 6C, SUPP. FIG. 6D, SUPP. FIG. 6E, SUPP. FIG. 6F, SUPP. FIG. 6G, SUPP. 6H, SUPP. FIG. 6I. Flow cytometry analysis of BM Lepr+ cells and osteoblasts did not reveal significant changes in their cellularity or in their expression of HSC-regulatory factors in CDH5-MAPK mice (SUPP. FIGS. 6A, SUPP. FIG. 6E, SUPP. FIG. 6G and SUPP. FIG. 6H). However, both Lepr+ cells and osteoblasts of CDH5-MAPK mice displayed an increased expression of NF-κB regulated target genes similar to the other BM cellular subsets, which was suppressed upon inhibition of endothelial NF-κB signaling (SUPP. FIG. 6F and SUPP. FIG. 6I).

SUPP. FIG. 7A, SUPP. FIG. 7B, SUPP. FIG. 7C, SUPP. FIG. 7D, SUPP. FIG. 7E, SUPP. FIG. 7F. To screen for novel candidate proteins that might regulate HSC function during inflammation, a proteomic analysis (SomaLogic) on plasma derived from Tie2.IkB-SS mice identified 82 proteins that were differentially expressed as compared to their littermate controls was performed. It was hypothesized that a potential pro-hematopoietic protein would display opposing trends in CDH5-MAPK mice as compared to Tie2.IkB-SS mice. Using this approach, 18 candidate factors were identified that were significantly altered and inversely correlated (i.e. down in CDH5-MAPK mice, up in Tie2.IkB-SS and vice versa) (SUPP. FIG. 7 FIG. 7A and SUPP. FIG. 7B). Among these, Clec11a/Stem Cell Growth Factor-α (SCGF) was the most significantly downregulated protein in CDH5-MAPK mice (Supp. FIG. 7C). It was confirmed the specificity of the SCGF aptamer and validated the observed decrease of plasma SCGF in CDH5-MAPK mice (SUPP. FIG. 7D). Notably, CDH5-MAPK::IkB mice displayed a restoration of their plasma SCGF levels, further indicating that SCGF could be a potential pro-hematopoietic factor that promotes recovery in CDH5-MAPK::IkB mice. (SUPP. FIG. 7E and SUPP. FIG. 7F).

SUPP. FIG. 8A, SUPP. FIG. 8B, SUPP. FIG. 8C, SUPP. FIG. 8D, SUPP. FIG. 2E. To determine if SCGF can restore hematopoietic defects in CDH5-MAPK mice, 4 μg of SCGF was subcutaneously infused for five consecutive days and phenotypic and functional attributes of their hematopoietic system were analyzed 24 hours following the last injection (SUPP. FIG. 8A). No significance was found for frequency and absolute numbers of cells (SUPP. FIG. 8B). SCGF infusion into littermate control mice confirmed that SCGF did not affect steady state hematopoiesis, however, infusion of SCGF into CDH5-MAPK mice had profound effects on their hematopoiesis (SUPP. FIG. 8C, SUPPL FIG. 8D, SUPPL FIG. 8E). SCGF infusion significantly increased the frequency of phenotypic HSCs and HSPCs in CDH5-MAPK mice (SUPP. FIG. 8C). SCGF infusion also resolved the peripheral blood myeloid bias in CDH5-MAPK mice and restored their blood counts (SUPP. FIG. 8D and SUPP. FIG. 8E).

SUPP. FIG. 9A, SUPP. FIG. 9B, SUPP. FIG. 9C, SUPP. FIG. 9D, SUPP. FIG. 9E, SUPP. FIG. 9F. Since SCGF has been shown to promote osteogenesis, it is likely that the decrease in plasma SCGF levels along with the BM inflammation observed in CDH5-MAPK mice could result in osteopenia. CDH5-MAPK mice indeed displayed an overall decrease in trabecular bone volume, trabecular numbers and thickness demonstrating that endothelial MAPK activation has a deleterious impact on bone health (SUPP. FIG. 9A, SUPP. FIG. 9B, SUPP. FIG. 9C, SUPP. FIG. 9D). SCGF did not affect bone formation in control mice but caused a significant increase in trabecular bone volume and trabecular numbers and thickness in CDH5-MAPK mice, confirming its role in promoting osteogenesis (SUPP. FIG. SUPP. FIG. 9A, SUPP. FIG. 9B, SUPP. FIG. 9C, SUPP. FIG. 9D). Notably, SCGF expression was absent in hematopoietic cells and BMECs, and was primarily expressed in BM stromal cells including BM Lepr+ and osteoblastic stromal subsets (SUPP. FIG. 9E). Analysis of SCGF expression in total stromal cells, Lepr+ cells and osteoblasts from BM of Tie2-IkB-SS, CDH5-MAPK, and CDH5-MAPK::IkB mice, however, revealed no significant changes in mRNA expression (SUPP. FIG. 9F) indicating that decreased plasma SCGF in CDH5-MAPK mice is not due to transcriptional alterations.

SUPP. FIG. 10, SUPP. FIG. 10B. Wild type mice were given a myelosuppressive dose of irradiation (650 Rads) 410 and infused every other day with either 0.5 μg, 1 μg, or 2 μg of SCGF for a total of 7 injections starting at Day +1 post-irradiation, and hematopoietic recovery was assessed for 21 days (Supp. FIG. 10A). The dose-response experiment indicated that infusion of 2 μg of SCGF resulted in a significantly enhanced recovery of white blood cells, red blood cells, and platelets, confirming that SCGF enhances hematopoietic recovery following myelosuppressive stress (SUPP. FIG. 10A). Utilizing this strategy, the schematic in SUPP. FIG. 10B shows the protocol by which it was tested whether SCGF can improve hematopoietic recovery and preserve HSPC activity in both control and CDH5-MAPK mice (SUPP. FIG. 10B).

DETAILED DESCRIPTION

Definitions

Figure 1B:
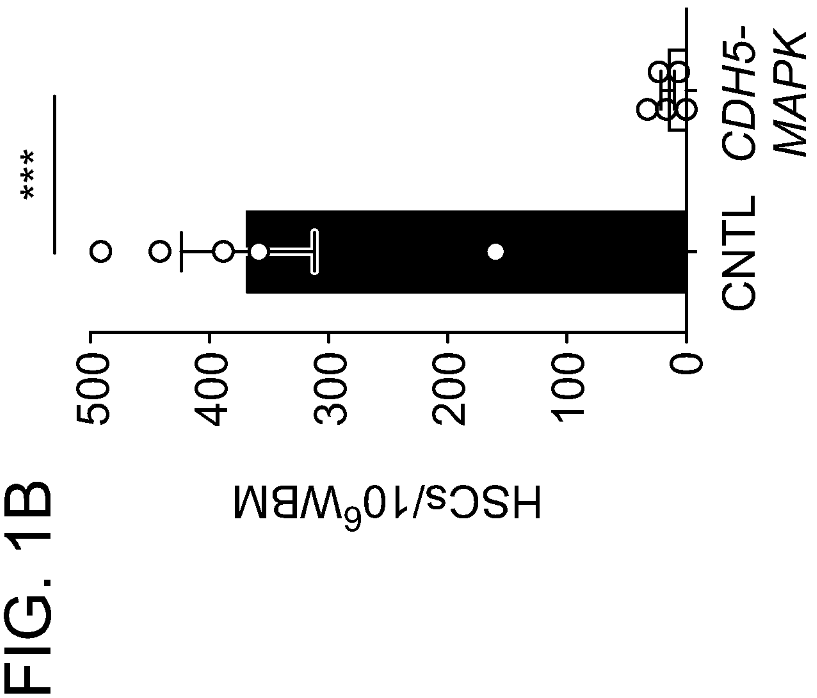

As used herein and in the appended claims, the singular forms "a", "an", and "the" include plural reference unless the context clearly dictates otherwise. Thus, for example, reference to a "peptide" is a reference to one or more peptides and equivalents thereof known to those skilled in the art, and so forth.

As used herein, the term "about" means plus or minus 20% of the numerical value of the number with which it is being used. Therefore, about 50% means in the range of 40%-60%, inclusive.

The term "adaptive immunity" as used herein refers to the protection of a host organism from a pathogen or toxin which is mediated by B cells and T cells, and is characterized by immunological memory. Adaptive immunity is highly specific to a given antigen and is highly adaptable.

"Administering" when used in conjunction with a therapeutic means to give or apply a therapeutic directly into or onto a target organ, tissue or cell, or to administer a therapeutic to a subject, whereby the therapeutic positively impacts the organ, tissue, cell, or subject to which it is targeted. Thus, as used herein, the term "administering", when used in conjunction with compositions comprising an angiocrine factor, can include, but is not limited to, providing the composition into or onto the target organ, tissue or cell; or providing a composition systemically to a patient by, e.g., intravenous injection, so that the therapeutic reaches the target organ, tissue or cell. "Administering" may be accomplished by parenteral, oral or topical administration, by inhalation, or by such methods in combination with other known techniques.

The term "agonist" as used herein refers to a chemical substance capable of activating a receptor to induce a full or partial pharmacological response. Receptors can be activated or inactivated by either endogenous or exogenous agonists and antagonists, resulting in stimulating or inhibiting a biological response. A physiological agonist is a substance that creates the same bodily responses, but does not bind to the same receptor. An endogenous agonist for a particular receptor is a compound naturally produced by the body which binds to and activates that receptor. A superagonist is a compound that is capable of producing a greater maximal response than the endogenous agonist for the target receptor, and thus an efficiency greater than 100%. This does not necessarily mean that it is more potent than the endogenous agonist, but is rather a comparison of the maximum possible response that can be produced inside a cell following receptor binding. Full agonists bind and activate a receptor, displaying full efficacy at that receptor. Partial agonists also bind and activate a given receptor, but have only partial efficacy at the receptor relative to a full agonist. An inverse agonist is an agent which binds to the same receptor binding-site as an agonist for that receptor and reverses constitutive activity of receptors. Inverse agonists exert the opposite pharmacological effect of a receptor agonist. An irreversible agonist is a type of agonist that binds permanently to a receptor in such a manner that the receptor is permanently activated. It is distinct from a mere agonist in that the association of an agonist to a receptor is reversible, whereas the binding of an irreversible agonist to a receptor is believed to be irreversible. This causes the compound to produce a brief burst of agonist activity, followed by desensitization and internalization of the receptor, which with long-term treatment produces an effect more like an antagonist. A selective agonist is specific for one certain type of receptor. The term "allogeneic" as used herein means that a donor and a recipient are of different genetic makeup, but of the same species. T The term "autologous" as used herein means derived from the same individual.

The term "amino acid" is used to refer to an organic molecule containing both an amino group and a carboxyl group; those that serve as the building blocks of naturally occurring proteins are alpha amino acids, in which both the amino and carboxyl groups are linked to the same carbon atom.

The terms "amino acid residue" or "residue" are used interchangeably to refer to an amino acid that is incorporated into a protein, a polypeptide, or a peptide, including, but not limited to, a naturally occurring amino acid and known analogs of natural amino acids that can function in a similar manner as naturally occurring amino acids.

The abbreviations used herein for amino acids are those abbreviations which are conventionally used: A=Ala=Alanine; R=Arg=Arginine; N=Asn=Asparagine; D=Asp=Aspartic acid; C=Cys=Cysteine; Q=Gln=Glutamine; E=Glu=Glutamic acid; G=Gly=Glycine; H=His=Histidine; I=Ile=Isoleucine; L=Leu=Leucine; K=Lys=Lysine; M=Met=Methionine; F=Phe=Phenyalanine; P=Pro=Proline; S=Ser=Serine; T=Thr=Threonine; W=Trp=Tryptophan; Y=Tyr=Tyrosine; V=Val=Valine. The amino acids may be L- or D-amino acids. An amino acid may be replaced by a synthetic amino acid which is altered so as to increase the half-life of the peptide or to increase the potency of the peptide, or to increase the bioavailability of the peptide.

The following represent groups of amino acids that are conservative substitutions for one another:

Alanine (A), Serine (S), Threonine (T);

Aspartic Acid (D), Glutamic Acid (E);

Asparagine (N), Glutamine (Q);

Arginine (R), Lysine (K);

Isoleucine (I), Leucine (L), Methionine (M), Valine (V); and

Phenylalanine (F), Tyrosine (Y), Tryptophan (W).

The term "angiogenesis" as used herein refers to the process by which new blood vessels take shape from existing blood vessels by "sprouting" of endothelial cells, thus expanding the vascular tree.

Figure 1A:
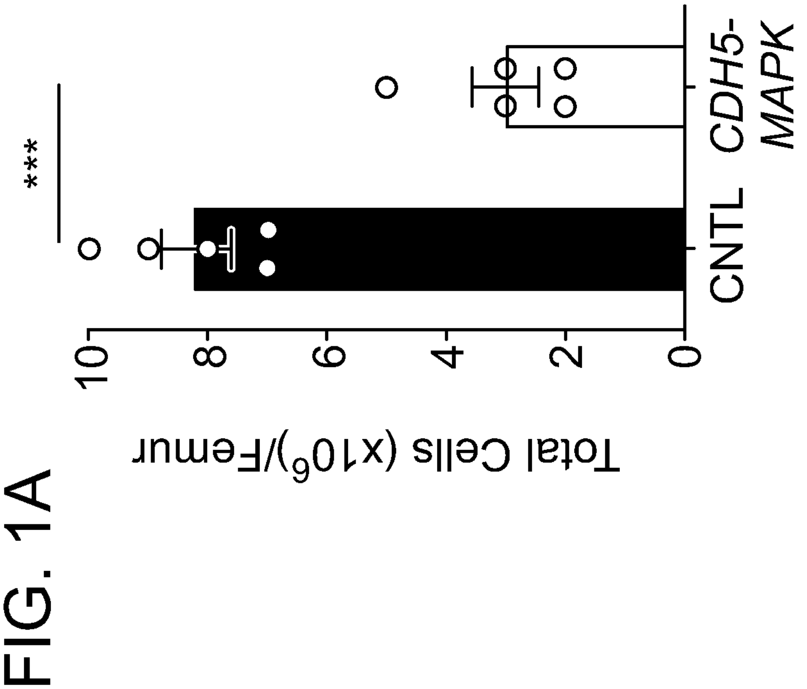
Figure 1C:
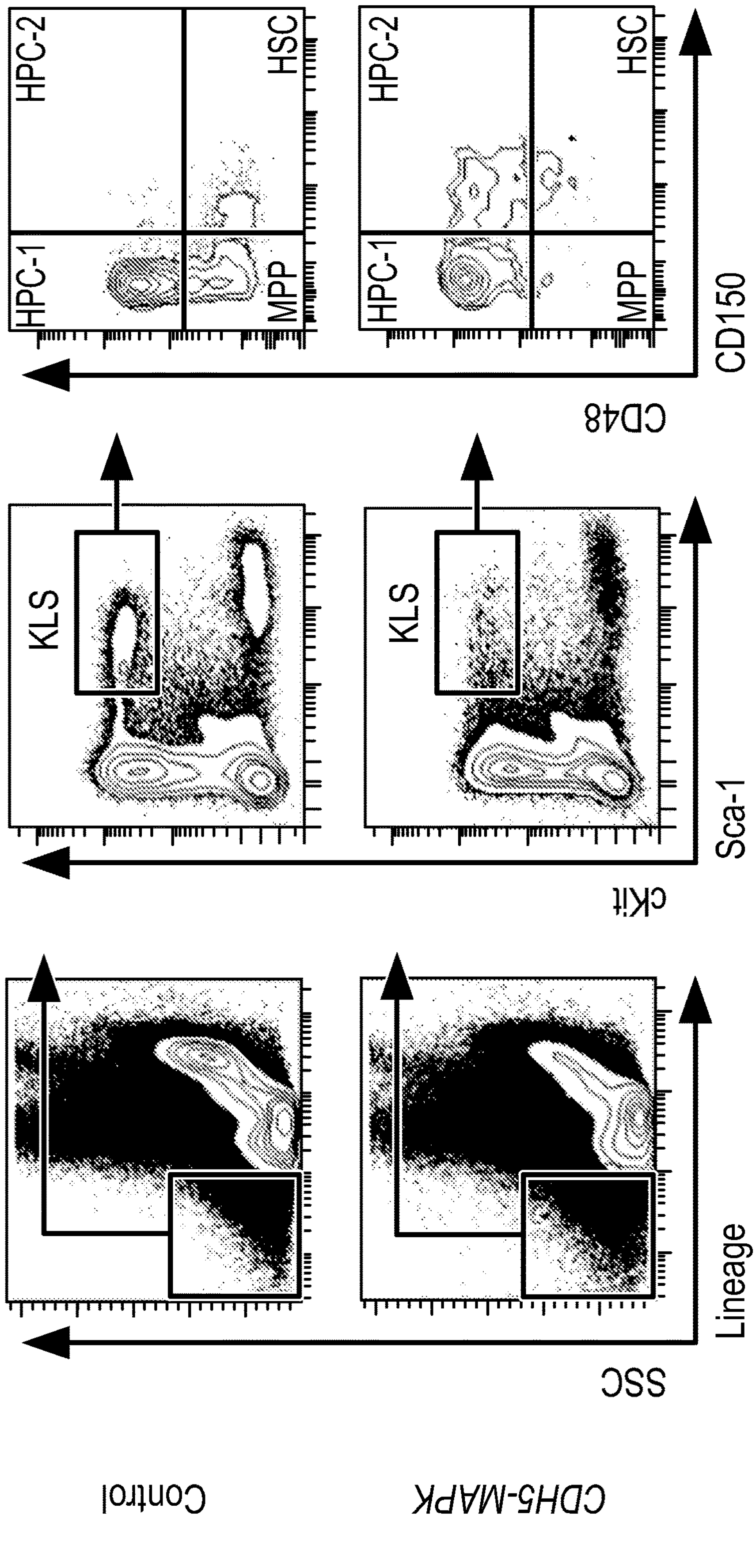
Figure 1D:
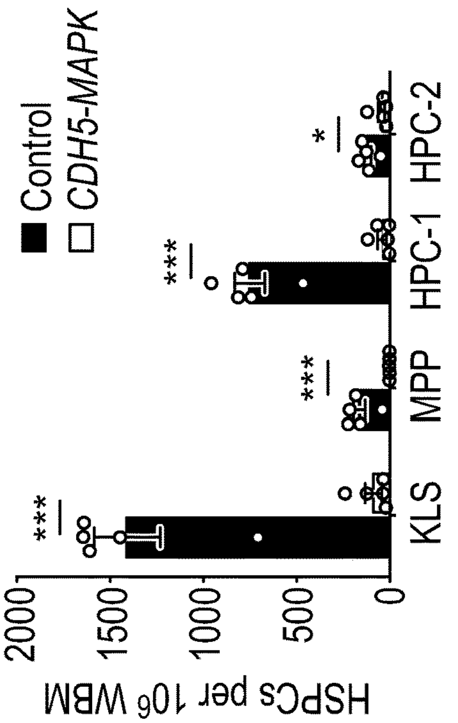
Figure 1E:
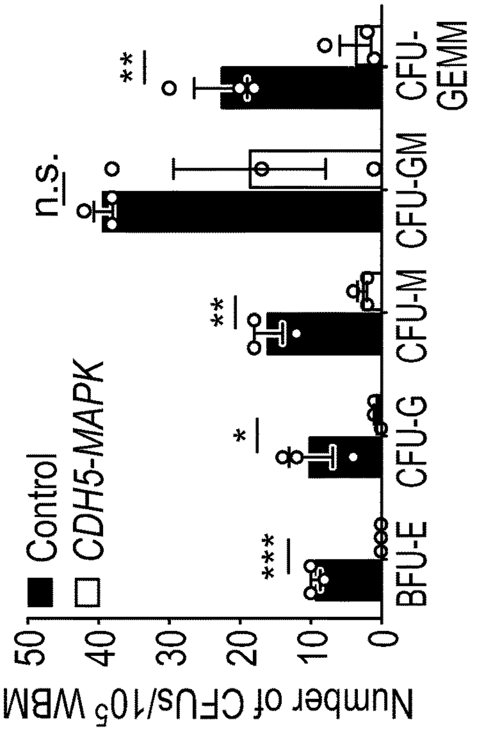

The term "angiocrine factor" as used herein refer to vascular niche-derived paracrine factors produced by endothelial cells that maintain organ homeostasis, balance the self-renewal and differentiation of stem cells, and orchestrate organ regeneration and tumor growth. Angiocrine factors comprise secreted and membrane-bound inhibitory and stimulatory growth factors, trophogens, chemokines, cytokines, extracellular matrix components, exosomes and other cellular products that are supplied by tissue-specific ECs to help regulate homeostatic and regenerative processes in a paracrine or juxtacrine manner. These factors also play a part in adaptive healing and fibrotic remodelling. Subsets of angiocrine factors can act as morphogens to determine the shape, architecture, size and patterning of regenerating organs. The angiocrine profile of each tissue-specific bed of ECs is different and reflects the diversity of cell types found adjacent to ECs in organs. Although subsets of angiocrine factors are produced constitutively, some angiogenic factors can modulate the production of other tissue-specific angiocrine factors. For example, VEGF-A induces the expression of defined angiocrine factors through interaction with VEGFR-1 and VEGFR-2 (FIG. 1E). Similarly, FGF-2 (through the activation of FGFR-1) and the angiopoietins (through their interaction with the receptor Tie2) drive the expression of unique clusters of angiocrine factors. TSP-1 functions in a complex manner and can act as an inhibitory angiogenic factor as well as directly influence the differentiation of stem and progenitor cells. The molecular programmes that govern the production of context-dependent angiocrine factors from organ-specific ECs remain undefined. Rafii, S., et al, "Angiocrine functions of organ-specific endothelial cells," Nature (2016) 529 (7586): 316-325).

The terms "animal," "patient," and "subject" as used herein include, but are not limited to, humans and non-human vertebrates such as wild, domestic, and farm animals. According to some embodiments, the terms "animal," "patient," and "subject" may refer to mammals, including humans.

The term "antibody" as used herein refers to a polypeptide or group of polypeptides comprised of at least one binding domain that is formed from the folding of polypeptide chains having three-dimensional binding spaces with internal surface shapes and charge distributions complementary to the features of an antigenic determinant of an antigen.

The basic structural unit of a whole antibody molecule consists of four polypeptide chains, two identical light (L) chains (each containing about 220 amino acids) and two identical heavy (H) chains (each usually containing about 440 amino acids). The two heavy chains and two light chains are held together by a combination of noncovalent and covalent (disulfide) bonds. The molecule is composed of two identical halves, each with an identical antigen-binding site composed of the N-terminal region of a light chain and the N-terminal region of a heavy chain. Both light and heavy chains usually cooperate to form the antigen binding surface. Human antibodies show two kinds of light chains, κ and λ; individual molecules of immunoglobulin generally are only one or the other.

An antibody may be an oligoclonal antibody, a polyclonal antibody, a monoclonal antibody, a chimeric antibody, a CDR-grafted antibody, a multi-specific antibody, a bi-specific antibody, a catalytic antibody, a chimeric antibody, a humanized antibody, a fully human antibody, an anti-idiotypic antibody, and an antibody that can be labeled in soluble or bound form, as well as fragments, variants or derivatives thereof, either alone or in combination with other amino acid sequences provided by known techniques. Monoclonal antibodies (mAbs) can be generated by fusing mouse spleen cells from an immunized donor with a mouse myeloma cell line to yield established mouse hybridoma clones that grow in selective media. A hybridoma cell is an immortalized hybrid cell resulting from the in vitro fusion of an antibody-secreting B cell with a myeloma cell. In vitro immunization, which refers to primary activation of antigen-specific B cells in culture, is another well-established means of producing mouse monoclonal antibodies. Diverse libraries of immunoglobulin heavy (VH) and light (Vκ and Vλ) chain variable genes from peripheral blood lymphocytes also can be amplified by polymerase chain reaction (PCR) amplification. Genes encoding single polypeptide chains in which the heavy and light chain variable domains are linked by a polypeptide spacer (single chain Fv or scFv) can be made by randomly combining heavy and light chain V-genes using PCR. A combinatorial library then can be cloned for display on the surface of filamentous bacteriophage by fusion to a minor coat protein at the tip of the phage. The technique of guided selection is based on human immunoglobulin V gene shuffling with rodent immunoglobulin V genes. The method entails (i) shuffling a repertoire of human λ light chains with the heavy chain variable region (VH) domain of a mouse monoclonal antibody reactive with an antigen of interest; (ii) selecting half-human Fabs on that antigen (iii) using the selected λ light chain genes as "docking domains" for a library of human heavy chains in a second shuffle to isolate clone Fab fragments having human light chain genes; (v) transfecting mouse myeloma cells by electroporation with mammalian cell expression vectors containing the genes; and (vi) expressing the V genes of the Fab reactive with the antigen as a complete IgGI, λ antibody molecule in the mouse myeloma. An antibody may be from any species. The term antibody also includes binding fragments of the antibodies of the invention; exemplary fragments include Fv, Fab, Fab', single stranded antibody (svFC), dimeric variable region (Diabody) and di-sulphide stabilized variable region (dsFv). Structural and functional domains can be identified by comparison of the nucleotide and/or amino acid sequence data to public or proprietary sequence databases. For example, computerized comparison methods can be used to identify sequence motifs or predicted protein conformation domains that occur in other proteins of known structure and/or function. Methods to identify protein sequences that fold into a known three-dimensional structure are known. See, for example, Bowie et al. *Science* 253:164 (1991), which is incorporated by reference in its entirety.

As used herein, the terms "antigen" or "immunogen" are used interchangeably to refer to a substance that elicits an immune response. An "antigenic determinant" or "epitope" is an antigenic site on a molecule. Sequential antigenic determinants/epitopes essentially are linear chains. In ordered structures, such as helical polymers or proteins, the antigenic determinants/epitopes essentially would be limited regions or patches in or on the surface of the structure involving amino acid side chains from different portions of the molecule which could come close to one another. These are conformational determinants.

The terms "apoptosis" or "programmed cell death" refer to a highly regulated and active process that contributes to biologic homeostasis comprised of a series of biochemical events that lead to a variety of morphological changes, including blebbing, changes to the cell membrane, such as loss of membrane asymmetry and attachment, cell shrinkage, nuclear fragmentation, chromatin condensation, and chromosomal DNA fragmentation, without damaging the organism.

Apoptotic cell death is induced by many different factors and involves numerous signaling pathways, some dependent on caspase proteases (a class of cysteine proteases) and others that are caspase independent. It can be triggered by many different cellular stimuli, including cell surface receptors, mitochondrial response to stress, and cytotoxic T cells, resulting in activation of apoptotic signaling pathways The caspases involved in apoptosis convey the apoptotic signal in a proteolytic cascade, with caspases cleaving and activating other caspases that then degrade other cellular targets that lead to cell death. The caspases at the upper end of the cascade include caspase-8 and caspase-9. Caspase-8 is the initial caspase involved in response to receptors with a death domain (DD) like Fas.

Receptors in the TNF receptor family are associated with the induction of apoptosis, as well as inflammatory signaling. The Fas receptor (CD95) mediates apoptotic signaling by Fas-ligand expressed on the surface of other cells. The Fas-FasL interaction plays an important role in the immune system and lack of this system leads to autoimmunity, indicating that Fas-mediated apoptosis removes self-reactive lymphocytes. Fas signaling also is involved in immune surveillance to remove transformed cells and virus infected cells. Binding of Fas to oligimerized FasL on another cell activates apoptotic signaling through a cytoplasmic domain termed the death domain (DD) that interacts with signaling adaptors including FAF, FADD and DAX to activate the caspase proteolytic cascade. Caspase-8 and caspase-10 first are activated to then cleave and activate downstream caspases and a variety of cellular substrates that lead to cell death.

Mitochondria participate in apoptotic signaling pathways through the release of mitochondrial proteins into the cytoplasm. Cytochrome c, a key protein in electron transport, is released from mitochondria in response to apoptotic signals, and activates Apaf-1, a protease released from mitochondria. Activated Apaf-1 activates caspase-9 and the rest of the caspase pathway. Smac/DIABLO is released from mitochondria and inhibits IAP proteins that normally interact with caspase-9 to inhibit apoptosis. Apoptosis regulation by Bel-2 family proteins occurs as family members form complexes that enter the mitochondrial membrane, regulating the release of cytochrome c and other proteins. TNF family receptors that cause apoptosis directly activate the caspase cascade, but can also activate Bid, a Bel-2 family member, which activates mitochondria-mediated apoptosis. Bax, another Bel-2 family member, is activated by this pathway to localize to the mitochondrial membrane and increase its permeability, releasing cytochrome c and other mitochondrial proteins. Bel-2 and Bel-xL prevent pore formation, blocking apoptosis. Like cytochrome c, AIF (apoptosis-inducing factor) is a protein found in mitochondria that is released from mitochondria by apoptotic stimuli. While cytochrome C is linked to caspase-dependent apoptotic signaling, AIF release stimulates caspase-independent apoptosis, moving into the nucleus where it binds DNA. DNA binding by AIF stimulates chromatin condensation, and DNA fragmentation, perhaps through recruitment of nucleases.

The mitochondrial stress pathway begins with the release of cytochrome c from mitochondria, which then interacts with Apaf-1, causing self-cleavage and activation of caspase-9. Caspase-3, -6 and-7 are downstream caspases that are activated by the upstream proteases and act themselves to cleave cellular targets.

Granzyme B and perforin proteins released by cytotoxic T cells induce apoptosis in target cells, forming transmembrane pores, and triggering apoptosis, perhaps through cleavage of caspases, although caspase-independent mechanisms of Granzyme B mediated apoptosis have been suggested.

Fragmentation of the nuclear genome by multiple nucleases activated by apoptotic signaling pathways to create a nucleosomal ladder is a cellular response characteristic of apoptosis. One nuclease involved in apoptosis is DNA fragmentation factor (DFF), a caspase-activated DNAse (CAD). DFF/CAD is activated through cleavage of its associated inhibitor ICAD by caspases proteases during apoptosis. DFF/CAD interacts with chromatin components such as topoisomerase II and histone H1 to condense chromatin structure and perhaps recruit CAD to chromatin. Another apoptosis activated protease is endonuclease G (EndoG). EndoG is encoded in the nuclear genome but is localized to mitochondria in normal cells. EndoG may play a role in the replication of the mitochondrial genome, as well as in apoptosis. Apoptotic signaling causes the release of EndoG from mitochondria. The EndoG and DFF/CAD pathways are independent since the EndoG pathway still occurs in cells lacking DFF.

Hypoxia, as well as hypoxia followed by reoxygenation can trigger cytochrome c release and apoptosis. Glycogen synthase kinase (GSK-3) a serine-threonine kinase ubiquitously expressed in most cell types, appears to mediate or potentiate apoptosis due to many stimuli that activate the mitochondrial cell death pathway. Loberg, R D, et al., J. Biol. Chem. 277 (44): 41667-673 (2002). It has been demonstrated to induce caspase 3 activation and to activate the proapoptotic tumor suppressor gene p53. It also has been suggested that GSK-3 promotes activation and translocation of the proapoptotic Bel-2 family member, Bax, which, upon agregation and mitochondrial localization, induces cytochrome c release. Akt is a critical regulator of GSK-3, and phosphorylation and inactivation of GSK-3 may mediate some of the antiapoptotic effects of Akt.

The term “autocrine signaling” as used herein refers to a type of cell signaling in which a cell secretes signal molecules that act on itself or on other adjacent cells of the same type.

The terms “autologous” or “autogeneic” as used interchangeably herein mean derived from the same organism.

The term “binding” and its other grammatical forms as used herein means a lasting attraction between chemical substances.

“Binding fragments” of an antibody can be produced by recombinant DNA techniques, or by enzymatic or chemical cleavage of intact antibodies. Binding fragments include Fab, Fab', $F(ab')_2$, Fv, and single-chain antibodies.

A “bispecific” or “bifunctional antibody is an antibody in which each of its binding sites is not identical. An antibody other than a “bispecific” or “bifunctional” antibody is understood to have each of its binding sites identical.

The term “binding specificity” as used herein involves both binding to a specific partner and not binding to other molecules. Functionally important binding may occur at a range of affinities from low to high, and design elements may suppress undesired cross-interactions. Post-translational modifications also can alter the chemistry and structure of interactions. “Promiscuous binding” may involve degrees of structural plasticity, which may result in different subsets of residues being important for binding to different partners. “Relative binding specificity” is a characteristic whereby in a biochemical system a molecule interacts with its targets or partners differentially, thereby impacting them distinctively depending on the identity of individual targets or partners.

The term “biomarker” (or “biosignature”) as used herein refers to peptides, proteins, nucleic acids, antibodies, genes, metabolites, or any other substances used as indicators of a biologic state. It is a characteristic that is measured objectively and evaluated as a cellular or molecular indicator of normal biologic processes, pathogenic processes, or pharmacologic responses to a therapeutic intervention. The term “indicator” as used herein refers to any substance, number or ratio derived from a series of observed facts that may reveal relative changes as a function of time; or a signal, sign, mark, note or symptom that is visible or evidence of the existence or presence thereof. Once a proposed biomarker has been validated, it may be used to diagnose disease risk, presence of disease in an individual, or to tailor treatments for the disease in an individual (choices of drug treatment or administration regimes). In evaluating potential drug therapies, a biomarker may be used as a surrogate for a natural endpoint, such as survival or irreversible morbidity. If a treatment alters the biomarker, and that alteration has a direct connection to improved health, the biomarker may serve as a surrogate endpoint for evaluating clinical benefit. Clinical endpoints are variables that can be used to measure how patients feel, function or survive. Surrogate endpoints are biomarkers that are intended to substitute for a clinical endpoint; these biomarkers are demonstrated to predict a clinical endpoint with a confidence level acceptable to regulators and the clinical community.

Bone Cells. Four cell types in bone are involved in its formation and maintenance. These are 1) osteoprogenitor cells, 2) osteoblasts, 3) osteocytes, and 4) osteoclasts.

Osteoprogenitor Cells. Osteoprogenitor cells arise from mesenchymal cells, and occur in the inner portion of the periosteum and in the endosteum of mature bone. They are found in regions of the embryonic mesenchymal compartment where bone formation is beginning and in areas near the surfaces of growing bones. Structurally, osteoprogenitor cells differ from the mesenchymal cells from which they have arisen. They are irregularly shaped and elongated cells having pale-staining cytoplasm and pale-staining nuclei. Osteoprogenitor cells, which multiply by mitosis, are identified chiefly by their location and by their association with osteoblasts. Some osteoprogenitor cells differentiate into osteocytes. While osteoblasts and osteocytes are no longer mitotic, it has been shown that a population of osteoprogenitor cells persists throughout life.

Osteoblasts. Osteoblasts, which are located on the surface of osteoid seams (the narrow region on the surface of a bone of newly formed organic matrix not yet mineralized), are derived from osteoprogenitor cells. They are immature, mononucleate, bone-forming cells that synthesize collagen and control mineralization. Osteoblasts can be distinguished from osteoprogenitor cells morphologically; generally they are larger than osteoprogenitor cells, and have a more rounded nucleus, a more prominent nucleolus, and cytoplasm that is much more basophilic. Osteoblasts make a protein mixture known as osteoid, primarily composed of type I collagen, which mineralizes to become bone. Osteoblasts also manufacture hormones, such as prostaglandins, alkaline phosphatase, an enzyme that has a role in the mineralization of bone, and matrix proteins.

Osteocytes. Osteocytes, star-shaped mature bone cells derived from ostoblasts and the most abundant cell found in compact bone, maintain the structure of bone. Osteocytes, like osteoblasts, are not capable of mitotic division. They are actively involved in the routine turnover of bony matrix and reside in small spaces, cavities, gaps or depressions in the bone matrix called lacuna.

Osteocytes maintain the bone matrix, regulate calcium homeostasis, and are thought to be part of the cellular feedback mechanism that directs bone to form in places where it is most needed. Bone adapts to applied forces by growing stronger in order to withstand them; osteocytes may detect mechanical deformation and mediate bone-formation by osteoblasts.

Osteoclasts. Osteoclasts, which are derived from a monocyte stem cell lineage and possess phagocytic-like mechanisms similar to macrophages, often are found in depressions in the bone referred to as Howship’s lacunae. They are large multinucleated cells specialized in bone resorption. During resorption, osteoclasts seal off an area of bone surface; then, when activated, they pump out hydrogen ions to produce a very acid environment, which dissolves the hydroxyapatite component. The number and activity of osteoclasts increase when calcium resorption is stimulated by injection of parathyroid hormone (PTH), while osteoclastic activity is suppressed by injection of calcitonin, a hormone produced by thyroid parafollicular cells.

Bone Matrix. The bone matrix accounts for about 90% of the total weight of compact bone and is composed of microcrystalline calcium phosphate resembling hydroxyapatite (60%) and fibrillar type I collagen (27%). The remaining 3% consists of minor collagen types and other proteins including osteocalcin, osteonectin, osteopontin, bone sialoprotein, as well as proteoglycans, glycosaminoglycans, and lipids. Extracellular matrix glycoproteins and proteoglycans in bone bind a variety of growth factors and cytokines, and serve as a repository of stored signals that act on osteoblasts and osteoclasts. Examples of growth factors and cytokines found in bone matrix include, but are not limited to, Bone Morphogenic Proteins (BMPs), Epidermal Growth Factors (EGFs), Fibroblast Growth Factors (FGFs), Platelet-Derived Growth Factors (PDGFs), Insulin-like Growth Factor-1 (IGF-1), Transforming Growth Factors (TGFs), Bone-Derived Growth Factors (BDGFs), Cartilage-Derived Growth Factor (CDGF), Skeletal Growth Factor (hSGF), Interleukin-1 (IL-1), and macrophage-derived factors. There is an emerging understanding that extracellular matrix molecules themselves can serve regulatory roles, providing both direct biological effects on cells as well as key spatial and contextual information.

The Periosteum and Endosteum. The periosteum is a fibrous connective tissue investment of bone, except at the bone's articular surface. Its adherence to the bone varies by location and age. In young bone, the periosteum is stripped off easily. In adult bone, it is more firmly adherent, especially so at the insertion of tendons and ligaments, where more periosteal fibers penetrate into the bone as the perforating fibers of Sharpey (bundles of collagenous fibers that pass into the outer circumferential lamellae of bone). The periosteum consists of two layers, the outer of which is composed of coarse, fibrous connective tissue containing few cells but numerous blood vessels and nerves. The inner layer, which is less vascular but more cellular, contains many elastic fibers. During growth, an osteogenic layer of primitive connective tissue forms the inner layer of the periosteum. In the adult, this is represented only by a row of scattered, flattened cells closely applied to the bone. The periosteum serves as a supporting bed for the blood vessels and nerves going to the bone and for the anchorage of tendons and ligaments. The osteogenic layer, which is considered a part of the periosteum, is known to furnish osteoblasts for growth and repair, and acts as an important limiting layer controlling and restricting the extend of bone formation. Because both the periosteum and its contained bone are regions of the connective tissue compartment, they are not separated from each other or from other connective tissues by basal laminar material or basement membranes. Perosteal stem cells have been shown to be important in bone regeneration and repair. (Zhang et al., 2005, J. Musculoskelet. Neuronal. Interact. 5(4): 360-362).

The endosteum lines the surface of cavities within a bone (marrow cavity and central canals) and also the surface of trabeculae in the marrow cavity. In growing bone, it consists of a delicate striatum of myelogenous reticular connective tissue, beneath which is a layer of osteoblasts. In the adult, the osteogenic cells become flattened and are indistinguishable as a separate layer. They are capable of transforming into osteogenic cells when there is a stimulus to bone formation, as after a fracture.

Components of bone. Bone is composed of cells and an intercellular matrix of organic and inorganic substances. The organic fraction consists of collagen, glycosaminoglycans, proteoglycans, and glycoproteins. The protein matrix of bone largely is composed of collagen, a family of fibrous proteins that have the ability to form insoluble and rigid fibers. The main collagen in bone is type I collagen. The inorganic component of bone, which is responsible for its rigidity and may constitute up to two-thirds of its fat-free dry weight, is composed chiefly of calcium phosphate and calcium carbonate, in the form of calcium hydroxyapatite, with small amounts of magnesium hydroxide, fluoride, and sulfate. The composition varies with age and with a number of dietary factors. The bone minerals form long fine crystals that add strength and rigidity to the collagen fibers; the process by which it is laid down is termed mineralization.

The term "bone marrow" as used herein refers to soft blood-forming tissue that fills the cavities of bones and contains fat and immature and mature blood cells, including white blood cells, red blood cells, and platelets. Bone marrow contains a variety of precursor and mature cell types, including hematopoietic cells, which are precursor cells of mature blood cells, and mesenchymal stem cells, otherwise known as stromal cells, that are precursors of a broad spectrum of connective tissue cells, both of which are capable of differentiating into other cell types. Hematopoietic stem cells (HSCs) in the bone marrow give rise to two main types of cells: the myeloid lineage (including monocytes, macrophages, neutrophils, basophils, eosinophils, erythrocytes, dendritic cells, and megakaryocytes or platelets) and the lymphoid lineage (including T cells, B cells, and natural killer cells).

Bone Remodeling. Bone constantly is broken down by osteoclasts and re-formed by osteoblasts in the adult. It has been reported that as much as 18% of bone is recycled each year through the process of renewal, known as bone remodeling, which maintains bone's rigidity. The balance in this dynamic process shifts as people grow older: in youth, it favors the formation of bone, but in old age, it favors resorption. As new bone material is added peripherally from the internal surface of the periosteum, there is a hollowing out of the internal region to form the bone marrow cavity. This destruction of bone tissue is due to osteoclasts that enter the bone through the blood vessels. Osteoclasts dissolve both the inorganic and the protein portions of the bone matrix. Each osteoclast extends numerous cellular processes into the matrix and pumps out hydrogen ions onto the surrounding material, thereby acidifying and solubilizing it. The blood vessels also import the blood-forming cells that will reside in the marrow for the duration of the organism's life.

The number and activity of osteoclasts must be tightly regulated. If there are too many active osteoclasts, too much bone will be dissolved, and osteoporosis will result. Conversely, if not enough osteoclasts are produced, the bones are not hollowed out for the marrow, and osteopetrosis (known as stone bone disease, a disorder whereby the bones harden and become denser) will result.

The terms "bone marrow transplant" (BMT) or "hematopoietic stem cell transplant" (HSCT) are used interchangeably to refer to a procedure in which bone marrow stem cells are collected from one individual (the donor) and given to another (the recipient). The stem cells can be collected either directly from the bone marrow or from the blood by leukapheresis. A bone marrow transplant may be autologous (using a patient's own stem cells that were collected from the marrow and saved before treatment), allogeneic (using stem cells donated by someone who is not an identical twin), or syngeneic (using stem cells donated by an identical twin).

The term "CD34" as used herein is a marker found on the surface of bone marrow stem cells.

The term "CD45" as used herein means the lymphocyte common antigen.

The term "Clec11a/Stem Cell Growth Factor-α" or "SCGF" refers to a secreted sulfated glycoprotein, which functions as a critical regulator of bone health and has been suggested as a growth factor for primitive hematopoietic progenitor cells.

The term "cancellous bone tissue" refers to an open, cell-porous network also called trabecular or spongy bone, which fills the interior of bone, and is composed of a network of rod- and plate-like elements that make the overall structure lighter and allows room for blood vessels and marrow so that the blood supply surrounds bone. Cancellous bone accounts for 20% of total bone mass but has nearly ten times the surface area of cortical bone. It does not contain haversian sites and osteons and has a porosity of about 30% to about 90%. In cancellous bone, the marrow spaces are relatively large and irregularly arranged, and the bone substance is in the form of slender anastomosing trabeculae and pointed spicules. The head of a bone, termed the epiphysis, has a spongy appearance and consists of slender irregular bone trabeculae, or bars, which anastomose to form a lattice work, the interstices of which contain the marrow, while the thin outer shell appears dense. The irregular marrow spaces of the epiphysis become continuous with the central medullary cavity of the bone shaft, termed the diaphysis, whose wall is formed by a thin plate of cortical bone.

The term "cell cycle" refers to the progress of cells through four phases: G1 (interphase), S (DNA synthesis phase), G2 (interphase) and M (mitosis phase). Nakamura-Ishizu, A., et al., Development (2014) 141: 4656-4666; citing Sisken, J E and Morasca, L., J. Cell Biol. (1965) 25: 179-189). Cells that proceed past the restriction point in the G1 phase enter the S phase, whereas those that do not pass the restriction point remain undivided. These undivided cells can withdraw from the cell cycle and enter the G0 phase, a state in which cells are termed quiescent or dormant (Id., citing Pardee, AB, Proc. Natl Acad. Sci. USA (1974) 71: 1286-90). Such non-cycling cells in the G0 phase can either reversibly re-enter the cell cycle and divide (Id., citing Cheung, T H and Rando, TA, Nat. Rev. Mol. Cell Biol. (2013) 14: 329-340) or remain dormant, losing the potential to cycle and, in some cases, becoming senescent (Id., citing Campisi, J. Cell (2005) 120: 513-22).

The term "cell lineage" or "lineage" as used herein refers to the developmental history of a differentiated cell as traced back to the cell from which it arises.

The term "chemokine" as used herein refers to a family of low molecular mass (8-11 kDa) structurally-related proteins with diverse immune and neural functions (Mackay C. R. Nat Immunol., Vol. 2: 95-101, (2001); Youn B. et al. Immunol Rev. (2000) Vol. 177: 150-174) that can be categorized into four subfamilies (C, CC, CXC and CX3C) based on the relative positions of conserved cysteine residues (Rossi D. et al. Annu Rev Immunol. (2000) 18: 217-242). Chemokines are essential molecules in directing leucocyte migration between blood, lymph nodes and tissues. They constitute a complex signaling network, because they are not always restricted to one type of receptor (Loetscher P. et al. J. Biol. Chem. (2001). 276: 2986-2991). Chemokines affect cells by activating surface receptors that are seven-transmembrane-domain G-protein-coupled receptors. Leukocyte responses to particular chemokines are determined by their expression of chemokine receptors. The binding of the chemokine to the receptor activates various signaling cascades, similar to the action of cytokines that culminate in the activation of a biological response. Secretion of the ligands for the CCR5 receptor, regulated upon activation normal T cell expressed and secreted (RANTES), macrophage inflammatory protein (MIP)-1α/and MIP-1β (Schrum S. et al. J Immunol. (1996) 157: 3598-3604) and the ligand for CXC chemokine receptor 3 (CXCR3), induced protein (IP)-10 (Taub D.D. et al. J Exp Med. (1993) 177:1809-1814) have been associated with unwanted heightened $T_{H1}$ responses. Additionally, elevated damaging pro-inflammatory cytokine levels of IL-2 and IFN-γ correlate with type 1 diabetes (T1D) (Rabinovitch A. et al. Cell Biochem Biophys. (2007) 48 (2-3): 159-63). Chemokines have been observed in $T_{H1}$ pancreatic infiltrates and other inflammatory lesions characterized by T cell infiltration (Bradley L. M. et al. J Immunol. (1999). 162:2511-2520).

The term "chemotherapy" as used herein refers to a treatment that uses drugs to destroy cancer cells, but is also used in bone marrow transplant patients without cancer in order to ensure successful engraftment.

The term "conditioning" as used herein refers to a combination of chemotherapy drugs, and sometimes radiation, given a few days prior to transplant that collectively prepare the body for transplant.

The term "contact" and its various grammatical forms as used herein refers to a state or condition of touching or of immediate or local proximity.

The term "cortical bone tissue" (also referred to as compact bone or dense bone), refers to the tissue of the hard outer layer of bones, so-called due to its minimal gaps and spaces. This tissue gives bones their smooth, white, and solid appearance. Cortical bone consists of haversian sites (the canals through which blood vessels and connective tissue pass in bone) and osteons (the basic units of structure of cortical bone comprising a haversian canal and its concentrically arranged lamellae), so that in cortical bone, bone surrounds the blood supply. Cortical bone has a porosity of about 5% to about 30%, inclusive and accounts for about 80% of the total bone mass of an adult skeleton. In cortical bone, the spaces or channels are narrow and the bone substance is densely packed.

The term "cytokine" as used herein refers to small soluble protein substances secreted by cells, which have a variety of effects on other cells. Cytokines mediate many important physiological functions, including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; tumor necrosis factor (TNF)-related molecules, including TNFα and lymphotoxin; immunoglobulin super-family members, including interleukin 1 (IL-1); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines.

The term "damage-associated molecule patterms" (DAMPs) as used herein refers to endogenous danger molecules that are released from damaged or dying cells, which activate the innate immune system by interacting with pattern recognition receptors (PRRs).

As used herein, the term "derived from" is meant to encompass any method for receiving, obtaining, or modifying something from a source of origin.

As used herein, the terms "detecting", "determining", and their other grammatical forms, are used to refer to methods performed for the identification or quantification of a biomarker, such as, for example, the presence or level of miRNA, or for the presence or absence of a condition in a biological sample. The amount of biomarker expression or activity detected in the sample can be none or below the level of detection of the assay or method.

The term "differentiation" as used herein refers to a process of development with an increase in the level of organization or complexity of a cell or tissue, accompanied by a more specialized function.

The terms "disease" or "disorder" as used herein refer to an impairment of health or a condition of abnormal functioning.

The term "endogenous" as used herein refers to that which is naturally occurring, incorporated within, housed within, adherent to, attached to, or resident in.

The term "engraftment" as used herein refers to a process in which normal growth of transplanted (donor) stem cells and production of blood cells in the patient's (recipient's) marrow spaces resumes after transplant.

As used herein, the term "enrich" is meant to refer to increasing the proportion of a desired substance, for example, to increase the relative frequency of a subtype of cell or cell component compared to its natural frequency in a cell population. Positive selection, negative selection, or both are generally considered necessary to any enrichment scheme. Selection methods include, without limitation, magnetic separation and fluorescence-activated cell sorting (FACS).

The term "erythropoiesis" as used herein refers to the formation of red blood cells in blood-forming tissue. In the early development of a fetus, erythropoiesis takes place in the yolk sac, spleen, and liver. After birth, all erythropoiesis occurs in the bone marrow. The erythroid line of differentiation in bone marrow and spleen starts with the early progenitor pro-erythroblasts that are derived from pluripotent stem cells. In adult bone marrow, definitive erythropoiesis begins when an HSC-derived common myeloid progenitor (a multipotent stem cell) commits to the erythroid lineage. The appearance of a pronormoblast (also called proerythroblast or ribriblast) marks the first stage of differentiation. This is followed by early, intermediate and late normoblast (erythroblast) stages, at which time the nucleus is expelled and the cell becomes a reticulocyte. Upon exiting the bone marrow, reticulocytes enter the circulation to become fully mature RBCs.

The term "exogenous" as used herein refers to that which is non-naturally occurring, or that is originating or produced outside of a specific cell, organism, or species.

The term "expand" and its various grammatical forms as used herein refers to a process by which dispersed living cells propagate in vitro in a culture medium that results in an increase in the number or amount of viable cells.

As used herein, the term "expression" and its various grammatical forms refers to the process by which a polynucleotide is transcribed from a DNA template (such as into an mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell. Expression may also refer to the post-translational modification of a polypeptide or protein.

The term "extracellular matrix" (or "ECM") as used herein refers to a scaffold in a cell's external environment with which the cell interacts via specific cell surface receptors. The extracellular matrix serves many functions, including, but not limited to, providing support and anchorage for cells, segregating one tissue from another tissue, and regulating intracellular communication. The extracellular matrix is composed of an interlocking mesh of fibrous proteins and glycosaminoglycans (GAGs). Examples of fibrous proteins found in the extracellular matrix include collagen, elastin, fribronectin, and laminin. Examples of GAGs found in the extracellular matrix include proteoglycans (e.g., heparin sulfate), chondroitin sulfate, keratin sulfate, and non-proteoglycan polysaccharide (e.g., hyaluronic acid). The term "proteoglycan" refers to a group of glycoproteins that contain a core protein to which is attached to one or more glycosaminoglycans.

The term "fragment" or "peptide fragment" as used herein refers to a small part derived, cut off, or broken from a larger peptide, polypeptide or protein, which retains the desired biological activity of the larger peptide, polypeptide or protein.

The term "graft" as used herein refers to a tissue or organ infused or transplanted from a donor to a recipient. It includes, but is not limited to, a self tissue transferred from one body site to another in the same individual ("autologous graft"), a tissue transferred between genetically identical individuals or sufficiently immunologically compatible to allow tissue transplant ("syngeneic graft"), a tissue transferred between genetically different members of the same species ("allogeneic graft" or "allograft"), and a tissue transferred between different species ("xenograft").

The term "growth factor" as used herein refers to extracellular polypeptide molecules that bind to a cell-surface receptor triggering an intracellular signaling pathway, leading to proliferation, differentiation, or other cellular response that stimulate the accumulation of proteins and other macromolecules, e.g., by increasing their rate of synthesis, decreasing their rate of degradation, or both. Exemplary growth factors include fibroblast growth factor (FGF), insulin-like growth factor (IGF-1), transforming growth factor beta (TGF-β), and vascular endothelial growth factor (VEGF)

Fibroblast Growth Factor (FGF). The fibroblast growth factor (FGF) family currently has over a dozen structurally related members. FGF1 is also known as acidic FGF; FGF2 is sometimes called basic FGF (bFGF); and FGF7 sometimes goes by the name keratinocyte growth factor. Over a dozen distinct FGF genes are known in vertebrates; they can generate hundreds of protein isoforms by varying their RNA splicing or initiation codons in different tissues. FGFs can activate a set of receptor tyrosine kinases called the fibroblast growth factor receptors (FGFRs). Receptor tyrosine kinases are proteins that extend through the cell membrane. The portion of the protein that binds the paracrine factor is on the extracellular side, while a dormant tyrosine kinase (i.e., a protein that can phosphorylate another protein by splitting ATP) is on the intracellular side. When the FGF receptor binds an FGF (and only when it binds an FGF), the dormant kinase is activated, and phosphorylates certain proteins within the responding cell, activating those proteins.

FGFs are associated with several developmental functions, including angiogenesis (blood vessel formation), mesoderm formation, and axon extension. While FGFs often can substitute for one another, their expression patterns give them separate functions. For example, FGF2 is especially important in angiogenesis, whereas FGF8 is involved in the development of the midbrain and limbs.

Insulin-Like Growth Factor (IGF-1). IGF-1, a hormone similar in molecular structure to insulin, has growth-promoting effects on almost every cell in the body, especially skeletal muscle, cartilage, bone, liver, kidney, nerves, skin, hematopoietic cell, and lungs. It plays an important role in childhood growth and continues to have anabolic effects in adults. IGF-1 is produced primarily by the liver as an endocrine hormone as well as in target tissues in a paracrine/autocrine fashion. Production is stimulated by growth hormone (GH) and can be retarded by undernutrition, growth hormone insensitivity, lack of growth hormone receptors, or failures of the downstream signaling molecules, including tyrosine-protein phosphatase non-receptor type 11 (also known as SHP2, which is encoded by the PTPN11 gene in humans) and signal transducer and activator of transcription 5B (STAT5B), a member of the STAT family of transcription factors. Its primary action is mediated by binding to its specific receptor, the Insulin-like growth factor 1 receptor (IGF1R), present on many cell types in many tissues. Binding to the IGF1R, a receptor tyrosine kinase, initiates intracellular signaling; IGF-1 is one of the most potent natural activators of the AKT signaling pathway, a stimulator of cell growth and proliferation, and a potent inhibitor of programmed cell death. IGF-1 is a primary mediator of the effects of growth hormone (GH). Growth hormone is made in the pituitary gland, released into the blood stream, and then stimulates the liver to produce IGF-1. IGF-1 then stimulates systemic body growth. In addition to its insulin-like effects, IGF-1 also can regulate cell growth and development, especially in nerve cells, as well as cellular DNA synthesis.

IGF-1 was shown to increase the expression levels of the chemokine receptor CXCR4 (receptor for stromal cell-derived factor-1, SDF-1) and to markedly increase the migratory response of MSCs to SDF-1 (Li, Y, et al. 2007 Biochem. Biophys. Res. Communic. 356(3): 780-784). The IGF-1-induced increase in MSC migration in response to SDF-1 was attenuated by PI3 kinase inhibitor (LY294002 and wortmannin) but not by mitogen-activated protein/ERK kinase inhibitor PD98059. Without being limited by any particular theory, the data indicate that IGF-1 increases MSC migratory responses via CXCR4 chemokine receptor signaling which is PI3/Akt dependent.

Transforming Growth Factor Beta (TGF-β). There are over 30 structurally related members of the TGF-β superfamily, and they regulate some of the most important interactions in development. The proteins encoded by TGF-β superfamily genes are processed such that the carboxy-terminal region contains the mature peptide. These peptides are dimerized into homodimers (with themselves) or heterodimers (with other TGF-β peptides) and are secreted from the cell. The TGF-βsuperfamily includes the TGF-β family, the activin family, the bone morphogenetic proteins (BMPs), the Vg-1 family, and other proteins, including glial-derived neurotrophic factor (GDNF, necessary for kidney and enteric neuron differentiation) and Müllerian inhibitory factor, which is involved in mammalian sex determination. TGF-β family members TGF-β1, 2, 3, and 5 are important in regulating the formation of the extracellular matrix between cells and for regulating cell division (both positively and negatively). TGF-β1 increases the amount of extracellular matrix epithelial cells make both by stimulating collagen and fibronectin synthesis and by inhibiting matrix degradation. TGF-βs may be critical in controlling where and when epithelia can branch to form the ducts of kidneys, lungs, and salivary glands.

Vascular Endothelial Growth Factor (VEGF). VEGFs are growth factors that mediate numerous functions of endothelial cells including proliferation, migration, invasion, survival, and permeability. The VEGFs and their corresponding receptors are key regulators in a cascade of molecular and cellular events that ultimately lead to the development of the vascular system, either by vasculogenesis, angiogenesis, or in the formation of the lymphatic vascular system. VEGF is a critical regulator in physiological angiogenesis and also plays a significant role in skeletal growth and repair.

VEGF's normal function creates new blood vessels during embryonic development, after injury, and to bypass blocked vessels. In the mature established vasculature, the endothelium plays an important role in the maintenance of homeostasis of the surrounding tissue by providing the communicative network to neighboring tissues to respond to requirements as needed. Furthermore, the vasculature provides growth factors, hormones, cytokines, chemokines and metabolites, and the like, needed by the surrounding tissue and acts as a barrier to limit the movement of molecules and cells.

The terms "immune reconstitution" or "reconstitution" as used herein refers to a process of rebuilding the immune system from transplanted HSCs after HSCT.

The terms "immune response" and "immune-mediated" are used interchangeably herein to refer to any functional expression of a subject's immune system, against either foreign or self-antigens, whether the consequences of these reactions are beneficial or harmful to the subject.

The term "immune system" as used herein refers to the body's system of defenses against disease. The innate immune system provides a non-specific first line of defense against pathogens. It comprises physical barriers (e.g. the skin) and both cellular (granulocytes, natural killer cells) and humoral (complement system) defense mechanisms. The reaction of the innate immune system is immediate, but unlike the adaptive immune system, it does not provide permanent immunity against pathogens.

The term "innate immunity" as used herein refers to the various innate resistance mechanisms that are encountered first by a pathogen, before adaptive immunity is induced, such as anatomical barriers, antimicrobial peptides, the complement system and macrophages and neutrophils carrying nonspecific pathogen-recognition receptors. Innate immunity is present in all individuals at all times, does not increase with repeated exposure to a given pathogen, and discriminates between groups of similar pathogens, rather than responding to a particular pathogen.

The terms "immunomodulatory", "immune modulator" and "immune modulatory" are used interchangeably herein to refer to a substance, agent, or cell that is capable of augmenting or diminishing immune responses directly or indirectly, e.g., by expressing chemokines, cytokines and other mediators of immune responses.

The term "immunosuppressive agent" as used herein refers to an agent that decreases the body's immune responses.

The term "immunosuppression" as used herein refers to a state of decreased immunity or a lowering of the body's immune response. The term "immunosuppressive therapy" as used herein refers to a treatment that lowers the activity of the body's immune system.

The term "inflammation" as used herein refers to the physiologic process by which vascularized tissues respond to injury. See, e.g., FUNDAMENTAL IMMUNOLOGY, 4th Ed., William E. Paul, ed. Lippincott-Raven Publishers, Philadelphia (1999) at 1051-1053, incorporated herein by reference. During the inflammatory process, cells involved in detoxification and repair are mobilized to the compromised site by inflammatory mediators. Inflammation is often characterized by a strong infiltration of leukocytes at the site of inflammation, particularly neutrophils (polymorphonuclear cells). These cells promote tissue damage by releasing toxic substances at the vascular wall or in uninjured tissue. Traditionally, inflammation has been divided into acute and chronic responses. The term "acute inflammation" as used herein refers to the rapid, short-lived (minutes to days), relatively uniform response to acute injury characterized by accumulations of fluid, plasma proteins, and neutrophilic leukocytes. The term "chronic inflammation" as used herein refers to inflammation that is of longer duration and which has a vague and indefinite termination. Chronic inflammation takes over when acute inflammation persists, either through incomplete clearance of the initial inflammatory agent or as a result of multiple acute events occurring in the same location. Chronic inflammation, which includes the influx of lymphocytes and macrophages and fibroblast growth, may result in tissue scarring at sites of prolonged or repeated inflammatory activity.

The term "inflammatory mediators" or "inflammatory cytokines" as used herein refers to molecular mediators of the inflammatory process. These soluble, diffusible molecules act both locally at the site of tissue damage and infection and at more distant sites. Some inflammatory mediators are activated by the inflammatory process, while others are synthesized and/or released from cellular sources in response to acute inflammation or by other soluble inflammatory mediators. Examples of inflammatory mediators of the inflammatory response include, but are not limited to, plasma proteases, complement, kinins, clotting and fibrinolytic proteins, lipid mediators, prostaglandins, leukotrienes, platelet-activating factor (PAF), peptides and amines, including, but not limited to, histamine, serotonin, and neuropeptides, proinflammatory cytokines, including, but not limited to, interleukin-1-beta (IL-1β), interleukin-4 (IL-4), interleukin-6 (IL-6), interleukin-8 (IL-8), tumor necrosis factor-alpha (TNF-α), interferon-gamma (IF-γ), and interleukin-12 (IL-12).

The term "infuse" and its other grammatical forms as used herein refers to introduction of a fluid other than blood into a vein.

The terms "inhibiting", "inhibit" or "inhibition" are used herein to refer to reducing the amount or rate of a process, to stopping the process entirely, or to decreasing, limiting, or blocking the action or function thereof. Inhibition may include a reduction or decrease of the amount, rate, action function, or process of a substance by at least about 5%, at least about 10%, at least about 15%, at least about 20%, at least about 25%, at least about 30%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, or at least about 99%.

The term "inhibitor" as used herein refers to a second molecule that binds to, contacts or otherwise interferes with activity of a first molecule thereby decreasing the first molecule's activity.

The term "insult," as used herein, refers to damage or harm to a structure or function of the body caused by an outside agent or force, which may be physical or chemical, or an interior condition The term "isolated" is used herein to refer to material, such as, but not limited to, a nucleic acid, peptide, polypeptide, or protein, which is: (1) substantially or essentially free from components that normally accompany or interact with it as found in its naturally occurring environment. The terms "substantially free" or "essentially free" are used herein to refer to considerably or significantly free of, or more than about 95%, 96%, 97%, 98%, 99% or 100% free. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material may be performed on the material within, or removed, from its natural state.

The term "Lineage-positive (Lin+) cells as used herein refers to a mix of all cells expressing mature cell lineage markers. The rest of the cells are lineage-negative (Lin−), meaning they are not stained by the lineage antibodies. All step and progenitor cell activity was identified within the Lin− population.

The term "lymphocyte common antigen" or CD45, means a receptor-linked protein tyrosine phosphatase expressed on all leukocytes.

The terms "major histocompatability complex" and "MHC" is used herein to refer to cell-surface molecules that display a molecular fraction known as an epitope or an antigen and mediate interactions of leukocytes with other leukocyte or body cells. MHCs are encoded by a large gene group and can be organized into three subgroups-class I, class II, and class III. In humans, the MHC gene complex is called HLA ("Human leukocyte antigen"); in mice, it is called H-2 (for "histocompatibility"). Both species have three main MHC class I genes, which are called HLA-A, HLA-B, and HLA-C in humans, and H2-K, H2-D and H2-L in the mouse. These encode the α chain of the respective MHC class I proteins. The other subunit of an MHC class I molecule is β2-microglobulin. The class II region includes the genes for the α and β chains (designated A and B) of the MHC class II molecules HLA-DR, HLA-DP, and HLA-DQ in humans. Also in the MHC class II region are the genes for the TAP1:TAP2 peptide transporter, the PSMB (or LMP) genes that encode proteasome subunits, the genes encoding the DMα and BMβ chains (DMA and DMB), the genes encosing the α and β chains of the DO molecule (DOA and DOB, respectively), and the gene encoding tapasin (TAPBP). The class II genes encode various other proteins with functions in immunity. The DMA and DMB genes encoding the subunits of the HLA-DM molecule that catalyzes peptide binding to MHC class II molecules are related to the MHC class II genes, as are the DOA and DOB genes that encode the subunits of the regulatory HLA-DO molecule. Janeways Immunobiology. 9th ed., GS, Garland Science, Taylor & Francis Group, 2017. pps. 232-233.

The term "matrix metalloproteinases" as used herein refers to a collection of zinc-dependent proteases involved in the breakdown and the remodelling of extracellular matrix components (Guiot, J. et al. Lung (2017) 195(3): 273-280, citing Oikonomidi et al. Curr Med Chem. 2009; 16(10): 1214-1228). For example, the MMP2 gene provides instructions for making matrix metallopeptidase 2. This enzyme is produced in cells throughout the body and becomes part of the extracellular matrix, which is an intricate lattice of proteins and other molecules that forms in the spaces between cells. One of the major known functions of MMP-2 is to cleave type IV collagen, which is a major structural component of basement membranes, the thin, sheet-like structures that separate and support cells as part of the extracellular matrix.

The term "mimic" as used herein refers to a compound or substance that chemically resembles a parent compound or substance and retains at least a degree of the desired function of the parent compound or substance. The term "mimic" may be used interchangeably with "mimetic", which refers to chemicals containing chemical moieties that mimic the function of a peptide. For example, if a peptide contains two charged chemical moieties having functional activity, a mimetic places two charged chemical moeties in a spatial orientation and constrained structure so that the charged chemical function is maintained in three-dimensional space.

The terms "modify" or "modulate" as used herein means to regulate, alter, adapt, or adjust to a certain measure or proportion. The terms "modified" or "modulated" as used herein in the context of cell types refers to changing the form or character of the cell type.

The term "myeloid cells" refers collectively to granulocytes and monocytes, which are differentiated descendants from common progenitors derived from hematopoietic stem cells in the bone marrow. Commitment to either lineage of myeloid cells is controlled by distinct transcription factors followed by terminal differentiation in response to specific colony-stimulating factors and release into the circulation. [Kawamoto, H., Minato, N. Intl J. Biochem. Cell Biol. (2004) 36 (8): 1374-70].

The term "myeloablative therapy" as used herein refers to a therapeutic regimen (such as high dose chemotherapy or high doses of irradiation) used to kill cells that live in the bone marrow, including cancer cells, which lowers the number of normal blood-forming cells in the bone marrow, resulting in fewer red blood cells, white blood cells, and platelets. The term "non-myeloablative" as used herein refers to the conditioning regimen prior to transplant in which limited amounts of chemotherapy are administered in order to prevent rejection of the donor bone marrow stem cells without destroying the recipient's bone marrow.

The term "myelosuppression" as used herein refers to a condition in which bone marrow activity is decreased, resulting in fewer red blood cells, white blood cells, and platelets. When myelosuppression is severe, it is called myeloablation.

Figure 11:
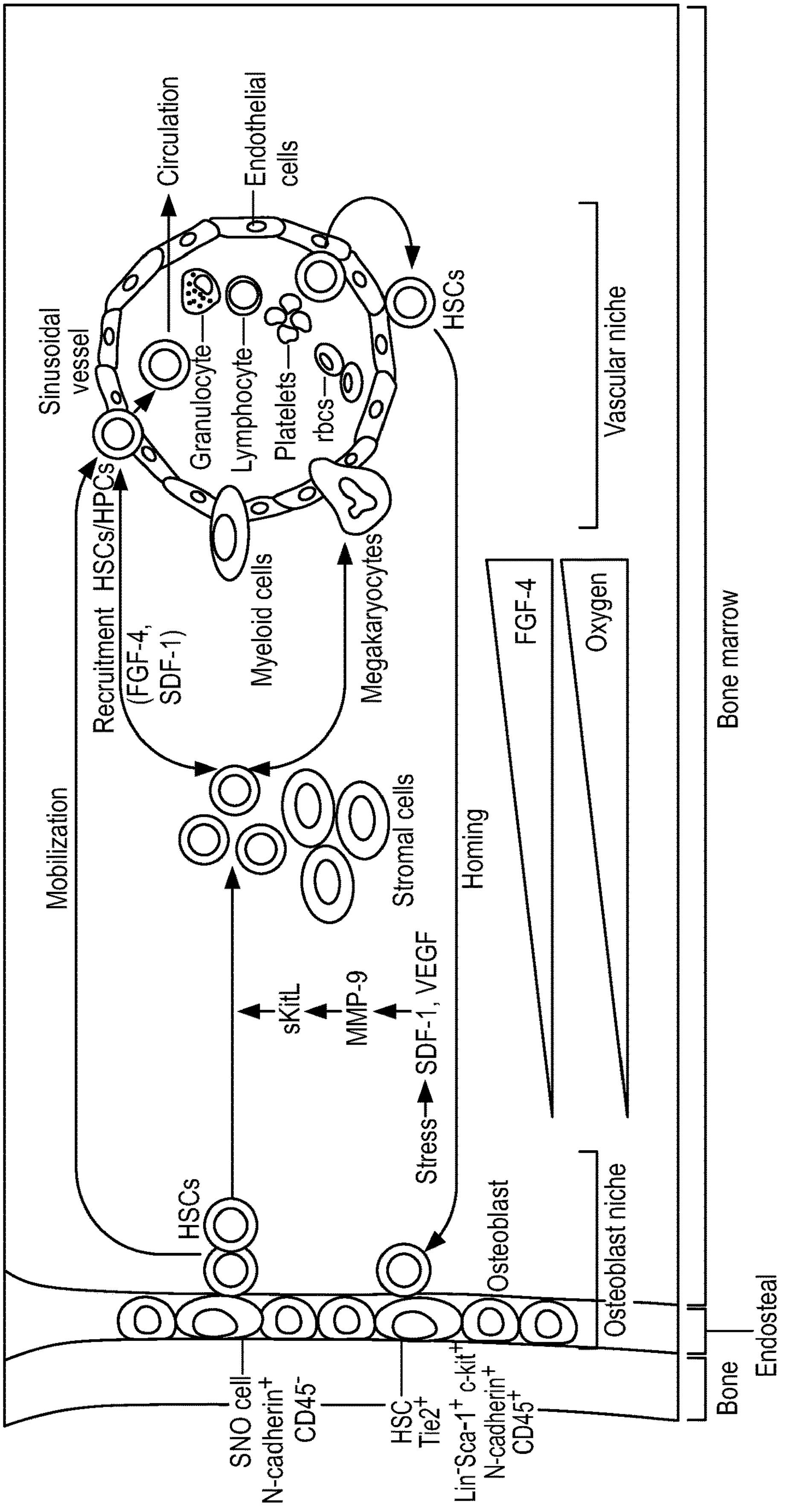
FIG. 11. Under normal physiological conditions, HSCs reside in either the osteoblastic or vascular niche. A portion of HSC daughter cells, in response to changes in levels of SDF-1 in the BM, will leave the niche and begin to mobilize and circulate. HSC homing is the reverse of mobilization, occurring in response to higher levels of SDF-1 in the BM. The osteoblastic niche may provide a quiescent microenvironment for HSC maintenance. In contrast, the vascular niche facilitates HSC transendothelial migration during mobilization or homing and may favor HSC proliferation and further differentiation. The process of recruiting HPCs to the vascular niche may depend on endothelium-derived FGF-4 and SDF-1. Higher FGF-4 and oxygen concentration gradients as the cells progress from the osteoblastic niche to the vascular niche might play a role in recruitment, proliferation, and differentiation of HSCs/HPCs. Under stress such as thrombocytopenia, SDF-1 and VEGF activate MMP-9, which converts membrane-associated Kit ligand into soluble Kit ligand (sKitL) and in turn promotes HSCs entry into the cell cycle, mobilization to the vascular niche, and differentiation. (Taken from Yin, T., & Li, L. (2006). The stem cell niches in bone. The Journal of clinical investigation, 116(5), 1195-1201. doi:10.1172/JCI28568).

The abbreviation "MAPK" as used herein refers to Mitogen-Activated Protein Kinase (MAPK) signaling which activates a three-tiered cascade with MAPK kinase kinases (MAP3K) activating MAPAK kinases (MAP2K) and finally MAPK. MAPKs are protein Ser/Thr kinases that convert extracellular stimuli into a wide range of cellular responses. (Cargnello, M. and Roux, P P, Microbiol. Mol. Biol. Rev. (2011) 75(1): 50-83). The major MAPK pathways involved in inflammatory diseases are extracellular regulating kinase (ERK), p38 MAPK, and c-Jun NH2-terminal kinase (JNK). Upstream kinases include TGFβ-activated kinase-1 (TAK1) and apoptosis signal-regulating kinase-1 (ASKI). Downstream of p38 MAPK is MAPK activated protein kinase 2 (MAPKAPK2 or MK2). (See FIG. 11, taken from Barnes, P J (2016) Pharmacological Revs.68: 788-815).

Different groups of MAPK-activated protein kinases (MAPKAPKs) have been defined downstream of mitogen-activated protein kinases (MAPKs). These enzymes transduce signals to target proteins that are not direct substrates of the MAPKs and, therefore, serve to relay phosphorylation-dependent signaling with MAPK cascades to diverse cellular functions. One of these groups is formed by the three MAPKAPKs: MK2, MK3 (also known as 3pK), and MK5 (also designated PRAK). Mitogen-activated protein kinase-activated protein kinase 2 (also referred to as "MAPKAPK2", "MAPKAP-K2", "MK2") is a kinase of the serine/threonine (Ser/Thr) protein kinase family. MK2 is highly homologous to MK3 (approximately 75% amino acid identity). The kinase domains of MK2 and MK3 are most similar (approximately 35% to 40% identity) to calcium/calmodulin-dependent protein kinase (CaMK), phosphorylase b kinase, and the C-terminal kinase domain (CTKD) of the ribosomal S6 kinase (RSK) isoforms. The MK2 gene encodes two alternatively spliced transcripts of 370 amino acids (MK2A) and 400 amino acids (MK2B). The MK3 gene encodes one transcript of 382 amino acids. The MK2- and MK3 proteins are highly homologous, yet MK2A possesses a shorter C-terminal region. The C-terminus of MK2B contains a functional bipartite nuclear localization sequence (NLS) (Lys-Lys-Xaa-Xaa-Xaa-Xaa-Xaa-Xaa-Xaa-Xaa-Xaa-Xaa-Lys-Arg-Arg-Lys-Lys; SEQ ID NO: 1) that is not present in the shorter MK2A isoform, indicating that alternative splicing determines the cellular localization of the MK2 isoforms. MK3 possesses a similar nuclear localization sequence. The nuclear localization sequence found in both MK2B and MK3 encompasses a D domain (Leu-Leu-Lys-Arg-Arg-Lys-Lys; SEQ ID NO: 2), which was shown to mediate the specific interaction of MK2B and MK3 with p38α and p38β. MK2B and MK3 also possess a functional nuclear export signal (NES) located N-terminal to the NLS and D domain. The NES in MK2B is sufficient to trigger nuclear export following stimulation, a process which may be inhibited by leptomycin B. The sequence N-terminal to the catalytic domain in MK2 and MK3 is proline rich and contains one (MK3) or two (MK2) putative Src homology 3 (SH3) domain-binding sites, which studies have shown, for MK2, to mediate binding to the SH3 domain of c-Abl in vitro. (Cargnello, M. and Roux, P P, Microbiol. Mol. Biol. Rev. (2011) 75(1): 50-83).

MK2B and MK3 are located predominantly in the nucleus of quiescent cells while MK2A is present in the cytoplasm. Both MK2B and MK3 are rapidly exported to the cytoplasm via a chromosome region maintenance protein (CRM1)-dependent mechanism upon stress stimulation. Nuclear export of MK2B appears to be mediated by kinase activation, as phosphomimetic mutation of Thr334 within the activation loop of the kinase enhances the cytoplasmic localization of MK2B. Without being limited by theory, it is thought that MK2B and MK3 may contain a constitutively active nuclear localization signal (NLS) and a phosphorylation-regulated nuclear export signal (NES). (Id.)

MK2 and MK3 appear to be expressed ubiquitously, with increased relative expression in the heart, lungs, kidney, reproductive organs (mammary and testis), skin and skeletal muscle tissues, as well as in immune-related cells such as white blood cells/leukocytes and dendritic cells.

Activation of MK2 and MK3 kinase activity. Various activators of p38α and p38β potently stimulate MK2 and MK3 activity. p38 mediates the in vitro and in vivo phosphorylation of MK2 on four proline-directed sites: Thr25, Thr222, Ser272, and Thr334. Of these sites, only Thr25 is not conserved in MK3. Without being limited by theory, while the function of phosphorylated Thr25 is unknown, its location between the two SH3 domain-binding sites suggests that it may regulate protein-protein interactions. Thr222 in MK2 (Thr201 in MK3) is located in the activation loop of the kinase domain and has been shown to be essential for MK2 and MK3 kinase activity. Thr334 in MK2 (Thr313 in MK3) is located C-terminal to the catalytic domain and is essential for kinase activity. The crystal structure of MK2 has been resolved and, without being limited by theory, suggests that Thr334 phosphorylation may serve as a switch for MK2 nuclear import and export. Phosphorylation of Thr334 also may weaken or interrupt binding of the C terminus of MK2 to the catalytic domain, exposing the NES and promoting nuclear export. (Id.)

Studies have shown that while p38 is capable of activating MK2 and MK3 in the nucleus, experimental evidence suggests that activation and nuclear export of MK2 and MK3 are coupled by a phosphorylation-dependent conformational switch that also dictates p38 stabilization and localization, and the cellular location of p38 itself is controlled by MK2 and possibly MK3. Additional studies have shown that nuclear p38 is exported to the cytoplasm in a complex with MK2 following phosphorylation and activation of MK2. The interaction between p38 and MK2 may be important for p38 stabilization since studies indicate that p38 levels are low in MK2-deficient cells and expression of a catalytically inactive MK2 protein restores p38 levels. Menon, M B, et al., J. Biol. Chem. (2010) 285: 33242-251Z).

Studies using MK2 knockout mice or MK2-deficient cells have shown that MK2 increases the production of inflammatory cytokines, including TNF-α, IL-1, and IL-6, by increasing the rate of translation of its mRNA. No significant reductions in the transcription, processing, and shedding of TNF-α could be detected in MK2-deficient mice. The p38 pathway is known to play an important role in regulating mRNA stability, and MK2 represents a likely target by which p38 mediates this function. Studies utilizing MK2-deficient mice indicated that the catalytic activity of MK2 is necessary for its effects on cytokine production and migration, suggesting that, without being limited by theory, MK2 phosphorylates targets involved in mRNA stability. Consistent with this, MK2 has been shown to bind and/or phosphorylate the heterogeneous nuclear ribonucleoprotein (hnRNP) A0, tristetraprolin (TTP), the poly(A)-binding protein PABP1, and HuR, a ubiquitously expressed member of the ELAV (Embryonic-Lethal Abnormal Visual in *Drosophila melanogaster*) family of RNA-binding protein. These substrates are known to bind or copurify with mRNAs that contain AU-rich elements in the 3' untranslated region, suggesting that MK2 may regulate the stability of AU-rich mRNAs such as TNF-α. It currently is unknown whether MK3 plays a similar role, but LPS treatment of MK2-deficient fibroblasts completely abolished hnRNP A0 phosphorylation, suggesting that MK3 is not able to compensate for the loss of MK2. ((Cargnello, M. and Roux, P P, Microbiol. Mol. Biol. Rev. (2011) 75(1): 50-83))

MK3 participates with MK2 in phosphorylation of the eukaryotic elongation factor 2 (eEF2) kinase. eEF2 kinase phosphorylates and inactivates eEF2. eEF2 activity is critical for the elongation of mRNA during translation, and phosphorylation of eEF2 on Thr56 results in the termination of mRNA translation. MK2 and MK3 phosphorylation of eEF2 kinase on Ser377 suggests that these enzymes may modulate eEF2 kinase activity and thereby regulate mRNA translation elongation. (Roux, P P, Blennis, J., Microbiol. & Molec. Biol. Revs. (2004) 68 (2): 320-344).

Transcriptional Regulation by MK2 and MK3. Nuclear MK2, similar to many MKs, contributes to the phosphorylation of cAMP response element binding (CREB), Activating Transcription Factor-1 (ATF-1), serum response factor (SRF), and transcription factor ER81. Comparison of wild-type and MK2-deficient cells revealed that MK2 is the major SRF kinase induced by stress, suggesting a role for MK2 in the stress-mediated immediate-early response. Both MK2 and MK3 interact with basic helix-loop-helix transcription factor E47 in vivo and phosphorylate E47 in vitro. MK2-mediated phosphorylation of E47 was found to repress the transcriptional activity of E47 and thereby inhibit E47-dependent gene expression, suggesting that MK2 and MK3 may regulate tissue-specific gene expression and cell differentiation. (Id.)

Other Targets of MK2 and MK3. Several other MK2 and MK3 substrates also have been identified, reflective of the diverse functions of MK2 and MK3 in several biological processes. The scaffolding protein 14-3-3ζ is a physiological MK2 substrate. Studies indicate that 14-3-3ζ interacts with a number of components of cell signaling pathways, including protein kinases, phosphatases, and transcription factors. Additional studies have shown that MK2-mediated phosphorylation of 14-3-3ζ on Ser58 compromises its binding activity, suggesting that MK2 may affect the regulation of several signaling molecules normally regulated by 14-3-3. (Cargnello, M. and Roux, P P, Microbiol. Mol. Biol. Rev. (2011) 75(1): 50-83))

Additional studies have shown that MK2 also interacts with and phosphorylates the p16 subunit of the seven-member Arp2 and Arp3 complex (p16-Arc) on Ser77. p16-Arc has roles in regulating the actin cytoskeleton, suggesting that MK2 may be involved in this process. (Id).

Further studies have shown that the small heat shock protein HSP27 (also known as HSPB1), lymphocyte-specific protein LSP-1, and vimentin are phosphorylated by MK2. HSPB1, also known as HSP27, forms large oligomers which may act as molecular chaperones and protect cells from heat shock and oxidative stress. Upon phosphorylation, HSPB1 loses its ability to form large oligomers and is unable to block actin polymerization, suggesting that MK2-mediated phosphorylation of HSPB1 serves a homeostatic function aimed at regulating actin dynamics that otherwise would be destabilized during stress. MK3 also was shown to phosphorylate HSPB1 in vitro and in vivo. (Gurgis, F M S, et al., Molecular Pharmacol. (2014) 85: 345-56); Guay, J. et al., (1997) J. Cell Sci. 110 (pt. 3): 357-68).

It was also shown that HSPB1 binds to polyubiquitin chains and to the 26S proteasome in vitro and in vivo. The ubiquitin-proteasome pathway is involved in the activation of transcription factor NF-kappa B (NF-κB) by degrading its main inhibitor, I kappa B-alpha (IκB-alpha), and it was shown that overexpression of HSPB1 increases NF-kappaB (NF-κB) nuclear relocalization, DNA binding, and transcriptional activity induced by etoposide, TNF-alpha, and Interleukin-1 beta (IL-1β). Additionally, previous studies have suggested that HSPB1, under stress conditions, favors the degradation of ubiquitinated proteins, such as phosphorylated I kappa B-alpha (IκB-alpha); and that this function of HSPB1 accounts for its anti-apoptotic properties through the enhancement of NF-kappa B (NF-κB) activity (Parcellier, A. et al., (2003) Mol Cell Biol, 23(16): 5790-5802).

NF-κB Signaling Pathway.

The abbreviation "NFκB" as used herein refers to which is a proinflammatory transcription factor. It switches on multiple inflammatory genes, including cytokines, chemokines, proteases, and inhibitors of apoptosis, resulting in amplification of the inflammatory response (Barnes, P J, (2016) Pharmacol. Rev. 68: 788-815). The molecular pathways involved in NF-κB activation include several kinases. The classic (canonical) pathway for inflammatory stimulai and infections to activate NF-κB signaling involve the IKK (inhibitor of κB kinase) complex, which is composed of two catalytic sybunits, IKK-α and IKK-β, and a regulatory subunit IKK-γ (or NFκB essential modulator (Id., citing Hayden, M S and Ghosh, S (2012) Genes Dev. 26: 203-234).

Figure 12A:
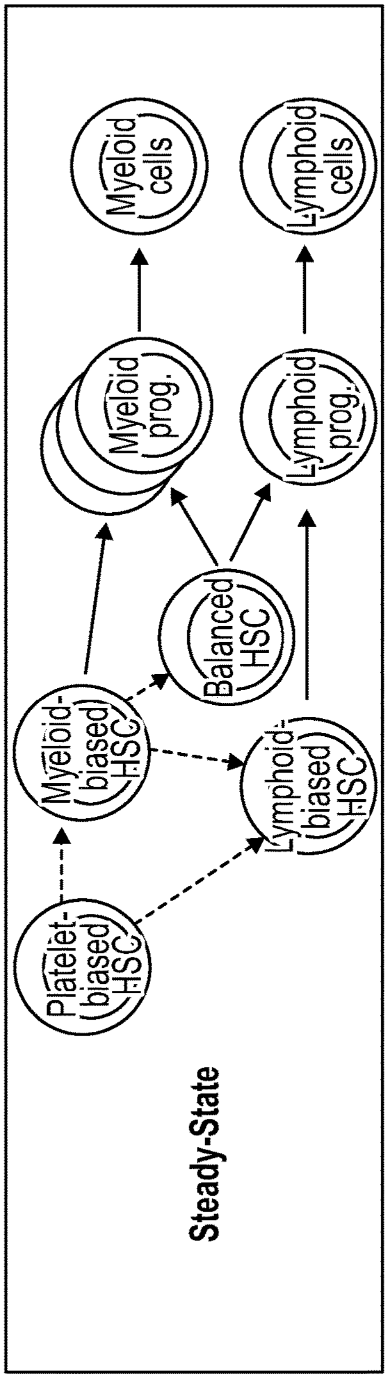
Figure 12B:
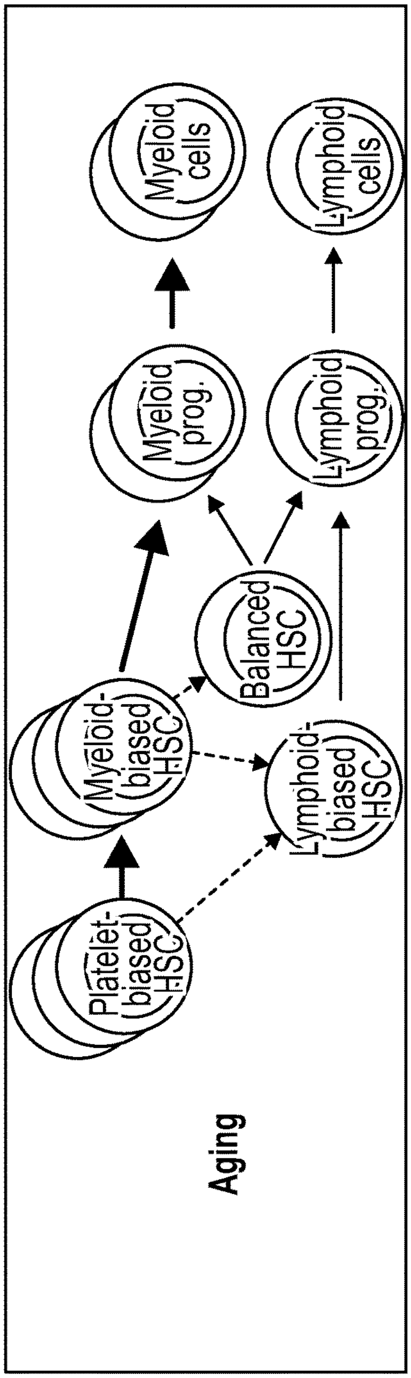
FIG. 12B. Inflammation enhances myeloid lineage production, including myeloid progenitors and mature myeloid cells, leading to myeloid bias in hematopoiesis.
Figure 12C:
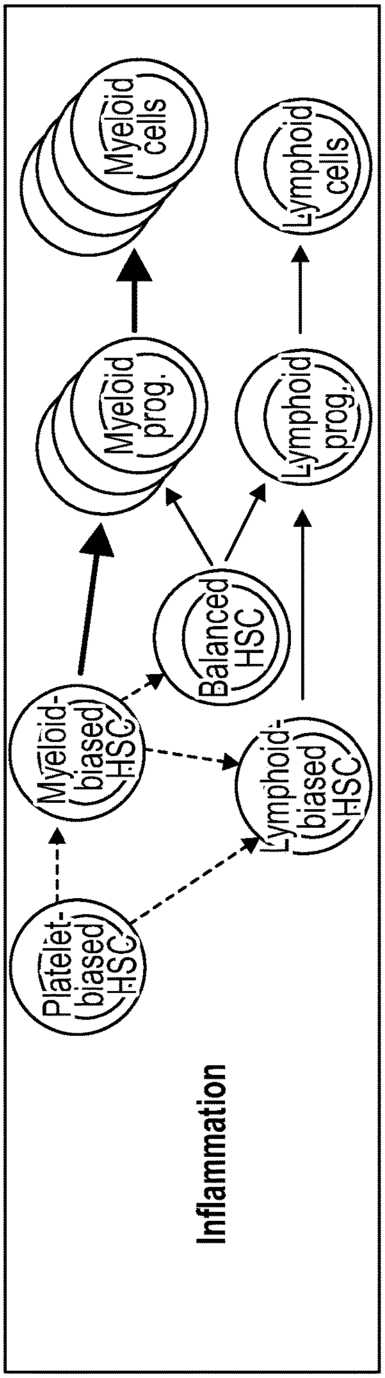
Figure 13:
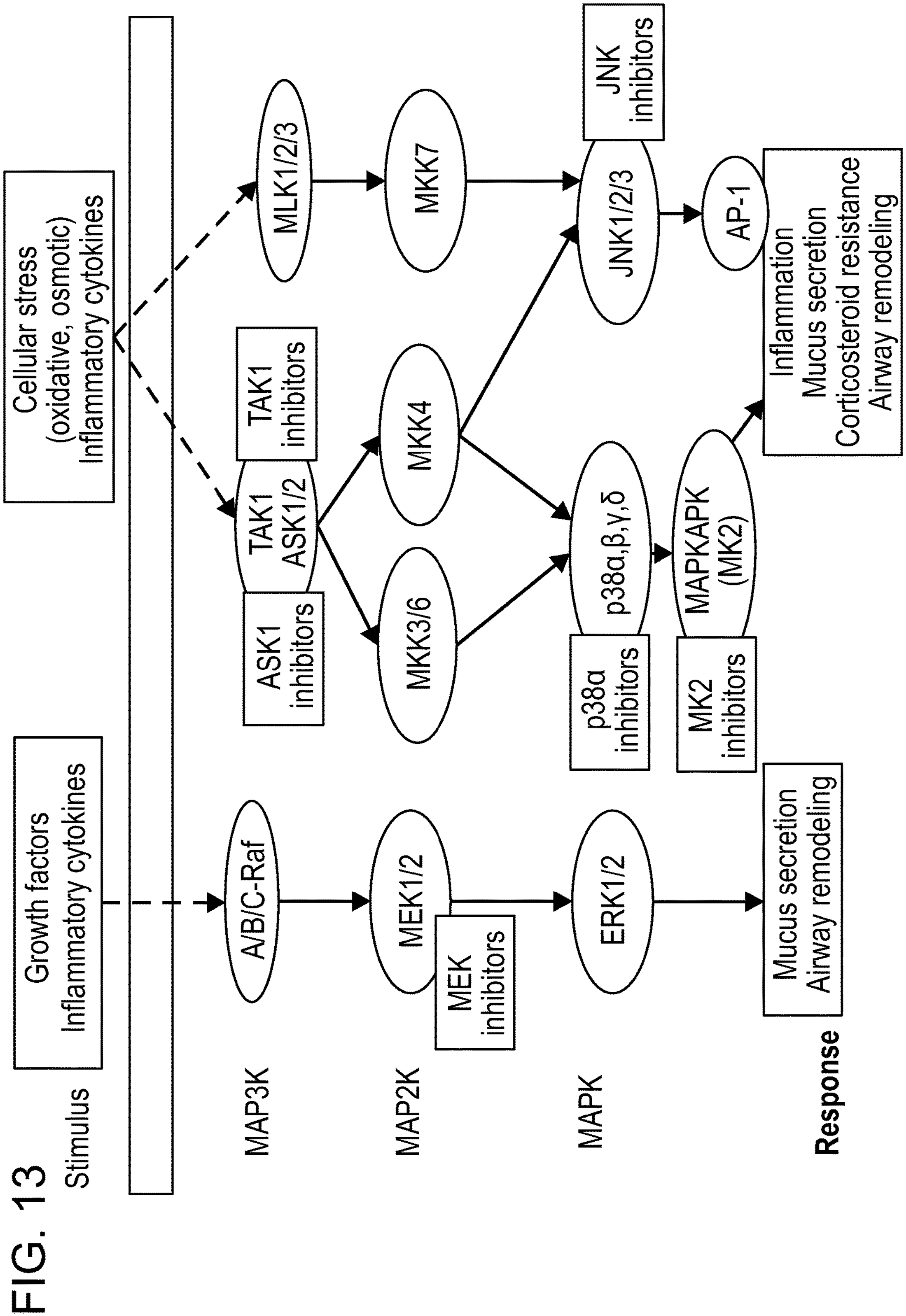
FIG. 13 is a schematic of mitogen-activated protein kinase signaling pathways. MAPK signaling is activated by external stimuli, such as growth factors and cellular stress, and activates a three-tiered cascade with MAPK kinase kinases (MAP3K), activating MAPK kinase (MAP2K) and finally MAPK. The major MAPK pathways involved in inflammatory diseases are ERK (extracellular regulating kinase), p38 MAPK, and JNK (c-Jun $NH_2$-terminal kinase). Downstream of p38 MAPK is MAPK activated protein kinase 2 (MAPKAPK2 or MK2). (Taken from Taken from Barnes, P J (2016) "Kinases as Novel Therapeutic Targets in Asthma and Chronic Obstructive Pulmonary Disease" Pharmacological Revs.68: 788-815).
Figure 14:
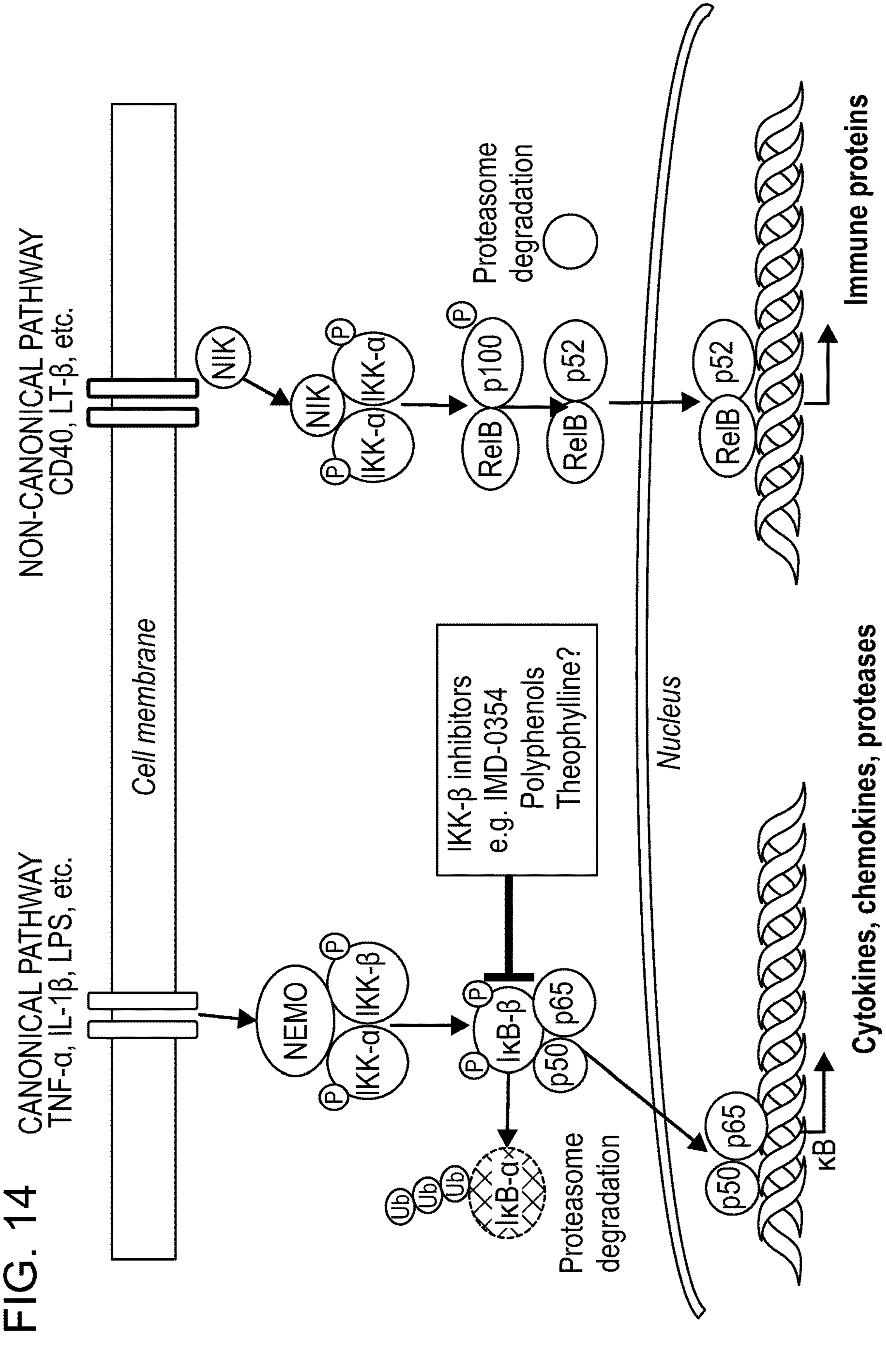
FIG. 14 is a schematic of nuclear factor-κB (NF κB) signaling pathways. The canonical (classic) pathway is activasted by inflammatory cytokines, such as tumor necrosis factor (TNF)-α, interleukin (IL)-1β, and lipopolysaccharide (LPS), leading to phosphorylation of inhibitor of κB kinases (IKKα, IKKβ, which are in a complex with NF-κB essential modulator (NEMO)), resulting in phosphorylation of inhibition of κB (IκB-β), which is ubiquinated and degraded by the proeasom releasing p65 and p50 to translocate to the nucleus, where they bind to a κB DNA recognition sequence, leading to the activation of cytokines, chemokine and protease genes. The noncanonical pathway is activated by CD40 and lymphotoxin (LT)-β, which activate NF-κB-inducing kinase (NIK), resulting in activation IKKα homodimers, which phosphorylate RelB/p100, generating RelB/p50 compleses that translocate to the nucleus and switch on immune genes. (Taken from Barnes, P J (2016) "Kinases as Novel Therapeutic Targets in Asthma and Chronic Obstructive Pulmonary Disease" Pharmacological Revs.68: 788-815).

The IKK complex phosphorylates Nf-KB-bound IκBs, targeting them for degradation by the proteasome and thereby releasing NF-κB dimers that are composed of p65 and p50 subunits, which translocate to the nucleus where they bind to κB recognition sites in the promoter reguions o inflammaoty and immune genes, resulting in their transcriptional activation (FIG. 12). This response depends mainly on the catalytic subunit IKK-β (also known as IKK2), which carries out IκB phosphorylation. The noncanonical (alternative) pathway involves the upstream kinase NF-κB-inducing kinase (NIK) that phosphorylates IKK-α homodimers and releases RelB and processes p100 to p52 in response to certain members of the TNF family, such as lymphotoxin-β (Id., citing Sun, S C. (2012) Immunol. Rev. 246: 125-140). This pathway switches on different gene sets and may mediate different immune functions from the canonical pathway. Dominant-negative IKK-β inhibits most of the proinflammatory functions of NF-κB, whereas inhibiting IKK-α has a role only in response to limited stimuli and in certain cells such as B-lymphocytes. The noncanonical pathway is involved in development of the immune system and in adaptive immune responses. The coactivator molecule CD40, which is expressed on antigen-presenting cells, such as dendritic cells and macrophages, activates the noncanonical pathway when it interacts with CD40L expressed on lymphocytes (Id., citing Lombardi, V et al. (2010) Int. Arch. Allergy Immnol. 151: 179-89).

The term 'NOD-like receptors" or NLRs as used herein refers to a large family of proteins containing a nucleotide-oligomerization domain (NOD) associated with various other domains, and whose general function is the detection of microbes and of cellular stress. The NOD subfamily is a subgroup of NLR proteins that contain a caspase activation and recruitment (CARD) domain, which is used for activation of downstream signaling.

The term "nucleic acid" is used herein to refer to a deoxyribonucleotide or ribonucleotide polymer in either single- or double-stranded form, and, unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleotide" is used herein to refer to a chemical compound that consists of a heterocyclic base, a sugar, and one or more phosphate groups. In the most common nucleotides, the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. Purines include adenine (A), and guanine (G); pyrimidines include cytosine (C), thymine (T), and uracil (U).

The term "osteogenesis" as used herein refers to the process by which osseous or bony tissue is formed. Osseuous tissue is a rigid form of connective tissue normally organized into definite structures, the bones. There are two major modes of osteogenesis, both of which involve the transformation of a preexisting mesenchymal tissue into bone tissue. The direct conversion of mesenchymal tissue into bone is called intramembranous ossification. This process occurs primarily in the bones of the skull. In other cases, mesenchymal cells differentiate into cartilage, which is later replaced by bone. The process by which a cartilage intermediate is formed and replaced by bone cells is called endochondral ossification.

Intramembraneous ossification is the characteristic way in which the flat bones of the scapula, the skull and the turtle shell are formed. In intramembraneous ossification, bones develop sheets of fibrous connective tissue. During intramembranous ossification in the skull, neural crest-derived mesenchymal cells proliferate and condense into compact nodules. Some of these cells develop into capillaries; others change their shape to become osteoblasts, committed bone precursor cells. The osteoblasts secrete a collagen-proteoglycan matrix that is able to bind calcium salts. Through this binding, the prebone (osteoid) matrix becomes calcified. In most cases, osteoblasts are separated from the region of calcification by a layer of the osteoid matrix they secrete. Occasionally, osteoblasts become trapped in the calcified matrix and become osteocytes. As calcification proceeds, bony spicules radiate out from the region where ossification began, the entire region of calcified spicules becomes surrounded by compact mesenchymal cells that form the periosteum, and the cells on the inner surface of the periosteum also become osteoblasts and deposit osteoid matrix parallel to that of the existing spicules. In this manner, many layers of bone are formed.

Intramembraneous ossification is characterized by invasion of capillaries into the mesenchymal zone, and the emergence and differentiation of mesenchymal cells into mature osteoblasts, which constitutively deposit bone matrix leading to the formation of bone spicules, which grow and develop, eventually fusing with other spicules to form trabeculae. As the trabeculae increase in size and number they become interconnected forming woven bone (a disorganized weak structure with a high proportion of osteocytes), which eventually is replaced by more organized, stronger, lamellar bone.

The molecular mechanism of intramembranous ossification involves bone morphogenetic proteins (BMPs) and the activation of a transcription factor called CBFA1. Bone morphogenetic proteins, for example, BMP2, BMP4, and BMP7, from the head epidermis are thought to instruct the neural crest-derived mesenchymal cells to become bone cells directly. BMPs activate the Cbfa1 gene in mesenchymal cells. The CBFA1 transcription factor is known to transform mesenchymal cells into osteoblasts. Studies have shown that the mRNA for mouse CBFA1 is largely restricted to the mesenchymal condensations that form bone, and is limited to the osteoblast lineage. CBFA1 is known to activate the genes for osteocalcin, osteopontin, and other bone-specific extracellular matrix proteins.

Endochondral Ossification (Intracartilaginous Ossification). Endochondral ossification, which involves the in vivo formation of cartilage tissue from aggregated mesenchymal cells, and the subsequent replacement of cartilage tissue by bone, can be divided into five stages. The skeletal components of the vertebral column, the pelvis, and the limbs are first formed of cartilage and later become bone.

First, the mesenchymal cells are committed to become cartilage cells. This commitment is caused by paracrine factors that induce the nearby mesodermal cells to express two transcription factors, Pax1 and Scleraxis. These transcription factors are known to activate cartilage-specific genes. For example, Scleraxis is expressed in the mesenchyme from the sclerotome, in the facial mesenchyme that forms cartilaginous precursors to bone, and in the limb mesenchyme.

During the second phase of endochondral ossification, the committed mesenchyme cells condense into compact nodules and differentiate into chondrocytes (cartilage cells that produce and maintain the cartilaginous matrix, which consists mainly of collagen and proteoglycans). Studies have shown that N-cadherin is important in the initiation of these condensations, and N-CAM is important for maintaining them. In humans, the SOX9 gene, which encodes a DNA-binding protein, is expressed in the precartilaginous condensations.

During the third phase of endochondral ossification, the chondrocytes proliferate rapidly to form the model for bone. As they divide, the chondrocytes secrete a cartilage-specific extracellular matrix.

In the fourth phase, the chondrocytes stop dividing and increase their volume dramatically, becoming hypertrophic chondrocytes. These large chondrocytes alter the matrix they produce (by adding collagen X and more fibronectin) to enable it to become mineralized by calcium carbonate.

The fifth phase involves the invasion of the cartilage model by blood vessels. The hypertrophic chondrocytes die by apoptosis, and this space becomes bone marrow. As the cartilage cells die, a group of cells that have surrounded the cartilage model differentiate into osteoblasts, which begin forming bone matrix on the partially degraded cartilage. Eventually, all the cartilage is replaced by bone. Thus, the cartilage tissue serves as a model for the bone that follows.

The replacement of chondrocytes by bone cells is dependent on the mineralization of the extracellular matrix. A number of events lead to the hypertrophy and mineralization of the chondrocytes, including an initial switch from aerobic to anaerobic respiration, which alters their cell metabolism and mitochondrial energy potential. Hypertrophic chondrocytes secrete numerous small membrane-bound vesicles into the extracellular matrix. These vesicles contain enzymes that are active in the generation of calcium and phosphate ions and initiate the mineralization process within the cartilaginous matrix. The hypertrophic chondrocytes, their metabolism and mitochondrial membranes altered, then die by apoptosis.

In the long bones of many mammals (including humans), endochondral ossification spreads outward in both directions from the center of the bone. As the ossification front nears the ends of the cartilage model, the chondrocytes near the ossification front proliferate prior to undergoing hypertrophy, pushing out the cartilaginous ends of the bone. The cartilaginous areas at the ends of the long bones are called epiphyseal growth plates. These plates contain three regions: a region of chondrocyte proliferation, a region of mature chondrocytes, and a region of hypertrophic chondrocytes. As the inner cartilage hypertrophies and the ossification front extends farther outward, the remaining cartilage in the epiphyseal growth plate proliferates. As long as the epiphyseal growth plates are able to produce chondrocytes, the bone continues to grow.

The term "osteopenia" as used herein refers to a reduced bone mass of less severity than osteoporosis. It is defined by bone densitometry as a T score of −1 to −2.5.

The term "osteoporosis" as used herein refers to a decrease in bone density in which the bones become more porous and fragile, with an increased risk of fracture. It is defined as a T score of ≤−2.5.

The term "organ" as used herein refers to a differentiated structure consisting of cells and tissues and performing some specific function in an organism.

As used herein, the term "paracrine signaling" refers to short range cell-cell communication via secreted signal molecules that act on adjacent cells.

The term "pathogen associated molecular patterns" (PAMPs) as used herein refer to molecules specifically associated with groups of pathogens that are recognized by cells of the innate immune system.

The terms "polypeptide" and "protein" are used herein in their broadest sense to refer to a sequence of subunit amino acids, amino acid analogs, or peptidomimetics. The subunits are linked by peptide bonds, except where noted. These terms also apply to amino acid polymers in which one or more amino acid residue is an artificial chemical analogue of a corresponding naturally occurring amino acid, as well as to naturally occurring amino acid polymers. The terms also are inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides may not be entirely linear. For instance, polypeptides may be branched as a result of ubiquitination, or they may be circular, with or without branching, generally as a result of posttranslational events, whether by natural processing or by events brought about by human manipulation, which do not occur naturally. Circular, branched and branched circular polypeptides may be synthesized by entirely synthetic methods The term "pharmaceutical composition" is used herein to refer to a composition that is employed to prevent, reduce in intensity, cure or otherwise treat a target condition or disease. The terms "formulation" and "composition" are used interchangeably herein to refer to a product of the described invention that comprises all active and inert ingredients.

The term "pharmaceutically acceptable," is used to refer to a carrier, diluent or excipient being compatible with the other ingredients of the formulation or composition (meaning capable of being combined with each other in a manner such that there is no interaction that would substantially reduce the efficacy of the composition under ordinary use conditions) and not deleterious to the recipient thereof. The carrier must be of sufficiently high purity and of sufficiently low toxicity to render it suitable for administration to the subject being treated. The carrier further should maintain the stability and bioavailability of an active agent. For example, the term "pharmaceutically acceptable" can mean approved by a regulatory agency of the Federal or a state government or listed in the U.S. Pharmacopeia or other generally recognized pharmacopeia for use.

The term "progenitor cell" as used herein refers to an immature cell in the bone marrow that may be isolated by growing suspensions of marrow cells in culture dishes with added growth factors. Progenitor cells mature into precursor cells that mature into blood cells. Progenitor cells are referred to as colony-forming units (CFU) or colony-forming cells (CFC). The specific lineage of a progenitor cell is indicated by a suffix, such as, but not limited to, CFU-E (erythrocytic), CFU-GM (granulocytic/macrophage), and CFU-GEMM (pluripotent hematopoietic progenitor).

The term "purification" and its various grammatical forms as used herein refers to the process of isolating or freeing from foreign, extraneous, or objectionable elements.

The term "quiescence" as used herein is a property that often characterizes tissue-resident stem cells and allows them to act as a dormant reserve that can replenish tissues during homeostasis. Quiescence is thought to be a fundamental characteristic of hematopoietic stem cells (HSCs), which possess multi-lineage differentiation and self-renewal potential, and are able to give rise to all cell types within the blood lineage (Nakamura-Ischizu, A. et al., Development (2014) 141: 4656-66, citing Pietras, E M. et al., J. Cell Biol. (2011) 195: 709-720). Precise regulation of the cell cycle of quiescent HSCs is required for the effective production of mature hematopoietic cells with minimal stem cell exhaustion (Id., citing Orford, K W and Scadden, D T, Nature Rev. Genet.(2008) 9: 115-128). Since proliferating cells are more susceptible to genetic mutations and become senescent once their turnovers reach their maximum, a limit known as the Hayflick limit (Id., citing Hayflick, L. and Moorhead, P S, Expl Cell Res., (1961) 25: 585-621), quiescence supposedly protects HSCs from malignant transformation and malfunction (Id., citing Wang, J C Y and Dick, J E, Trends Cell Biol. (2005) 15: 494-501). Both cell-intrinsic and -extrinsic signals induced in response to various stresses, such as inflammation or blood loss, permit quiescent HSCs to re-enter the cell cycle, proliferate and differentiate (Id., citing Morrison, S J and Weissman, IL Immunity (1994) 1: 661-673; Suda, T. et al., Proc. Nat. Acad. Sci. USA (1983) 80: 6689-93).

The term "reference sequence" refers to a sequence used as a basis for sequence comparison. A reference sequence may be a subset or the entirety of a specified sequence.

The term "relapse" as used herein refers to the reappearance of a disease after a period of remission.

The term "remission" as used herein refers to the decrease or disappearance of a disease and its symptoms.

The term "splice-site variant" as used herein refers to a genetic alteration in the DNA sequence that occurs at the boundary of an exon and an intron (splice site) that can result in an altered protein-coding sequence.

"The term "steady state" as used herein refers to a state of dynamic equilibrium, where rate of loss quals the rate of gain.

The term "stem cells" as used herein refers to undifferentiated cells having high proliferative potential with the ability to self-renew that can generate daughter cells that can undergo terminal differentiation into more than one distinct cell phenotype. Stem cells are distinguished from other cell types by two characteristics. First, they are unspecialized cells capable of renewing themselves through cell division, sometimes after long periods of inactivity. Second, under certain physiologic or experimental conditions, they can be induced to become tissue- or organ-specific cells with special functions. In some organs, such as the gut and bone marrow, stem cells regularly divide to repair and replace worn out or damaged tissues. In other organs, however, such as the pancreas and the heart, stem cells only divide under special conditions.

Adult (somatic) stem cells are undifferentiated cells found among differentiated cells in a tissue or organ. Their primary role in vivo is to maintain and repair the tissue in which they are found. Adult stem cells have been identified in many organs and tissues, including brain, bone marrow, peripheral blood, blood vessels, skeletal muscles, skin, teeth, gastrointestinal tract, liver, ovarian epithelium, and testis. Adult stem cells are thought to reside in a specific area of each tissue, known as a stem cell niche, where they may remain quiescent (non-dividing) for long periods of time until they are activated by a normal need for more cells to maintain tissue, or by disease or tissue injury.

Bone Marrow Stem Cells. The term "bone marrow stem cells" as used herein refers to stem cells derived from the bone marrow and include HSCs and MSCs. The mononuclear fraction of bone marrow contains stromal cells, hematopoietic precursors, and endothelial precursors.

Peripheral Blood Stem Cells. The term "peripheral blood stem cells" as used herein refers to stem cells derived from peripheral blood. Peripheral blood houses adult (somatic) stem cells which are undifferentiated cells found among differentiated cells in a tissue or organ. Examples of peripheral blood stem cells include, but not limited to, hematopoietic stem cells, and mesenchymal stem cells [Dzierzak E. et al., "Of lineage and legacy: the development of mammalian hematopoietic stem cells", Nature Immunol., Vol. 9(2): 129-136, (2008)].

Hematopoietic Stem Cells. As used herein, the term "hematopoietic stem cells" (also known as the colony-forming unit of the myeloid and lymphoid cells (CFU-M,L), or $CD34^+$ cells) are rare pluripotent cells within the blood-forming organs that are responsible for the continued production of blood cells during life [Li Y. et al., "Inflammatory signaling regulates embryonic hematopoietic stem and progenitor cell production", Genes Dev., Vol. 28(23): 2596-2612, (2014)]. HSCs can generate a variety of cell types, including erythrocytes, neutrophils, basophils, eosinophils, platelets, mast cells, monocytes, tissue macrophages, osteoclasts, and the T and B lymphocytes. The regulation of hematopoietic stem cells is a complex process involving self-renewal, survival and proliferation, lineage commitment and differentiation and is coordinated by diverse mechanisms including intrinsic cellular programming and external stimuli, such as adhesive interactions with the micro-environmental stroma and the actions of cytokines.

Different paracrine factors (cytokines) are important in causing hematopoietic stem cells to differentiate along particular pathways. The cytokines can be made by several cell types, but they are collected and concentrated by the extracellular matrix of the stromal (mesenchymal) cells at the sites of hematopoiesis. For example, granulocyte-macrophage colony-stimulating factor (GM-CSF) and the multilineage growth factor IL-3 both bind to the heparan sulfate glycosaminoglycan of the bone marrow stroma. The extracellular matrix then presents these factors to the stem cells in concentrations high enough to bind to their receptors [Alvarez S. et al., "GM-CSF and IL-3 activities in schistosomal liver granulomas are controlled by stroma-associated heparan sulfate proteoglycans", J Leukoc Biol., Vol. 59(3): 435-441, (1996)].

Mesenchymal Stem Cells. Mesenchymal stem cells (MSCs) (also known as bone marrow stromal stem cells or skeletal stem cells) are non-blood adult stem cells found in a variety of tissues. They are characterized by their spindle-shape morphologically; by the expression of specific markers on their cell surface; and by their ability, under appropriate conditions, to differentiates along a minimum of three lineages (osteogenic, chondrogenic, and adipogenic) [Najar M. et al., "Mesenchymal stromal cells and immunomodulation: A gathering of regulatory immune cells", Cytotherapy, Vol. 18(2): 160-171, (2016)]. No single marker that definitely delineates MSCs in vivo has been identified due to the lack of consensus regarding the MSC phenotype, but it generally is considered that MSCs are positive for cell surface markers CD105, CD166, CD90, and CD44 and that MSCs are negative for typical hematopoietic antigens, such as CD45, CD34, and CD14. As for the differentiation potential of MSCs, studies have reported that populations of bone marrow-derived MSCs have the capacity to develop into terminally differentiated mesenchymal phenotypes both in vitro and in vivo, including bone, cartilage, tendon, muscle, adipose tissue, and hematopoietic supporting stroma. Studies using transgenic and knockout mice and human musculoskeletal disorders have reported that MSC differentiate into multiple lineages during embryonic development and adult homeostasis [Najar M. et al., "Mesenchymal stromal cells and immunomodulation: A gathering of regulatory immune cells", Cytotherapy, Vol. 18(2): 160-171, (2016)].

Analysis of the in vitro differentiation of MSCs under appropriate conditions that recapitulate the in vivo process have led to the identification of various factors essential for stem cell commitment. Among them, secreted molecules and their receptors (e.g., transforming growth factor-(3), extracellular matrix molecules (e.g., collagens and proteoglycans), the actin cytoskeleton, and intracellular transcription factors (e.g., Cbfa1/Runx2, PPARy, Sox9, and MEF2) have been shown to play important roles in driving the commitment of multipotent MSCs into specific lineages, and maintaining their differentiated phenotypes [Davis L. A. et al., "Mesodermal fate decisions of a stem cell: the Wnt switch", Cell Mol Life Sci., Vol. 65(17): 2568-2574, (2008)].

The term "stem cell niche" as used herein refers to the specific area of each tissue within which adult stem cells reside, where they may remain quiescent (non-dividing) for long periods of time until they are activated by a normal need for more cells to maintain tissue, or by disease or tissue injury. Cells of the stem-cell niche interact with the stem cells to maintain them or promote their differentiation.

The term "stem cell rescue" or "rescue transplant" as used herein refers to a method of replacing blood-forming stem cells that were destroyed by treatment with high doses of anticancer drugs or radiation therapy. It is usually done using the patient's own stem cells that were saved before treatment. The stem cells help the bone marrow recover and make healthy blood cells. A stem cell rescue may allow more chemotherapy or radiation therapy to be given so that more cancer cells are killed.

As used herein, the phrase "subject in need" of treatment for a particular condition is a subject having that condition, diagnosed as having that condition, or at risk of developing that condition. According to some embodiments, the phrase "subject in need" of such treatment also is used to refer to a patient who (i) will be administered a composition of the described invention; (ii) is receiving a composition of the described invention; or (iii) has received at least one a composition of the described invention, unless the context and usage of the phrase indicates otherwise.

The term "suspension" as used herein refers to a dispersion (mixture) in which a finely-divided species is combined with another species, with the former being so finely divided and mixed that it doesn't rapidly settle out.

The term "target" as used herein refers to a biological entity, such as, for example, but not limited to, a protein, cell, organ, or nucleic acid, whose activity can be modified by an external stimulus. Depending upon the nature of the stimulus, there may be no direct change in the target, or a conformational change in the target may be induced.

As used herein, the term "therapeutic agent" or "active agent" refers to refers to the ingredient, component or constituent of the compositions of the described invention responsible for the intended therapeutic effect.

The term "therapeutic component" as used herein refers to a therapeutically effective dosage (i.e., dose and frequency of administration) that eliminates, reduces, or prevents the progression of a particular disease manifestation in a percentage of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest, reduction, or elimination of the progression of a disease manifestation.

As used herein, the term "tissue" refers to a collection of similar cells and the intercellular substances surrounding them. For example, connective tissue is the supporting or framework tissue of the body formed of fibrous and ground substance with numerous cells of various kinds. It is derived from the mesenchyme, and this in turn from the mesoderm. The varieties of connective tissue include, without limitation, areolar or loose; adipose; sense, regular or irregular, white fibrous; elastic; mucous; lymphoid tissue; cartilage and bone.

The term "toll-like receptor" as used herein refers to innate receptors on macrophages, dendritic cells, and some other cells that recognize pathogens and their products. Recognition stimulates the receptor-bearing cells to produce cytokines that help initiate immunr responses.

The term "transplantation" and its various grammatical forms as used herein refers to a surgical procedure in which tissue or an organ is transferred from one area of a person's body to another area, or from one person (the donor) to another person (the recipient).

The terms "treat," "treated," or "treating" as used herein refers to both therapeutic treatment and/or prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

The term "vasculogenesis" as used herein refers to the process of new blood vessel formaton.

The term "volume/volume percentage is a measure of the concentration of a substance in a solution. It is expressed as the ratio of the volume of the solute to the total volume of the solution multiplied by 100. Volume percent (vol/vol % or v/v %) should be used whenever a solution is prepared by mixing pure liquid solutions.

The abbreviation "WBM" stands for whole bone marrow.

The term "weight by weight percentage" or wt/wt % is used herein to refer to the ratio of weight of a solute to the total weight of the solution.

As used herein, the terms "wild type," "naturally occurring," or grammatical equivalents thereof, are meant to refer to an amino acid sequence or a nucleotide sequence that is found in nature and includes allelic variations; that is, an amino acid sequence or a nucleotide sequence that usually has not been intentionally modified. Accordingly, the term "non-naturally occurring," "synthetic," "recombinant," or grammatical equivalents thereof, are used interchangeably to refer to an amino acid sequence or a nucleotide sequence that is not found in nature; that is, an amino acid sequence or a nucleotide sequence that usually has been intentionally modified. It is understood that once a recombinant nucleic acid is made and reintroduced into a host cell or organism, it will replicate non-recombinantly, i.e., using the in vivo cellular machinery of the host cell rather than in vitro manipulations, however, such nucleic acids, once produced recombinantly, although subsequently replicated non-recombinantly, are still considered recombinant for the purpose of the described invention.

Methods

According to one aspect, the described invention provides a method for improving hematopoietic reconstitution of BM after a myelosuppressive insult comprising inhibiting endothelial cell-specific NF-κB within the bone marrow.

According to some embodiments, the myelosuppressive insult comprises sublethal radiation, chemotherapy, or both. According to some embodiments, the myelosuppressive insult comprises sublethal irradiation. According to some embodiments, the myelosuppressive insult comprises total body irradiation. According to some embodiments, the myelosuppressive insult comprises total lymphoid irradiation. According to some embodiments, the myelosuppressive insult comprises exposure to radiation. According to some embodiments, radiation can be derived from any suitable source, such as opposite Cobalt-60 sources.

According to some embodiments, the myelosuppressive insult is myeloablative.

According to some embodiments, the myelosuppressive insult comprises about 1 joule of energy aborbed per kilogram of matter (Gy) to about 30 Gy. According to some embodiments, the myelosuppressive insult comprises about 1 Gy, about 2 Gy, about 3 Gy, about 4 Gy, about 5 Gy, about 6 Gy, about 7 Gy, about 8 Gy, about 9 Gy, about 10 Gy, about 11 Gy, about 12 Gy, about 13 Gy, about 14 Gy, about 15 Gy, about 16 Gy, about 17 Gy, about 18 Gy, about 19 Gy, about 20 Gy, about 21 Gy, about 22 Gy, about 23 Gy, about 24 Gy, about 25 Gy, about 26 Gy, about 27 Gy, about 28 Gy, about 29 Gy, about 30 Gy. According to some embodiments, the myelosuppressive insult comprises about 1 Gy to about 16 Gy.

According to some embodiments, the myelosuppressive insult comprises single dose total body irradiation. According to some embodiments, the myelosuppressive insult comprises fractionated dose total body irradiation. According to some embodiments, the myelosuppressive insult comprising irradiation is delivered over the course of 1 day, 2 days, 3 days, 4 days, 5, days, 6 days, 7, days, 8 days, 9 days, 10 days, 11 days, 12 days, 13 days, or 14 days. According to some embodiments, the myelosuppressive insult comprising irradiation is delivered over the course of 2 days to about 6 days. According to some embodiments, the myelosuppressive insult results after the final delivery of the radiation.

According to some embodiments when the myelosuppressive insult comprises irradiation, the irradiation dose is about 1 Gy to about 16 Gy. According to some embodiments when the myelosuppressive insult comprises irradiation, the total irradiation dosage is about 1 Gy to about 16 Gy. According to some embodiments wherein the myelosuppressive insult comprises irradiation, the total irradiation dosage is about 1 Gy to about 16 Gy delivered over the course of about 2 days to about 6 days. According to some embodiments, irradiation further comprises lung shielding.

According to some embodiments, the myelosuppressive insult comprises chemotherapy. According to some embodiments, the myelosuppressive insult comprises high-dose chemotherapy. According to some embodiments, the myelosuppressive insult comprises chemotherapy with alkylating agents. According to some embodiments, the myelosuppressive insult comprises high-dose chemotherapy with alkylating agents.

According to some embodiments, after a myelosuppressive insult, the bone marrow of the subject comprises inflammation in an HSC niche. According to some embodiments, the myelosuppressive insult comprises myeloablation. According to some embodiments, the myelosuppressive insult results in the inability for autologous hematologic recovery.

According to some embodiments, NF-κB inhibition in endothelial cells within the BM is effective to suppress downstream NF-κB signaling in the bone marrow (BM). According to some embodiments, the NF-κB inhibition in endothelial cells within the BM is effective to downregulate target NFκB genes within the BM. According to some embodiments, the NF-κB inhibition in endothelial cells within the BM is effective to suppress downstream NF-κB signaling in the BM and to downregulate target NFκB genes in endothelial cells in the BM. According to some embodiments, the NF-κB inhibition in endothelial cells within the BM protects the hematopoietic compartment and enhances recovery following myelosuppressive injury.

According to some embodiments, the hematopoietic cell population in the bone marrow comprises bone marrow endothelial cells (BMECs), hematopoietic stem cells (HSCs) and stromal cells (MSCs).

According to some embodiments, BMECs comprise bone marrow (BM) stromal cells, BM Lepr+ cells, and BM osteoblasts. According to some embodiments, the immunophenotype of BMECs is CD45− Ter119− CD31+ VEcadherin+. According to some embodiments, BM stromal cells comprise BM Lepr+ and BM osteoblastic stromal subsets. According to some embodiments, the immunophenotype of BM stromal cells is CD45− Ter119− CD31− VEcadherin−. According to some embodiments, the immunophenotype of BM Lepr+ cells within the BM stromal population is CD45- Ter119− CD31− Lepr+. According to some embodiments, the immunophenotype of BM osteoblasts is CD45− Ter19− CD31− SCA1− CD51+.

According to some embodiments, hematopoietic stem and progenitor cells (HSPCs) comprise hematopoietic stem cells (HSCs) and hematopoietic progenitor cells (HPCs). According to some embodiments the immunophenotype of HSCs comprises Lineage-CD48-CD150bright.

According to some embodiments, the immunophenotype of HSCs is Lineage-(Ter119/CD11b/GR1/B220/CD3)− CD41−cKIT+SCA1+CD48−CD150+.

According to some embodiments, the immunophenotype of KLS HSPCs is Lin− cKIT+SCA1+. According to some embodiments, the KLS compartment is enriched in HSCs.

According to some embodiments, markers of mature hematopoietic stem cell lineages include B220, CD4, CD8, Gr-1, Mac-1, and Ter-119.

According to some embodiments, the BMECs impact BM function and hematopoiesis during inflammatory stress within the BM. According to some embodiments, endothelial MAPK can be constituitively activated in adult endothelium. According to some embodiments, BM endothelial niche activity is reduced by chronic activation of endothelial MAPK. According to some embodiments, reduced BM endothelial niche activity leads to defects in steady state hematopoiesis and HSC function.

According to some embodiments, chronic activation of endothelial MAPK leads to an inflammatory stress response that disrupts the endothelial network. According to some embodiments, the inflammatory stress response comprises one or more of increased vascular dilatation, decreased vascular integrity comprising increased BM vascular leakiness, and increased levels of inflammatory mediators including sICAM, VCAM and IL1b. According to some embodiments, chronic activation of endothelial MAPK leads to inflammation via downstream activation of canonical NF-κB signaling. According to some embodiments, downstream activation of canonical NF-κB signaling comprises one or more of an increase in p65 phosphorylation within the endothelium with no significant changes in total iκBα levels, an increase in MEK1DD driven ERK1/2 phosphorylation, or an increase in level of expression of NF-κB signaling targets including pro-inflammatory cytokines and chemokines IL-1a, IL-1b, Cxcl1, Cxcl3, Ccl12, and Ccl22.

According to some embodiments, constituitive activation of endothelial MAPK decreases bone marrow cellularity and decreases the frequency and absolute numbers of hematopoietic stem cells (HSCs), hematopoietic stem and progenitor cells (HSPCs) comprising KLS cells, multipotent progenitors (MPPs), and hematopoietic progenitor cell subsets (HPC-1 and HPC-2) as compared to littermate controls. According to some embodiments, the immunophenotype of the MMPs is cKIT+Lin−SCA1+CD150−CD48−. According to some embodiments the immunophenotype of HPC-1 is cKIT+Lin−SCA1+CD150−CD48+. According to some embodiments, the immunophenotype of HPC-2 is cKIT+ Lin−SCA1+CD150+CD48+

According to some embodiments, BM endothelial cells comprising constitutively activated endothelial MAPK comprise a decreased long-term HSC engraftment potential compared to controls. According to some embodiments, the HSCs and HSPCs from animals with constitutively activated endothelial MAPK comprise a loss of quiescence and increased apoptosis compared to littermate controls.

According to some embodiments, inhibition of endothelial NF-κB signaling is effective to restore BM vascular integrity in chronically MAPK activated endothelium. According to some embodiments, increased expression of IkB-SS suppresses p65 nuclear translocation in chronically activated MAPK endothelium.

According to some embodiments, restoration of BM endothelial niche integrity in chronically activated MAPK epithelium suppressed by IkBSS effects functional recovery of HSCs and the hematopoietic system. According to some embodiment, the functional recovery of HSCs comprises restoration of BM cellularity. According to some embodiment, the functional recovery of HSCs comprises restoration of BM cellularity and frequency of phenotypic HSCs and HSPCs.

According to some embodiments, functional recovery of HSCs comprising recovery of long-term engraftment potential and a reversal of myeloid-biased differentiation. According to some embodiment, the functional recovery of HSCs comprises restoration of BM cellularity and frequency of phenotypic HSCs and HSPCs, recovery of long-term engraftment potential, and a reversal of myeloid-biased differentiation.

According to some embodiments, sublethal myelosuppressive injury followed by post-myelosuppressive hematopoietic reconstitution with endothelium comprising downstream NF-κB activation delays hematopoietic recovery. According to some embodiment, the analysis of hematopoietic recovery is by peripheral blood analysis. According to some embodiments, endothelial-specific inhibition of NF-κB protects the hematopoietic compartment and enhances recovery following myelosuppressive injury. According to some embodiments, the endothelial-specific inhibition of NFκB is by IkBSS. According to some embodiments, the analysis is by peripheral blood analysis.

According to some embodiments, the vascular niche within the BM and HSCs plays a role in maintaining lineage-committed hematopoietic progenitors that sustains steady state peripheral blood output.

According to some embodiments, subjects with chronically activated endothelial MAPK with activated downstream NF-κB signaling in the BM and spleen display a decrease in immunophenotypically defined BM multipotent progenitors (MPPs), common lymphoid progenitors (CLPs), common myeloid progenitors (CMPs), granulocyte/macrophage progenitors (GMPs), megakaryocyte/erythroid progenitors (MEPs) and B cell progenitor subsets; and an increased percentage of CD11b+GR1+ cells within CD45+ BM cells. According to some embodiments, B cell progenitor subsets comprise SIgM-B220+ B cells, Pre-Pro B cells, Pro B cells and Pre B cells. According to some embodiments, IkB suppression of endothelial NFκB signaling within the bone marrow restores hematopoietic defects in BM and peripheral blood, i.e., increases immunophenotypically defined BM multipotent progenitors (MPPs), common lymphoid progrenitors (CLPs), common myeloid progenitors (CMPs), granulocyte/macrophage progenitors (GMPs), megakaryocyte/erythroid progenitors (MEPs) and B cell progenitor subsets; and a reduced percentage of CD11b+ GR1+ cells within CD45+ BM cells.

According to some embodiments, downstream endothelial NF-κB activation induces a generalized inflammatory stress response within the BM microenvironment. According to some embodiments, downstream endothelial NF-κB activation induces a generalized inflammatory stress response within the BM microenvironment in subjects with chronically activated endothelial MAPK within the bone marrow. According to some embodiments, the generalized inflammatory stress response comprises upregulation of target NFκB genes in hematopoietic cells (CD45+), stromal cells (CD45−Ter119−CD31−VEcadherin−) and unfractionated whole bone marrow cells. According to some embodiments, the generalized inflammatory stress response comprises one or more of: an increase in hypoxia and ROS levels with a loss of quiescence and increased apoptosis in HPSCs, a loss of cell cycling and increased apoptosis of BM stromal cells; a decrease in number of BM stromal cells, a loss of quiescence and an increase in numbers of BM endothelial cells. According to some embodiments, suppression of endothelial NF-κB signaling restores the defects to HSPCs and BM niche cells comprising endothelium and BM stromal subsets, induced by inflammation.

According to some embodiments, endothelial MAPK activation followed by downstream endothelial NF-κB activation caused an increased expression of NF-κB regulated target genes in Lepr+ cells and osteoblasts. According to some embodiments, the increased expression of NF-κB regulated target genes in Lepr+ cells and osteoblasts was suppressed by inhibition of endothelial NF-κB signaling. According to some embodiments, pro-inflammatory genes that showed increased expression within the BM endothelial, hematopoietic and stromal compartments upon endothelial MAPK activation include I11b, Csf1, Cdkn1a, and csf2. I11b and csf1 have been reported to directly impact HSC function and promote a myeloid biased differentiation at the expense of lymphopoiesis. Chronic H11 exposure has been shown to cause enhanced HSC cycling and exhaustion.

According to some embodiments, endothelial MAPK activation followed by downstream endothelial NF-κB activation causes hematopoietic defects in HSPCs comprising increased HSPC cycling, impaired HSPC repopulating ability and a myeloid-biased differentiation. According to some embodiments, inhibition of endothelial NF-κB signaling: decreases expression of I11b within endothelial cells, stromal cells, and hematopoietic cells; wherein the decrease in endothelial I11b expression correlated with a significant down-regulation of inflammation, and decreased Csf1 expression in stromal cells and hematopoietic cells.

According to some embodiments, candidate proteins that regulate HSC function and promote recovery after inflammation include one or more of Clec11α, Hapln1, Hspd1, Igfbp1, Bgn, Wnt7a, Sparc, RP53, Bmpr1a, Ighm, Thbs4, Camk2d, Sirt2, Camk2b, Slitrk5, Dctpp1, Hnrnpa2b,Erap1.

The protein encoded by C-type lectin domain containing 11A (CLEC11A) is a secreted sulfated glycoprotein and functions as a growth factor for primitive hematopoietic progenitor cells; an alternative splice variant has been described.

Hapln1 (hyaluronan and proteoglycan link protein 1) stabilizes the aggrehgates of proteoglycan monomers with hyaluronic acid in the extracellular cartilage matrix.

Heat shock protein family D (SP60) member 1 Hspd1 is a chaperonin implicated in mitochondrial protein import and macromolecular assembly; together with Hsp10, it facilitates the correct folding of imported proteins. It may also prevent misfolding and promote refolding and proper assembly of unfolded polypeptides generated under stress conditions in the mitochondrial matrix.

Insulin like growth factor binding protein 1 (IGFBP-1) is an IGF-binding protein; IGF-binding proteins prolong the half-life of the IGFs and have been shown to either inhibit or stimulate the growth promoting effects of IGFs on cell culture. They alter the interaction of IGFs with their cell surface receptors and promote cell migration.

Biglycan, also known as Bone/Cartilage proteoglycan-1 (Bgn) may be involved in collagen fiber assembly.

The Wnt-7a gene is a member of the WNT gene family, which consists of strucxturally related genes that encode secreted signaling proteins. These proteins have been implicated in oncogenesis and in several development processes, including regulation of cell fate and patterning during embryogenesis. Protein Wnt Family Member 7A (Wnt7a) is the gene product of the Wnt-7a gene. It is a ligand of Wnt/β-catenin signaling pathways. Its expression is increased by hypoxia culture conditions. (Wu, D J et al, Sci Rep (2018) 8(1): 15792).

SPARC (Secreted Protein Acidic and Cysteine Rich) is a ptotein coding gene. The protein appears to regulate cell growth through interactions with the extracellular matrix and cytokines.

RP53 gene (also known as retinol dehydrogenase 12 gene, short chain dehydrogenase/reductase family 7C member 2) is a protein coding gene. The protein encoded by this gene is an NADPH-dependent retinal reductase, whose highest activity is toward 9-cis and all-trans-retinol. The encoded enzyme also plays a role in the metabolism of short-chain aldehydes but does not exhibit steroid dehydrogenase activity.

Bone morphogenetic protein receptor type 1A (Bmpr1a) is one of a family of transmembrane serine/threonine kinases. The ligands of these receptors are members of the TGF-beta superfamily.

The Ighm gene encodes the constant region of immunoglobulin heavy chain mu. Thbs4 (thrombospondin 4) is an adhesive glycoprotein that mediates cell-to-cell and cell-to matrix interactions. It binds to structural ECM proteins and modulates the ECM in response to tissue damage.

Calcium/calmodulin dependent protein kinase II delta (camk2d) belongs to the serine/threonine protein kinase family and to the Ca(2+)/calmodulin-dependent protein kinase subfamily.

Sirtuin 2 (sirt2) is an NAD-dependent protein deacetylase. It plays a major role in the control of cell cycle progression and genomic stability. It functions in the antephase checkpoint, preventing precocious mitotic entry in response to microtubule stress agents. The functions of human sirtuins have not yet been determined; however yeast sirtuin proteins are known to regulate epigenetic gene silencing.

Calcium/calmodulin dependent protein Kinase II beta (Camk2b) belongs to the serine/threonine protein kinase family and to the Ca(2+)/calmodulin-dependent protein kinase family.

SLIT and NTRK Like Family Member 5 (SLitrk5) is an integral membrain protein with 2 N-terminal leucine-rich repeat (LRR) domains similar to those of SLIT proteins. Most SLITRKs, including SLITRK5, also have C-terminal regions that share homology with neurotrophin receptors. SLITRKs are expressed predominantly in neural tissues and have nrurite-modulating activity.

The protein encoded by the DCTPP1 gene is dCTP pyrophosphatase (Dctpp1), which converts dCTP to dCMP and inorganic pyrophosphate. Ribosomal protein S3 (Rps3) is involved in translation as a component of the 40S small ribosomal subunit. It has endonuclease activity and plays a role in repair of damaged DNA.

Heterogeneous nuclear ribonucleoprotein A2/B1 (Hnrnpa2B1) is a ubiquitously expressed RNA binding protein that complexes with heterogeneous nuclear RNA. These proteins are associated with pre-mRNAs in the nucleus and appear to influence pre-mRNA processing and other aspects of mRNA metabolism and transport.

Endoplasmic reticulum aminopeptidase 1 (Erap1), the protein encoded by the ERAP1 gene, is an aminopeptidase involved in trimming HLA class I-binding precursors so that they can be presented on MHC class I molecules.

According to some embodiments, Clec11a/stem cell growth factor α (SCGF) is a potential pro-hematopoietic factor that regulates HSC function following endothelial inflammation.

According to some embodiments, in subjects with downstream NF-κB activation, infusion of SCGF increased the frequency of phenotypic HSCs. According to some embodiments, in subjects with downstream NF-κB activation, infusion of SCGF increased the frequency of HSPCs reflected in an enhanced colony-forming ability of BM cells. According to some embodiments, in subjects with downstream NF-κB activation, infusion of SCGF resolved peripheral blood myeloid bias and restored blood counts. According to some embodiments, in subjects with downstream NF-κB activation, infusion of SCGF restored long-term engraftment potential of BM cells. According to some embodiments, in subjects with downstream NF-κB activation, infusion of SCGF resolved vascular dilation and suppressed vascular leakiness within the BM microenvironment. According to some embodiments, in subjects with downstream NF-κB activation, infusion of SCGF decreased expression of NF-κB target genes within the BM. According to some embodiments, inflammation-induced lineage skewing of HSCs is reversible upon exposure to a wild type BM microenvironment during serial transplantations. According to some embodiments, in subjects with downstream NF-κB activation, infusion of SCGF resulted in decreased nuclear p65 levels within BM endothelium. According to some embodiments, in subjects with downstream NF-κB activation, infusion of SCGF suppresses endothelial inflammation and restores vascular integrity, which leads to a recovery of their hematopoietic system.

According to some embodiments, in subjects with downstream NF-κB activation, infusion of SCGF caused a significant increase in bone health comprising an increase in trabecular bone volume and trabecular numbers and thickness. According to some embodiments, in subjects with downstream NF-κB activation, infusion of SCGF, SCGF was primarily expressed in BM stromal cells including BM Lepr+ and osteoblastic stromal subsets.

According to some embodiments, following myelosuppressive stress, infusion of SCGF enhanced recovery of white blood cells, red blood cells, and platelets. According to some embodiments, the myelosuppressive stress is a myelosuppresive dose of irradiation (650 Rads). According to some embodiments, following myelosuppressive irradiation of both control and endothelial MAPK activated mice with downstream endothelial NF-κB activation, infusion of SCGF improved hematopoietic recovery comprising preservation of vascular integrity and increased BM cellularity. According to some embodiments, the improvement was after 28 days following myelosuppressive injury.

According to some embodiments, a competitive BM transplant can be performed in which donor WBM cells derived from endothelial MAPK activated mice with downstream endothelial NF-κB activation or from littermate controls ($2.5\times10^6$) are transplanted along with CD45.1 competitor WBM cells ($5\times10^5$) into lethally irradiated (950 Rads) CD45.1 mice on day 28 post-irradiation.

According to some embodiments, the EBM are depleted of terminally differentiated hematopoietic cells.

According to some embodiments, BM endothelium is immunmopurified from a cell suspension, and BM ECs selected by antibody capture.

According to some embodiments, following the competitive BM transplant, infusion of SCGF enhances long-term engraftment potential ability and multi-lineage reconstitution ability for hematopoietic cells derived from both endothelial MAPK activated mice with downstream endothelial NF-κB activation or from littermate controls. According to some embodiments, SCGF infusion following the competitive BM transplant maintains the serial repopulation ability of hematopoietic cells derived from endothelial MAPK activated mice with downstream endothelial NF-κB activation during secondary transplantation assays. According to some embodiments, SCGF infusion following the competitive BM transplant preserves HSC functionality in endothelial MAPK activated mice with downstream endothelial NF-κB activation at steady-state. According to some embodiments, SCGF infusion following the competitive BM transplant preserves HSC functionality in endothelial MAPK activated mice with downstream endothelial NF-κB activation following myelosuppressive injury. According to some embodiments, SCGF infusion following the competitive BM transplant preserves HSC functionality in control mice following myelosuppressive injury.

According to some embodiments, the methods described herein are effective to preserve vascular integrity, compared to a control. According to some embodiments, the methods described herein are effective to increase bone marrow cellularity, compared to a control. According to some embodiments, the methods described herein are effective to enhance long-term engraftment potential, compared to a control. According to some embodiments, the methods described herein are effective to effect multi-lineage reconstitution, compared to a control. According to some embodiments, the methods described herein are effective to inhibit vascular inflammation, compared to a control. According to some embodiments, the methods described herein are effective to preserve HSC function, compared to a control.

According to some embodiments, the methods described are effective to preserve vascular integrity. According to some embodiments, the methods described herein are effective to preserve vascular integrity by at least 0.01%, by at least 0.10%, by at least 1%, by at least 2%, by at least 3%, by at least 4%, by at least 5%, by at least 6%, by at least 7%, by at least 8%, by at least 9%, by at least 10%, by at least 11%, by at least 12%, by at least 13%, by at least 14%, by at least 15%, by at least 16%, by at least 17%, by at least 18%, by at by at least 19%, by at least 20%, by at least 21%, by at least 22%, by at least 23%, by at least 24%, by at least 25%, by at least 26%, by at least 27%, by at least 28%, by at least 29%, by at least 30%, by at least 31%, by at least 32%, by at least 33%, by at least 34%, by at least 35%, by at least 36%, by at least 37%, by at least 38%, by at least 39%, by at least 40%, by at least 41%, by at least 42%, by at least 43%, by at least 44%, by at least 45%, by at least 46%, by at least 47%, by at least 48%, by at least 49%, by at least 50%, %, by at least 51%, by at least 52%, by at least 53%, by at least 54%, by at least 55%, by at least 56%, by at least 57%, by at least 58%, by at least 59%, by at least 60%, by at least 61%, by at least 62%, by at least 63%, by at least 64%, by at least 65%, by at least 66%, by at least 67%, by at least 68%, by at least 69%, by at least 70%, by at least 71%, by at least 72%, by at least 73%, by at least 74%, by at least 75%, by at least 76%, by at least 77%, by at least 78%, by at least 79%, by at least 80%, by at least 81%, by at least 82%, by at least 83%, by at least 84%, by at least 85%, by at least 86%, by at least 87%, by at least 88%, by at least 89%, by at least 90%, by at least 91%, by at least 92%, by at least 93%, by at least 94%, by at least 95%, by at least 96%, by at least 97%, by at least 98%, by at least 99%, or by at least 100%, compared to a control.

According to some embodiments, the methods described herein are effective to increase bone marrow cellularity. According to some embodiments, the methods described herein are effective to increase bone marrow cellularity by at least 0.01%, by at least 0.10%, by at least 1%, by at least 2%, by at least 3%, by at least 4%, by at least 5%, by at least 6%, by at least 7%, by at least 8%, by at least 9%, by at least 10%, by at least 11%, by at least 12%, by at least 13%, by at least 14%, by at least 15%, by at least 16%, by at least 17%, by at least 18%, by at by at least 19%, by at least 20%, by at least 21%, by at least 22%, by at least 23%, by at least 24%, by at least 25%, by at least 26%, by at least 27%, by at least 28%, by at least 29%, by at least 30%, by at least 31%, by at least 32%, by at least 33%, by at least 34%, by at least 35%, by at least 36%, by at least 37%, by at least 38%, by at least 39%, by at least 40%, by at least 41%, by at least 42%, by at least 43%, by at least 44%, by at least 45%, by at least 46%, by at least 47%, by at least 48%, by at least 49%, by at least 50%, %, by at least 51%, by at least 52%, by at least 53%, by at least 54%, by at least 55%, by at least 56%, by at least 57%, by at least 58%, by at least 59%, by at least 60%, by at least 61%, by at least 62%, by at least 63%, by at least 64%, by at least 65%, by at least 66%, by at least 67%, by at least 68%, by at least 69%, by at least 70%, by at least 71%, by at least 72%, by at least 73%, by at least 74%, by at least 75%, by at least 76%, by at least 77%, by at least 78%, by at least 79%, by at least 80%, by at least 81%, by at least 82%, by at least 83%, by at least 84%, by at least 85%, by at least 86%, by at least 87%, by at least 88%, by at least 89%, by at least 90%, by at least 91%, by at least 92%, by at least 93%, by at least 94%, by at least 95%, by at least 96%, by at least 97%, by at least 98%, by at least 99%, or by at least 100% compared to a control.

According to some embodiments, the methods described herein are effective to enhance long-term engraftment potential. According to some embodiments, the methods described herein are effective to enhance long-term engraftment potential by at least 0.01%, by at least 0.10%, by at least 1%, by at least 2%, by at least 3%, by at least 4%, by at least 5%, by at least 6%, by at least 7%, by at least 8%, by at least 9%, by at least 10%, by at least 11%, by at least 12%, by at least 13%, by at least 14%, by at least 15%, by at least 16%, by at least 17%, by at least 18%, by at by at least 19%, by at least 20%, by at least 21%, by at least 22%, by at least 23%, by at least 24%, by at least 25%, by at least 26%, by at least 27%, by at least 28%, by at least 29%, by at least 30%, by at least 31%, by at least 32%, by at least 33%, by at least 34%, by at least 35%, by at least 36%, by at least 37%, by at least 38%, by at least 39%, by at least 40%, by at least 41%, by at least 42%, by at least 43%, by at least 44%, by at least 45%, by at least 46%, by at least 47%, by at least 48%, by at least 49%, by at least 50%, %, by at least 51%, by at least 52%, by at least 53%, by at least 54%, by at least 55%, by at least 56%, by at least 57%, by at least 58%, by at least 59%, by at least 60%, by at least 61%, by at least 62%, by at least 63%, by at least 64%, by at least 65%, by at least 66%, by at least 67%, by at least 68%, by at least 69%, by at least 70%, by at least 71%, by at least 72%, by at least 73%, by at least 74%, by at least 75%, by at least 76%, by at least 77%, by at least 78%, by at least 79%, by at least 80%, by at least 81%, by at least 82%, by at least 83%, by at least 84%, by at least 85%, by at least 86%, by at least 87%, by at least 88%, by at least 89%, by at least 90%, by at least 91%, by at least 92%, by at least 93%, by at least 94%, by at least 95%, by at least 96%, by at least 97%, by at least 98%, by at least 99%, or by at least 100%, compared to a control.

According to some embodiments, the methods described are effective to effect multi-lineage reconstitution. According to some embodiments, the methods described herein are effective to effect multi-lineage reconstitution by at least 0.01%, by at least 0.10%, by at least 1%, by at least 2%, by at least 3%, by at least 4%, by at least 5%, by at least 6%, by at least 7%, by at least 8%, by at least 9%, by at least 10%, by at least 11%, by at least 12%, by at least 13%, by at least 14%, by at least 15%, by at least 16%, by at least 17%, by at least 18%, by at by at least 19%, by at least 20%, by at least 21%, by at least 22%, by at least 23%, by at least 24%, by at least 25%, by at least 26%, by at least 27%, by at least 28%, by at least 29%, by at least 30%, by at least 31%, by at least 32%, by at least 33%, by at least 34%, by at least 35%, by at least 36%, by at least 37%, by at least 38%, by at least 39%, by at least 40%, by at least 41%, by at least 42%, by at least 43%, by at least 44%, by at least 45%, by at least 46%, by at least 47%, by at least 48%, by at least 49%, by at least 50%, by at least 51%, by at least 52%, by at least 53%, by at least 54%, by at least 55%, by at least 56%, by at least 57%, by at least 58%, by at least 59%, by at least 60%, by at least 61%, by at least 62%, by at least 63%, by at least 64%, by at least 65%, by at least 66%, by at least 67%, by at least 68%, by at least 69%, by at least 70%, by at least 71%, by at least 72%, by at least 73%, by at least 74%, by at least 75%, by at least 76%, by at least 77%, by at least 78%, by at least 79%, by at least 80%, by at least 81%, by at least 82%, by at least 83%, by at least 84%, by at least 85%, by at least 86%, by at least 87%, by at least 88%, by at least 89%, by at least 90%, by at least 91%, by at least 92%, by at least 93%, by at least 94%, by at least 95%, by at least 96%, by at least 97%, by at least 98%, by at least 99%, or by at least 100% compared to a control.

According to some embodiments, the methods described are effective to inhibit vascular inflammation. According to some embodiments, the methods described herein are effective to inhibit vascular inflammation by at least 0.01%, by at least 0.10%, by at least 1%, by at least 2%, by at least 3%, by at least 4%, by at least 5%, by at least 6%, by at least 7%, by at least 8%, by at least 9%, by at least 10%, by at least 11%, by at least 12%, by at least 13%, by at least 14%, by at least 15%, by at least 16%, by at least 17%, by at least 18%, by at by at least 19%, by at least 20%, by at least 21%, by at least 22%, by at least 23%, by at least 24%, by at least 25%, by at least 26%, by at least 27%, by at least 28%, by at least 29%, by at least 30%, by at least 31%, by at least 32%, by at least 33%, by at least 34%, by at least 35%, by at least 36%, by at least 37%, by at least 38%, by at least 39%, by at least 40%, by at least 41%, by at least 42%, by at least 43%, by at least 44%, by at least 45%, by at least 46%, by at least 47%, by at least 48%, by at least 49%, by at least 50%, %, by at least 51%, by at least 52%, by at least 53%, by at least 54%, by at least 55%, by at least 56%, by at least 57%, by at least 58%, by at least 59%, by at least 60%, by at least 61%, by at least 62%, by at least 63%, by at least 64%, by at least 65%, by at least 66%, by at least 67%, by at least 68%, by at least 69%, by at least 70%, by at least 71%, by at least 72%, by at least 73%, by at least 74%, by at least 75%, by at least 76%, by at least 77%, by at least 78%, by at least 79%, by at least 80%, by at least 81%, by at least 82%, by at least 83%, by at least 84%, by at least 85%, by at least 86%, by at least 87%, by at least 88%, by at least 89%, by at least 90%, by at least 91%, by at least 92%, by at least 93%, by at least 94%, by at least 95%, by at least 96%, by at least 97%, by at least 98%, by at least 99%, or by at least 100%, compared to a control.

According to some embodiments, the methods described are effective to preserve HSC function. According to some embodiments, the methods described herein are effective to preserve HSC function by at least 0.01%, by at least 0.10%, by at least 1%, by at least 2%, by at least 3%, by at least 4%, by at least 5%, by at least 6%, by at least 7%, by at least 8%, by at least 9%, by at least 10%, by at least 11%, by at least 12%, by at least 13%, by at least 14%, by at least 15%, by at least 16%, by at least 17%, by at least 18%, by at by at least 19%, by at least 20%, by at least 21%, by at least 22%, by at least 23%, by at least 24%, by at least 25%, by at least 26%, by at least 27%, by at least 28%, by at least 29%, by at least 30%, by at least 31%, by at least 32%, by at least 33%, by at least 34%, by at least 35%, by at least 36%, by at least 37%, by at least 38%, by at least 39%, by at least 40%, by at least 41%, by at least 42%, by at least 43%, by at least 44%, by at least 45%, by at least 46%, by at least 47%, by at least 48%, by at least 49%, by at least 50%, by at least 51%, by at least 52%, by at least 53%, by at least 54%, by at least 55%, by at least 56%, by at least 57%, by at least 58%, by at least 59%, by at least 60%, by at %, by at least 61%, by at least 62%, by at least 63%, by at least 64%, by at least 65%, by at least 66%, by at least 67%, by at least 68%, by at least 69%, by at least 70%, by at least 71%, by at least 72%, by at least 73%, by at least 74%, by at least 75%, by at least 76%, by at least 77%, by at least 78%, by at least 79%, by at least 80%, by at least 81%, by at least 82%, by at least 83%, by at least 84%, by at least 85%, by at least 86%, by at least 87%, by at least 88%, by at least 89%, by at least 90%, by at least 91%, by at least 92%, by at least 93%, by at least 94%, by at least 95%, by at least 96%, by at least 97%, by at least 98%, by at least 99%, or by at least 100% compared to a control.

According to some embodiments, the methods described herein can reduce, or inhibit activation of endothelial MAPK in a subject subjected to a myeoablative insult. According to some embodiments, the methods described herein can reduce, or inhibit, activation of canonical NF-κB signaling in a subject subjected to a myeoablative insult. According to some embodiments, the methods described herein According to some embodiments, the methods described herein can modulate ROS levels and hypoxia in a subject subjected to a myeoablative insult. According to some embodiments, the methods described herein can reduce expression of I11b within endothelial cells of a subject subjected to a myeoablative insult.

Compositions

According to another aspect, the described invention provides a composition comprising a protein, splice variant, biologically active fragment, agonist, or mimic effective to regulate HSC function and promote recovery after inflammation. According to some embodiments, the protein, splice variant, biologically active fragment, agonist or mimic effective to regulate HSC function and promotes recovery after inflammation is an angiocrine factor. According to some embodiments, the angiocrine factor comprises one or more of SCGF; OPG; SEM-III; IL-33; BMP-2; a matrix metalloproteinase, a TIMP metallopeptidase inhibitor; SCF, nidogen-1, IL-7, CXCL12; tenascin-C, FGF-2, Jag-1; NOS2; PDGF; TGF; FGF1; Noggin; BMP-4; angioprotein-1; VCAM-1; E-selectin; von Willebrand factor; Thrombospondin-1; IGFBP2; or ICAM-1. According to some embodiments, the protein, splice variant, or biologically active fragment effective to regulate HSC function and promotes recovery after inflammation is one or more of Clec11a, Hapln1, Hspd1, Igfbpd1, Bgn, Wnt7a, Sparc, Rps3, Bmpr1a, Ighm, Thbs4, Camk2d, Sirt2, Camk2b, Slitrk5, Dctpp1, Hnrnps2b, Erap1.

According to some embodiments, the angiocrine factor comprises stem cell growth factor-α (SCGF), also known as Clec11A, LSLCL, or P47. In nature, SCGF is encoded by the CLEC11A gene. For example, the murine mRNA sequence for SCGF can be found at accession no. NM_009131[1] (SEQ ID NO. 3), and the murine protein sequence can be found at accession no. NP_033157[2] (SEQ ID NO. 4). The human mRNA sequence for SCGF can be found at accession no. NM_002975[3] (SEQ ID NO. 5), and the human protein sequence can be found at accession no.

[1] ORIGIN

```
   1 aagagaagct gaggagatca aaagttgaga cagagcagat caggagggaa ggcagaagag
  61 aaagcctggc agaaagaagg tccaaggggc ttgtgagctg cccaccagac tgggacactt
 121 gctaggtcta tacagcagtc ctacccctgg cattctgacc tctctactat ttgggtgctg
 181 ggaagcccag ctggatgcag gcagcctggc tcttgggggc cctagtggtc cctcagcttt
 241 tgagttttgg tcatggagcc cgaggtcctg ggagggagtg ggagggaggc tggggaggtg
 301 ccctggagga ggagagagag cgggagtcac agatgttgaa gaatctccag gaggccctag
 361 ggctgcccac tggggtggga aatgaggata atcttgctga aaaccctgaa gacaaagagg
 421 tctgggagac cacagagact caaggggaag aagaggaaga ggaaatcacc acagcacctt
 481 cttctagtcc caacccttc cccagccctt ctcccacacc agaggacact gtcacttaca
 541 tcttgggccg cttggccagc ctcgatgcag gcctacacca attgcacgtc cgtctgcacg
 601 ttttggacac ccgtgtggtt gagctgaccc aggggctgcg gcagctgcgg gatgctgcga
 661 gtgacacccg cgactcagtg caagccctga aggaggtcca ggaccgtgct gagcaggagc
 721 acggccgctt ggagggctgc ctgaagggcc tgcgccttgg ccacaagtgc ttcctgctct
 781 cgcgagactt cgagacccag gcggcggcgc aggcgcggtg caaggcgcga ggtgggagct
 841 tagcacagcc tgcggaccgc cagcaaatgg atgcgctaag ccggtactta cgcgccgctc
 901 tcgcccccta caactggccg gtgtggctgg gagtgcacga tcggcgctcc gaggggctct
 961 accttttcga gaacggccag cgcgtgtctt tcttcgcctg gcaccgcgca ttcagcctgg
1021 agtccggcgc ccagcctagt gcggcaacac atccactcag cccggatcag cccaatggcg
1081 gcgtcctgga gaactgcgtg gcccaggcct cagacgacgg ttcttggtgg gaccatgact
1141 gtgagcggcg cctctacttc gtctgcgagt tccccttcta gagaaccggt ctctgcccag
1201 gagctctagt gcacattttg caccgtacac cgcgcaccct attgttaggg gcctgggagt
1261 cgctcagaga ttaagcgtga ccatgaatac attttaatca gaagaggttt tttattttag
1321 atactggcac ccagactgat tggggccagg tgtgctcctg agattgcttc caagatgcat
1381 tatcagccca gggattttaa aggcaaaccc cacaagattg catgtagcct gcttacatgt
```

-continued

```
1441 aggccggagc ataaaaattt aacatatatg tcttgaagtt gtcctagtca tcctttgagc

1501 agaggaagca agattagtta caaaaacaga aatcgcagtt agtcttacaa ctaaatttgc

1561 taggacagca aattttacaa ggccaatcaa tttcagaata gtcttcaata tctgggagaa

1621 tgaggaagta gatggactgt tagtgtacag cccacacaag ctaggggctt tcgtctgagg

1681 catattttgc tttggttttt caagcagtga gtctaaactt ttaaatgtaa tattaaccac

1741 catacgtaca atgtgcattc cgcaccctga actccacccc gtgcatcttc cactctgcac

1801 tctatagtgc accctgcatc ttgagccctc cttgggccag aactgccgcc aatcccggct

1861 ggtcccccag ccccagactt ctccatgtcc ccacctgtct ttgaaacttc aaggtctcaa

1921 ataggcccag tgccaataaa tccttttaaa atataaaaaa aaaaaaaaaa
```

[2] ORIGIN

```
  1 mqaawllgal vvpqllsfgh gargpgrewe ggwggaleee reresqmlkn iqealglptg

 61 vgnednlaen pedkevwett etqgeeeeee ittapssspn pfpspsptpe dtvtyilgrl

121 asldaglhql hvrlhvldtr vveltqglrq lrdaasdtrd svqalkevqd raeqehgrle

181 gclkglrlgh kcfllsrdfe tqaaaqarck arggslaqpa drqqmdalsr ylraalapyn

241 wpvwlgvhdr rseglylfen gqrvsffawh rafslesgaq psaathplsp dqpnggvlen

301 cvaqasddgs wwdhdcerrl yfvcefpf
```

[3] ORIGIN

```
  1 agagacgagg agaggaacag gaagagagaa gctgggagaa tcgggaacct gggggctagt

 61 gacctgcaca cagggcaggg gcactcggca gttcccagag gccacccctc ccaccccaga

121 catccagaca tctggaactt tgggtgccaa gagtccagct taatgcaggc agcctggctt

181 ttgggggctt tggtggtccc ccagctcttg ggctttggcc atggggctcg gggagcagag

241 agggagtggg agggaggctg gggaggtgcc caggaggagg agcgggagag ggaggccctg

301 atgctgaagc atctgcagga agccctagga ctgcctgctg ggagggggga tgagaatcct

361 gccggaactg ttgagggaaa agaggactgg gagatggagg aggaccaggg ggaggaagag

421 gaggaggaag caacgccaac cccatcctcc ggccccagcc cctctcccac ccctgaggac

481 atcgtcactt acatcctggg ccgcctggcc ggcctggacg caggcctgca ccagctgcac

541 gtccgtctgc acgcgttgga cacccgcgtg gtcgagctga cccaggggct gcggcagctg

601 cggaacgcgg caggcgacac ccgcgatgcc gtgcaagccc tgcaggaggc gcagggtcgc

661 gccgagcgcg agcacggccg cttggagggc tgcctgaagg ggctgcgcct gggccacaag
```

NP_002966[4] (SEQ ID NO. 6). According to some embodiments the angiocrine factor is obtained from commercial sources. For example Clec11a (SCGF) protein may be sourced from R&D Systems 3729-SC/CF The proteins described herein may be chemically synthesized or recombinantly expressed. Synthetic polypeptides, prepared using the well-known techniques of solid phase, liquid phase, or peptide condensation techniques, or any combination thereof, can include natural and unnatural amino acids. Amino acids used for peptide synthesis may be standard Boc (N-α-amino protected N-α-t-butyloxycarbonyl) amino acid resin with the standard deprotecting, neutralization, coupling and wash protocols of the original solid phase procedure of Merrifield (1963, J. Am. Chem. Soc. 85:2149-2154), or the base-labile N-α-amino protected 9-fluorenylmethoxycarbonyl (Fmoc) amino acids first described by Carpino and Han (1972, J. Org. Chem. 37:3403-3409). Both Fmoc and Boc N-α-amino protected amino acids can be obtained from Sigma, Cambridge Research Biochemical, or other chemical companies familiar to those skilled in the art. In addition, the polypeptides can be synthesized with other N-α-protecting groups that are familiar to those skilled in this art. Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161-214, or using automated synthesizers. The polypeptides may comprise D-amino acids (which are resistant to L-amino acid-specific proteases in vivo), a combination of D- and L-amino acids, and various "designer" amino acids (e.g., β-methyl amino acids, C-α-methyl amino acids, and N-α-methyl amino acids, etc.) to convey special properties. Synthetic amino acids include ornithine for lysine, and norleucine for leucine or isoleucine. In addition, the polypeptides can have peptidomimetic bonds, such as ester bonds, to prepare peptides with novel properties. For example, a peptide may be generated that 721 tgcttcctgc tctcgcgcga cttcgaagct caggcggcgg cgcaggcgcg gtgcacggcg 781 cggggcggga gcctggcgca gccggcagac cgccagcaga tggaggcgct cactcggtac 841 ctgcgcgcgg cgctcgctcc ctacaactgg cccgtgtggc tgggcgtgca cgatcggcgc 901 gccgagggcc tctacctctt cgaaaacggc cagcgcgtgt ccttcttcgc ctggcatcgc 961 tcaccccgcc ccgagctcgg cgcccagccc agcgcctcgc cgcatccgct cagcccggac 1021 cagcccaacg gtggcacgct cgagaactgc gtggcgcagg cctctgacga cggctcctgg 1081 tgggaccacg actgccagcg gcgtctctac tacgtctgcg agttcccctt ctagcggggc 1141 cggtaccccg cctccctgcc catcccacca cccggccttt ccctgcgccg tgcccaccct 1201 cctccggaat ctcccttccc ttcctggcca cgaatggcag cgtcctcccc gacccccagt 1261 ctgggcgctt ctgggagggc tcttgcggtg ccggcactcc tccttgttag tgtctttcct 1321 tgaaggggcg ggcaccaggc taggtccggt gccaataaat ccttgtggaa tctga

4 ORIGIN 1 mqaawllgal vvpqllgfgh gargaerewe ggwggaqeee rerealmlkh lqealglpag 61 rgdenpagtv egkedwemee dqgeeeeeea tptpssgpsp sptpedivty ilgrlaglda 121 glhqlhvrlh aldtrvvelt qglrqlrnaa gdtrdavqal qeaggraere hgrlegclkg 181 lrlghkcfll srdfeaqaaa qarctarggs laqpadrqqm ealtrylraa lapynwpvwl 241 gvhdrraegl ylfengqrvs ffawhrsprp elgaqpsasp hplspdqpng gtlencvaga 301 sddgswwdhd cqrrlyyvce fpf incorporates a reduced peptide bond, i.e., R1-CH2-NH-R2, where R1 and R2 are amino acid residues or sequences. According to some embodiments, a reduced peptide bond may be introduced as a dipeptide subunit. Such a polypeptide would be resistant to protease activity, and would possess an extended half-life in vivo.

According to some embodiments the source of the angiocrine factor is via isolation or purification from naturally occurring sources, such as biological tissue. According to some embodiments, the source of the angiocrine factor is a tissue autologous to the recipient subject. According to some embodiments, the source of the angiocrine factor is a tissue allogeneic to the recipient subject. According to some embodiments, the source tissue is mammalian. According to some embodiments, the source tissue is human. According to some embodiments, the source tissue is murine. According to some embodiments, the source of the angiocrine factor is whole bone marrow. According to some embodiments, the source of the angiocrine factor is whole bone marrow obtained from one or more areas, such as the femur and the tibia. According to some embodiments, the source of the angiocrine factor is bone marrow stromal cells According to some embodiments, wherein the angiocrine factor is SCGF, then the source of the SCGF is via isolation or purification from naturally occurring sources, such as biological tissue. According to some embodiments, the source of SCGF is a tissue autologous to the recipient subject. According to some embodiments, the source of the SCGF is a tissue allogeneic to the recipient subject. According to some embodiments, the tissue is mammalian. According to some embodiments, the tissue is human. According to some embodiments, the tissue is murine. According to some embodiments, the source of SCGFs is whole bone marrow. According to some embodiments, the source of SCGFs is whole bone marrow obtained from one or more areas, such as the femur and the tibia.

For example, if the source of SCGF is from bone marrow tissue then, briefly, intact marrow plugs can be flushed from long bones and subjected to enzymatic digestion until digested marrow cells are obtained. Then samples can be cultured with growth medium to enhance progenitor survival and proliferation. Differentation can be induced by replacing medium with adipogenic, osteogenic, or chondrogenic differentiation medium (for example StemPro MSC differentiation kits; Life Technologies) and stained to identify cells expressing SCGF. SCGF protein is expressed by bone marrow stromal cells, bone marrow Lepr+ cells, osteoblasts, osteocytes, hypertrophic chondrocytes, and bone marrow ECs, such as by type H ECs, sinusoidal ECs and arterial ECs.

According to some embodiments the angiocrine factor can be isolated or purified through any methods known in the art. Examples include the use of ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

For example, if the angriocrine factor is SCGF, then SCGF cells can be sorted through known flow cytometry methods and highest expressing cells can be obtained to develop a stable cell line expressing SCGF, for example, BM Lepr+ stromal cells. Stable cells lines with high SCGF expression can be cultured in culture medium, centrifuged to eliminate cellular debris, and stored with agents, such as phenylmethylsulfonyl fluoride to inhibit protease activity. The secreted SCGF can be affinity purified using beads, such as anti-Flag M2beads, eluted, and concentrated with a centrifugal filter device, quantified by SDS-PAGE and stored in low temperatures, such as −80° C.

According to some embodiments the source of the angiocrine factor is via isolation or purification from engineered sources. Engineered sources are cells that are genetically engineered (i.e., transduced or transformed or transfected) with vectors, such as a cloning vector or an expression vector, to produce an angiocrine factor as described herein. According to some embodiments, a host cell can be genetically engineered with a vector to produce an angiocrine factor as used herein by recombination techniques.

According to some embodiments, the host cell can be any host cell appropriate to be transfected, transformed or transduced with a vector to produce an angiocrine factor as used herein. The host cell can be a higher eukaryotic cell, such as a mammalian cell, or a lower eukaryotic cell, such as a yeast cell, or the host cell can be a prokaryotic cell, such as a bacterial cell. Exemplary host cells include but are not limited to bacterial cells, such as *E. coli, Streptomyces, Salmonella typhimurium*; fungal cells, such as yeast; insect cells such as *Drosophila* S2 and Sf9; animal cells such as CHO, COS or Bowes melanoma; adenoviruses; plant cells, etc.

According to some embodiments, the vector can be a cloning vector or an expression vector. The vector, for example, in the form of a plasmid, a viral particle, a phage, etc. According to some embodiments, the vector is an expression vector wherein the expression vector is any appropriate expression vector that will express an angiocrine factor as used herein. Exemplary expression vectors include but are not limited to chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. Further exemplary vectors include Bacterial: pQE70, pQE60, pQE-9 (Qiagen), pBS, pDIO, phagescript, psiX174, pbluescript SK, PBSKS, pNH8A, pNH16a, pNH18A, pNH46A (Stratagene); pTRC99a, pKK2233, pKK233-3, pDR540, pRIT5 (Pharmacia). Eukaryotic: PWLNEO, pSV2CAT, pOG44, pXT1, pSG (Stratagene) pSVK3, PBPV, PMSG, pSVL (Pharmacia). According to some embodiments, the vector is inserted with the sequence for an angiocrine factor. According to some embodiments, the vector is inserted with the sequence for an angiocrine factor wherein the angiocrine sequence has been inserted, in a forward or reverse orientation. According to some embodiments, the vector is a cell culture system. According to some embodiments, the vector is a mammalian cell culture system. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements. The angiocrine factor DNA sequence may be inserted into the vector by a variety of procedures. In general, the DNA sequence is inserted into an appropriate restriction endonuclease site(s) by procedures known in the art.

According to some embodiments, the vector further comprises regulatory sequence such as a promotor, enhancer, and the like, which operably links to the angriocrine sequence of an angiocrine factor as used herein. According to some embodiments, the vector comprises a promotor sequence or region. According to some embodiments, promotors are used herein to initiate DNA synthesis. According to some embodiments, promoters are used herein to describe a group of transcriptional control modules that are clustered around the initiation site for RNA polymerase II. According to some embodiments, promoters are discrete functional modules, each consisting of approximately 7-20 bp of DNA, containing one or more recognitions sites for transcriptional activator or repressor proteins. According to some embodiments, at least one region in each promoter functions to position the start site for RNA synthesis. Exemplary functional regions include the TATA box, or in some promoters that lack the TATA box, the promoter for the mammalian terminal deoxynucleotidyl transferase gene and the promoter for the SV40 late genes, a discrete element overlying the start site itself, may be used to indicate the place of initiation. According to some embodiments, viral or mammalian cellular or bacterial phage promoters are used to achieve expression of of the target sequence, and are known in the art, provided that the levels of expression are sufficient for a given purpose. Exemplary promoters include viral promoters such as the human cytomegalovirus (CMV) immediate early gene promoter, the SV40 early promoter, the Rous sarcoma virus long terminal repeat, rat insulin promoter and glyceraldehyde-3-phosphate dehydrogenase are used wherein viral promoters may obtain high-level expression of the coding sequence of interest. According to some embodiments, a promotor is used wherein the promoter can be regulated in response to specific physiologic signals can permit inducible expression of the gene product.

According to some embodiments, promoters used herein utilize additional promoter elements that regulate the frequency of transcriptional initiation. For example, additional promoter elements located in the region 30-110 bp upstream of the start site. The spacing between promoter elements frequently is flexible, therefore, according to some embodiments, the additional promoter elements are identified by ensuring that the promoter function is preserved when elements are inverted or moved relative to one another. For example, in the tk promoter, the spacing between promoter elements can be increased to 50 bp apart before activity begins to decline. According to some embodiments, individual additional promoter elements may function either co-operatively or independently to activate transcription. According to some embodiments, promotor regions or sequences can be selected from any desired gene using CAT (chloramphenicol transferase) vectors or other vectors with selectable markers. Exemplary promotors include bacterial promoters such as lacI, lacZ, T3, T7, gpt, lambda PRI PL and trp; Eukaryotic promoters such as CMV immediate early, HSV thymidine kinase, early and late SV40, LTRs from retrovirus, and mouse metallothionein-I.

According to some embodiments, the vector comprises an enhancer sequence or region. According to some embodiments, the enhancer sequence increases transcription of the DNA encoding the angiocrine factor of the present invention by higher eukaryotes. According to some embodiments, enhancers are cis-acting elements of DNA, usually about from 10 to 300 bp that act on a promoter to increase its transcription. According to some embodiments, enhancers are used, wherein enhancers are genetic elements that increase transcription from a promoter located at a distant position on the same molecule of DNA. Enhancers, like promoters, are composed of many individual elements, each of which binds to one or more transcriptional proteins. The basic distinction between enhancers and promoters is operational. An enhancer region as a whole must be able to stimulate transcription at a distance; whereas this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous. Examples include but are not limited to the SV40 enhancer on the late side of the replication origin bp 100 to 270, a cytomegalovirus early promoter enhancer, the polyoma enhancer on the late side of the replication origin, and adenovirus enhancers.

According to some embodiments, any promoter/enhancer combination could be used to drive the expression of the target gene (CLEC11A). Promoter/enhancer combinations can be found in publically available databases, such as in the Eukaryotic Promoter Data Base EPDB. Eukaryotic cells can support cytoplasmic transcription from certain bacterial promoters if the appropriate bacterial polymerase is provided, either as part of the delivery complex or as an additional genetic expression construct.

According to some embodiments, the vector comprises one or more of origins of replication comprising a promoter, an enhancer or both, transcription initiation signals, transcription termination signals, poly-A regions, amplication regions, selectable markers, multipurpose cloning sites, and the like.

According to some embodiments, if the expression vector utilizes a cDNA insert, the expression vector further comprises a polyadenylation signal wherein the polyadenylation signal effects proper polyadenylation of the gene transcript. According to some embodiments, any such sequence may be employed as known in the art. Exemplary polyadynylation signals include the human growth hormone and SV40 polyadenylation signals.

According to some embodiments, the vector comprises a ribosome-binding site for translation initiation and a transcription terminator. According to some embodiments, the expression vector also comprises a terminator or a termination signal wherein the terminator serves to enhance message levels and to minimize transcriptional overlap.

According to some embodiments, a transformant is used wherein the transformant is transformed with the expression vector as described herein. The transformant can be from any organism species appropriate. According to some embodiments, a transformant is prepared by transforming an appropriate host with the expression vector as described herein. Exemplary transformants include but are not limited to *E. coli* strains such as HB101, JM109, MC1061, BL21, XL1-Blue, SURE, DH1, DH5; yeast strains such as HIS/LI, HF7c; insect cells such as BmN, Sf cells; and mammalian cells such as CHO, COS, MOP, c127, Jurkat, WOP, HeLa, Namalwa cells. An appropriate method of transformation should be selected depending on the host. For example, the calcium phosphate precipitation or electroporation method for *E. coli*; the lithium acetate method, spheroplast fusion or electroporation for yeast; viral infection for insect cells; the calcium phosphate precipitation, protoplast fusion, lipofection, the erythrocyte ghost method, liposome fusion, the DEAE-dextran method, electroporation or viral infection for mammalian cells.

According to some embodiments, the vector is assembled in appropriate phase with translation initiation, termination, and/or leader sequences and/or signals. According to some embodiments, the vector is assembled in appropriate phase with translation initiation, termination, and/or leader sequences and/or signals in an operable reading phase with a functional promoter.

According to some embodiments, the host cell is engineered with a vector by methods known in the art, such as, by calcium phosphate transfection, DEAE-Dextran mediated transfection, or electroporation, delivered in a or on a lipid delivery vehicle or a nanoparticle. According to some embodiments, the engineered host cells are cultured in a conventional nutrient media enriched as appropriate for activating promoters, selecting transformants or amplifying the angiocrine factor genes. The culture conditions, such as temperature, pH and the like, will be apparent to the ordinarily skilled artisan.

According to some embodiments, the engineered host cell will produce an engineered cell line. According to some embodiments, following transformation of a suitable host strain to attain an engineered cell line, stabilization of the engineered cell line, and growth of the stable engineered cell line to an appropriate cell density, the selected promoter is induced by appropriate means (e.g., temperature shift or chemical induction) and the engineered cells are cultured for an additional period to produce the angiocrine factor as described herein. According to some embodiments, a cell line is stabilized by the use of any number of dominant drug selection markers for establishing permanent, stable cell clones expressing the products. Such stabilization methods are known in the art, as is an element that links expression of the drug selection markers to expression of the angiocrine factor as described herein.

According to some embodiments, cell-free translation systems can also be employed to produce such angiocrine factors as described herein using RNAs derived from the DNA constructs of the angiocrine factor of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

According to some embodiments, angiocrine factor of the present invention can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

According to some embodiments, for example, if the angiocrine factor is SCGF, the target gene for SCGF can be determined as described herein. According to some embodiments, the target gene can be detected as described herein. According to some embodiments, the target gene can be synthesized from mRNA by PCR on the cDNA from mammalian mRNA as a template, using a forward and a reverse primer synthesized based on the nucleotide sequence shown in SEQ ID NO. 7 and SEQ ID NO. 8. Exemplary mammals to be used in the invention include, but are not limited to, human and murine. SCGF mRNA preparation, cDNA synthesis and PCR can be carried out by conventional methods, such as the use of SuperScript III (Invitrogen). Primers for murine SCFG mRNA can be (forward) 5'-AGG TCC TGG GAG GGA GTG-3' (SEQ ID NO. 7) and (reverse) 5'-GGG CCT CCT GGA GAT TCT T-3' (SEQ ID NO. 8). Primers for human SCFG mRNA can be (forward) 5'-AGG TCC TGG GAG GGA GTG-3' (SEQ ID NO. 7) and (reverse) 5'-GGG CCT CCT GGA GAT TCT T-3' (SEQ ID NO. 8). SCGF DNA can be cloned into a vector, such as a commercially available pcDNA I or pcDNA3 vector (Invitrogen), transfected into HEK293 cells, and subjected to stable cell line selection. Stable clones with high SCGF expression can be cultured in culture medium, centrifuged to eliminate cellular debris, and stored with agents, such as phenylmethylsulfonyl fluoride to inhibit protease activity. The secreted recombinant SCGF can be affinity purified using beads, such as anti-Flag M2beads, eluted, and concentrated with a centrifugal filter device, quantified by SDS-PAGE and stored in low temperatures, such as −80° C.

Formulations/Administration

According to some embodiments, the angiocrine factor, splice variant, fragment, agonist or mimic thereof may be formulated into a composition in a free base, neutral or salt form or ester.

Pharmaceutically acceptable salts include the acid addition salts, e.g., those formed with the free amino groups of a proteinaceous composition, or which are formed with inorganic acids such as for example, hydrochloric or phosphoric acids, or such organic acids as acetic, oxalic, tartaric, fumaric, or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective.

According to some embodiments, the composition of the described invention may be formulated with an excipient, carrier or vehicle including, but not limited to, a solvent. The terms "excipient", "carrier", or "vehicle" as used herein refers to carrier materials suitable for formulation and administration of the composition described herein. Carriers and vehicles useful herein include any such materials known in the art which are nontoxic and do not interact with other components. As used herein the phrase "pharmaceutically acceptable carrier" refers to any substantially non-toxic carrier useable for formulation and administration of the composition of the present invention in which the angiocrine factor of the present invention will remain stable and bioavailable.

The pharmaceutically acceptable carrier must be of sufficiently high purity and of sufficiently low toxicity to render it suitable for administration to the mammal being treated. It further should maintain the stability and bioavailability of the angiocrine factor. Exemplary pharmaceutically acceptable carriers for the compositions of the described invention include, without limitation, buffers, diluents and other suitable additives. The term "buffer" as used herein refers to a solution or liquid whose chemical makeup neutralizes acids or bases without a significant change in pH. Examples of buffers envisioned by the present invention include, but are not limited to, Dulbecco's phosphate buffered saline (PBS), Ringer's solution, 5% dextrose in water (D5W), normal/physiologic saline (0.9% NaCl). According to some embodiments, the infusion solution is isotonic to subject tissues. According to some embodiments, the infusion solution is hypertonic to subject tissues. Compositions of the described invention can include pharmaceutically acceptable carriers such as sterile aqueous solutions, non-aqueous solutions in common solvents such as alcohols, or solutions in a liquid oil base.

According to some embodiments, the composition is a pharmaceutical composition comprising a pharmaceutically acceptable carrier. According to some embodiments, the carrier of the composition of the present invention may include a release agent such as sustained release or delayed release carrier. According to such embodiments, the carrier can be any material capable of sustained or delayed release of the active to provide a more efficient administration, e.g., resulting in less frequent and/or decreased dosage of the composition, improve ease of handling, and extend or delay effects on diseases, disorders, conditions, syndromes, and the like, being treated, prevented or promoted. Non-limiting examples of such carriers include liposomes, microsponges, microspheres, or microcapsules of natural and synthetic polymers and the like. Liposomes may be formed from a variety of phospholipids such as cholesterol, stearylamines or phosphatidylcholines.

According to some embodiments, the pharmaceutical composition is formulated as a syringeable composition. According to some embodiments, the pharmaceutical composition can be administered parenterally, meaning introduced into the body by way of an injection, including, for example, subcutaneously (i.e., an injection beneath the skin), intramuscularly (i.e., an injection into a muscle); intravenously (i.e., an injection into a vein); or by infusion techniques. Injectable preparations, such as sterile injectable aqueous or oleaginous suspensions, may be formulated according to the known art using suitable dispersing or wetting agents and suspending agents.

According to some embodiments, the pharmaceutical composition is administered locally or systemically. According to some embodiments, the composition can be administered buccally, transdermally, intrathecally, topically, mucosally, orally, by inhalation (e.g., aerosol inhalation), via a catheter, via a lavage, in lipid compositions (e.g., nanoparticles, liposomes), or by other method or any combination of the forgoing as would be known to one of ordinary skill in the art (see, for example, Remington's Pharmaceutical Sciences, 18th Ed. Mack Printing Company, 1990, incorporated herein by reference).

According to some embodiments, the compositions described herein are formulated depending on the administration method of the composition. For example, if the pharmaceutical composition is to be delivered orally, the compositions described herein can be formulated in an oral dosage form. Exemplary oral dosage forms include powder, tablet, capsule, syrup, pill, or granule(s). In another example, if the pharmaceutical composition is delivered parentally, the compositions described herein can be formulated in a parental dosage form.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it may be desirable to include isotonic agents, for example, sugars or sodium chloride. Prolonged absorption of the injectable compositions can be brought about by the use in the compositions of agents delaying absorption, for example, aluminum monostearate and gelatin.

According to some embodiments, if the pharmaceutical composition is formulated for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. According to some embodiments, sterile aqueous media that can be employed will be known to those of skill in the art in light of the present disclosure. According to some embodiments, formulations should meet sterility, pyrogenicity, and general safety and purity standards as required by FDA Office of Biologies standards.

According to some embodiments, the parental pharmaceutical compositions are formulated to be sterile. Sterile injectable solutions can be prepared by incorporating the active compounds in the required amount in the appropriate solvent with the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, exemplary methods of preparation include vacuum-drying and freeze-drying techniques which yield a powder of the active ingredient plus any additional desired ingredient from a previously sterile-filtered solution thereof. A powdered composition can be combined with a liquid carrier such as, e.g., water or a saline solution, with or without a stabilizing agent.

For example, according to some embodiments, if the pharmaceutical composition of the described invention is to be administered parenterally, the pharmaceutical composition comprising an angiocrine factor may be suspended in PBS and either added to IV fluid or injected at the proposed site of infusion.

According to some embodiments, the pharmaceutical composition comprises an additional therapeutic agent. According to some embodiments, the additional therapeutic is selected from the group consisting of an anti-inflammatory agent, an analgesic agent, an anti-infective agent, a growth factor, an immunosuppressive, and a combination thereof. According to some embodiments, the pharmaceutical composition comprises a therapeutic amount of the additional therapeutic agent.

According to some embodiments, the pharmaceutical composition further comprises a therapeutic amount of an anti-inflammatory agent wherein the anti-inflammatory agent is effective to reduce or inhibit inflammation.

According to some embodiments, the anti-inflammatory agent comprises a steroidal anti-inflammatory agent. The term "steroidal anti-inflammatory agent", as used herein, refer to any one of numerous compounds containing a 17-carbon 4-ring system and includes the sterols, various hormones (as anabolic steroids), and glycosides. Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflucortolone valerate, fluadrenolone, fluclorolone acetonide, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures and combinations thereof.

According to some embodiments, the anti-inflammatory agent comprises a nonsteroidal anti-inflammatory agent. The term "non-steroidal anti-inflammatory agent" as used herein refers to a large group of agents that are aspirin-like in their action, including, but not limited to, ibuprofen (Advil®), naproxen sodium (Aleve®), and acetaminophen (Tylenol®). Additional examples of non-steroidal anti-inflammatory agents that are usable in the context of the described invention include, without limitation, oxicams, such as piroxicam, isoxicam, tenoxicam, sudoxicam, and CP-14, 304; disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone, and mixtures and combinations thereof.

According to another embodiment, the anti-inflammatory agent comprises anti-inflammatory cytokines and/or pro-inflammatory mediators. Accord to some embodiments, the anti-inflammatory agent comprises without limitation, Transforming Growth Factor-beta3 (TGF-$\beta$3), an anti-Tumor Necrosis Factor-alpha (TNF-$\alpha$) agent, or a combination thereof.

According to some embodiments, the pharmaceutical composition further comprises a therapeutic amount of analgesic agent wherein the analgesic agent is effective to reduce, inhibit, or relieve pain by elevating the pain threshold without disturbing consciousness or altering other sensory modalities. According to some such embodiments, the analgesic agent is a non-opioid analgesic. "Non-opioid analgesics" are natural or synthetic substances that reduce pain but are not opioid analgesics. Examples of non-opioid analgesics include, but are not limited to, etodolac, indomethacin, sulindac, tolmetin, nabumetone, piroxicam, acetaminophen, fenoprofen, flurbiprofen, ibuprofen, ketoprofen, naproxen, naproxen sodium, oxaprozin, aspirin, choline magnesium trisalicylate, diflunisal, meclofenamic acid, mefenamic acid, and phenylbutazone, and combinations and mixtures thereof.

According to some other embodiments, the analgesic is an opioid analgesic. “Opioid analgesics”, “opioids”, or “narcotic analgesics” are natural or synthetic substances that bind to opioid receptors in the central nervous system, producing an agonist action. Examples of opioid analgesics include, but are not limited to, codeine, fentanyl, hydromorphone, levorphanol, meperidine, methadone, morphine, oxycodone, oxymorphone, propoxyphene, buprenorphine, butorphanol, dezocine, nalbuphine, and pentazocine, and combinations and mixtures thereof.

According to some embodiments, the pharmaceutical composition further comprises a therapeutic amount of an anti-infective agent wherein the anti-infective agent is effective to reduce, inhibit the growth of, or to destroy bacteria, fungus, and other microorganisms. According to some embodiments, the anti-infective agent is selected from the group consisting of an antibiotic agent, antimicrobial agent, antifungal agent, anti-viral agent, anti-protozoal agent, and a combination thereof.

According to some embodiments, the anti-infective agent comprises an antibiotic agent. Examples of antibiotic agents include, but are not limited to, Penicillin G; Methicillin; Nafcillin; Oxacillin; Cloxacillin; Dicloxacillin; Ampicillin; Amoxicillin; Ticarcillin; Carbenicillin; Mezlocillin; Azlocillin; Piperacillin; Imipenem; Aztreonam; Cephalothin; Cefaclor; Cefoxitin; Cefuroxime; Cefonicid; Cefmetazole; Cefotetan; Cefprozil; Loracarbef; Cefetamet; Cefoperazone; Cefotaxime; Ceftizoxime; Ceftriaxone; Ceftazidime; Cefepime; Cefixime; Cefpodoxime; Cefsulodin; Fleroxacin; Nalidixic acid; Norfloxacin; Ciprofloxacin; Ofloxacin; Enoxacin; Lomefloxacin; Cinoxacin; Doxycycline; Minocycline; Tetracycline; Amikacin; Gentamicin; Kanamycin; Netilmicin; Tobramycin; Streptomycin; Azithromycin; Clarithromycin; Erythromycin; Erythromycin estolate; Erythromycin ethyl succinate; Erythromycin glucoheptonate; Erythromycin lactobionate; Erythromycin stearate; Vancomycin; Teicoplanin; Chloramphenicol; Clindamycin; Trimethoprim; Sulfamethoxazole; Nitrofurantoin; Rifampin; Mupirocin; Metronidazole; Cephalexin; Roxithromycin; Co-amoxiclavuanate; combinations of Piperacillin and Tazobactam; and their various salts, acids, bases, and other derivatives thereof; and combinations and mixtures thereof.

According to some embodiments, the anti-infective agent comprises an antibacterial agent agent. Exemplary antibacterial agents include but are not limited to, penicillins, cephalosporins, carbacephems, cephamycins, carbapenems, monobactams, aminoglycosides, glycopeptides, quinolones, tetracyclines, macrolides, and fluoroquinolones, and combinations and mixtures thereof.

According to some embodiments, the anti-infective agent comprises an anti-fungal agent. The term “anti-fungal agent” as used herein means any of a group of chemical substances having the capacity to inhibit the growth of or to destroy fungi. Exemplary anti-fungal agents include but are not limited to Amphotericin B, Candicidin, Dermostatin, Filipin, Fungichromin, Hachimycin, Hamycin, Lucensomycin, Mepartricin, Natamycin, Nystatin, Pecilocin, Perimycin, Azaserine, Griseofulvin, Oligomycins, Neomycin, Pyrrolnitrin, Siccanin, Tubercidin, Viridin, Butenafine, Naftifine, Terbinafine, Bifonazole, Butoconazole, Chlordantoin, Chlormidazole, Cloconazole, Clotrimazole, Econazole, Enilconazole, Fenticonazole, Flutrimazole, Isoconazole, Ketoconazole, Lanoconazole, Miconazole, Omoconazole, Oxiconazole, Sertaconazole, Sulconazole, Tioconazole, Tolciclate, Tolindate, Tolnaftate, Fluconawle, Itraconazole, Saperconazole, Terconazole, Acrisorcin, Amorolfine, Biphenamine, Bromosalicylchloranilide, Buclosamide, Calcium Propionate, Chlorphenesin, Ciclopirox, Cloxyquin, Coparaffinate, Diamthazole, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Triacetin, Ujothion, Undecylenic Acid, and Zinc Propionate, and combinations and mixtures thereof.

According to some embodiments, the anti-infective agent comprises an anti-protozoal agent. The term “anti-protozoal agent” as used herein means any of a group of chemical substances having the capacity to inhibit the growth of or to destroy protozoans used chiefly in the treatment of protozoal diseases. Examples of antiprotozoal agents, without limitation, include pyrimethamine (Daraprim®) sulfadiazine, and Leucovorin, and mixtures and combinations thereof.

According to some embodiments, the anti-infective agent comprises an antiviral agent. The term “anti-viral agent” as used herein means any of a group of chemical substances having the capacity to inhibit the replication of or to destroy viruses used chiefly in the treatment of viral diseases. Anti-viral agents include, but are not limited to, Acyclovir, Cidofovir, Cytarabine, Dideoxyadenosine, Didanosine, Edoxudine, Famciclovir, Floxuridine, Ganciclovir, Idoxuridine, Inosine Pranobex, Lamivudine, MADU, Penciclovir, Sorivudine, Stavudine, Trifluridine, Valacyclovir, Vidarabine, Zalcitabine, Acemannan, Acetylleucine, Amantadine, Amidinomycin, Delavirdine, Foscamet, Indinavir, Interferons (e.g., IFN-alpha), Kethoxal, Lysozyme, Methisazone, Moroxydine, Nevirapine, Podophyllotoxin, Ribavirin, Rimantadine, Ritonavir2, Saquinavir, Stailimycin, Statolon, Tromantadine, Zidovudine (AZT) and Xenazoic Acid, and mixtures and combinations thereof.

According to some embodiments, the pharmaceutical composition further comprises a therapeutic amount of a growth factor. According to some embodiments, the growth factor is selected from the group consisting of platelet-derived growth factor (PDGF), fibroblast growth factor (FGF), granulocyte colony stimulating factor (G-CSF), granulocyte macrophage colony stimulating factor (GM-CSF), and a combination thereof.

According to some embodiments, the growth factor comprises an exogenous hematopoietic growth factor. According to some embodiments, the exogenous hematopoietic growth factor comprising G-CSF, GM-CSF, GM-CSF/IL-3 fusion protein (PIXY321), rhGM-CSF, IL-1, IL-3, IL-6, IL-11, SCF, FTL3-ligand, erythropoietin (EPO), thrombopoietin (TPO), stroma, and a combination thereof.

According to some embodiments, the pharmaceutical composition is administered with a co-therapy. According to some embodiments, the pharmaceutical composition is administered with a therapeutic amount of a co-therapy. According to some embodiments, the pharmaceutical composition herein is administered before the co-therapy. According to some embodiments, the pharmaceutical composition herein is administered after a co-therapy. According to some embodiments, the pharmaceutical composition herein is administered concurrently with the co-therapy.

According to some embodiments, the adjunct therapy is a stem cell therapy. According to some embodiments, the pharmaceutical composition is administered with a therapeutic amount of the stem cell therapy, wherein the therapeutic amount is effective to promote or induce stem cell rescue.

According to some embodiments, a stem cell transplant may be formulated by any appropriate methods. In brief, stem cell therapy comprises the steps of isolating hematopoietic stem cells from a population of mononuclear cells isolated from a tissue source, enriching the isolated population of mononuclear cells for hematopoietic stem cells by positive or negative selection, and infusing the enriched isolated population of hematopoietic stem cells to the subject. According to some embodiments, the tissue source is autologous. According to some embodiments, the tissue source is allogeneic. The specifities of the above described method depends on the tissue source of the stem cells.

Autologous Tissue. According to some embodiments, the tissue source comprises autologous tissue. According to some embodiments, the autologous tissue is harvested prior to myeoablative insult. According to some embodiments, the harvested autologous tissue comprising stem cells further undergoes purging to deplete contaminating tumor cells. According to some embodiments, if malignant cells exist in the harvested tissue, the stem cells are enriched through the use of anti-CD34 specific monoclonal antibodies and immunobeads ("positive selection") and/or the malignant cells are removed through the use of antitumor monoclonal antibodies ("negative selection").

Allogeneic Tissue. According to some embodiments, the tissue source comprises allogeneic tissue. According to some embodiments, the donor allogeneic tissue is screened for histocompatibility with the recipient subject. According to some embodiments, histocompability is screened through histocompatibility matching wherein the donor and the recipient subject are human leukocyte antigen (HLA) identical or nearly identical or similar. According to some embodiments, if malignant cells exist in the harvested tissue, the harvested tissue is purged as described above. According to some embodiments, histo-incompatible material may be removed from the harvested material. According to some embodiments, the allogeneic harvested tissue may also undergo ex-vivo T cell depletion (TCD).

Bone marrow tissue. According to some embodiments, the tissue source comprises bone marrow wherein the tissue is either allogeneic or autologous. According to some embodiments, any known method to harvest bone marrow tissue may be used. For example, bone marrow for transplantation may be obtained ("harvested") by multiple aspirations of the iliac crest over 2-3 hours under general or spinal anesthesia. Approximately 10-40×$10^9$ nucleated cells (2×$10^8$/kg of recipient weight), up to a maximum of 20 mL/kg of donor weight, will be obtained. The marrow aspirate will primarily consist of stromal cells, undifferentiated stem cells, early committed progenitor cells, T lymphocytes and erythroid, myeloid, monocytic, megakaryocytic, and lymphoid cell lines in various stages of development. Particulate material in the marrow will be removed by filtration. If an ABO blood group incompatibility exists, plasmapheresis may be utilized to remove isohemagglutinins, while differential centrifugation can be utilized to remove incompatible erythrocytes. Special processing ("purging") may also be performed to reduce the marrow burden of tumor cells, T lymphocytes, or other specific components that may have a deleterious effect on the recipient subject. After processing, harvested, processed tissue comprising the stem cells will be immediately administered to the recipient via intravenous infusion or will be cryopreserved and stored for later transfusion.

Peripheral blood. According to some embodiments, the tissue source is peripheral blood wherein the tissue is either allogeneic or autologous. According to some embodiments, any known method to harvest peripheral blood may be used. According to some embodiments, the population of mononuclear cells is obtained after treatment with a hematopoietic stem cell mobilizing agent. According to some such embodiments, the hematopoietic stem cell mobilizing agent comprises G-CSF, GM-CSF (e.g., Sargramostim (LEUKINE®)), or a pharmaceutically acceptable analog or derivative thereof. According to some embodiments, the hematopoietic stem cell mobilizing agent is a recombinant analog or derivative of a colony stimulating factor. According to some embodiments, the hematopoietic stem cell mobilizing agent is filgrastim (NEUPOGEN®). According to some embodiments, the hematopoietic stem cell mobilizing agent is one or more of plerixafor (MOZOBIL®), eltrombopag (PROMACTA®), Romiplostim (NPLATE®), pegfilgrastim (NEULASTA®), darbepoietin alfa (ARANESP®). Then, the donor's buffy coat comprising stem cells then may be isolated by leukapheresis. After processing, the enriched population of hematopoietic stem cells will be immediately administered to the recipient via intravenous infusion or will be cryopreserved frozen and stored for later transfusion.

Doses/Dosage Regimes

According to some embodiments, pharmaceutical compositions may comprise, between about 0.01% to about 99.99% (wt/wt %) of the angiocrine factor, biologically active fragment, splice variant, agonist or mimic thereof depending on the weight of the unit and the administration route, between about 10% to about 90% (wt/wt %), between about 20% to about 80% (wt/wt %), between about 30% to about 70% (wt/wt %), or between about 40% to about 60% (wt/wt %), inclusive and any range derivable therein. For example, the pharmaceutical compositions may comprise about 0.01%, about 0.10%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, by at about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, %, about 51%, about 52%, about 53%, about 54%, about 55%, about 56%, about 57%, about 58%, about 59%, about 60%, by at %, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100% (wt/wt %), of the angiocrine factor, splice variant, biologically active fragment, agonist or mimetic.

According to some embodiments, the amount of angiocrine factor, splice variant, biologically active fragment, agonist or mimetic thereof in a therapeutically useful composition can be prepared so that a suitable dosage will be contained in a unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

According to some embodiments, the actual dosage amount of a composition of the present disclosure administered to a subject can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject.

Subjects. The compositions and methods described herein are intended for use with any subject that may experience the described benefits. Thus, "subjects," "patients," and "individuals" (used interchangeably) include humans as well as non-human subjects, particularly domesticated animals.

According to some embodiments, the subject and/or animal is a mammal, e g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish. In some embodiments, the subject and/or animal may comprise fluorescently-tagged cells (with e.g. GFP). In some embodiments, the subject and/or animal is a transgenic animal comprising a fluorescent cell.

According to some embodiments, the subject and/or animal is a human. According to some embodiments, the human is a pediatric human. According to some embodiments, the human is an adult human. According to some embodiments, the human is a geriatric human. In other embodiments, the human may be referred to as a patient.

According to some embodiments, the subject is a non-human animal, and therefore the described invention pertains to veterinary use. According to some embodiments, the non-human animal is a household pet. According to some embodiments, the non-human animal is a livestock animal.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

Examples

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods

Animals C57BL/6J (CD45.2; stock no. 000664), B6.SJL-Ptprc$^{a}$ Pepc$^{b}$/BoyJ (CD45.1; stock no. 002014), and C57BL/6-Gt(ROSA)26Sor$^{tm(Map2kl*,EGFP)Rsky/J}$ (Map$^{fl/fl}$) (stock no. 012352) mice were purchased from The Jackson Laboratory (Bar Harbor, ME). (Srinivasan, L. et al. PI3 kinase signals BCR-dependent mature B cell survival. Cell 139, 573 ¬-586, doi:10.1016/j.cell.2009.08.041 (2009)). Cdh5(PAC)-creERT2 mice were obtained from Ralf H. Adams at The Max Planck Institute for Molecular Biomedicine. (Benedito, R. et al. The notch ligands D114 and Jagged1 have opposing effects on angiogenesis. Cell 137, 1124-1135, doi:10.1016/j.cell.2009.03.025 (2009)). Tie2.IkB-SS mice were obtained from Jan Kitajewski at Columbia University. (Brown, K., Gerstberger, S., Carlson, L., Franzoso, G. & Siebenlist, U. Control of I kappa B, alpha proteolysis by site-specific, signal-induced phosphorylation. Science 267, 1485-1488, doi:10.1126/science.7878466 (1995)). Lepr-cre mice were obtained from Sean J Morrison at the University of Texas Southwestern Medical Center, Cdh5(PAC)-creERT2, and Tie2.IκB-SS mice were bred and maintained on a C57BL/6J (CD45.2) genetic background. (DeFalco, J. et al. Virus-assisted mapping of neural inputs to a feeding center in the hypothalamus. Science 291, 2608-2613, doi:10.1126/science.1056602 (2001)). All mice were housed in Positive Individual Ventilation (PIV) cages with HEPA-filtered air exchange (Thoren Caging Systems, Inc.) and maintained on Pico Lab Rodent Diet 20 (Lab Diet 5053) and water ad libitum. To induce Cdh5(PAC)-creERT2-mediated recombination, Tamoxifen (Sigma-Aldrich T5648) solubilized in Sunflower Oil (Sigma-Aldrich S5007) was administered via intraperitoneal injection (150 mg/kg body weight) at a dose of 30 mg/mL for three consecutive days at 8-12 weeks of age or animals fed Custom Teklad 2020 Feed supplemented with 0.025% w/w tamoxifen (Envigo) ad libitum at 6-10 weeks of age for four consecutive weeks. Age matched cre-negative littermate mice also underwent the same tamoxifen induction regimen and were utilized as controls. Mice were allowed to recover for 4 weeks post¬tamoxifen induction prior to experimental analysis. All mice were maintained in specific-pathogen-free housing. Total body γ-irradiation (TBI) was administered from a 137$^{Cs}$ source at doses indicated in the subsequent methodology. Irradiated recipients were given PicoLab Mouse 20 antibiotic feed (0.025% Trimethoprim and 0.124% Sulfamethoxazole; LabDiet) 24 hours prior to irradiation and subsequently maintained for four weeks. Experiments were conducted in accordance with the Association for Assessment and Accreditation of Laboratory Animal Care, Intl. (AAALAC) and National Institutes of Health (NIH) Office of Laboratory Animal Welfare (OLAW) guidelines and under the approval of Weill Cornell Medical College and the Institutional Animal Care and Use Committee (IACUC).

Buffers and Media

Magnetic activated cell sorting (MACS) buffer. PBS without Ca++/Mg++ (pH 7.2) (Corning 21-040,CV) containing 0.5% W/V bovine serum albumin (BSA; Fisher Scientific BP1605) and 2 mM EDTA (Corning 46-034-CI).

Digestion Buffer. 1× Hanks Balanced Salt Solution (Life Technologies 14065) containing 20 mM HEPES (Corning 25-060-CI), 2.5 mg/mL Collagenase A (Roche 11088793001), and 1 unit/mL Dispase II (Roche 04942078001).

Endothelial growth medium. A 1:1 ratio of Low-glucose DMEM (ThermoFisher Scientific 11885-084) and Ham's F-12 (Corning 10-080), supplemented with 20% heat-inactivated FBS (Denville Scientific FB5002-H), 1% antibiotic-antimycotic (Corning 30-004-CI), 1% non-essential amino acids (Corning 25¬025-CI), 10 mM HEPES (Corning 25-060-CI), 100 μg/mL heparin (Sigma-Aldrich H3149), and 50 μg/mL endothelial cell growth supplement (Alfa Aesar BT-203)].

Hematopoietic, BMEC and Stromal Cell Quantification

To quantify total hematopoietic cells, femurs were gently crushed with a mortar and pestle and enzymatically dissassociated for 15 min at 37° C. in Digestion Buffer following which cell suspensions were filtered (40 μm; Corning 352340) and washed in MACS buffer. Viable cell numbers were quantified using a hemocytometer with Trypan Blue (Life Technologies) exclusion. To quantify hematopoietic stem and progenitor cells (HSPCs) in the BM, femurs and tibiae were flushed using a 26G×½ needle with MACS buffer. To quantify splenic HSPCs, spleens were gently crushed and filtered over a 40 λm filter to obtain single cell suspensions. To quantify BMECs, total BM stromal cells, BM Lepr+ cells and BM osteoblasts, femurs were gently crushed with a mortar and pestle and enzymatically dissassociated for 15 min at 37° C. in Digestion buffer following which cell suspensions were filtered (40 λm; Corning 352340) and washed in MACS buffer. Cells were surface stained using fluorochrome-conjugated antibodies as per manufacturer recommendations. Cell populations were analyzed using flow cytometry.

Flow Cytometry

Prior to cell surface staining, Fc receptors were blocked using an antibody against CD16/32 (93; Biolegend) in MACS buffer for 10 minutes at 4° C. For CMP/GMP/MEP staining, samples were blocked with 10% normal rat serum for 10 minutes at 4° C. Blocked samples were subsequently stained with fluorochrome-conjugated antibodies in MACS buffer for 30 mins at 4° C. as described. Samples stained with biotinylated anti-Lepr antibody were washed and stained with Streptavidin-conjugated fluorochromes for 15 minutes at 4° C. Stained cells were washed in MACS buffer and fixed in 1% paraformaldehyde (PFA) in PBS (pH 7.2) with 2 mM EDTA. Sample data was collected and analyzed using a LSR II SORP (BD Biosciences) or Fortessa (BD Biosciences) with FACS DIVA 8.0.1 software (BD Biosciences). Gates were established using unstained controls and standard fluorescence minus one strategies. A list of antibody clones utilized in the study are included in Supp. Table 2.

Cell Populations were Defined as Shown in Table 6.

TABLE 6

Definitions of Cell Populations

| Cells | Cell Type | Surface marker phenotype |
|---|---|---|
| HSCs | Hematopoietic stem cells | Lineage (Ter119/CD11b/GR1/B220/CD3)− CD41− cKIT+ SCA1+ CD48− CD150+ |
| KLS | Hematopoietic stem and progenitor cells | Lineage− cKIT+ SCA1+ |
| MPP | Multipotent progenitors that express the receptor tyrosine kinase FLT3; can produce both lymphoid and myeloid cells | Lineage− cKIT+ SCA1+ CD48− CD150− |
| HPC-1 | hematopoietic progenitor cell subset 1 | Lineage− cKIT+ SCA1+ CD48+ CD150− |
| HPC-2 | hematopoietic progenitor cell subset 2 | Lineage− cKIT+ SCA1+ CD48+ CD150+ |
| CLP* | Common lymphoid progenitor; | Lineage− cKITlowSCA1lowFLT3+ IL7Rα+ |
| CMP | Common myeloid progenitor | Lineage− cKIT+ SCA1− CD34+ CD 16/32− |
| GMP | Granulocyte-macrophage progenitors | Lineage− cKIT+ SCA1− CD34+ CD 16/32+ |
| MEP | Metakaryocyte/erythrocyte progenitor | Lineage− cKIT+ SCA1− CD34− CD 16/32− |
| Pre Pro B | A B cell progenitor subset | slgM− B220+ CD43+ CD24− |
| Pro B | A B cell progenitor subset | slgM− B220+ CD43+ CD24+ |
| Pre B | A B cell progenitor subset | slgM− B220+ CD43− CD24+ |
| Myeloid | Peripheral blood cell type (granulocytes and monocytes) | CD45+ CD11B+ GR1+ |
| B Cells | Antibody producting antigen specific lymphocyte responsible for adaptive immune responses | CD45+ B220+ |
| T Cells | Antigen specific lymphocyte responsible for cell-mediated adaptive immune ractions | CD45+ CD3+ |
| BM ECs | Bone marrow endothelial cells | CD45− Ter119− CD31+ VEcadherin+ |
| BM Stromal Cells | Nonlymphoid cell that provides soluble and cell-bound signals | CD45− Ter119− CD31− VEcadherin− |
| BM Lepr+ Cells | Within the BM stromal population. Include Nestin+ and CXCL12 abundant reticular cells; are an important source of KitL and SDF1 for HSC maintenance. | CD45− Ter119− CD31− Lepr+ |
| Osteo-blasts | immature, mononucleate, bone-forming cells that synthesize collagen and control mineralization derived from osteoprogenitors, which arise from MSCs | CD45− Ter119− CD31− SCA1− CD51+ |

* HSCs differentiate into MPPs. Differentiation ofMPPs into CLPs requires signaling through the FLT3 receptor expressed on MPPs. (CLPs) derivedfrom MPPS comprise a subset that can generate B, T and NKcells; a second subset that can generate only Band T cells; and a third subset that is committed exclusively to B cells. The B cell commited CLPs give rise to proB cells. Developmental stages of the B cell lineage are: early pro-B cell, late pro-B cell, large pre-B cell, small pre-B cell, immature B cell and Mature B cell.

Progenitor Activity

Colony-forming units (CFUs) in semi-solid methylcellulose were quantified to assess hematopoietic progenitor activity. WBM was flushed from femurs and tibiae using a 26G×½ needle with MACS buffer. Viable cell counts were determined with a hemocytometer using Trypan Blue (Life Technologies). WBM cells ($5\times10^4$ Cells/well) were plated in duplicate in Methocult GF M3434 methylcellulose (StemCell Technologies) according to the manufacturer's suggestions. Colonies were scored for phenotypic CFU-GEMM, CFU-GM, CFU-G, CFU-M, and BFU-E colonies using a SZX16 604 Stereo-Microscope (Olympus).

Competitive Transplantation and Limiting Dilutions

Adult CD45.1 recipient mice were pre-conditioned with lethal-irradiation (950 Rads) 16 hours prior to transplantation. WBM was isolated from femurs by gentle crushing with a mortar and pestle and was enzymatically disassociated for 15 min at 37° C. in Digestion buffer following which cell suspensions were filtered (40 μm; Corning 352340) and washed in MACS to obtain single cell suspensions. Viable cell numbers were quantified using a hemocytometer with Trypan Blue (Life Technologies) for live/dead exclusion. For competitive transplantation experiments at steady-state (1:1 ratio), $5\times10^5$ donor WBM cells (CD45.2) were transplanted with $5\times10^5$ competitor WBM cells (CD45.1) via retro-orbital sinus injections into CD45.1 recipient mice pre-conditioned with myeloablative irradiation (950 Rads). For competitive transplantation experiments following myelosuppressive injury (5:1 ratio), $2.5\times10^6$ donor WBM cells (CD45.2) were transplanted with $5\times10^5$ competitor WBM cells (CD45.1). Retro-orbital sinus bleeds using 75 mm heparinized glass capillary tubes (Kimble-Chase) were used to assess multi-lineage hematopoietic engraftment. Peripheral blood was depleted of red blood cells using RBC Lysis Buffer (Biolegend 420301) and stained with fluorochrome-conjugated antibodies according to the manufacturer's recommendations. The hematopoietic engraftment antibody FIG. includes CD45.1 (A20; Biolegend), CD45.2 (104; Biolegend), and TER119 (TER119; Biolegend). Multilineage engraftment FIG.s include CD45.2 (104; Biolegend), GR1 (RB6-8C5; Biolegend), CD11B (M1/70; Biolegend), B220 (RA3-6B2; Biolegend), CD3 (17A2; Biolegend), CD4 (GK1.5; Biolegend), and CD8 (53-6.7; Biolegend). For limiting dilution analysis, indicated numbers of WBM were non-competitively transplanted via retro-orbital sinus injections into pre-conditioned CD45.1 recipient mice. Percent negative responding/dead mice were monitored for a four-month post-transplant period. Multilineage hematopoietic engraftment in surviving mice was confirmed by flow cytometry in red blood cell (RBC)-lysed peripheral blood using antibodies raised against CD45.2 (104; Biolegend), GR1 (RB6-8C5; Biolegend), CD11B (M1/70; Biolegend), B220 (RA3-6B2; Biolegend), and CD3 (17A2; Biolegend). HSC frequency and statistical significance was calculated using Extreme Limiting Dilution Analysis (ELDA) software (bioinfwehi.edu.au). (Hu, Y. & Smyth, G. K. ELDA: extreme limiting dilution analysis for comparing depleted and enriched populations in stem cell and other assays. J Immunol Methods 347, 70-78, doi: 10.1016/j.jim.2009.06.008 (2009)).

Vascular permeability. Bone marrow vascular integrity was examined as previously described (Poulos, M. G. et al. "Endothelial transplantation rejuvenates aged hematopoietic stem cell function." J. Clin. Invest. (2017) 127: 4164-78. Doi: 10.1172/jci93940). In short, 0.5% w/v Evans Blue Dye (Sigma-Aldrich E2129) in PBS (pH 7.2) was injected via tail vein at 25 mg dye/kg total body weight. Three hours post-injection, mice were sacrificed via cervical dislocation and cardiac perfused with 10 mL PBS (pH 7.2). Femurs were crushed in a mortar and pestle with 600 μL formamide and incubated at 55° C. overnight. Extractions were briefly vortexed and centrifuged at 16,000×g for 5 min at room temperature. Supernatant was removed and absorbance (Abs) was measured at 620 nm and 740 nm. Sample Abs was corrected for Heme-containing proteins [Abs620−(1.426×$Abs_{740}$+0.03)] and blanked using non-injected controls [corrected sample Abs620− corrected non-injected control Abs620]. Evan's Blue Dye extravasation was calculated using a standard curve and normalized to femur weight.

Immunohistochemistry. To label the vasculature, mice were intravenously administered 25 μg of Alexa Fluor 647-conjugated CD144/VEcadherin antibody (Clone BV13; Biolegend) via retro-orbital sinus injections. Animals were sacrificed 10 min post-injection and cardiac perfused with 10 mL PBS (pH 7.2). Femurs were fixed overnight in 4% PFA in PBS (pH 7.2), decalcified in 10% EDTA for 72 hours at room temperature, cryopreserved in 30% sucrose for 48 hours at 4° C., and embedded in 50% optimal cutting temperature (OCT) and 50% sucrose. Longitudinal femur sections (12 μm) were cut using a CM 3050S Cryostat (Leica), counter-stained with 1 μg/mL 4-6, Diamidino-2-Phenylindole (DAPI) (Biolegend), and mounted using Prolong Gold anti-fade solution (Life Technologies). Sections were imaged on a LSM 710 confocal microscope (Zeiss).

Whole Mount immunofluorescence. Mice were intravenously administered 25 μg of Alexa Fluor-conjugated CD144/VEcadherin antibody (Clone BV13; Biolegend) via retro-orbital sinus injections. After 10 minutes, mice were euthanized and cardiac perfused with 4% PFA following which femurs were isolated, stripped of muscle and connective tissue, and fixed in 4% PFA for 30 minutes at room temperature. Bones were washed in 1×PBS 3×5 minutes and cryopreserved in 15% sucrose for 24 hours at 4° C., and further cryopreserved in 30% sucrose for 24 hours at 4° C. Bones were then embedded in a 50% OCT and 50% sucrose solution and flash frozen in liquid nitrogen. Bones were shaved longitudinally on a Leica CM 3050S cryostat in order to fully expose the bone marrow cavity for antibody penetration. Shaved bones were unmounted and washed 3×5 minutes in 1×PBS until OCT was completely melted. Exposed bones were blocked for 2 hours at room temperature in blocking buffer [20% Normal Goat Serum (Jackson Laboratories) in 1×PBS containing 0.5% Triton X-100], protected from light. Bones were then stained with fluorochrome conjugated primary antibodies (see Table 7) diluted in blocking buffer by immersion incubation in 1.5 mL Eppendorf microcentrifuge tubes for 48 hours at 4° C. Bones were washed 3×10 minutes in 1×PBS. 40 μm Z-stack images were acquired on a Nikon C2 confocal laser scanning microscope. The immunophenotype of HSCs was defined as $Lineage^{neg}CD48^{neg}hCD150^{bright}$ and their distance relative to the nearest vascular cell (VE-cadherin/CD144+) was measured for quantification.

TABLE 7

Whole Mount Immunofluorescence materials

| Antibody (stock) | Fluor | Clone | Dilution | Company |
|---|---|---|---|---|
| Ter119 (Img/mL) | Pac-Blue | Ter119 | 1:100 | Biolegend |
| CD41 (1 mg/mL) | Pac-Blue | MWReG30 | 1:100 | Biolegend |
| CD11b (1 mg/mL) | Pac-Blue | M1/70 | 1:100 | Biolegend |
| GR1 (1 mg/mL) | Pac-Blue | RB6-8C5 | 1:100 | Biolegend |
| B220 (1 mg/mL) | Pac-Blue | RA3-6B2 | 1:100 | Biolegend |

TABLE 7-continued

| Whole Mount Immunofluorescence materials | | | | |
|---|---|---|---|---|
| Antibody (stock) | Fluor | Clone | Dilution | Company |
| CD3 (1 mg/mL) | Pac-Blue | 17A2 | 1:50 | Biolegend |
| CD48 (1 mg/mL) | Pac-Blue | HM48-1 | 1:100 | Biolegend |
| CD150 (0.2 mg/mL) | PE/Dazzle 594 | TC15-12F12.2 | 1:50 | Biolegend |
| CD144 (1 mg/mL) | AF647 | BV13 | 25 ug (intravital) | Biolegend |

Proteomic Analysis

Plasma proteome analysis was performed at SomaLogics (Boulder, CO) using the aptamer-based SomaScan platform, as previously described. (Gold, L. et al. Aptamer-based multiplexed proteomic technology for biomarker discovery. PloS one 5, e15004, doi:10.1371/journal.pone.0015004 (2010).). To generate plasma, mice were bled via the retro-orbital sinus using 75 mm heparinized glass capillary tubes (Kimble-Chase) into EDTA containing microcentrifuge tubes (5 μM final concentration). Whole blood was centrifuged at 2200×g for 15 minutes at room temperature and plasma was collected and stored at −80° C. Cryopreserved mouse plasma EDTA samples were analyzed using the SomaScan Assay 1.1K platform; proteomic data is presented as relative fluorescent units (RFUs). To identify differentially expressed proteins, two-sided Student's t-test was performed with the threshold of significance set at $P<0.075$ using SomaSuite Software (SomaLogics). Core analysis was performed on the entire dataset (p-value cut-off <0.05) using Ingenuity pathway analysis (Qiagen) to identify biological processes that are significantly enriched in CDH5-MAPK mice. (giagenbioinformatics.com).

Lentivirus

Myristoylated-Akt1 (myrAkt1) lentivirus was generated by co-transfecting pCCL-myrAkt1 backbone (13 μg) (see Kobayashi, H. et al. Angiocrine factors from Akt-activated endothelial cells balance self-renewal and differentiation of haematopoietic stem cells. Nature cell biology 12, 1046-1056, doi:10.1038/ncb2108 (2010)) with RRE (5 μg), REV (2.5 μg), and VSV-G (3 μg) packaging plasmids on a 10 cm dish of 80% confluent 293T/17 cells (ATCC CRL-11268) using Lipofectamine 2000 (ThermoFisher Scientific 12566-014) according to the manufacturer's suggestions. Forty-eight hours post-transfection, supernatants were processed using Lenti-X Concentrator (ClonTech 631232) according to the manufacturer's suggestions. Precipitated myrAkt] lentivirus was resuspended in 0.5 mL TNE Buffer (50 mM Tris pH 8.0, 1 mM EDTA, 130 mM NaCl), aliquoted, and stored at −80° C. Viral titers were determined using Lenti-X p24 Rapid Titer Kit (ClonTech 632200). IkB-SS expressing lentiviral vector was generated by sub-cloning the sequence of human IκBα super suppressor (Addgene #15264) into pLVX Puro Vector (Clontech #632164). IkB-SS lentivirus was generated by co-transfecting pLVX-PuroIkB-SS vector with RRE, REV and VSV-G packaging plasmids in 293T cells as described earlier. pLVX Puro Vector (Clontech #632164) was utilized to generate the 'Puro empty' lentivirus.

Endothelial cell cultures Primary bone marrow endothelial cell (BMEC) cultures were generated from Cdh5(PAC)-creERT2; Mapkfl/fl, as described previously. (Poulos, M. G. et al. Endothelial transplantation rejuvenates aged hematopoietic stem cell function. J Clin Invest (2017)127, 4163-4178, doi:10.1172/jci93940). Briefly, femurs and tibiae were gently crushed using a mortar and pestle and digested with Digestion buffer for 15 minutes at 37° C., filtered (40 μm; Corning 352340), and washed in MACS buffer. WBM was depleted of terminally differentiated hematopoietic cells using a murine Lineage Cell Depletion Kit (Miltenyi Biotec 130-090-858) according to the manufacturer's recommendations. BM endothelium was immunopurified from cell suspensions using sheep anti-rat IgG Dynabeads (ThermoFisher Scientific 11035) pre-captured with a CD31 antibody (MEC13.3; Biolegend) in MACS buffer according to the manufacturer's suggestions. CD31 selected BM ECs were cultured in endothelial growth media and transduced with 104 pg myrAkt1 lentivirus per $3\times10^4$ ECs/cm$^2$. Akt-transduced BMECs were selected for seven days in serum- and cytokine-free StemSpan SFEM (StemCell Technologies, Inc. 09650) media. BMEC lines were stained with antibodies against cadherein 5, also known as VECAD (BV13; Biolegend), CD31 (390; Biolegend), and CD45 (30-F11; Biolegend) and FACS sorted for purity (BMEC defined as CD45−CD31+VEcadherin+). Established BMEC lines were transduced either with GFP lentivirus (Control BMECs) or GFP-Cre lentivirus (CDH5-MAPK BMECs) and the resultant GFP+ cells were FACS sorted to purity. Control and CDH5-MAPK BMECs were subsequently transduced with either Puro-empty or Puro-IκB-SS lentivirus to generate, respectively, Control, IkB, CDH5-MAPK and CDH5-MAPK::IkB cell lines. Transduced cell lines were selected with 2 μg/mL puromycin for 5 days. Cells were cultured in endothelial growth medium at 37° C., 5% $CO_2$, and 20% $O_2$ in 70% relative humidity. Growth media was changed every two days and cells were passaged 1:2 at 95% confluency with Accutase Cell Detachment Solution (Biolegend 423201) according to the manufacturer's suggestions.

Immunoblots

Established BMEC lines were serum starved in low-glucose DMEM for 36 hours prior to preparing cell lysates. Cultured cells were washed with ice-cold PBS (pH 7.2) and lysed in RIPA buffer (150 mM NaCl, 1% IGEPAL CA-630, 0.5% deoxycholate, 0.1% sodium dodecyl sulfate (SDS), and 50 mM TrisHCl, pH 8.0) with PhosStop Phosphatase Inhibitor (Roche 04906845001) and Complete EDTA-free Protease Inhibitor Cocktail (Roche 11836170001) for 20 minutes at 4° C., sonicated, and centrifuged for 10 minutes at 21,000×g at 4° C. to remove insoluble debris. Supernatants were stored at −80° C. Protein concentrations were determined using the DC Protein Assay (BioRad 5000111), and 5 μg total protein was denatured for 3 minutes at 95° C. in Laemmli Buffer, resolved on 12.5% SDS-acrylamide gels and electroblotted to nitrocellulose. Transferred blots were blocked for 1 hour in 5% non-fat dry milk in PBS (pH 7.2) with 0.05% IGEPAL CA-630 (Sigma-Aldrich 18896) and incubated overnight at 4° C. in 5% non-fat dry milk in PBS (pH 7.2) with 0.05% IGEPAL CA-630 with primary antibodies raised against phospho-p65 (Ser536) at 1:1000 (Cell Signaling 3033), p65 at 1:1000 (Cell Signaling 4764), phospho-ERK1/2 (Thr202/Tyr204) at 1:2000 (Cell Signaling 4370), ERK1/2 at 1:1000 (Cell Signaling 9102), Total IκBα at 1:1000 (Cell Signaling 4814), and Tubulin at 1:1000 (Cell Signaling 2146). Blots were washed 3×10 mins in PBS (pH 7.2) with 0.05% IGEPAL CA-630 at room temperature and incubated in 5% non-fat dry milk in PBS (pH 7.2) with 0.05% IGEPAL CA-630 and anti-rabbit or anti-mouse IgG (H+L) horseradish peroxidase (Jackson ImmunoResearch Laboratories) secondary antibodies at a dilution of 1:10,000 for 1 hour at room temperature. Blots were washed 3×10 minutes in PBS (pH 7.2) with 0.05% IGEPAL CA-630 at room temperature and developed using Amersham ECL Prime Western Blotting Detection Reagent (GE Healthcare RPN2232), according to the manufacturer's suggestions. All blots were developed using Carestream Kodak BioMax Light Film (Sigma-Aldrich).

Quantification of nuclear p65 p65, also known as Re1A, is one of the five components that form the NF-κB (nuclear factor kappa-light-chain-enhancer of activated B cells) transcription factor family. For assessment of nuclear p65, BMECs were plated in endothelial growth medium in chamber slides (Nunc Lab-Tek II CC Chamber Slide; Catalog #154941). At ~70% confluency, cells were serum starved in low-glucose DMEM for 36 hours following which cells were washed in PBS (pH 7.2) and fixed in 4% PFA in PBS (pH 7.2) for 15 minutes at room temperature. Cells were then permeabilized with 5% normal goat serum containing 1% Triton X-100 in PBS (pH 7.2) for 30 minutes. Cells were then stained with p65 antibody (C22B4; Cell Signaling, 1:100 dilution) in Antibody dilution buffer (1% Triton™ X-100 in PBS containing 1% BSA) for 1 hour at room temperature. Cells were washed 3 times with PBS and stained with goat anti-rabbit Alexa Fluor 647 (Thermo Scientific #A-21245, 1:250 dilution) in Antibody dilution buffer for 30 minutes at room temperature. Cells were washed 3 times with PBS and counterstained with DAPI at 1 μg/mL and mounted using Prolong Gold anti-fade solution (Life Technologies). To determine the effect of SCGF on nuclear p65 levels, BMECs derived from CDH5-MAPK mice were incubated with 0.4 μg/mL SCGF (or vehicle control) for 36 hours in low glucose DMEM. Concentration matched isotype control antibody (Cell Signaling #3900) was used for establishing background fluorescence. Images were acquired on a Nikon C2 confocal laser scanning microscope. Nuclear p65 levels were quantified using Image J as described previously. (Wessel, A. W. & Hanson, E. P. A method for the quantitative analysis of stimulation-induced 988 nuclear translocation of the p65 subunit of NF-kappaB from patient-derived dermal fibroblasts. 989 Methods Mol Biol 1280, 413-426, doi:10.1007/978-1-4939-2422-6_25 (2015). 990).

Gene expression analysis WBM was flushed from femurs and tibiae using a 26G×½ needle with MACS buffer and depleted of red blood cells using 1×RBC Lysis Buffer (Biolegend 420301) according to the manufacturer's recommendations. Total RNA was isolated from $4\times10^6$ RBC-lysed WBM cells using RNeasy plus Mini Kit (Qiagen 74134) according to manufacturer's instructions. Briefly, cells were lysed in 600 μL of Buffer RLT and homogenized using QIAshredder columns (Qiagen 79654). For RNA isolation from CD45 cells, stromal cells, Lepr+ cells and osteoblasts, cells were directly sorted into Trizol LS using FACS and RNA was purified using manufacturer's recommendations. RNA was isolated from 100,000 CD45+ cells per sample and 1000 cells per sample for stromal cells, Lepr+ cells and osteoblasts. For WBM and CD45 cells, total RNA was reverse transcribed using RT2 First Strand Kit (Qiagen 330401). cDNA generated from 100 ng total RNA was subsequently loaded on to RT2 PCR profiler arrays to evaluate gene expression of NF-kB signaling targets (Qiagen PAMM-225ZC). For stromal cells, Lepr+ cells and osteoblasts, cDNA was generated and amplified using the Ovation Pico WTA System V2 (Nugen) according to the manufacturer's suggested protocol and 100 ng amplified cDNA was utilized for the qPCR arrays. qPCR was performed using RT2 SYBR Green qPCR Mastermix (Qiagen 330522) in a ViiA 7 qPCR system (Applied Biosystems) with recommended cycling parameters. Qiagen's online data analysis tool was utilized to calculate fold changes, generate unsupervised hierarchical clustering and gene expression heat maps (qiagen.com). Reference genes for normalization were selected from a FIG. of 5 housekeeping genes (Actb, B2m, Gapdh, Gusb and Hsp90a1b) using 'Automatic selection of housekeeping genes' in the Qiagen online tool which selects the most stable reference gene for each condition. Fold changes were calculated using the $2^{-\Delta\Delta CT}$ method. Confirmation of I11b and Csf1 expression was performed by RT-qPCR using primers obtained from Qiagen (Cat #PPM03109F-200 and PPM03116C-200). For evaluation of cre and IkB-SS transgene expression in hematopoietic cells, RNA was isolated from 100,000 CD45+ cells per sample. Total RNA was reverse transcribed using RT2 First Strand Kit (Qiagen 330401). cDNA equivalent to RNA content of 2000 cells was utilized for RT-PCR analysis. Primers for RT PCR analysis of cre and IkB-SS expression (FIG. 6) are as follows:

TABLE 1

Primers Target Sequences

| Target | Forward (F) or Reverse (R) | Target Sequence (5' to 3') |
|---|---|---|
| Ptprc | F | CAGGGTCCACCTACATAAATGCCA (SEQ ID NO: 9) |
| Ptprc | R | CCTTCTTCACATCGTGTGACCATGAC (SEQ ID NO: 10) |
| Cdh5 | F | GAGAGACTGGATTTGGAATCAAATGCAC (SEQ ID NO: 11) |
| Cdh5 | R | CTCATAGGCAAGCACATTCCCTGTG (SEQ ID NO: 12) |
| Cre | F | ATGGCCAATTTACTGACCGTACACCA (SEQ ID NO: 13) |
| Cre | R | ACGATGAAGCATGTTTAGCTGGCCCA (SEQ ID NO: 14) |
| Actb | F | TGGCACCACACCTTCTACAATGAGC (SEQ ID NO: 15) |
| Actb | R | TGGCACCACACCTTCTACAATGAGC (SEQ ID NO: 15) |
| IkB-SS | F | AGACCTGGCTTTCCTCAACTTCC (SEQ ID NO: 16) |
| IkB-SS | R | CAGCACCCAAGGACACCAAAAGC (SEQ ID NO: 17) |

Peripheral Hematopoietic Recovery Mice were irradiated with sublethal-irradiation (650 Rads) from a $137^{Cs}$ source for evaluating hematopoietic recovery following myelosuppressive injury. Peripheral blood was collected using 75 mm heparinized glass capillary tubes (Kimble-Chase) via retro-orbital sinus bleeds at indicated time points. WBC, RBC, and platelet populations were analyzed using an Advia120 (Bayer Healthcare).

Reactive oxygen species estimation To examine reactive oxygen species (ROS), mice were intravitally-labeled for 10 minutes with 25 μg Alexa Fluor 647-conjugated CD144/VE-Cadherin antibody (BV13; Biolegend) via retro-orbital injection. Mice were sacrificed and femurs were either flushed (for HSPC analysis) or gently crushed and enzymatically disassociated (for BMEC and stromal cell analysis) in Digestion buffer for 15 minutes at 37° C. with gentle agitation. Cell suspensions were filtered (40 μm) and washed in MACS buffer followed by surface staining using the indicated antibodies for 20 minutes at 4° C. Stained cell suspensions were washed in MACS buffer and then incubated with 5 μM CellROX Orange (ThermoFisher Scientific) in Stemspan SFEM (StemCell Technologies) at 37° C. for 30 minutes, washed with MACS buffer, and resuspended in PBS containing 2 mM EDTA. ROS levels in the indicated cell types were estimated using Flow Cytometry.

Hypoxyprobe. To evaluate bone marrow oxygenation status, mice were co-injected with 100 mg/kg of Pimonidazole HCl (Hypoxyprobe-1; Hypoxyprobe, Inc.) and 25 μg Alexa Fluor 647-conjugated CD144/VE-Cadherin (BV13; Biolegend) via retro-orbital injection. Following 20 min, mice were euthanized and femurs were isolated. Femurs were either flushed (for HSPC analysis) or gently crushed and enzymatically disassociated (for BMEC and stromal cell analysis) in Digestion buffer for 15 minutes at 37° C. with gentle agitation. Following surface staining, cells were fixed and permeabilized using the BD Cytofix/Cytoperm Kit (BD Biosciences) and stained with a monoclonal antibody raised against Hypoxyprobe-1 at a 1:100 dilution (HP-Red549; Hypoxyprobe, Inc.) according to the manufacturer's suggestions. Hypoxyprobe levels in the indicated cell types were estimated using Flow Cytometry.

Cell cycle and apoptosis. For cell cycle analysis of BMECs, stromal cells and HSPCs, cells were surface stained, fixed and permeabilized using the BD Cytofix/Cytoperm Kit (BD Biosciences) as described in the preceding section following which the cells were stained with an antibody raised against Ki67 (B56, BD 561284) and counterstained with Hoechst 33342 (BD Biosciences), according to the manufacturer's recommendations. For cell cycle analysis of HSCs, WBM cells were first depleted of lineage positive cells using a lineage-cell depletion kit (Miltenyi Biotec #130-110-470) prior to surface staining. Cells were analyzed using flow cytometry with a low acquisition rate (350 events/second). Cell cycle status was classified as follows: G0 (Ki-67negative; 2N DNA content), G1 (Ki-67+; 2N DNA content), and S/G2/M (Ki-67+; >2N DNA content). Percentage of singlet cells in the Sub-G0/G1 area were classified as apoptotic.

Plasma ELISA. For aptamer-based sandwich ELISAs, streptavidin-coated 96-well plates (ThermoFisher Scientific 15124) were incubated at 4° C. overnight with 20 nM biotinylated aClec11a aptamer (SomaLogics; Boulder, CO) in SBT buffer (40 mM HEPES pH 7.5, 120 mM NaCl, 5 mM KCl, 5 mM MgCl2, and 0.05% Tween 20) according to the manufacturer's recommendations. Plates were washed three times with SBT buffer and blocked with 100 μM biotin (Sigma-Aldrich B4501) in SBT buffer for 10 minutes at room temp. Plates were washed three times at 100 RPM for 1 min with SBT buffer and blocked with 3% BSA in SBT buffer for 30 minutes at room temperature. Plates were washed three times at 100 RPM for 1 minute with SBT buffer. Mouse plasma biological replicates were diluted 1:80 in SBT buffer (optimal plasma dilution range determined in-house) and incubated at 450 RPM for 2 hours at 37° C. SBT alone was used to determine background signal. Plates were then washed three times at 100 RPM for 1 minute in TBST buffer (Tris-HCl pH 7.6, 150 mM NaCl, 0.05% Tween-20) and incubated at 450 RPM for 1 hour at room temp with 1 μg/mL αClec11a polyclonal antibody (R&D Systems AF3729) in 3% BSA in TBST buffer. Plates were washed three times at 100 RPM for 1 minute in TBST buffer and incubated at 450 RPM for 30 minutes at room temp with 8 ng/mL peroxidase conjugated donkey-αgoat secondary antibody (Jackson ImmunoResearch 705-035-147) in 3% BSA in TBST buffer (optimal secondary antibody dilution range determined in-house). Plates were washed three times at 100 RPM for 1 minute in TBST buffer and incubated in 1-Step Ultra TMB substrate (ThermoFisher Scientific 34028) for 12 minutes at room temperature. Sulfuric acid was added to a final concentration of 1M to stop the reaction and absorbance was read at 450 nm.

Direct ELISAs were adapted from a previously described protocol. (Yue, R., Shen, B. & Morrison, S. J. Clec11a/osteolectin is an osteogenic growth factor that promotes the maintenance of the adult skeleton. Elife 5, doi:10.7554/eLife.18782 (2016)). Mouse plasma was diluted 1:50 in PBS (pH 7.2) (optimal plasma dilution range determined in-house to achieve maximum signal-to-noise ratio), coated on Corning 1×8 Stripwell 96-well plates (Sigma-Aldrich CLS2592) and incubate overnight at 4° C. PBS (pH 7.2) alone was used to determine background signal. Plates were washed three times in PBS (pH 7.2) with 0.01% Tween-20 and blocked for 2 hours at room temp with ELISA Blocker blocking buffer (ThermoFisher Scientific N502). Plates were washed three times in PBS (pH 7.2) with 0.01% Tween-20 and incubated for 2 hours at room temperature with 1 μg/mL αClec11a polyclonal antibody (R&D Systems AF3729) in PBS (pH 7.2) with 0.01% Tween-20. Following primary antibody incubation, plates were washed three times in PBS (pH 7.2) with 0.01% Tween-20 and incubated for 1 hour at room temperature with 8 ng/mL peroxidase-conjugated donkey-αgoat secondary antibody (Jackson ImmunoResearch 705-035-147) in PBS (pH 7.2) with 0.01% Tween-20 (optimal secondary antibody dilution range determined in-house). Plates were then washed three times in PBS (pH 7.2) with 0.01% Tween-20 and incubated in 1-Step Ultra TMB substrate (ThermoFisher Scientific 34028) for 12 minutes at room temperature. Sulfuric acid was added to a final concentration of 1M to stop the reaction and absorbance was read at 450 nm. Recombinant murine Clec11a protein (R&D Systems 3729-SC/CF) was used to establish standard curves and determine protein concentration.

Clec11a/SCGF Infusion

Recombinant murine Clec11a (SCGF) protein (R&D Systems 3729-SC/CF) was resuspended in PBS (pH 7.2) to 100 μg/mL and stored at −80° C. as single-use aliquots. For steady state analysis, 100 μL of either 4 μg SCGF in PBS (pH 7.2) or PBS alone was injected subcutaneously on five consecutive days prior to analysis. Total SCGF protein dosing in steady state animals was adapted from a previous report.[63] For regeneration analysis, 100 μL of either 2 μg SCGF in PBS (pH 7.2) or PBS alone was injected subcutaneously on days 1, 3, 5, 7, 9, 11, and 13 post-TBI (650 Rads). SCGF dosing following myelosuppressive injury was determined by a dose-response experiment (SUPP. FIG. 10A and SUPP. FIG. 10B).

μCT Analysis Femurs were isolated, fixed in 4% PFA for 24 hours at 4° C. and stored in 70% ethanol at 4° C. A Scanco Medical CT 35 system with an isotropic voxel size of 7 μm was used to image the distal femur. Scans used an x-ray tube potential of 55 kVp, an x-ray intensity of 0.145 mA, and an integration time of 600 ms. For trabecular bone analysis, an upper 2.1-mm region beginning 280 μm proximal to the growth plate was contoured. For cortical bone analysis, a region 0.6 mm in length centered on the mid-shaft was used. Trabecular and cortical bones were thresholded at 211 and 350 per mgHA/cm$^3$, respectively. 3D images were obtained from contoured 2D images by methods based on distance transformation of the binarized images.

Quantification and Statistical Analysis

Sample sizes for phenotypic and functional analysis of mouse hematopoietic parameters were determined based on prior estimates of variance and effect sizes observed in previous experiments. Number of animals needed was calculated based on the ability to detect a two-fold change in the Mean with 80% power, with the threshold for significance (a) set at 0.05. All experimental findings were confirmed in at least 2 independent cohorts of mice and the data presented in the manuscript represent pooled data from independent experiments. Statistical comparisons between two groups were performed using two-tailed Student's t-test. Multiple comparisons were made using a One-way ANOVA analysis with a Tukey's Correction. Data is presented as the mean±standard error of the mean (SEM), unless otherwise noted. Statistical significance is indicated as * (p<0.05),  (p<0.01), * (p<0.001), and n.s. (not significant). Statistical analysis was performed using Prism 6 (GraphPad Software). HSC frequency and 95% confidence intervals were determined using Extreme Limiting Dilution Analysis (ELDA) software (bioinf.wehi.edu.au). (Hu, Y. & Smyth, G. K. ELDA: extreme limiting dilution analysis for comparing depleted and enriched populations in stem cell and other assays. J Immunol Methods 347, 70-78, doi:10.1016/j.jim.2009.06.008 (2009)).

Results

Figure 1F:
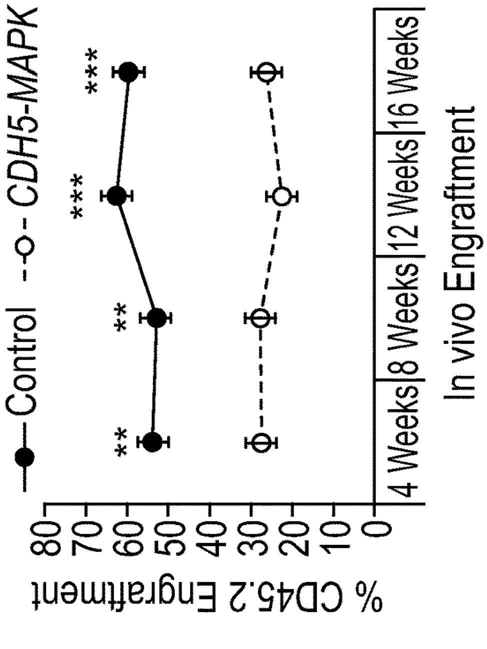
Figure 1G:
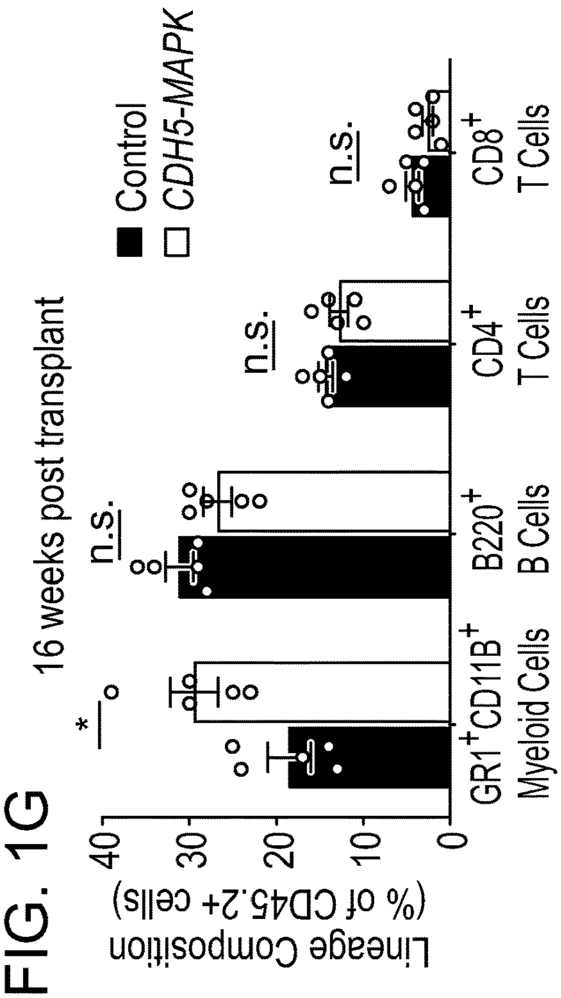

Endothelial MAPK activation impairs HSC function and hematopoiesis. To determine whether endothelial MAPK activation affects HSC activity and hematopoiesis, a mouse model was generated wherein MAPK signaling was constitutively activated specifically in adult endothelium. Mice carrying a Rosa26 Stop/Floxed MEK1DD cassette (an inducible S218D/S222D MAPKK1 mutant that renders ERK-MAPK signaling constitutively active) were crossed to a tamoxifen inducible cre transgenic mouse under the control of the adult endothelial-specific VEcadherin promoter (Cdh5(PAC)-creERT2) to generate CDH5-MAPK mice. To activate MAPK signaling in endothelial cells, 6-10 week old male and female mice were maintained on tamoxifen-impregnated feed (250 mg/kg) for 4 weeks and were allowed to recover for 4 weeks before experimental analysis. CDH5, MAPK mice displayed significantly decreased bone marrow cellularity and a significant decline in the frequency and absolute numbers of immunophenotypically defined HSCs (defined as cKIT+LineageNeg CD41−SCA1+CD150+ CD48Neg), as well as hematopoietic stem and progenitor cells (HSPCs) including KLS cells (cKIT+LineageNeg SCA1+), multipotent progenitors (MPPs; cKIT+LineageNeg SCA1+CD150 NegCD48Neg) and hematopoietic progenitor cell subsets (HPC-1 and HPC-2 defined as cKIT+ LineageNeg SCA1+CD150 NegCD48+ and cKIT+LineageNeg SCA1+CD150+CD48+, respectively), as compared to their littermate controls (FIG. 1A, FIG. 1B, FIG. 1C and FIG. 1D, SUPP. FIG. 1A). The decline in frequency of phenotypic HSPCs in CDH5-MAPK mice manifested as a functional loss of progenitor activity by methylcellulose-based colony assays (FIG. 1E). Competitive BM transplantation revealed that BM cells from CDH5-MAPK mice displayed diminished long-term engraftment potential and a significant myeloid-biased peripheral blood output (FIG. 1F and FIG. 1G). Furthermore, limiting dilution transplantation assays confirmed that endothelial MAPK activation significantly reduced the frequency of bona fide long-term HSCs (LT,HSCs) that are able to give rise to stable (>4 months; >1% CD45.2 engraftment), multi-lineage engraftment, in CDH5-MAPK mice as compared to control mice, (FIG. 1H and FIG. 1I). Cell cycle analysis demonstrated that HSCs and HSPCs from CDH5-MAPK mice displayed a loss of quiescence and increased apoptosis as compared to their littermate controls (FIG. 1J, FIG. 1K, SUPP. FIG. 1B, SUPP. FIG. 1C, SUPP. FIG. 1D, SUPP. FIG. 1E and SUPP. FIG. 1F). Taken together, these data suggest that chronic activation of endothelial MAPK adversely impacts niche activity leading to defects in steady state hematopoiesis and HSC function.

Figure 2A:
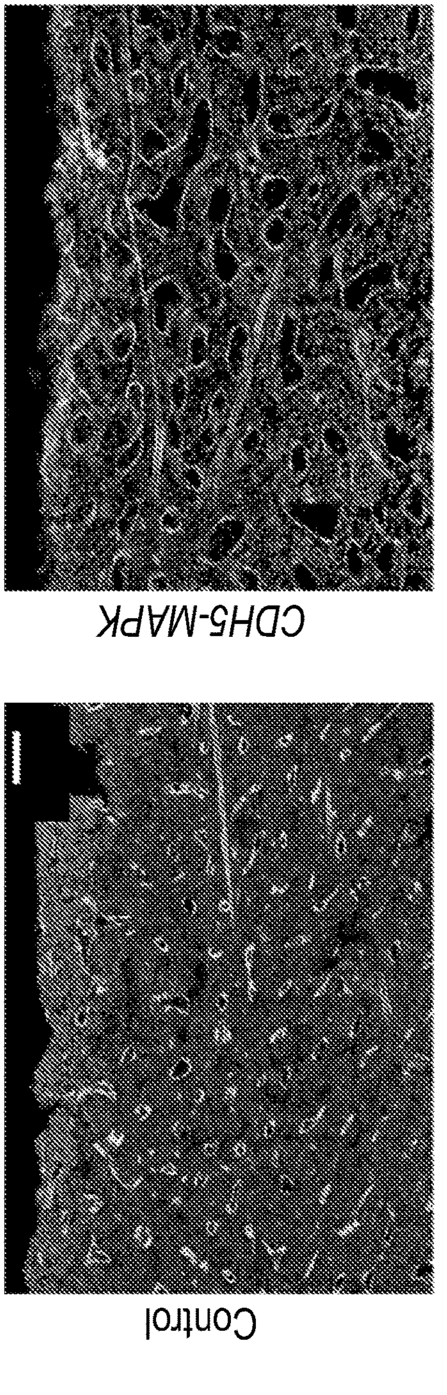
FIG. 2A, FIG. 2B, FIG. 2C, FIG. 2D, FIG. 2E, FIG. 2F, FIG. 2G, FIG. 2H, FIG. 2I, FIG. 2J show that CDH5-MAPK mice display systemic and BM-localized inflammation.
Figure 2B:
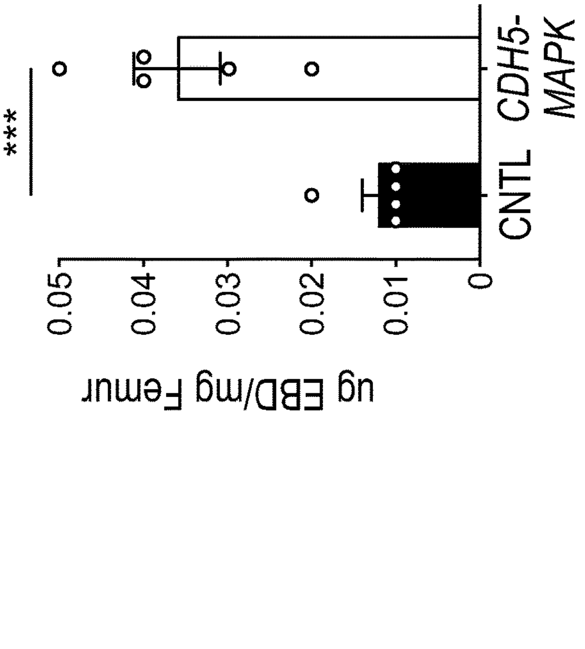
Figure 2C:
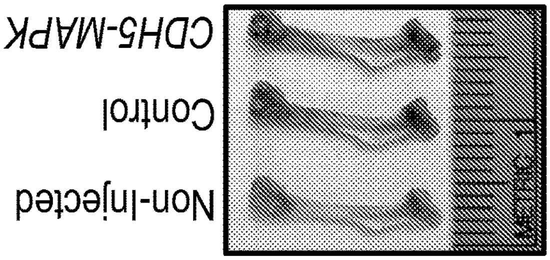
Figure 2D:
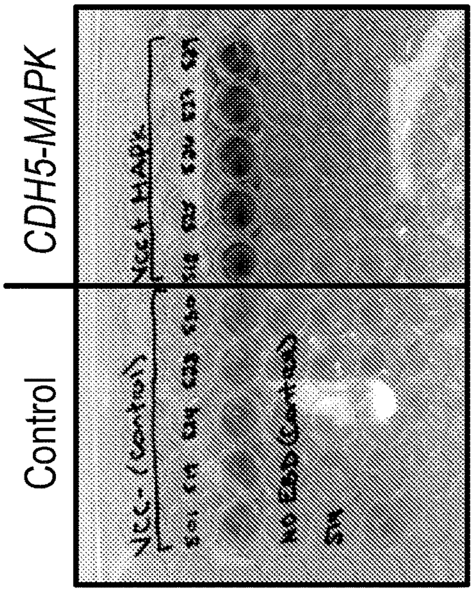

Endothelial MAPK drives an NF-kB dependent inflammatory stress response. The hematopoietic defects observed in CDH5-MAPK mice suggest that constitutive MAPK activation likely affects the integrity of the BM endothelial niche. Immunofluorescence analysis of the BM confirmed that MAPK activation led to disruption of the endothelial network, including an increase in vascular dilatation (FIG. 2A). Analysis of vascular integrity by a modified Evan's Blue assay revealed that CDH5-MAPK mice develop a significant increase in BM vascular leakiness, indicative of a loss of vascular integrity (FIG. 2B, FIG. 2C and FIG. 2D). Notably, increased vascular dilation and enhanced leakiness are hallmarks of an inflammatory stress[30]. Plasma proteome analysis of CDH5-MAPK mice demonstrated significantly increased levels of inflammatory mediators including sICAM, VCAM and IL1b (FIG. 2E and Supp. Table 1). Ingenuity Pathway Analysis of the differentially expressed proteins revealed that 'Inflammatory Response' was the most significantly enriched disease process in CDH5-MAPK mice (p values $1.3\times10^{-13}$, Activation z-score 2.32), within which 'Inflammation of organ' (p-value $5.7\times10^{-16}$, Activation z-score 0.21) and 'Inflammation of absolute anatomical origin' (p-value $2.8\times10^{-15}$, Activation z-score 0.84) were the top affected processes (FIG. 2F), indicating that endothelial MAPK activation leads to an inflammatory stress response. NF-κB signaling plays pivotal roles in driving inflammatory responses and recent reports indicate that endothelial MAPK activation can lead to inflammation via downstream activation of canonical NF-κB signaling. (Sanchez, A. et al. Map3k8 controls granulocyte colony-stimulating factor production and neutrophil precursor proliferation in lipopolysaccharide-induced emergency granulopoiesis. Sci Rep 7, 5010, doi:10.1038/s41598-017-04538-3 (2017).; Roth Flach, R. J. et al. Endothelial protein kinase MAP4K4 promotes vascular inflammation and atherosclerosis. Nat Commun 6, 8995, doi:10.1038/ncomms9995 (2015); Vandoorne, K. et al. Imaging the Vascular Bone Marrow Niche During Inflammatory Stress. Circ Res 123, 415-427, doi:10.1161/circresaha.118.313302 (2018); Baker, R. G., Hayden, M. S. & Ghosh, S. NF-kappaB, inflammation, and metabolic disease. Cell metabolism 13, 11-22, doi:10.1016/j.cmet.2010.12.008 (2011); Bottero, V., Withoff, S. & Verma, I. M. NF-kappaB and the regulation of hematopoiesis. Cell death and differentiation 13, 785-797, doi:10.1038/sj.cdd.4401888 (2006)).

Figure 2E:
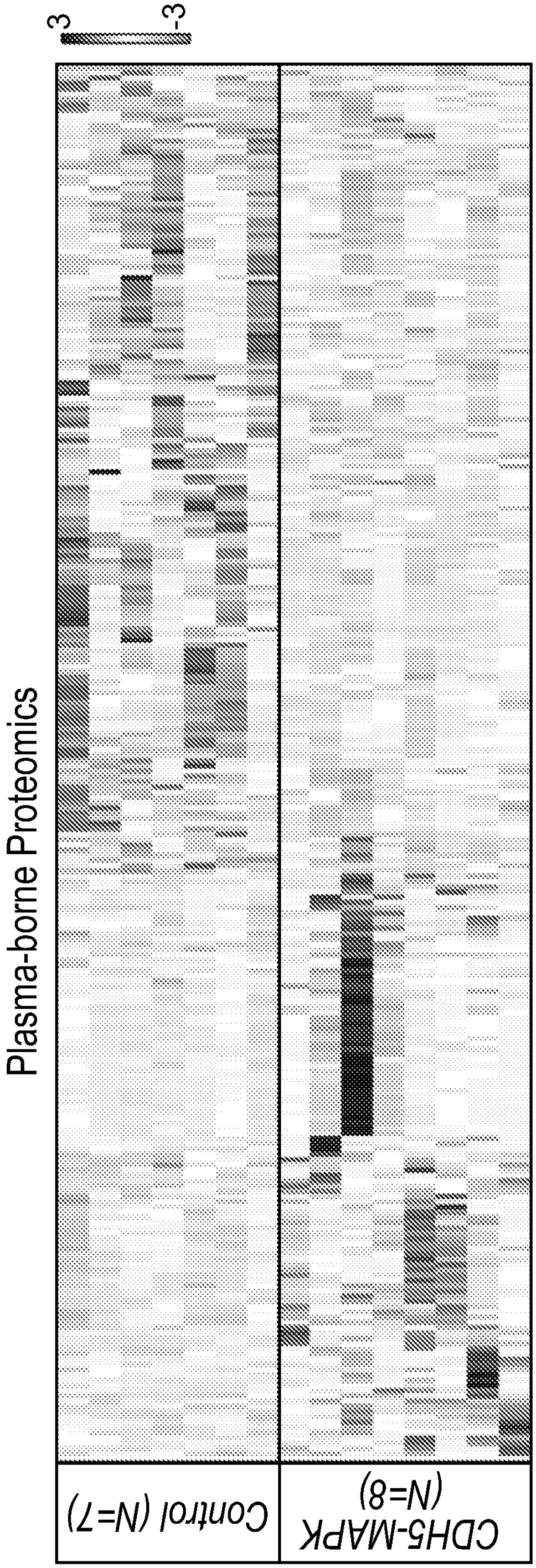
Figure 2F:
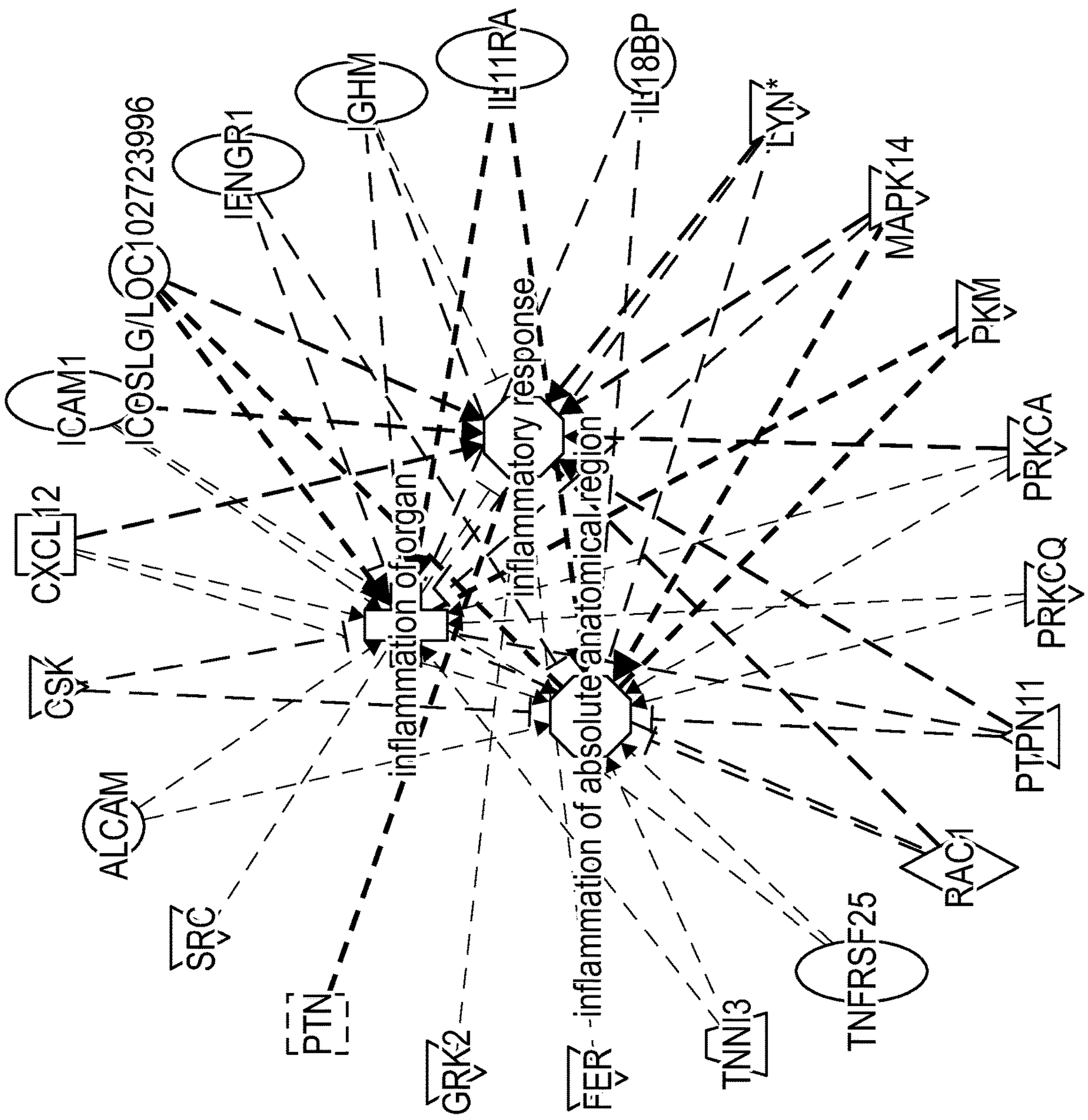
Figures 2G, 2H:
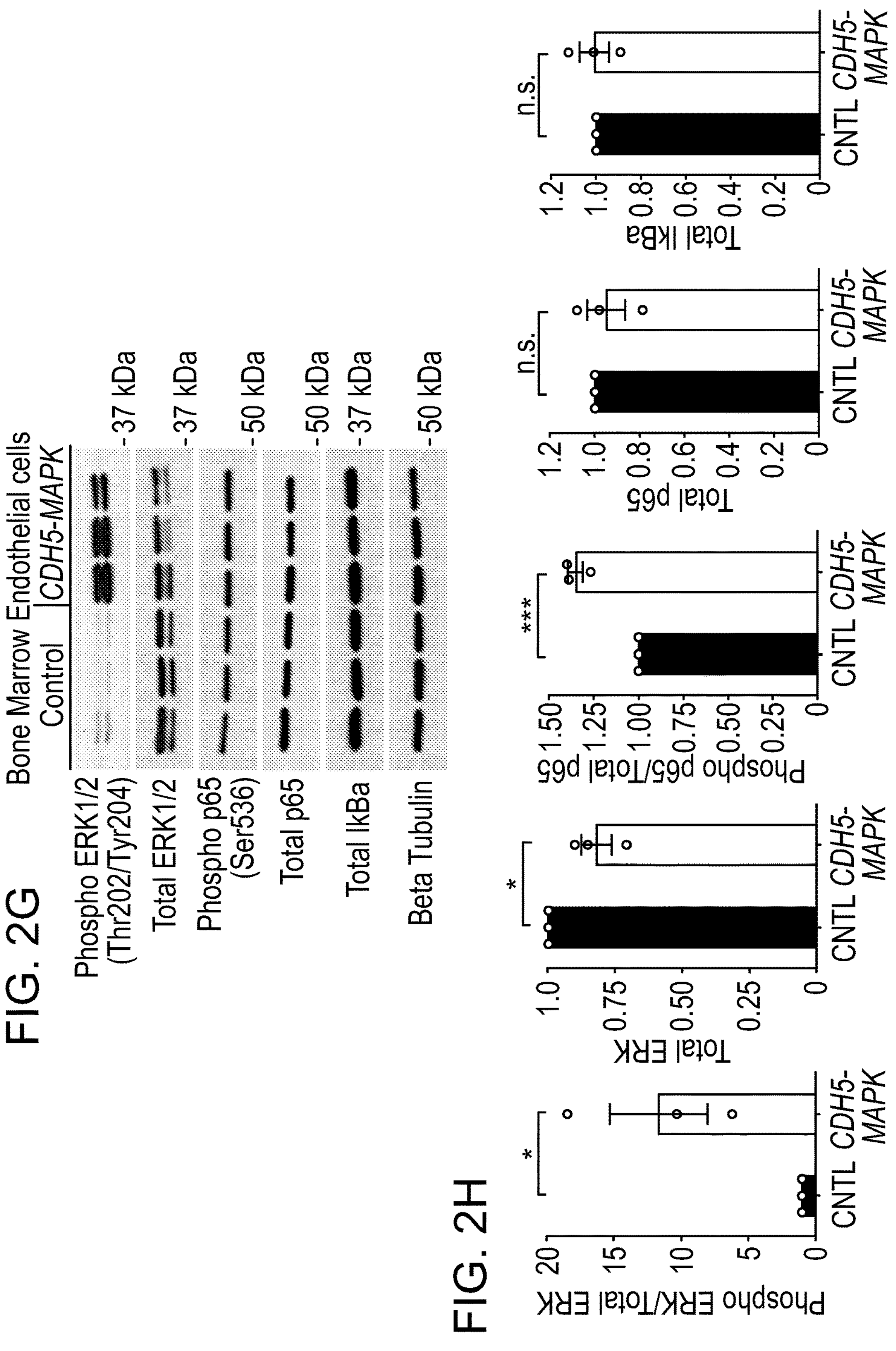
Figure 2I:
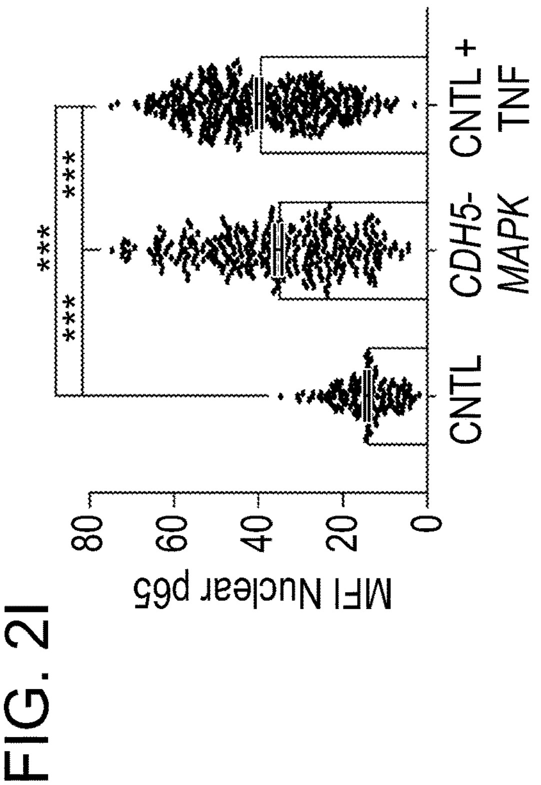
Figure 2J:
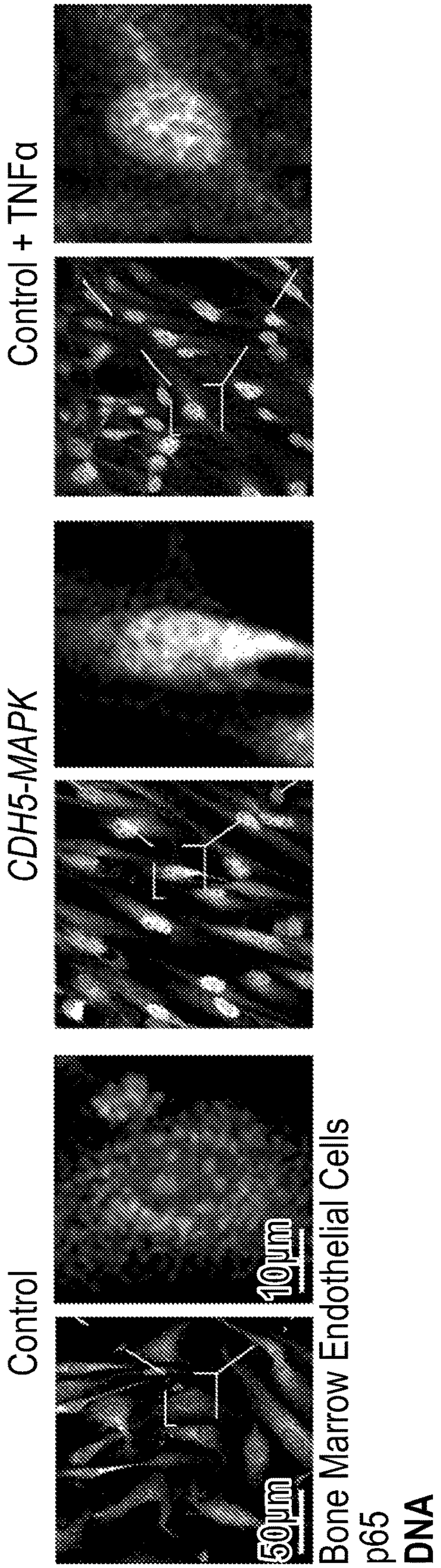

To verify this possibility, immunoblot analysis of endothelium derived from the BM of CDH5-MAPK mice was performed which confirmed an increase in MEK1DD driven ERK1/2 phosphorylation (FIG. 2G and FIG. 2H) and revealed a modest but consistent increase in p65-phosphorylation with no significant changes in total IκBα levels. These features are indicative of sustained activation of NF-κB signaling wherein endogenous feedback mechanisms increase the synthesis of total IκBα levels. (Brown, K., Park, S., Kanno, T., Franzoso, G. & Siebenlist, U. Mutual regulation of the transcriptional activator NF-kappa B and its inhibitor, I kappa B-alpha. Proc Natl Acad Sci USA 90, 2532-2536, doi:10.1073/pnas.90.6.2532 (1993); Wu, C. & Ghosh, S. Differential phosphorylation of the signal-responsive domain of I kappa B alpha and I kappa B beta by I kappa B kinases. J Biol Chem 278, 31980-31987, 983 doi:10.1074/jbc.M304278200 (2003); Yang, F., Tang, E., Guan, K. & Wang, C. Y. IKK beta plays an essential role in the phosphorylation of Re1A/p65 on serine 536 induced by lipopolysaccharide. J Immunol 170, 5630-5635, doi: 10.4049/jimmunol.170.11.5630 (2003)). Quantification of p65 nuclear translocation by immunofluorescence analysis demonstrated an increase in nuclear p65 within endothelium of CDH5-MAPK mice, confirming activation of NF-κB signaling downstream of endothelial MAPK activation (FIG. 2I and FIG. 2J). (Wessel, A. W. & Hanson, E. P. A method for the quantitative analysis of stimulation-induced 988 nuclear translocation of the p65 subunit of NF-kappaB from patient-derived dermal fibroblasts. 989 Methods Mol Biol 1280, 413-426, doi:10.1007/978-1-4939-2422-6_25 (2015)). Collectively, these findings suggest that increased NF-κB signaling within the endothelium of CDH5-MAPK mice likely drives an inflammatory stress response leading to vascular and hematopoietic defects.

Figure 3A:
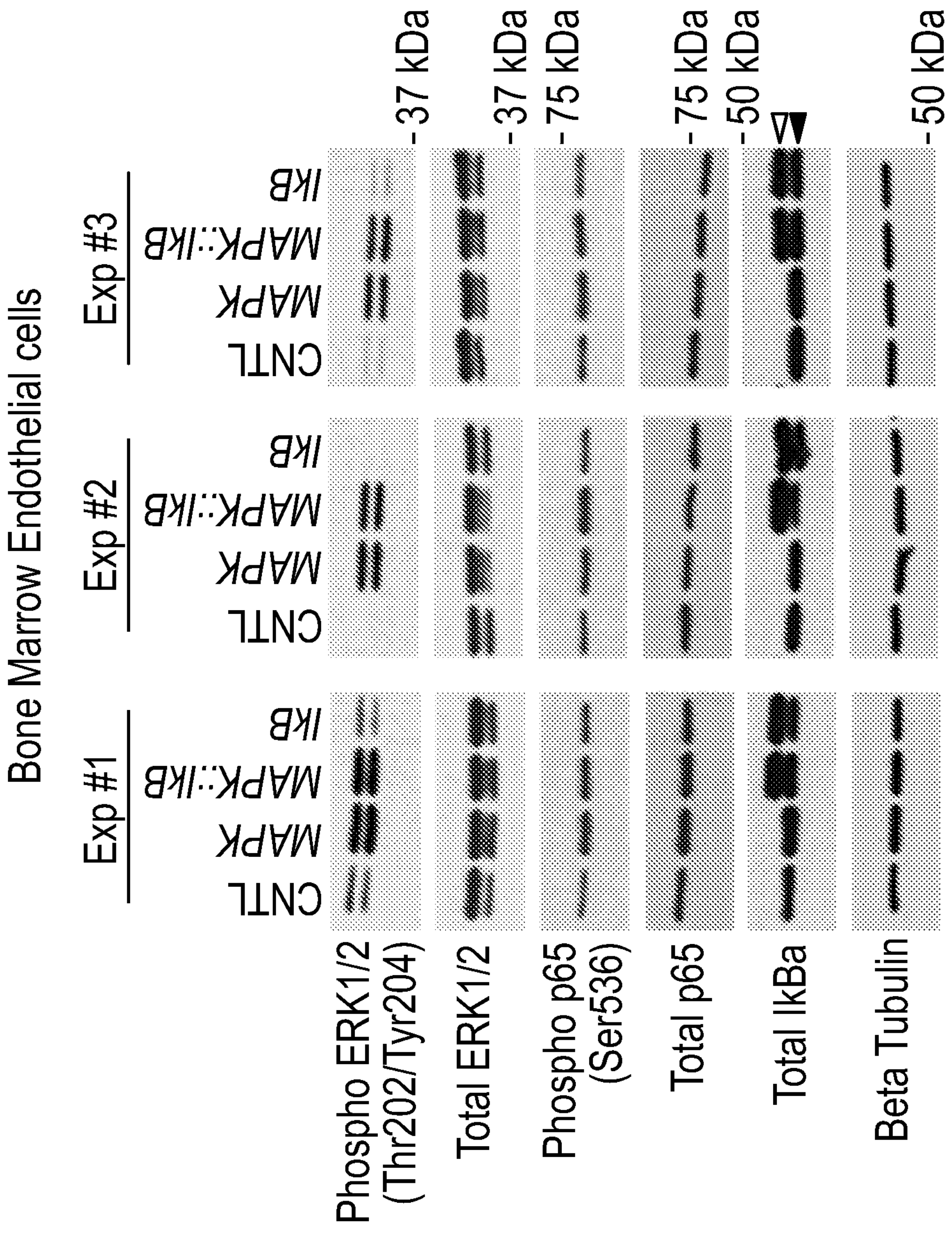
FIG. 3A, FIG. 3B, FIG. 3C, FIG. 3D, FIG. 3E, FIG. 3F, FIG. 3G show that endothelial NF-κB inhibition resolves endothelial inflammation and restores vascular integrity in CDH5-MAPK mice.
Figure 3B:
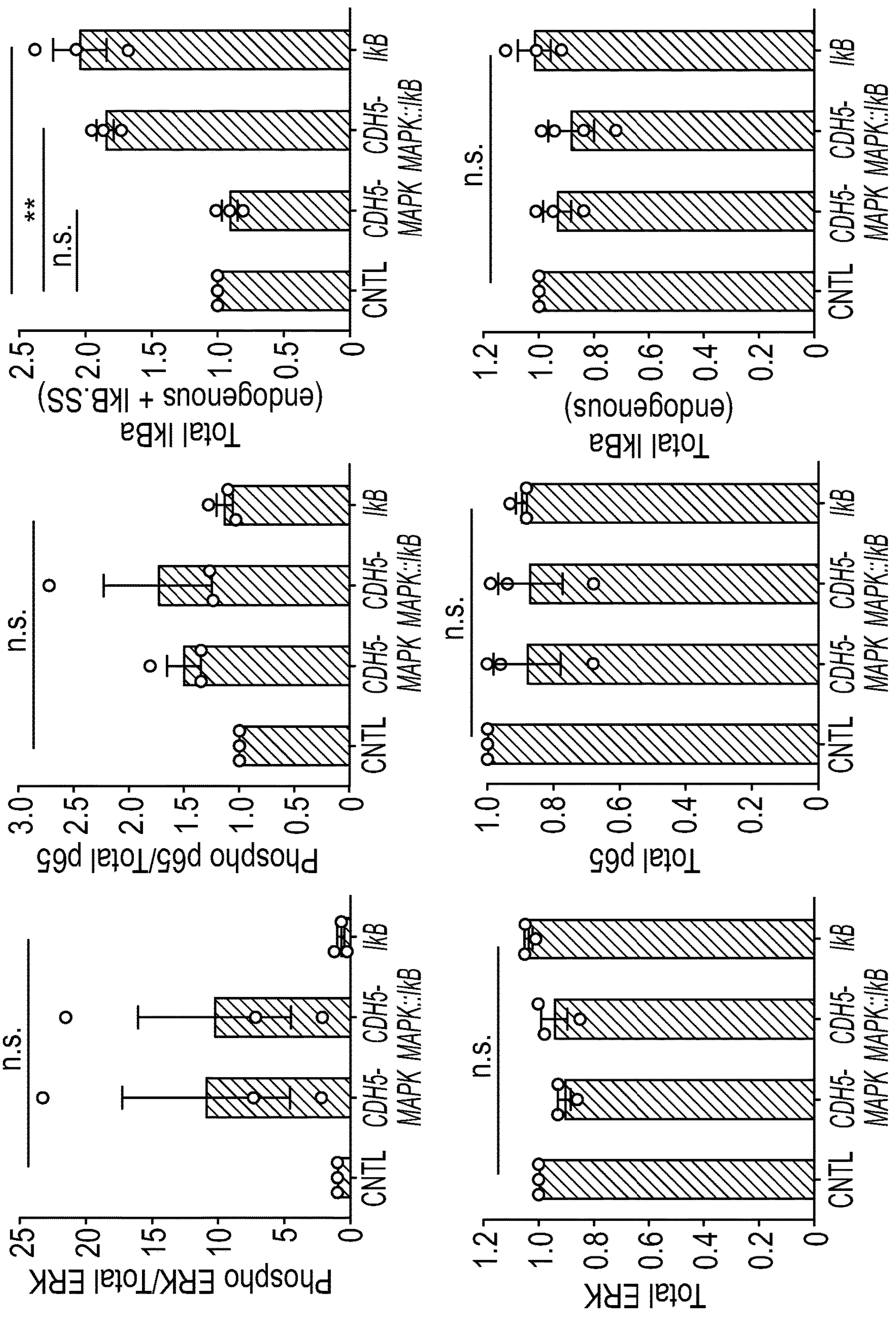
Figure 3C:
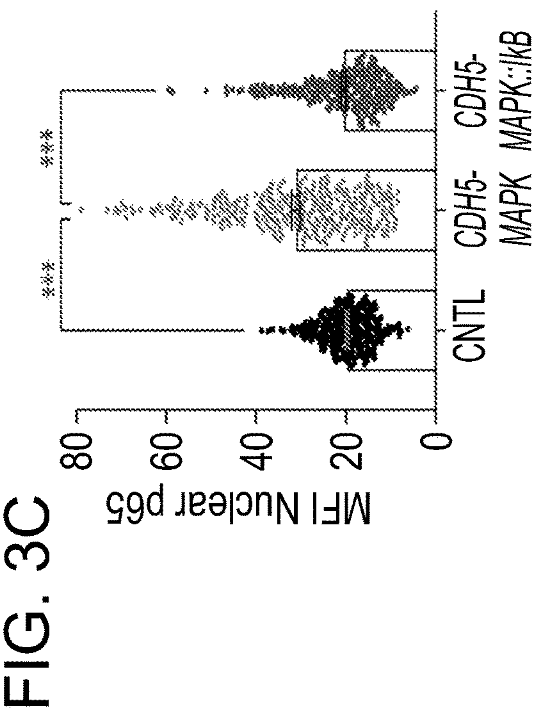
Figure 3D:
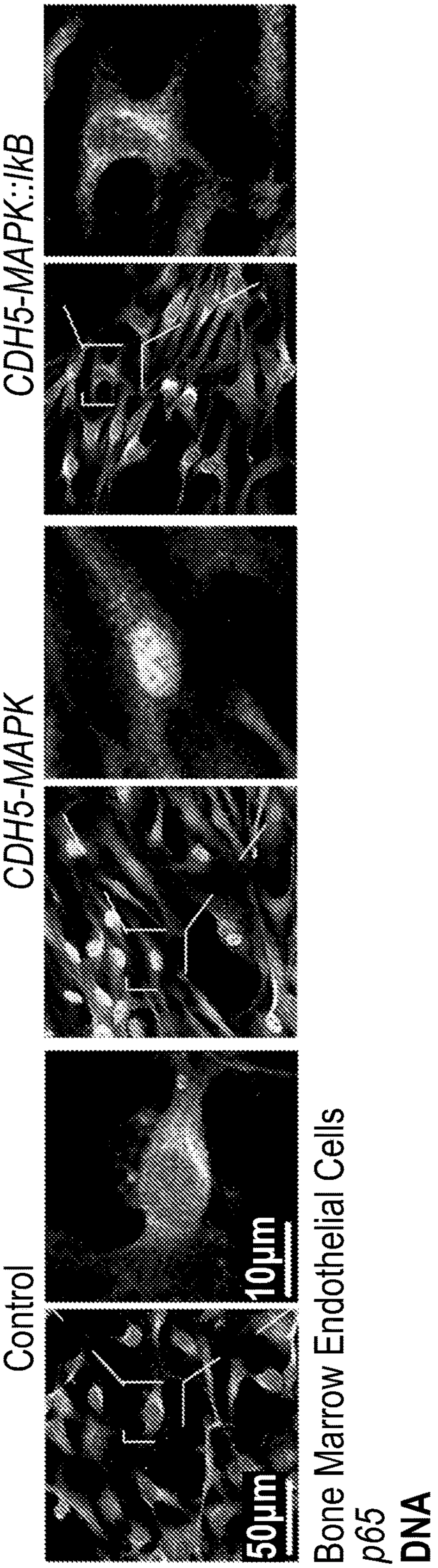
Figure 3E:
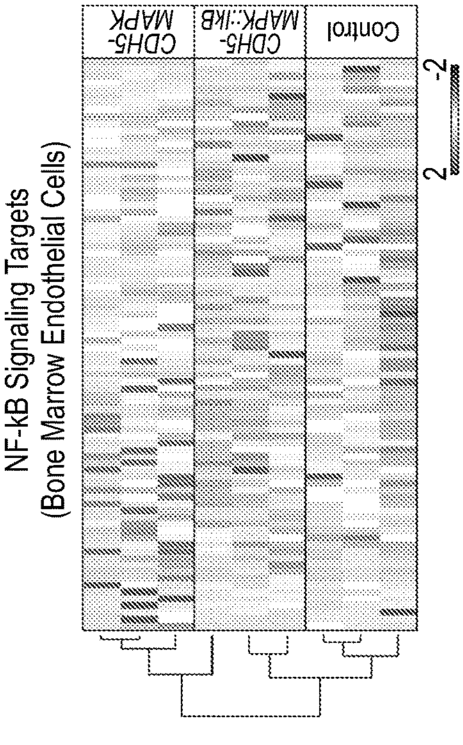
Figure 3F:
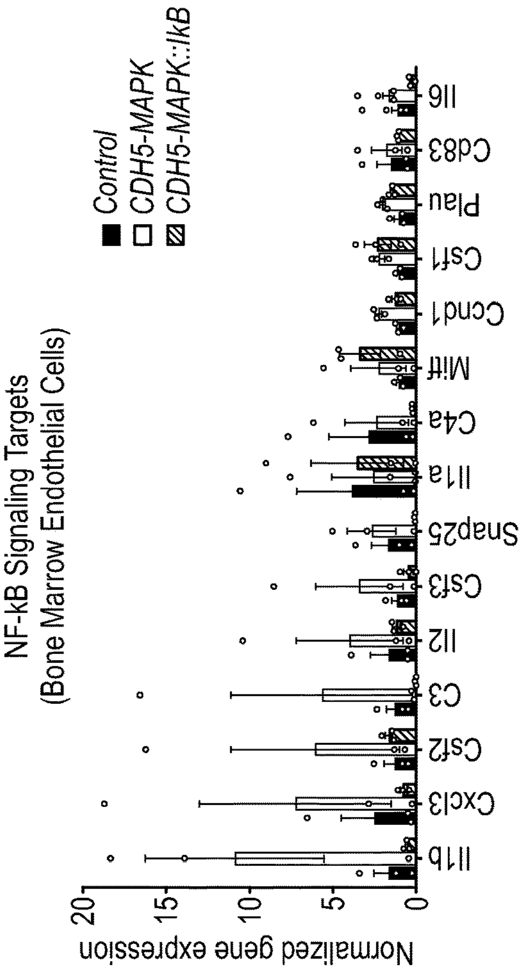
Figure 3G:
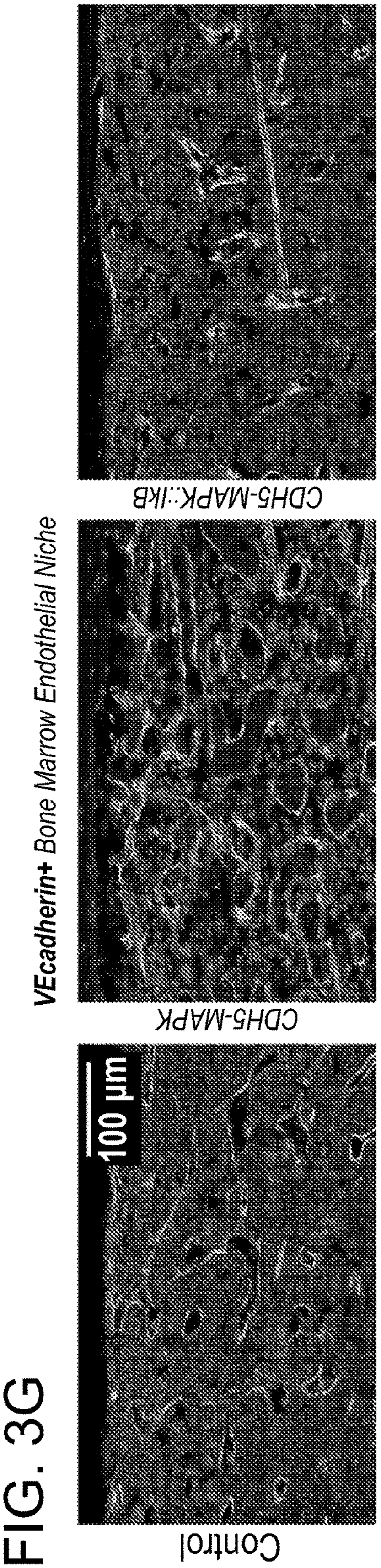

Endothelial NF-κB inhibition resolves vascular defects in CDH5-MAPK mice. Next, whether suppression of NF-κB signaling within the endothelium of CDH5-MAPK mice is sufficient to restore their vascular defects was determined. To this end, endothelial cells derived from BM of control and CDH5-MAPK mice was transduced with a lentivirus expressing a dominant negative IκBαS32A/S36A super suppressor (IkB-SS) construct that sequesters NF-kB (p65/p50) in the cytoplasm preventing its nuclear translocation. (Boehm, J. S. et al. Integrative genomic approaches identify IκBKE as a breast cancer oncogene. 991 Cell 129, 1065-1079, doi:10.1016/j.cell.2007.03.052 (2007); Brown, K., Gerstberger, S., Carlson, L., Franzoso, G. & Siebenlist, U. Control of I kappa B, alpha proteolysis by site-specific, signal-induced phosphorylation. Science 267, 1485-1488, doi:10.1126/science.7878466 (1995)). Immunoblot analysis confirmed the expression of IkB-SS transgene and revealed no significant alterations in ERK1/2 or p65 phosphorylation levels due to transgene expression (FIG. 3A and FIG. 3B). Immunofluorescence analysis confirmed that expression of IkB-SS decreased p65 nuclear translocation in endothelium derived from CDH5-MAPK mice (FIG. 3C and FIG. 3D). These data suggested that increased NF-κB signaling within the endothelium of CDH5-MAPK mice in vivo could be suppressed by expression of IkB-SS within the endothelium. To test this hypothesis, CDH5-MAPK mice were crossed with Tie2.IkB-SS mice (CDH5-MAPK::IkB mice) wherein the IkB-SS transgene is selectively expressed within endothelium of adult mice. (Brown, K., Gerstberger, S., Carlson, L., Franzoso, G. & Siebenlist, U. Control of I kappa B, alpha proteolysis by site-specific, signal-induced phosphorylation. Science 267, 1485-1488, doi:10.1126/science.7878466 (1995)).Analysis of NF-κB regulated target gene expression within bone marrow derived endothelial cells (BMECs; defined as CD45−Ter119−CD31+VEcadherin+) of CDH5-MAPK mice revealed increased levels of NF-kB signaling targets, including the pro-inflammatory cytokines and chemokines I11a, I11b, Cxcl1, Cxcl3, Ccl2, and Ccl22 (FIG. 3E and FIG. 3F, Supp. Table 2). Importantly, BMECs derived from CDH5-MAPK::IkB mice demonstrated an overall decrease in expression of NF-kB target genes indicating that IkB-SS transgene expression within BMECs of CDH5-MAPK mice decreased their NF-κB signaling (FIG. 3E and FIG. 3F, Supp. Table 2). Furthermore, immunofluorescence analysis of the BM endothelial niche demonstrated a normalization of the vascular dilation in CDH5-MAPK::IkB mice, confirming that inhibition of endothelial NF-κB signaling is sufficient to restore BM vascular integrity in CDH5-MAPK mice (FIG. 3G). Collectively, these findings confirmed that the detrimental effects of endothelial MAPK activation on the BM vascular niche are primarily mediated by downstream activation of endothelial NF-κB dependent inflammatory stress.

Figures 4A, 4B, 4C:
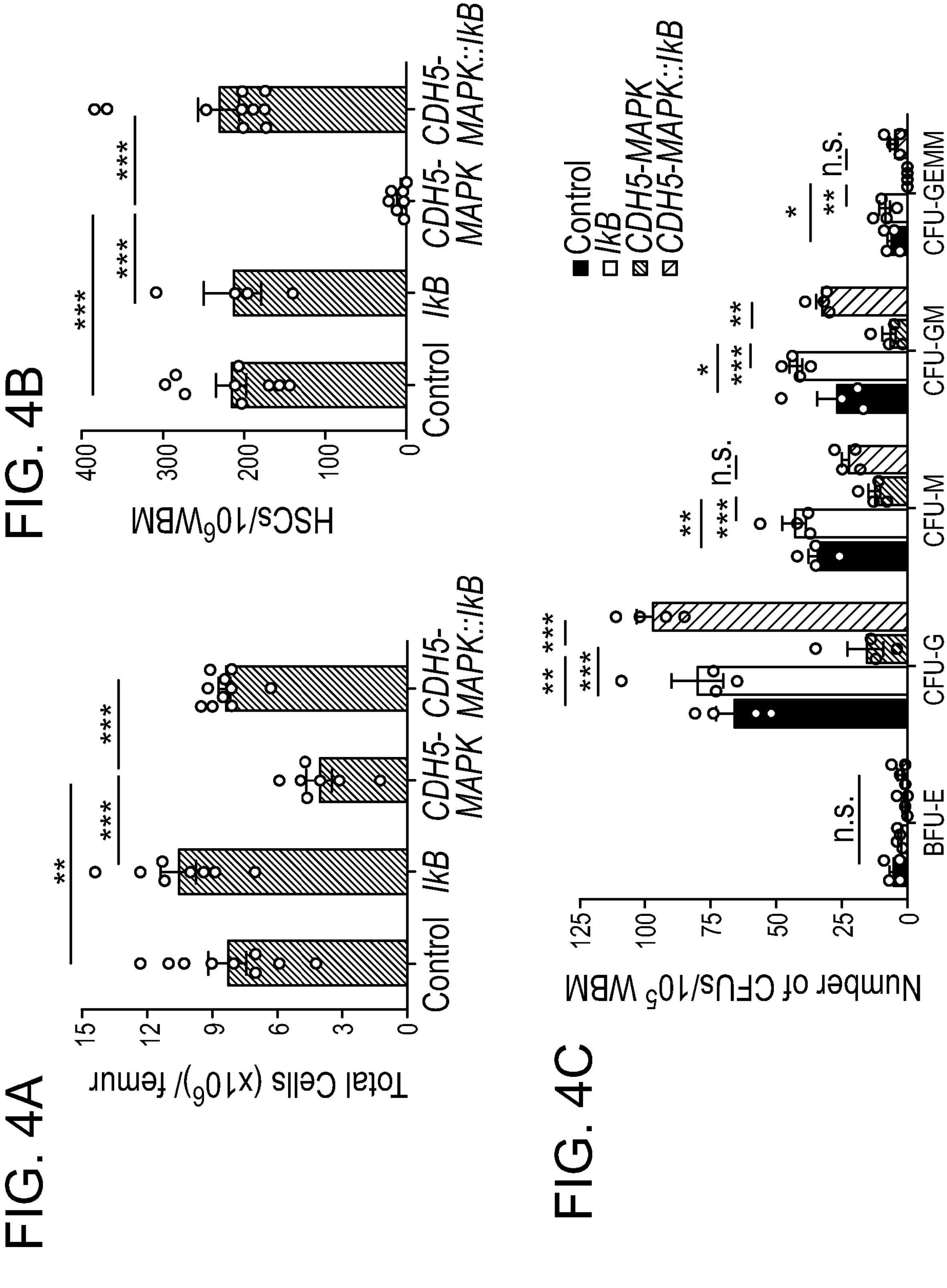
Figure 4J:
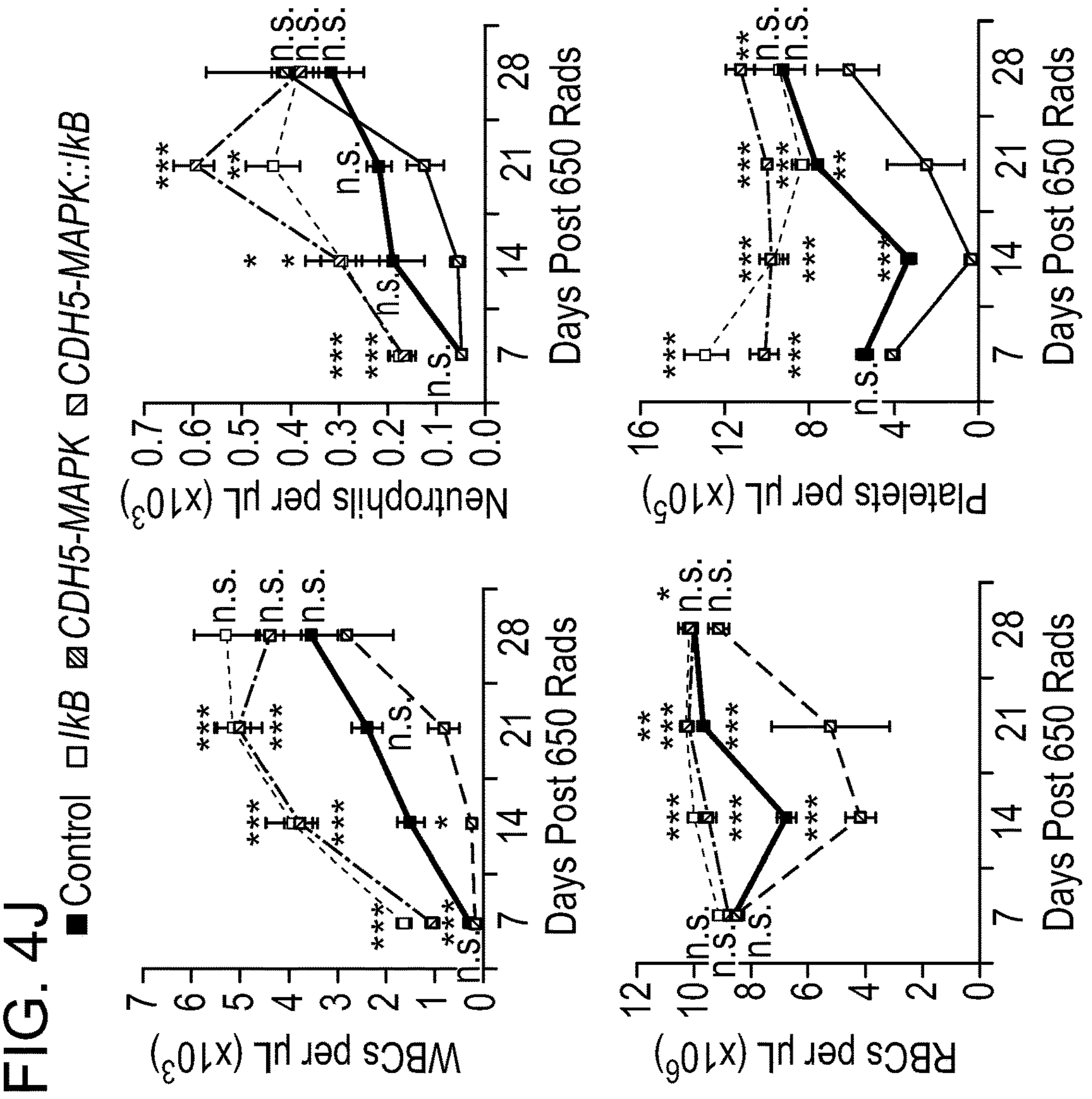
Figure 4I:
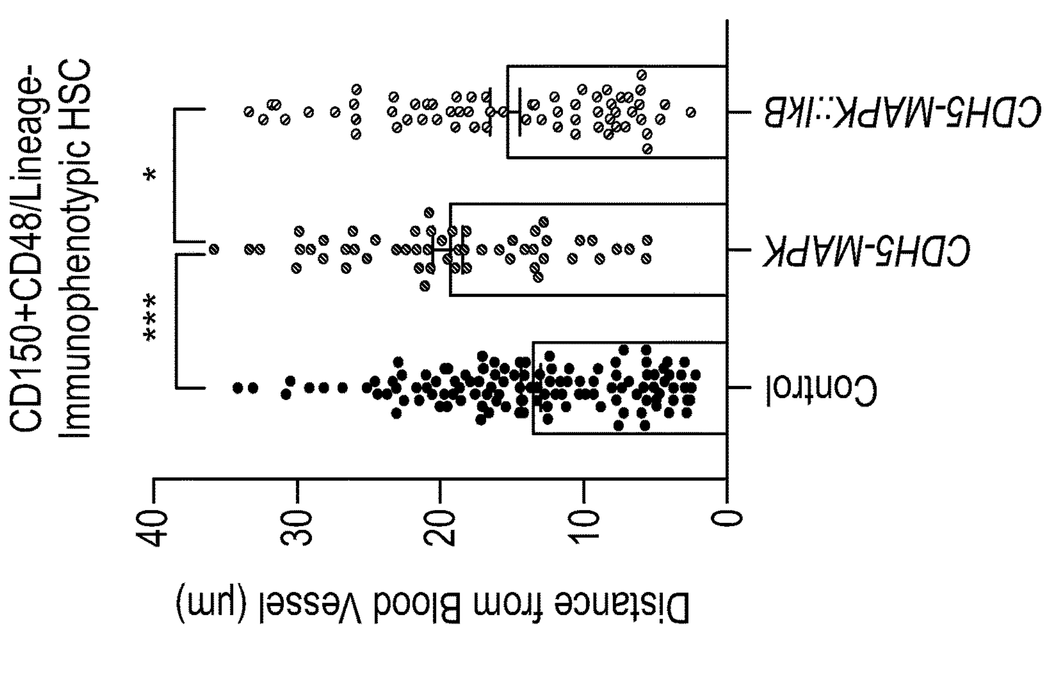

Endothelial NF-κB inhibition restores HSC activity in CDH5-MAPK mice. Then, it was studied whether restoration of BM endothelial niche integrity in CDH5-MAPK::IkB mice resulted in a functional recovery of HSCs and the hematopoietic system. Hematopoietic analysis of CDH5-MAPK::IkB mice demonstrated a restoration of BM cellularity and frequency of phenotypic HSCs and HSPCs (FIG. 4A and FIG. 4B; SUPP. FIG. 2A). The phenotypic recovery of progenitors within BM of CDH5-MAPK::IkB mice was also reflected in their progenitor activity in methylcellulose-based colony assays (FIG. 4C). Additionally, HSC functionality assayed by competitive BM transplantations demonstrated a complete recovery of long-term engraftment potential and a reversal of myeloid-biased differentiation in CDH5-MAPK::IkB mice (FIG. 4D and FIG. 4E; SUPP. FIG. 2B). WBM cells derived from CDH5-MAPK::IkB mice were also able to maintain their serial repopulation 180 and multi-lineage reconstitution abilities during secondary transplantation assays (SUPP. FIG. 2C and SUPP. FIG. 2D). Moreover, limiting dilution BM transplantation confirmed the restoration in frequency of bona fide LT,HSCs that were able to give rise to long-term multi-lineage engraftment in CDH5-MAPK::IkB mice (FIG. 4F and FIG. 4G). Under homeostatic conditions, HSCs predominantly reside in a perivascular niche wherein they receive instructive cues from endothelial and perivascular niche cells that regulate their quiescence and self-renewal. To determine whether inflammation within BM endothelium of CDH5-MAPK disrupted HSC-niche interactions, a whole mount immunofluorescence imaging of HSCs was performed which revealed an increase in average distance of HSCs from the vasculature (FIG. 4H and FIG. 4I). Notably, CDH5-MAPK::IkB mice demonstrated a restoration of HSC proximity to the vascular niche (FIG. 4H and FIG. 4I). These data demonstrate that restoration of BM endothelial integrity in CDH5-MAPK::IkB mice resulted in a normalization of HSC-niche interactions and a restoration of HSC functionality. To determine whether inflammation associated with endothelial MAPK activation influences post-myelosuppressive hematopoietic reconstitution, CDH5-MAPK, Tie2.IkB-SS, and CDH5-MAPK::IkB mice and littermate controls was subjected to sublethal myelosuppressive injury and assessed their hematopoietic recovery. Analysis of peripheral blood revealed that CDH5-MAPK mice displayed a significant delay in hematopoietic recovery indicating that sustained endothelial MAPK activation is deleterious for recovery following myelosuppressive injury (FIG. 4J). However, endothelial-specific NF-κB inhibition in CDH5-MAPK mice protected white blood cell, neutrophil, red blood cell, and platelet loss following irradiation as compared to CDH5-MAPK and control mice (FIG. 4J). Notably, the rate of hematopoietic recovery in CDH5-MAPK::IkB mice is similar to the recovery observed in Tie2.IkB-SS mice, which have been previously demonstrated to display a robust protection of the hematopoietic system following myelosuppressive injury. (Poulos, M. G. et al. Endothelial-specific inhibition of NF-kappaB enhances functional haematopoiesis. Nat Commun (2016) 7, 13829, doi:10.1038/ncomms13829). These data suggest that endothelial inflammation in CDH5-MAPK mice delays hematopoietic recovery whereas endothelial-specific NF-κB inhibition in CDH5-MAPK mice protects their hematopoietic compartment and enhances recovery following myelosuppressive injury.

Endothelial inflammation impairs hematopoietic progenitor activity. Along with HSCs, the vascular niche within the BM plays a crucial role in maintaining a diverse array of lineage-committed hematopoietic progenitors that sustain steady state peripheral blood output. (Wei, Q. & Frenette, P. S. Niches for Hematopoietic Stem Cells and Their Progeny. Immunity (2018) 48, 632-648, doi:10.1016/j.immuni.2018.03.024; Crane, G. M., Jeffery, E. & Morrison, S. J. Adult haematopoietic stem cell niches. Nature reviews. Immunology (2017) 17, 573-590, doi:10.1038/nri.2017.53; Comazzetto, S. et al. Restricted Hematopoietic Progenitors and Erythropoiesis Require SCF from Leptin Receptor+ Niche Cells in the Bone Marrow. Cell stem cell (2019) 24, 477-486.e476, doi:10.1016/j.stem.2018.11.022). Moreover, the vascular niche within the spleen has been shown to be a vital component for extramedullary hematopoiesis. (Inra, C. N. et al. A perisinusoidal niche for extramedullary haematopoiesis in the spleen. Nature (2015) 527, 466-471, doi: 10.1038/nature15530).

Figures 5A, 5B, 5C, 5D:
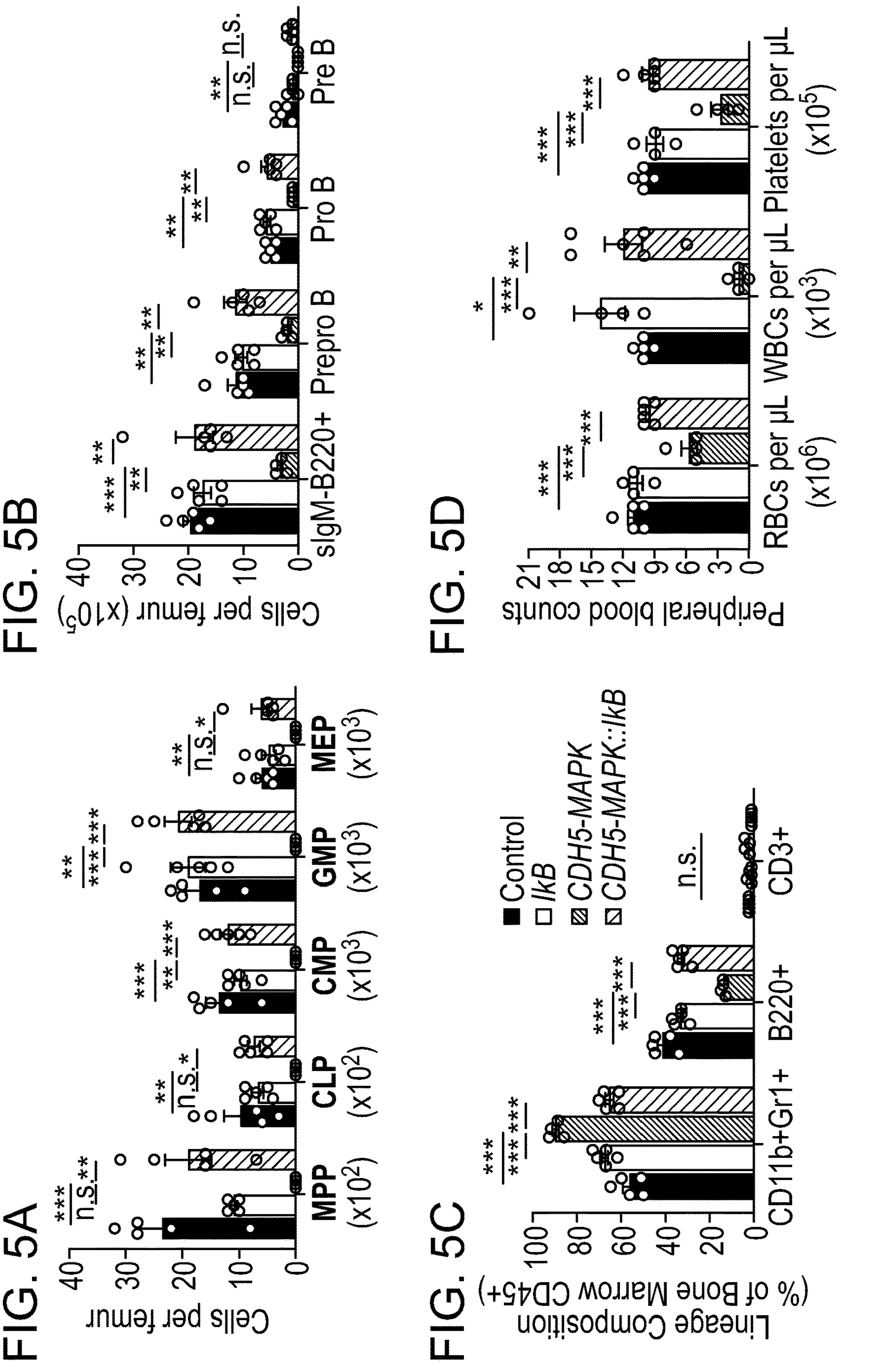
FIG. 5A, FIG. 5B, FIG. 5C, FIG. 5D, FIG. 5E, FIG. 5F, FIG. 5G, FIG. 5H, FIG. 5I, FIG. 5L show that endothelial NF-κB inhibition restores hematopoietic progenitor activity in CDH5-MAPK mice.
Figure 5E:
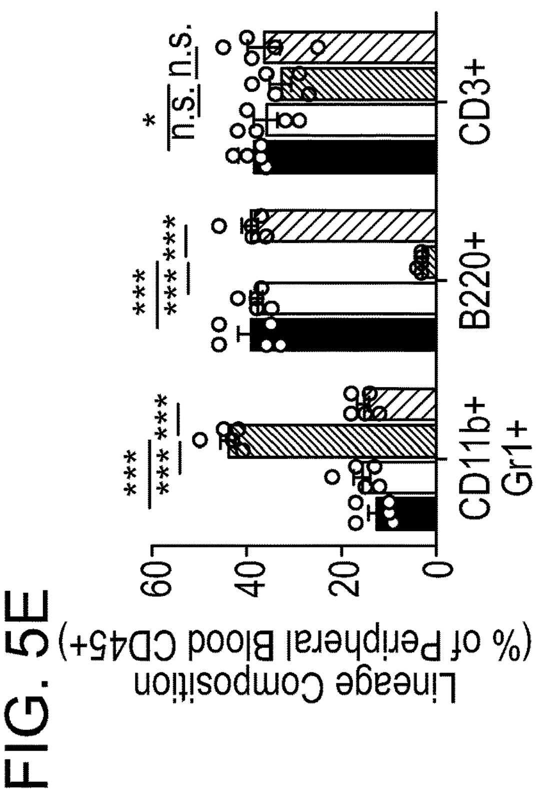
Figure 5F:
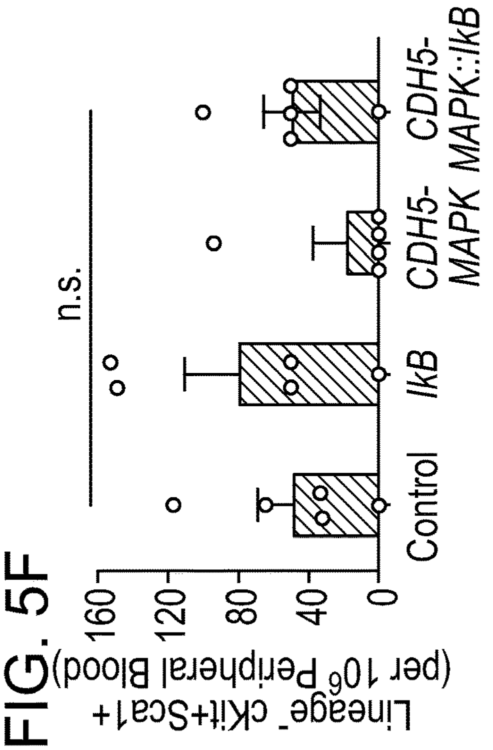
Figure 5G:
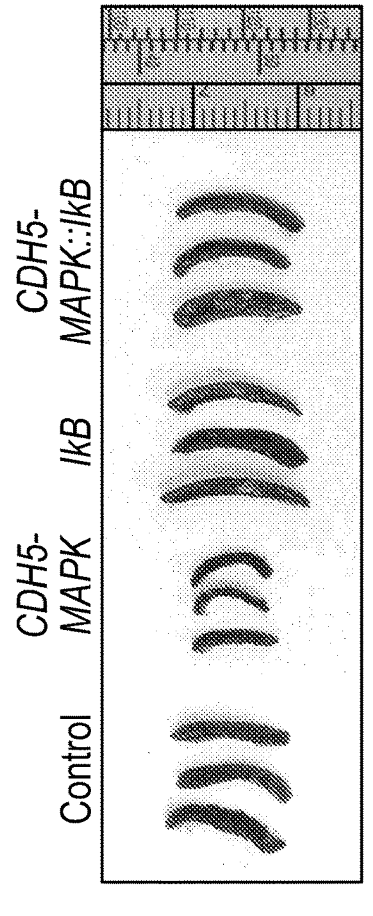
Figure 5H:
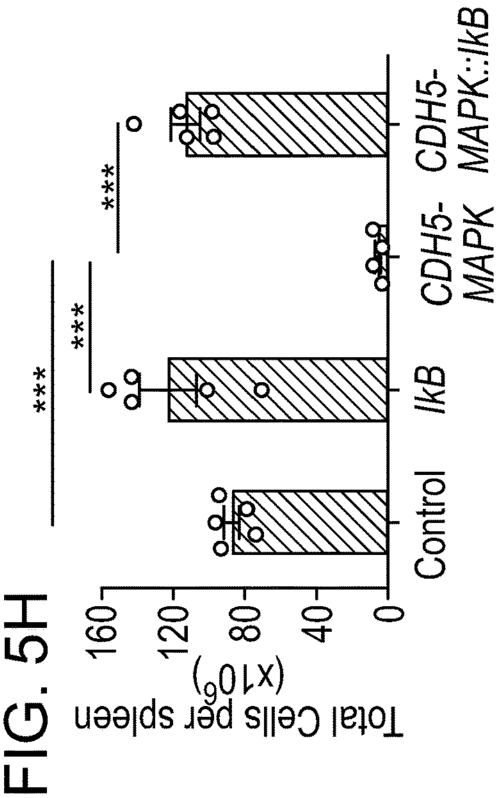
Figure 5I:
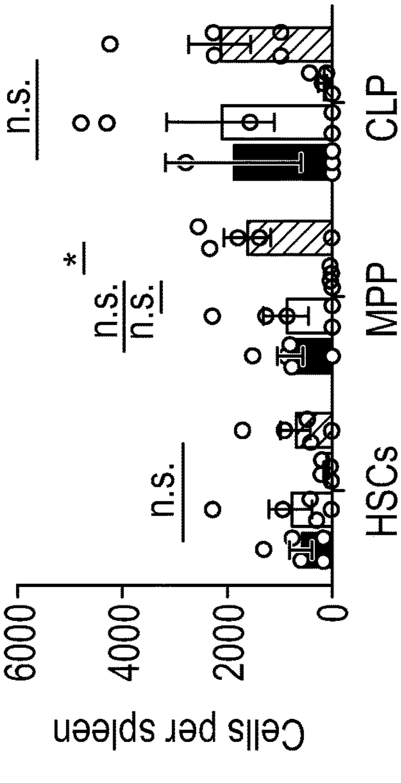
Figure 5J:
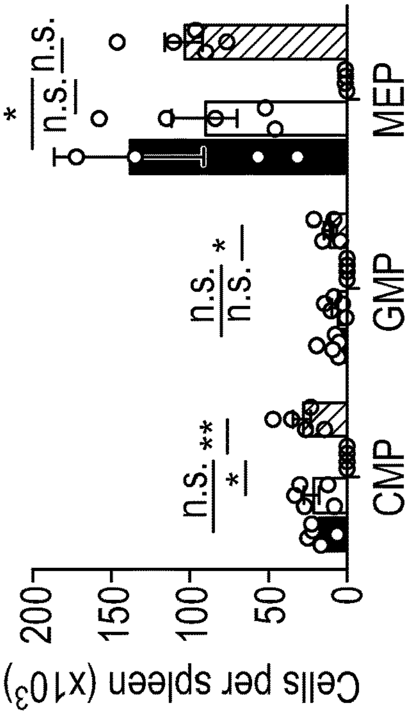
Figure 5K:
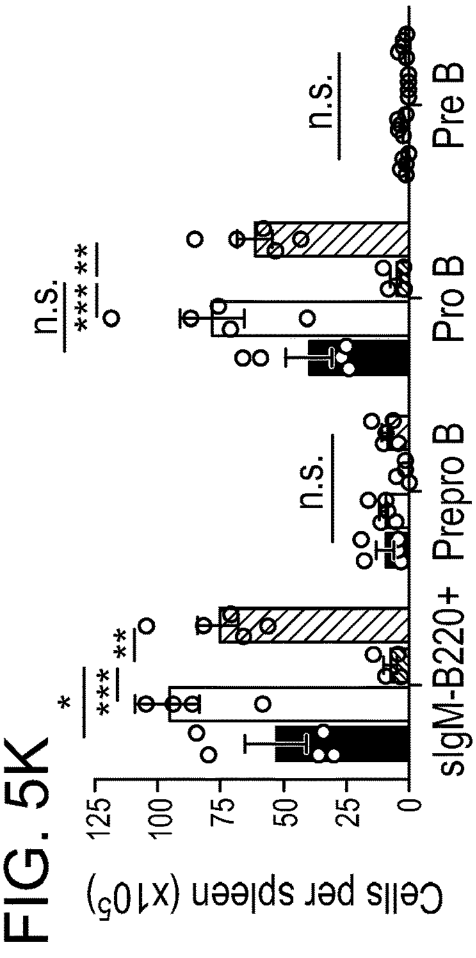
Figure 5L:
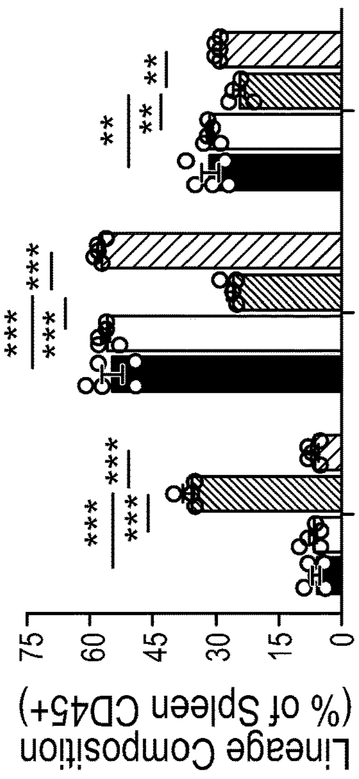

The effects of endothelial MAPK activation on hematopoietic progenitors within the BM and spleen of CDH5-MAPK mice was next studied. CDH5-MAPK mice displayed a decline in immunophenotypically defined BM multipotent progenitors (MPPs), common lymphoid progenitors (CLPs), common myeloid progenitors (CMPs), granulocyte/macrophage progenitors (GMPs), megakaryocyte/erythroid progenitors (MEPs), and B cell progenitor subsets (sIgM-B220+ B cells, Pre-Pro B cells, Pro B cells and Pre B cells) which was functionally reflected in their decreased peripheral blood counts.(FIG. 5A, FIG. 5B, FIG. 5C and FIG. 5D; SUPP. FIG. 2E, SUPP. FIG. 2F). Hematopoietic cells within BM of CDH5-MAPK mice also manifested a myeloid-biased output (increased percentage of CD11b+GR1+ cells within CD45+ BM cells), likely mediated by the effects of inflammatory cytokines that promote myeloid-biased differentiation of HSCs (FIG. 5C). The lineage-skewing in the BM was also reflected in their peripheral blood lineage composition (FIG. 5E). Collectively, these findings indicate that endothelial MAPK activation resulted in decreased blood counts due to loss of HSC and progenitor activity and was associated with a myeloid-biased output. Importantly, the BM and peripheral blood defects observed in CDH5-MAPK mice were completely restored in CDH5-MAPK::IkB mice. We next sought to determine whether impaired hematopoiesis within BM of CDH5-MAPK mice could result in HSPC mobilization and extramedullary hematopoiesis. Peripheral blood analysis did not reveal significant differences in circulating KLS HSPCs demonstrating that endothelial MAPK activation did not lead to HSPC mobilization (FIG. 5F). Analysis of the spleen in CDH5-MAPK mice revealed significant decreases in size and cellularity along with a decrease in frequency of HSCs and hematopoietic subsets, indicating an absence of extramedullary hematopoiesis (FIG. 5G, FIG. 5H, FIG. 5I and FIG. 5K). Lineage composition of CD45+ cells in the spleen revealed a myeloid bias (CD11b+GR1+ cells), confirming that endothelial MAPK-dependent inflammation adversely impacts niche activity and hematopoiesis within the spleen (FIG. 5I). Notably, CDH5-MAPK::IkB mice demonstrated a restoration of the defects observed in the spleen of CDH5-MAPK mice (FIG. 5G, FIG. 5I, FIG. 5H, FIG. 5I, FIG. 5J, FIG. K and FIG. 5L). These data demonstrate that CDH5-MAPK mice manifest hematopoietic defects, both in primary (bone marrow) and secondary (spleen) hematopoietic organs, and that suppression of endothelial NF-κB signaling overrides the hematopoietic defects resulting from endothelial MAPK activation.

Figure 6A:
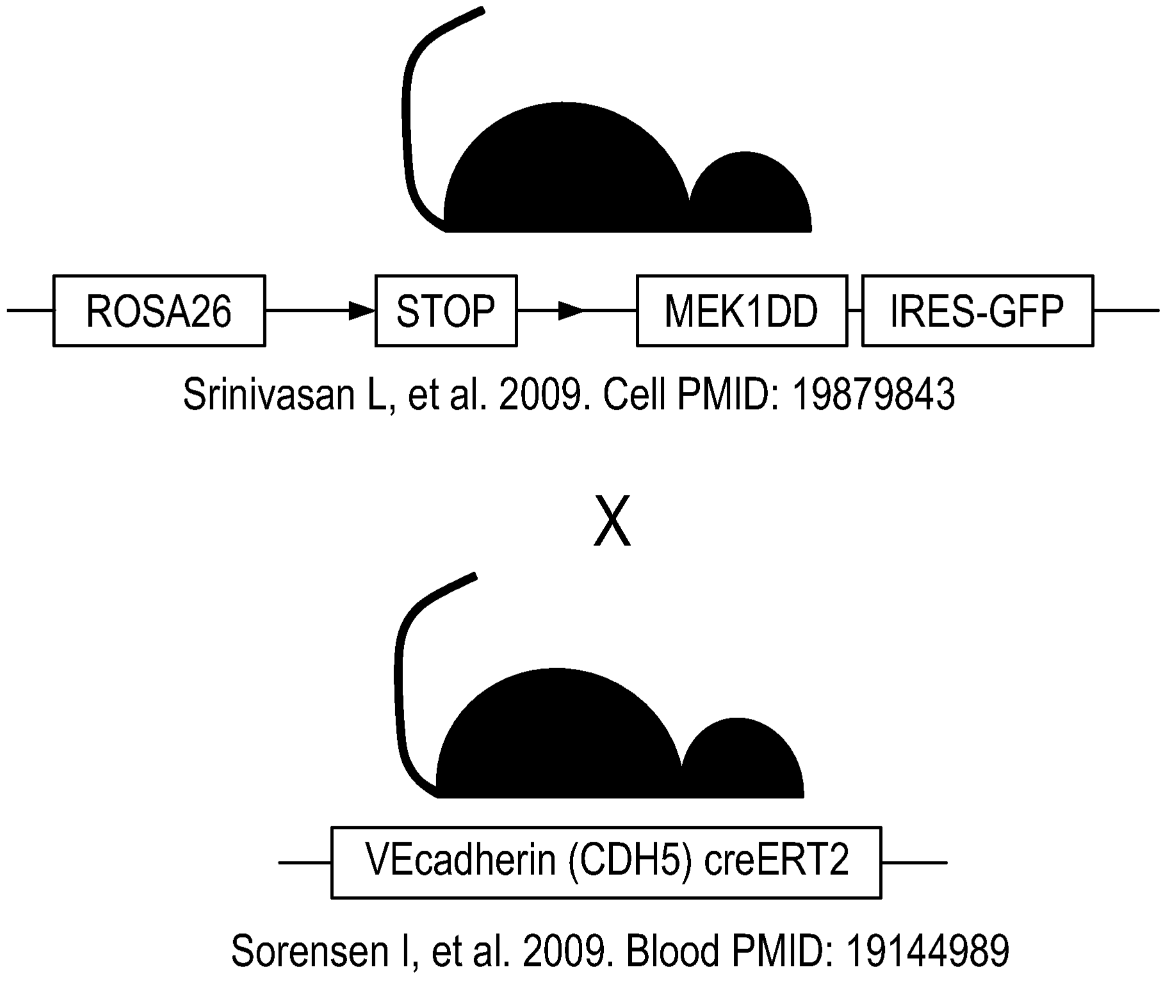
FIG. 6A, FIG. 6B, FIG. 6C, FIG. 6D, FIG. 6E, FIG. 6F, FIG. 6G show that CDH5-MAPK and Tie2.IkB-SS mice demonstrate endothelial-specific expression of transgenes.
Figure 6B:
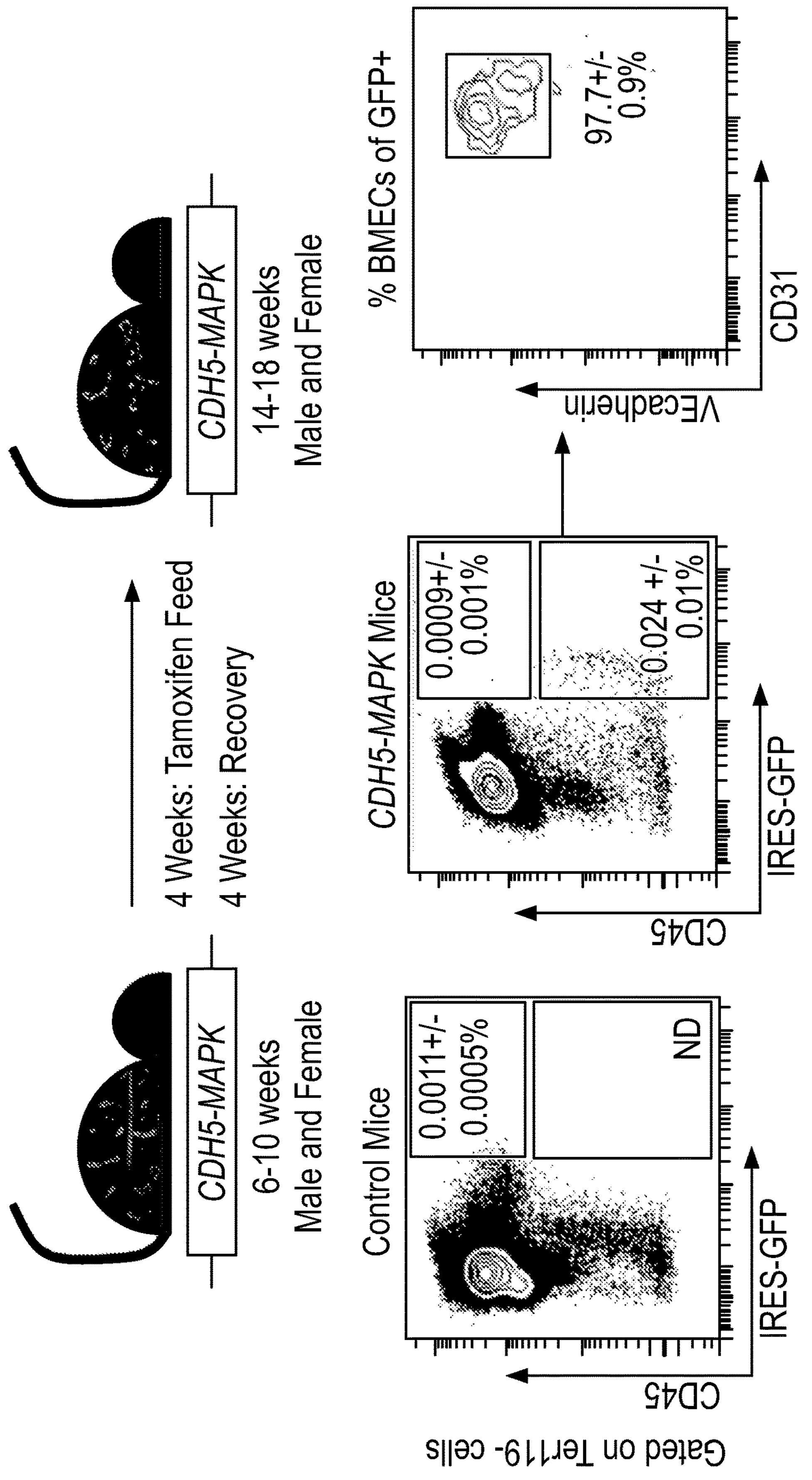
Figures 6C, 6D, 6E:
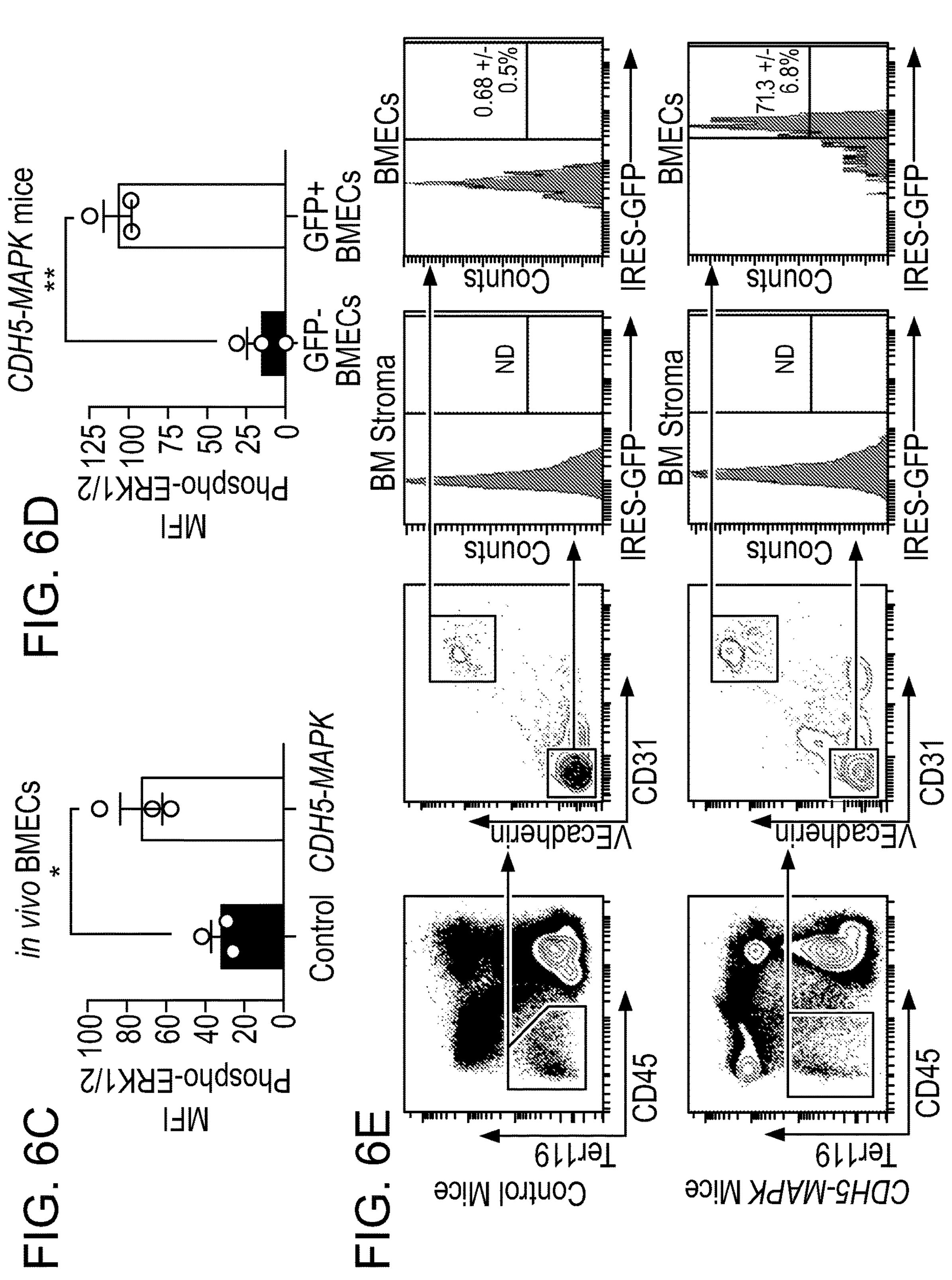

Endothelial MAPK activation drives an inflammatory stress response within the bone marrow. The HSC and hematopoietic defects along with the vascular dilation within BM of CDH5-MAPK 238 mice (FIG. 1 and FIG. 2) raised the possibility that downstream endothelial NF-κB activation induces a generalized inflammatory stress response within the BM microenvironment. In support of this idea, RT¬qPCR analysis revealed an overall upregulation of NF-kB target genes in hematopoietic cells (CD45+), stromal cells (CD45−Ter119−CD31−VEcadherin−) as well as in unfractionated whole bone marrow (WBM) cells of CDH5-MAPK mice (SUPP. FIG. 3A, SUPP. FIG. 3B, SUPP. FIG. 3C, SUPP. FIG. 3D, SUPP. FIG. 3E and SUPP. FIG. 3F, Supp. Table 2), demonstrating that endothelial MAPK activation drives a generalized inflammatory response within the BM. The striking increase in expression of NF-kB target genes within the WBM of CDH5-MAPK mice (SUPP. FIG. 3E and SUPP. FIG. 3F) raised the possibility of promiscuous expression of MEK1DD transgene within hematopoietic cells of CDH5-MAPK mice. To verify this possibility, the fidelity of transgene expression in CDH5,MAPK mice was verified by using the endogenous Rosa26:eGFP reporter system to track cre mediated 248 recombination (FIG. 6). GFP expression was strictly confined to endothelial cells within the bone marrow with no detectable expression in any of the hematopoietic subsets analyzed including HSCs as well as myeloid cells, B cells and T cells (FIG. 6A, FIG. 6B, FIG. 6C, FIG. 6D and FIG. 6E; SUPP. FIG. 4A and SUPP. FIG. 4B). Flow cytometric analysis demonstrated that tamoxifen administration resulted in activation of endothelial MAPK signaling in vivo (FIG. 6C), and also confirmed the fidelity of the GFP reporter system to track recombination efficiency (FIG. 6D). Moreover, RT PCR analysis of FACS sorted cells demonstrated that cre expression was restricted to endothelial cells and not detected in hematopoietic cells of CDH5-MAPK mice (FIG. 6G). These findings confirm previous reports that Cdh5(PAC)-creERT2 mice demonstrate faithful endothelium-restricted expression in adult mice, with no off-target expression in HSCs or hematopoietic cells. (Sorensen, I., Adams, R. H. & Gossler, A. DLL1-mediated Notch activation regulates endothelial identity in mouse fetal arteries. Blood (2009) 113, 5680-5688, doi:10.1182/blood-2008-08-174508; Langen, U. H. et al. Cell-matrix signals specify bone endothelial cells during developmental osteogenesis. Nature cell biology (2017) 19, 189-201, doi:10.1038/ncb3476. 46 Payne, S., De Val, S. & Neal, A. Endothelial-Specific Cre Mouse Models. Arterioscler Thromb Vase Biol (2018) 38, 2550-2561, doi:10.1161/atvbaha.118.309669; Kilani, B. et al. Comparison of endothelial promoter efficiency and specificity in mice reveals a subset of Pdgfb-positive hematopoietic cells. J Thromb Haemost (2019) 17, 827-840, doi:10.1111/jth.14417).

Figure 6F:
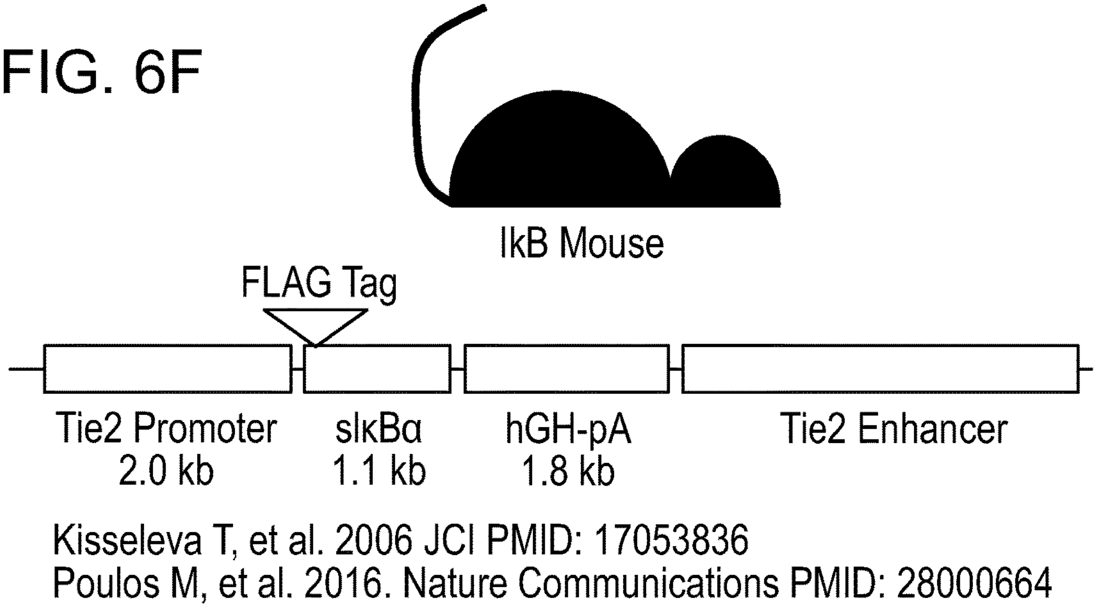
Figure 6G:
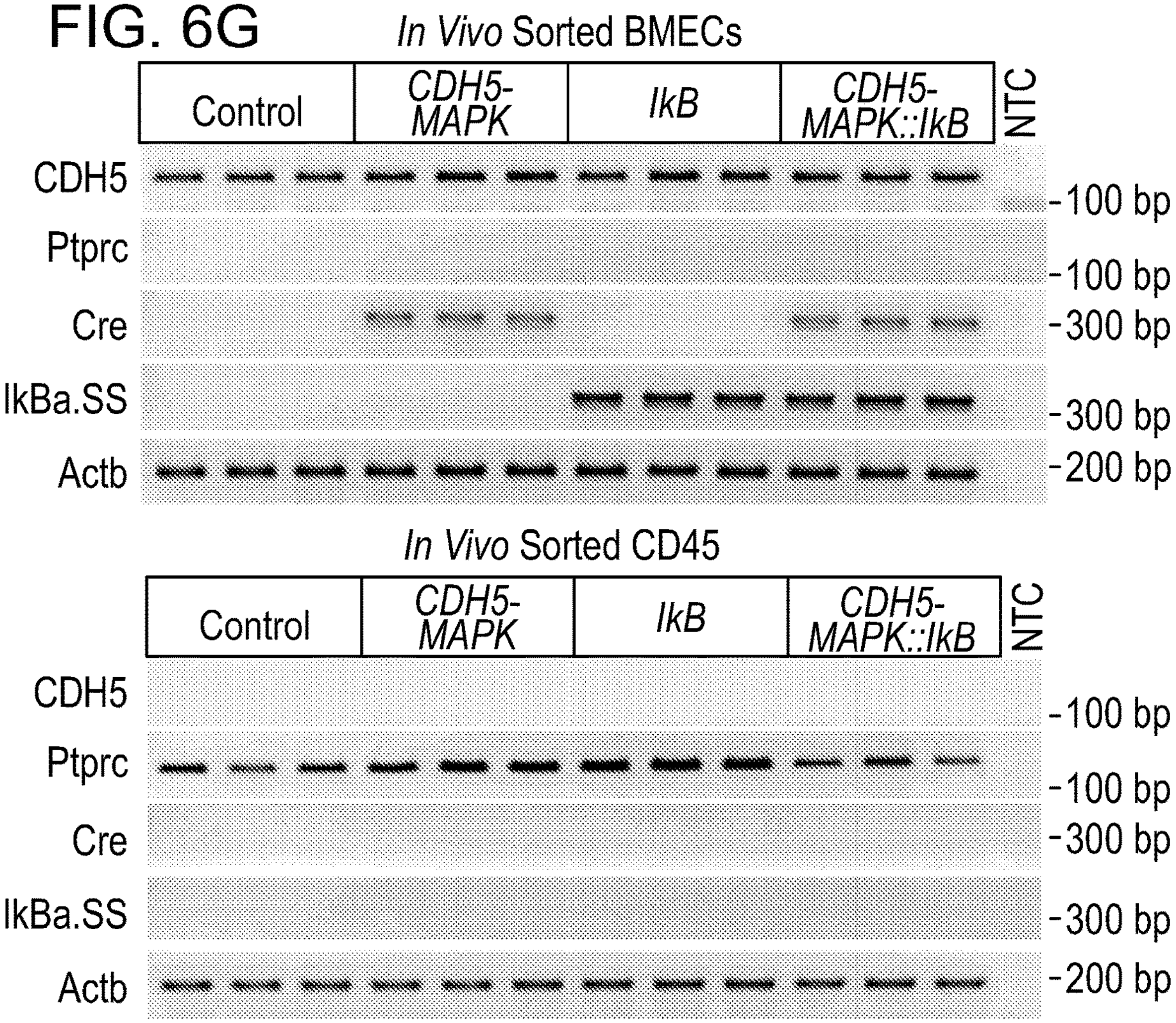

Expression of the IkB-SS transgene in Tie2.IkB-SS mice was confirmed to be restricted to endothelial cells with no detectable expression in hematopoietic cells (FIG. 6F and FIG. 6G). The lack of Tie2 driven transgene expression in adult hematopoietic cells is consistent with previous reports. (Forde, A., Constien, R., Grone, H. J., Hammerling, G. & Arnold, B. Temporal Cre-mediated recombination exclusively in endothelial cells using Tie2 regulatory elements. Genesis (2002) 33, 191 ¬-197, doi:10.1002/gene.10117; Tang, Y., Harrington, A., Yang, X., Friesel, R. E. & Liaw, L. The contribution of the Tie2+ lineage to primitive and definitive hematopoietic cells. Genesis (2010) 48, 563-567, doi:10.1002/dvg.20654; Gareus, R. et al. Endothelial cell-specific NF-kappaB inhibition protects mice from atherosclerosis. Cell metabolism (2008) 8, 372-383, doi:10.1016/j.cmet.2008.08.016; Korhonen, H. et al. Anaphylactic shock depends on endothelial Gq/G11. J Exp Med (2009) 206, 411 ¬-420, doi:10.1084/jem.20082150; Poulos, M. G. et al. Endothelial-specific inhibition of NF-kappaB enhances functional haematopoiesis. Nat Commun (2016) 7, 13829, doi:10.1038/ncomms13829).

Collectively, these observations confirm that HSC and hematopoietic defects in CDH5-MAPK mice are exclusively mediated from an endothelial NF-κB dependent inflammatory stress within the BM. Importantly, endothelial-specific suppression of NF-κB signaling in CDH5-MAPK::IkB mice resolved the BM inflammation as indicated by unsupervised hierarchical clustering as well as the overall decrease in expression of NF-kB signaling targets (SUPP. FIG. 3A, SUPP. FIG. 3B, SUPP. FIG. 3C, SUPP. FIG. 3D, SUPP FIG. 3E and FIG. 3F, Supp. Table 2). Collectively, these results highlight that endothelial cells, despite being a rare population within the BM (FIG. 6B), have a profound impact on HSC function and hematopoiesis during inflammatory stress.

Endothelial NF-κB inhibition resolves inflammation-induced hypoxic injury. The precise mechanisms by which BM inflammation impacts niche activity and HSC function remain poorly understood. Chronic inflammation is known to cause organ damage by inducing tissue hypoxia. (Bartels, K., Grenz, A. & Eltzschig, H. K. Hypoxia and inflammation are two sides of the same coin. Proc Natl Acad Sci USA (2013) 110, 18351-18352, doi:10.1073/pnas.1318345110; Karhausen, J., Haase, V. H. & Colgan, S. P. Inflammatory hypoxia: role of hypoxia-inducible factor. Cell Cycle (2005) 4, 256-258; Eltzschig, H. K. & Carmeliet, P. Hypoxia and inflammation. N Engl J Med (2011) 364, 656-665, doi:10.1056/NEJMra0910283). Furthermore, increased generation of reactive oxygen species (ROS) at sites of inflammation leads to endothelial dysfunction, vascular leakiness and tissue injury. (Mittal, M., Siddiqui, M. R., Tran, K., Reddy, S. P. & Malik, A. B. Reactive oxygen species in 1035 inflammation and tissue injury. Antioxid Redox Signal (2014) 20, 1126-1167, doi:10.1089/ars.2012.5149). Importantly, excessive ROS and hypoxia have been shown to adversely impact HSPC function by promoting loss of quiescence and exhaustion. (Bigarella, C. L., Liang, R. & Ghaffari, S. Stem cells and the impact of ROS signaling. Development (2014) 141, 4206-4218, doi:10.1242/dev.107086; Takubo, K. et al. Regulation of the HIF-1alpha level is essential for hematopoietic stem cells. Cell stem cell (2010) 7, 391-402, doi:10.1016/j.stem.2010.06.020; Ludin, A. et al. Reactive oxygen species regulate hematopoietic stem cell self-renewal, migration and development, as well as their bone marrow microenvironment. Antioxid Redox Signal (2014) 21, 1605-1619, doi:10.1089/ars.2014.5941).

To obtain insights into the mechanisms by which BM inflammation causes hematopoietic and vascular defects in CDH5-MAPK mice, the oxygenation status and ROS levels of HSPCs and BM niche cells was examined (FIG. 7). HSPCs of CDH5-MAPK mice demonstrated a significant increase in hypoxia and ROS levels along with a loss of quiescence and increased apoptosis (FIG. 7A, FIG. 7B, FIG. 7C and FIG. 7D; Supp. FIG. 5). Notably, both BM endothelial cells and BM stromal cells also displayed increased hypoxia (FIG. 7E), indicating that hypoxic injury induced by inflammation impacted both HSPCs and BM niche cells of CDH5-MAPK mice and was restored upon suppression of endothelial NFκB signaling. Interestingly, niche cells did not display significant changes in ROS levels (FIG. 7F), indicative of a either an unaltered production in response to the inflammatory stress or a higher ROS detoxification ability or an impaired production in response to the inflammatory stress, as compared to HSPCs. However, BM stromal cells demonstrated a loss of cycling and increased apoptosis in CDH5,MAPK mice (FIG. 7G and FIG. 7H). Contrarily, the quiescent nature of BM endothelium observed under homeostatic conditions was disrupted in CDH5-MAPK mice likely due to the direct effect of MAPK activation driven cell-cycle entry (FIG. 7G). The alterations in cell-cycle status of niche cells in CDH5,MAPK mice were reflected in their BM cellularity wherein endothelial cells displayed an increase in absolute numbers whereas stromal cells were reduced (FIG. 7I and FIG. 7K). Notably, the defects observed in niche cells of CDH5-MAPK mice were restored in CDH5-MAPK::IkB mice (FIG. 7E and FIG. 7H).

Figures 7A, 7B, 7C, 7D, 7E, 7F:
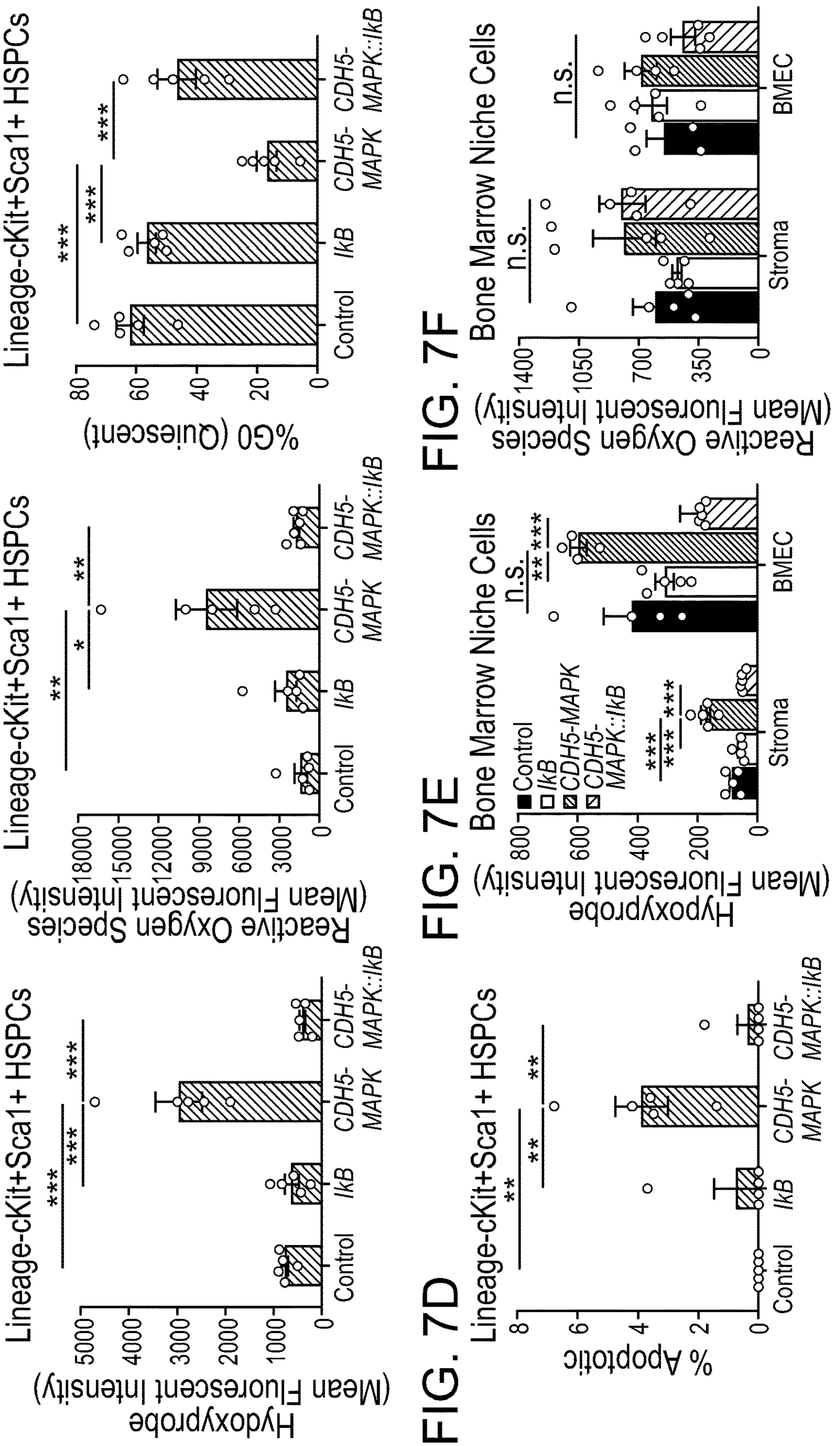
FIG. 7A, FIG. 7B, FIG. 7C, FIG. 7D, FIG. 7E, FIG. 7F, FIG. 7G, FIG. 7H, FIG. 7I, FIG. 7J, FIG. 7K, FIG. 7L, FIG. 7M, FIG. 7N, FIG. 7O, FIG. 7P, FIG. 7Q show that endothelial NF-κB inhibition rescues hypoxic injury of HSPCs and BM niche cells.
Figure 7G:
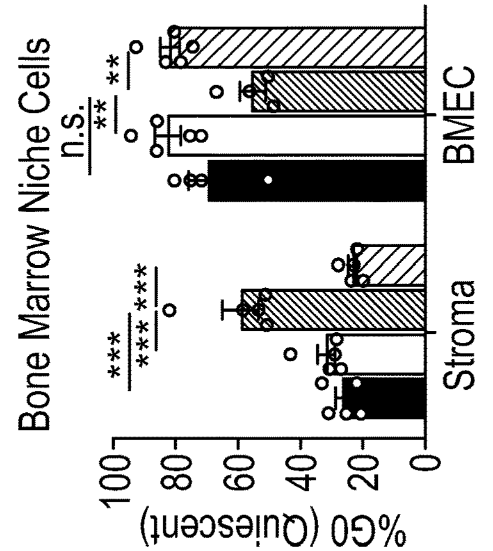
Figure 7H:
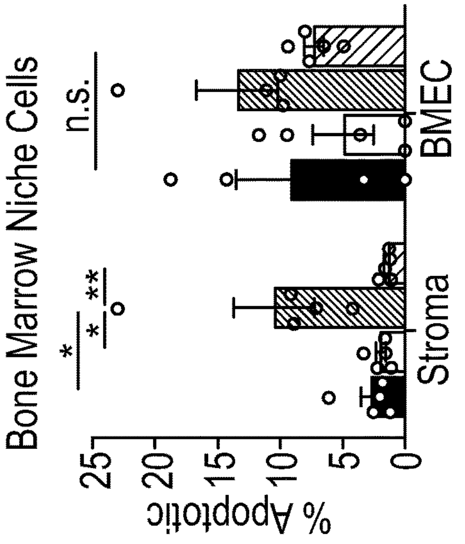
Figure 7I:
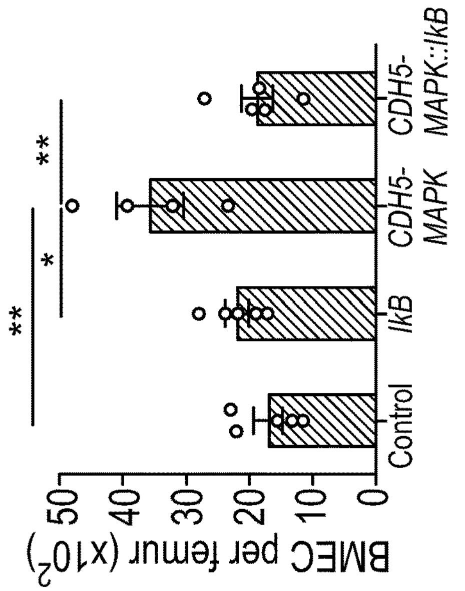
Figure 7J:
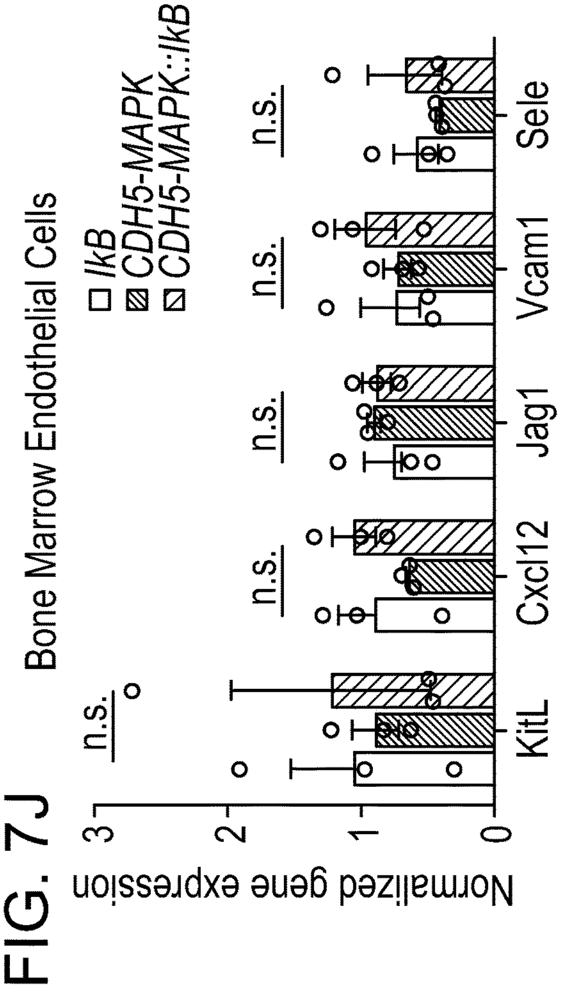
Figure 7K:
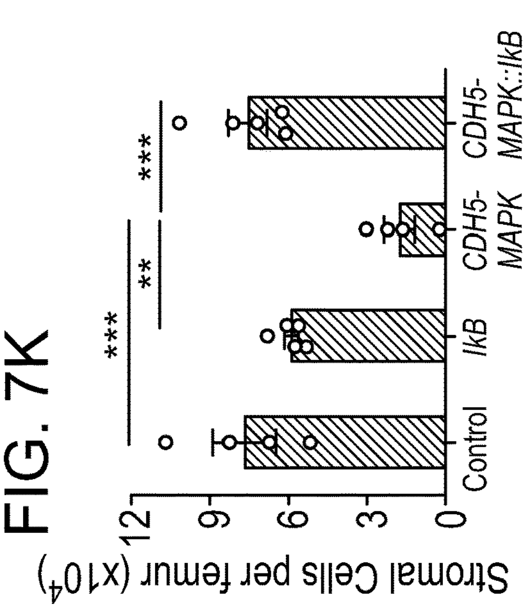
Figure 7L:
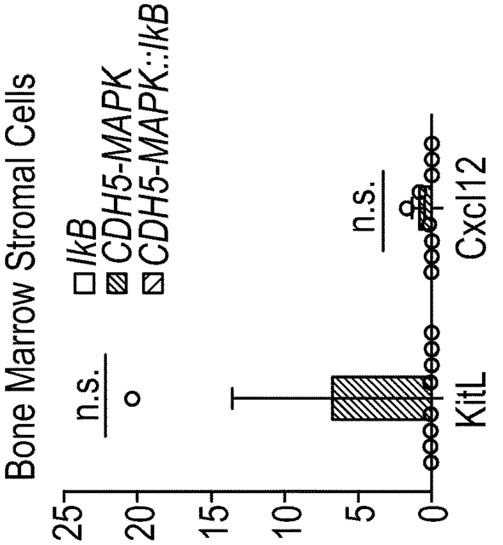

BM niche cells, including endothelium and various BM stromal subsets are known to play critical roles in HSC maintenance by expressing pro-HSC factors such as KitL and SDF1. (Morrison, S. J. & Scadden, D. T. The bone marrow niche for haematopoietic stem cells. Nature (2014) 505, 327-334, doi:10.1038/nature12984). To determine whether endothelial MAPK activation altered the levels of these HSC-regulatory factors, we assessed their expression in candidate BM niche cells by RT-qPCR. However, no significant alterations in their expression were observed in either BMECs or BM stromal cells amongst the genotypes (FIG. 7J, FIG. 7K and FIG. 7L). Within the BM stromal population, Lepr+ cells (which include Nestin+ and CXCL12 abundant reticular cells) have been shown to be an important source of KitL and SDF1 for HSC maintenance. (Zhou, B. O., Yue, R., Murphy, M. M., Peyer, J. G. & Morrison, S. J. Leptin-receptor-expressing mesenchymal stromal cells represent the main source of bone formed by adult bone marrow. Cell stem cell (2014) 15, 154-168, doi:10.1016/j.stem.2014.06.008). SDF1 is also known to be expressed by CD45−Ter119−CD31−Sca1−CD51+ BM osteoblast cells. (Ding, L. & Morrison, S. J. Haematopoietic stem cells and early lymphoid progenitors occupy distinct bone marrow niches. Nature (2013) 495, 231-235, doi:10.1038/nature11885).

Analysis of BM Lepr+ cells and osteoblasts did not reveal significant changes in their cellularity or in their expression of HSC-regulatory factors in CDH5-MAPK mice (SUPP. FIG. 6A, SUPP. FIG. 6B, SUPP FIG. 6C, SUPP FIG. 6D and SUPP FIG. 6E, SUPP FIG. 6F and SUPP FIG. 6H). However, both Lepr+ cells and osteoblasts of CDH5-MAPK mice displayed an increased expression of NF-κB regulated target genes similar to the other BM cellular subsets, which was suppressed upon inhibition of endothelial NF-κB signaling (SUPP. FIG. 6F, SUPP. FIG. 6H). Collectively, these results demonstrate that the niche and HSPC defects observed in CDH5-MAPK mice correlate with inflammation-induced alterations in ROS levels and hypoxia, and that inhibition of NF-κB signaling within endothelial cells of CDH5,306 MAPK resolves these defects.

Figure 7M:
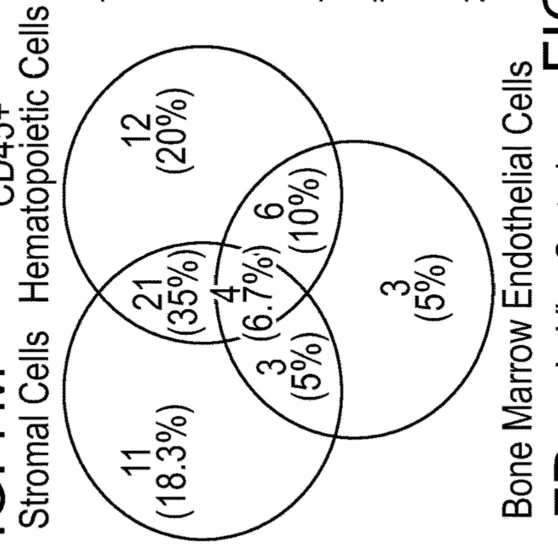
Figure 7N:
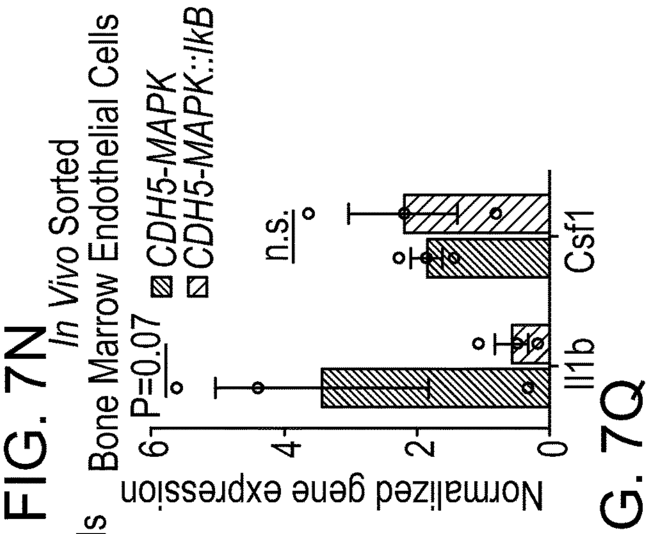
Figure 7O:
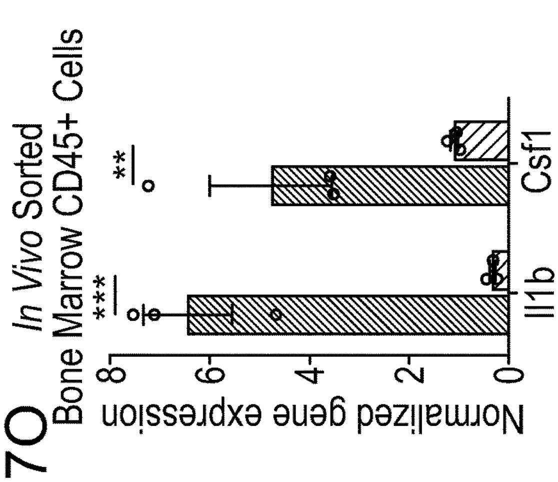
Figure 7P:
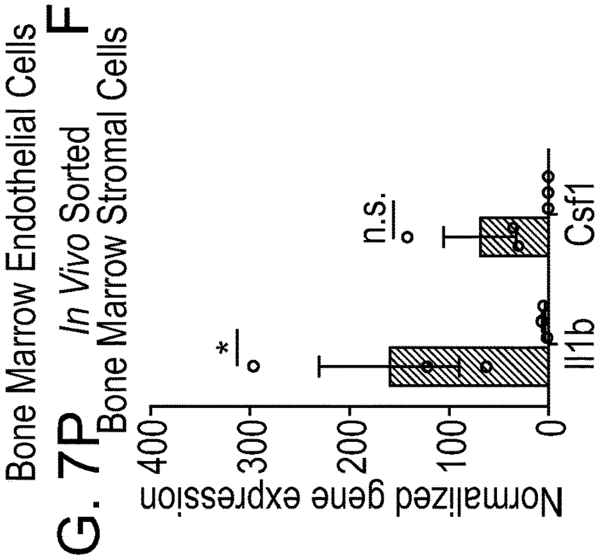
Figure 7Q:

To identify pro-inflammatory genes that potentially mediate HSPC and niche defects in CDH5,308 MAPK mice, the qPCR array data (Supp. Table 2) was surveyed for genes that showed increased expression within the BM endothelial, hematopoietic and stromal compartments; I11b, Csf1, Cdkn1a, and Csf2 were significantly upregulated in all three cellular subsets upon endothelial MAPK activation (FIG. 7M). I11b and Csf1 have been previously reported to directly impact HSC function and promote a myeloid-biased differentiation at the expense of lymphopoiesis. (Pietras, E. M. et al. Chronic interleukin-1 exposure drives haematopoietic stem cells towards precocious myeloid differentiation at the expense of self-renewal. Nature cell biology (2016) 18, 607 ¬-618, doi:10.1038/ncb3346; Mossadegh-Keller, N. et al. M-CSF instructs myeloid lineage fate in single haematopoietic stem cells. Nature (2013) 497, 239-243, doi:10.1038/nature12026). Chronic I11 exposure has also been shown to cause enhanced HSC cycling and exhaustion. (Pietras, E. M. et al. Chronic interleukin-1 exposure drives haematopoietic stem cells towards precocious myeloid differentiation at the expense of self-renewal. Nature cell biology (2016) 18, 607 ¬-618, doi:10.1038/ncb3346). The hematopoietic defects observed in CDH5,MAPK mice including increased HSPC cycling, impaired repopulating ability and a myeloid-biased differentiation suggest that I11b and Csf1 possibly mediate HSPC defects in CDH5-MAPK mice, and their suppression in CDH5-MAPK::IkB mice potentially restores hematopoietic function. To verify this possibility, RT-qPCR analysis was performed and confirmed that inhibition of endothelial NF-κB signaling in CDH5-MAPK mice decreased the expression of I11b within endothelial cells, stromal cells and hematopoietic cells, while Csf1 expression was decreased in stromal cells and hematopoietic cells (FIG. 7N, FIG. 7O and FIG. 7P). Notably, although endothelial Csf1 expression was not decreased, the decrease in endothelial I11b expression correlated with a significant down-regulation of inflammation within the unfractionated WBM cells of CDH5-MAPK::IkB mice (FIG. 7Q, SUPP. FIG. 3E), suggesting that endothelial I11b likely plays a key role in mediating BM inflammation in CDH5-MAPK mice. However, the diverse changes observed in the plasma proteome of CDH5-MAPK mice suggest that chronic inflammation possibly involves a balance of multiple pro- and anti-inflammatory mediators that regulate inflammatory responses and HSC function (FIG. 2E and FIG. 2F).

SCGF suppresses BM inflammation and restores HSC function in CDH5-MAPK mice. Given that crossing CDH5-MAPK mice to Tie2.IkB-SS mice resolved their inflammation and restored vascular and hematopoietic defects, we utilized these models to screen for novel candidate proteins that might regulate HSC function during inflammation. To this end, a proteomic analysis (SomaLogic) on plasma derived from Tie2.IkB-SS mice identified 82 proteins that were differentially expressed as compared to their littermate controls was performed (data not shown). It was hypothesized that a potential pro-hematopoietic protein would display opposing trends in CDH5-MAPK mice as compared to Tie2.IkB-SS mice. Using this approach, 18 candidate factors were identified that were significantly altered and inversely correlated (i.e. down in CDH5-MAPK mice, up in Tie2.IkB-SS and vice versa) (SUPP. FIG. 7A and SUPP. 7B). Among these, Clec11a/Stem Cell Growth Factor-α (SCGF) was the most significantly downregulated protein in CDH5-MAPK mice (SUPP. FIG. 7C).

SCGF has recently been identified as a potential rejuvenation factor for restoration of bone formation in aged mice. (Yue, R., Shen, B. & Morrison, S. J. Clec11a/osteolectin is an osteogenic growth factor that promotes the maintenance of the adult skeleton. Elife 5, doi:10.7554/eLife.18782 (2016)). Although SCGF has been reported to be dispensable for steady state hematopoiesis, plasma levels of SCGF have been reported to be down regulated in patients with severe malarial anemia and decreased levels of plasma SCGF correlated with poor hematopoietic recovery following bone marrow transplantation, indicating that SCGF could play key roles during stress hematopoiesis. (Yue, R., Shen, B. & Morrison, S. J. Clec11a/osteolectin is an osteogenic growth factor that promotes the maintenance of the adult skeleton. Elife (2016) 5, doi:10.7554/eLife.18782; Keller, C. C. et al. Suppression of a novel hematopoietic mediator in children with severe malarial anemia. Infect Immun (2009) 77, 3864-3871, doi:10.1128/IAI.00342-09; Ito, C. et al. Serum stem cell growth factor for monitoring hematopoietic recovery following stem cell transplantation. Bone Marrow Transplant (2003) 32, 391-398, doi:10.1038/sj.bmt.1704152). It was confirmed the specificity of the SCGF aptamer and validated the observed decrease of plasma SCGF in CDH5-MAPK mice (SUPP. FIG. 7D). Notably, CDH5-MAPK::IkB mice displayed a restoration of their plasma SCGF levels, further indicating that SCGF could be a potential pro-hematopoietic factor that promotes recovery in CDH5-MAPK::IkB mice. (SUPP. FIG. 7E).

Figures 8A, 8B, 8C, 8D:
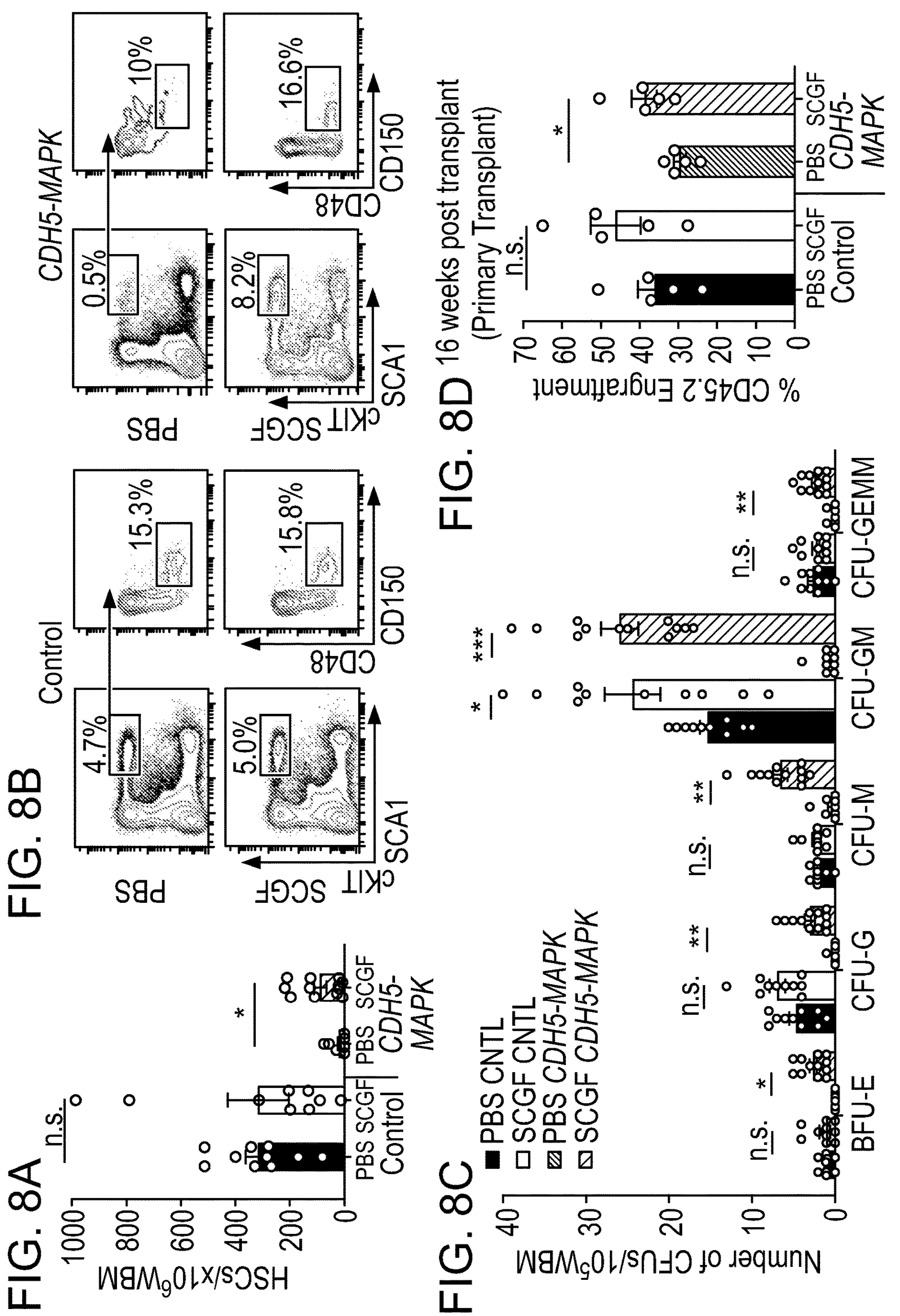
FIG. 8A, FIG. 8B, FIG. 8C, FIG. 8D, FIG. 8E, FIG. 8F, FIG. 8G, FIG. 8H, FIG. 8I, FIG. 8J, FIG. 8L show that SCGF infusion resolves hematopoietic and vascular defects in CDH5-MAPK mice.
Figure 8E:
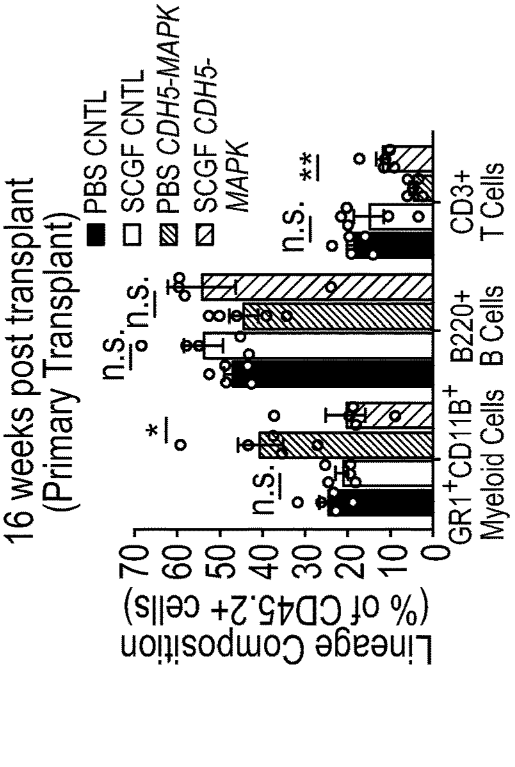
Figure 8F:
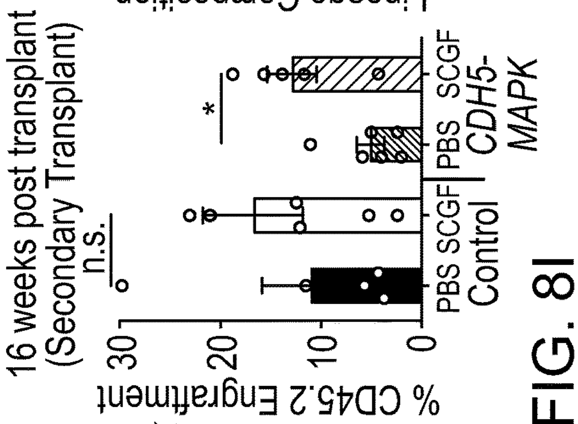
Figure 8G:
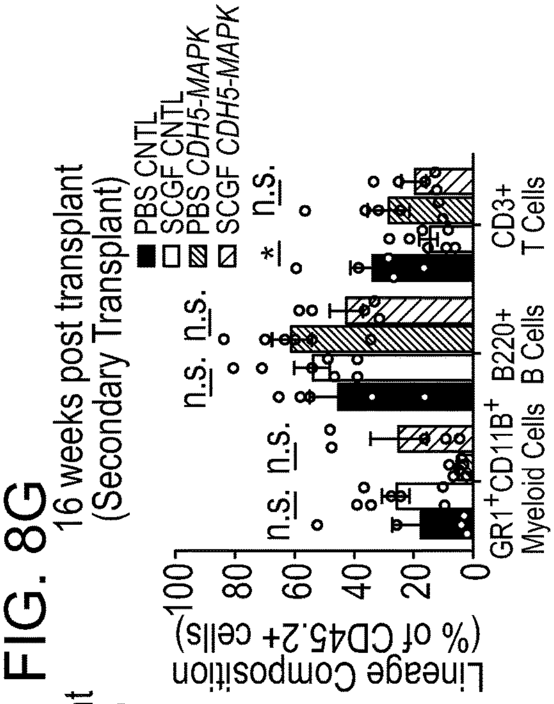

To determine if SCGF can restore hematopoietic defects in CDH5-MAPK mice, 4 μg of SCGF was subcutaneously infused for five consecutive days and analyzed phenotypic and functional attributes of their hematopoietic system 24 hours following the last injection (SUPP. FIG. 8A). SCGF infusion into littermate control mice confirmed that SCGF did not affect steady state hematopoiesis as previously reported (FIG. 8 and SUPP. FIG. 8). (Yue, R., Shen, B. & Morrison, S. J. Clec11a/osteolectin is an osteogenic growth factor that promotes the maintenance of the adult skeleton. Elife (2016) 5, doi:10.7554/eLife.18782). However, infusion of SCGF into CDH5-MAPK mice had profound effects on their hematopoiesis (FIG. 8 and SUPP. FIG. 8). SCGF infusion significantly increased the frequency of phenotypic HSCs and HSPCs in CDH5-MAPK mice (FIG. 8A and FIG. 8B; SUPP. FIG. 8C). The increase in HSPC frequency was reflected in the enhanced colony-forming ability of BM cells isolated from SCGF treated CDH5-MAPK mice (FIG. 8C). SCGF infusion also resolved the peripheral blood myeloid bias in CDH5-MAPK mice and restored their blood counts (SUPP. FIG. 8D, SUPP. FIG. 8E). Moreover, competitive BM transplantation demonstrated that SCGF infusion into CDH5-MAPK mice restored their long-term engraftment potential with a significant decrease in myeloid bias (FIG. 8D and FIG. 8E). The increased engraftment potential of BM cells derived from SCGF treated CDH5-MAPK mice was also maintained during secondary transplantation assays indicating a preservation of serial repopulation ability (FIG. 8F and FIG. 8G). Interestingly, the myeloid-biased output of CDH5-MAPK mice observed in primary transplantations was resolved in secondary transplantations indicating that inflammation induced lineage-skewing of HSCs is not permanent and is reversible upon exposure to a wild type BM microenvironment during serial transplantations (FIG. 8F and FIG. 8G).

Figure 8H:
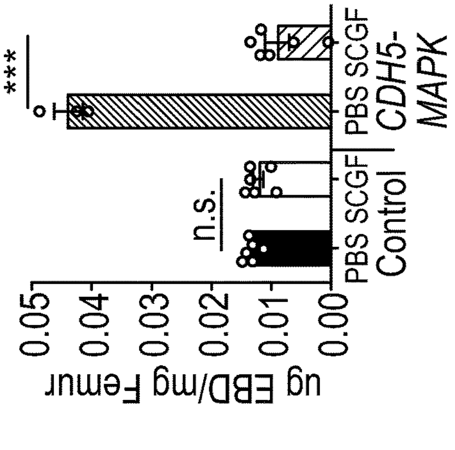
Figure 8I:
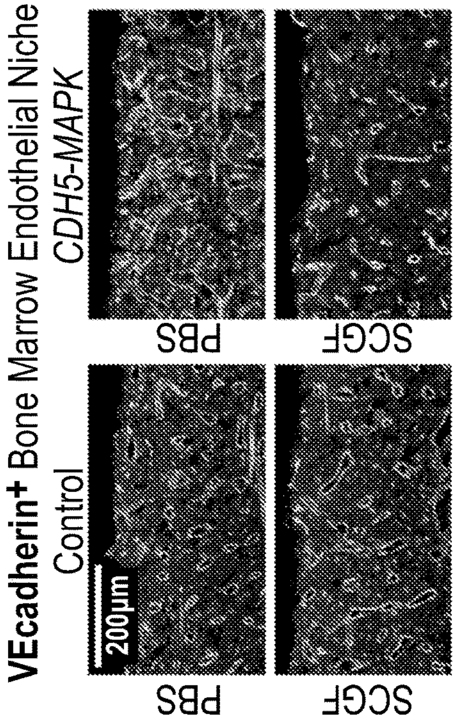
Figure 8J:
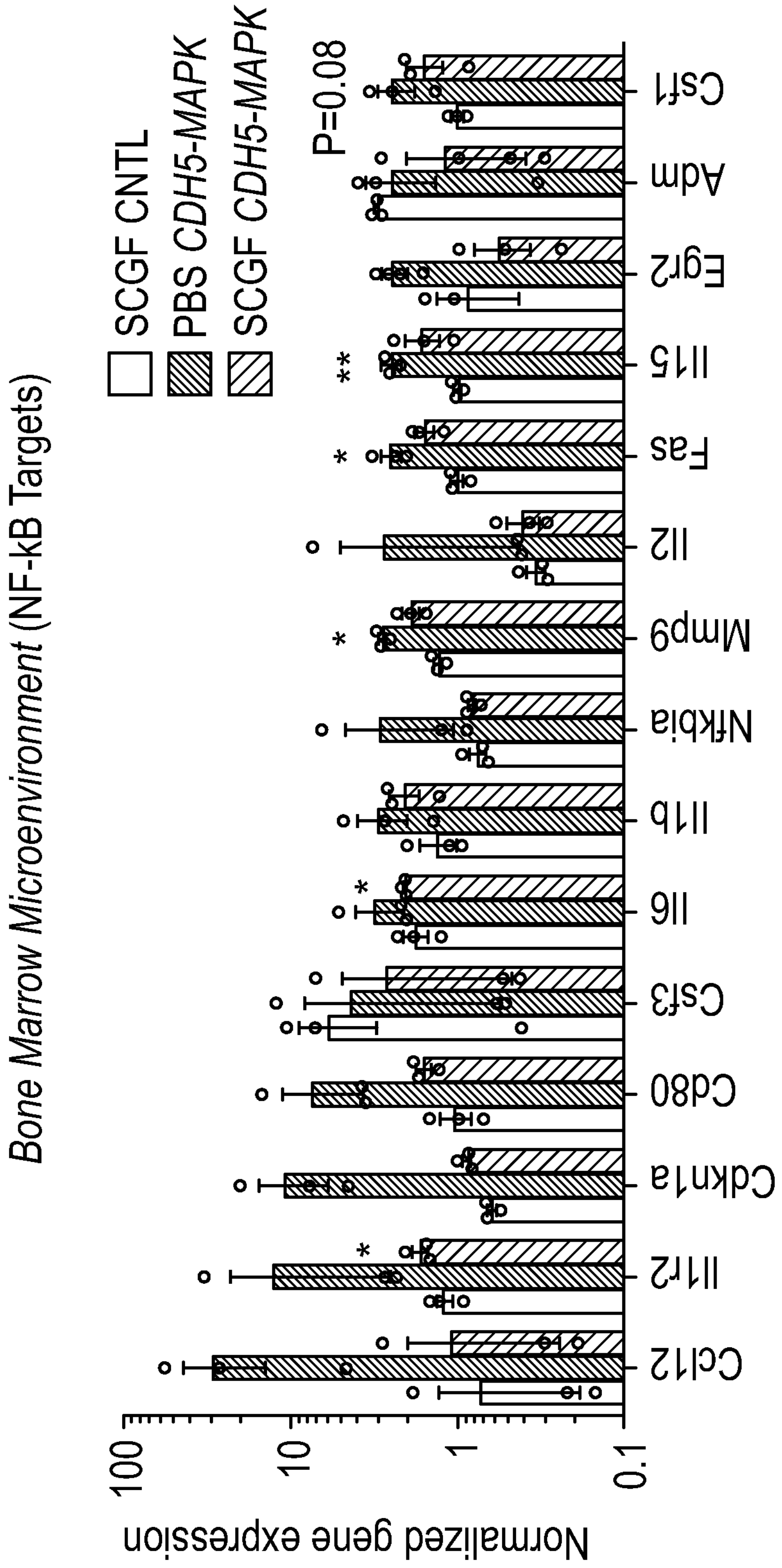
Figure 8K:
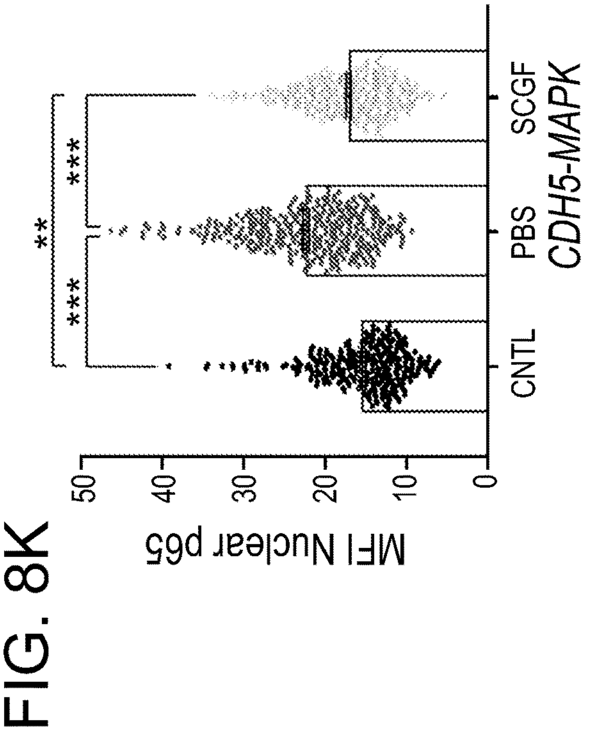
Figure 8L:
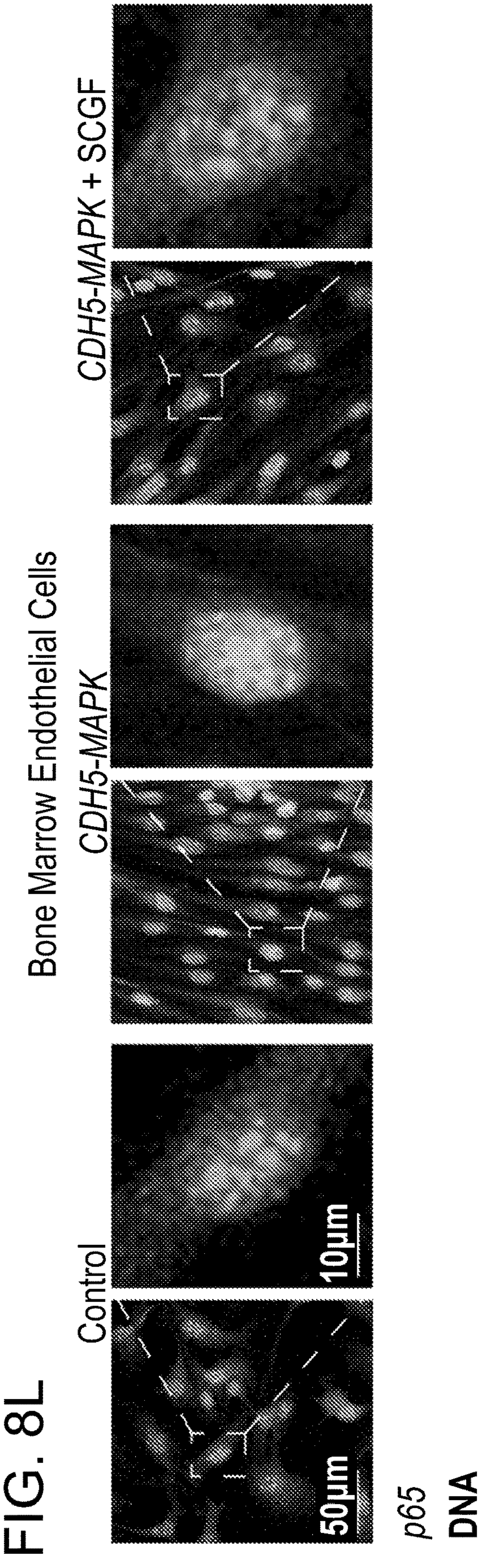

Given that SCGF knockout mice display normal hematopoietic parameters and accelerated bone loss (Yue, R., Shen, B. & Morrison, S. J. Clec11a/osteolectin is an osteogenic growth factor that promotes the maintenance of the adult skeleton. Elife (2016) 5, doi:10.7554/eLife.18782) and the lack of discernible effects on hematopoiesis in SCGF-infused control mice (FIG. 8A, FIG. 8B, FIG. 8C, FIG. 8D, FIG. 8E, FIG. 8F and FIG. 8G), it is likely that the hematopoietic recovery observed in SCGF-infused CDH5-MAPK mice is possibly mediated by its effect on the vascular niche. Analysis of the endothelial niche revealed that infusion of SCGF resolved the vascular dilation and suppressed vascular leakiness within the BM microenvironment of CDH5-MAPK mice (FIG. 8H, FIG. 8I). The vascular recovery mediated by SCGF infusion was also associated with an overall decrease in expression of NF-kB target genes within the BM of CDH5-MAPK mice (FIG. 8J). The striking vascular recovery mediated by SCGF infusion raised the possibility that SCGF directly acts on the endothelium of CDH5-MAPK mice to suppress their NF-kB signaling. Immunofluorescence analysis demonstrated that SCGF treatment resulted in decreased nuclear p65 levels within BM endothelium isolated from CDH5-MAPK mice confirming a direct effect of SCGF on endothelial cells (FIG. 8K, FIG. 8L). Taken together, these data indicate that infusion of SCGF into CDH5-MAPK mice suppresses endothelial inflammation and restores vascular integrity, which leads to a recovery of their hematopoietic system.

Figures 9A, 9B:
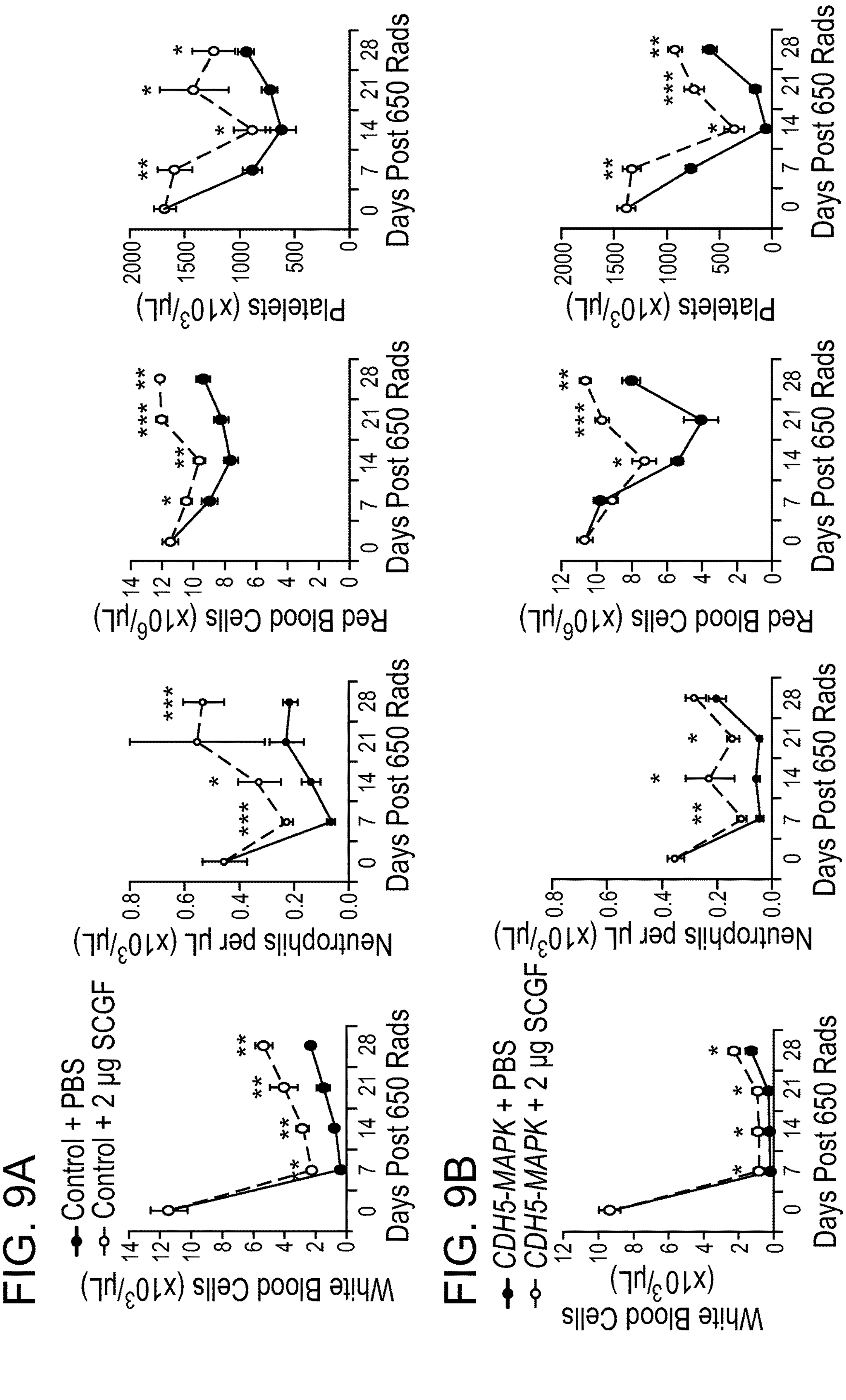
FIG. 9A, FIG. 9B, FIG. 9C, FIG. 9D, FIG. 9E, FIG. 9F, FIG. 9G, FIG. 9H, FIG. 9I, FIG. 9J, show that SCGF enhances hematopoietic regeneration following myelosuppressive injury.
Figure 9C:
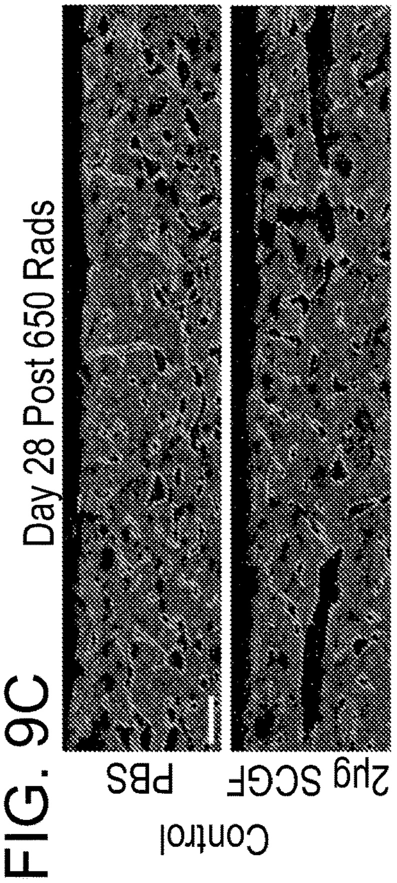
Figure 9D:
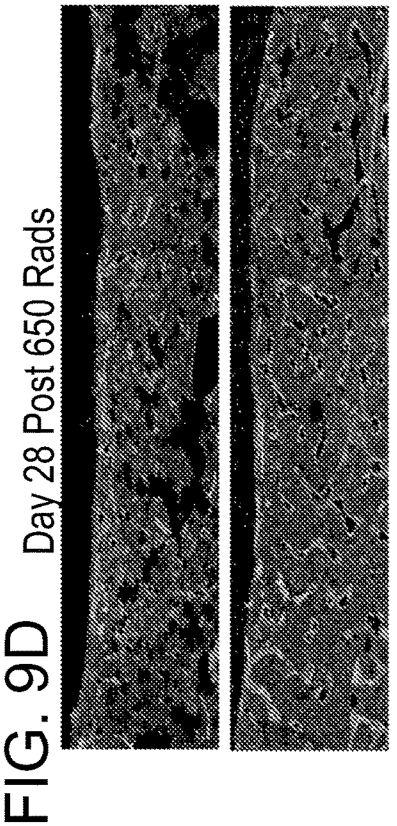
Figure 9E:
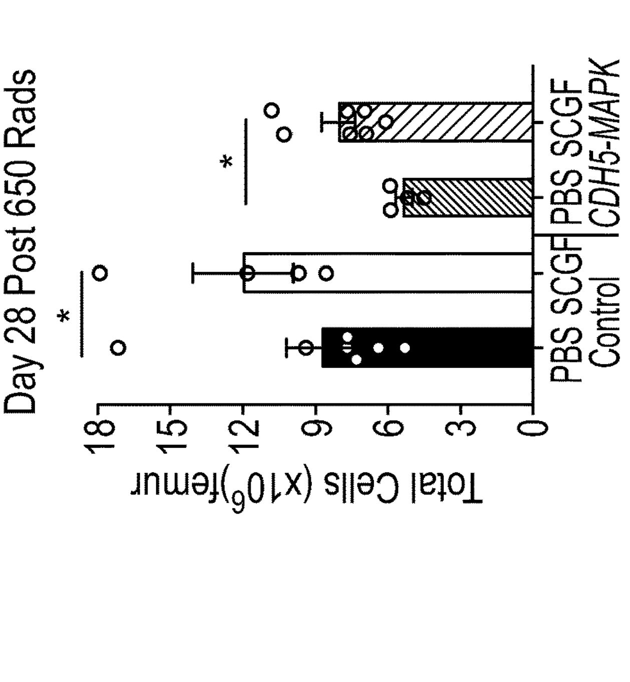
Figure 9F:
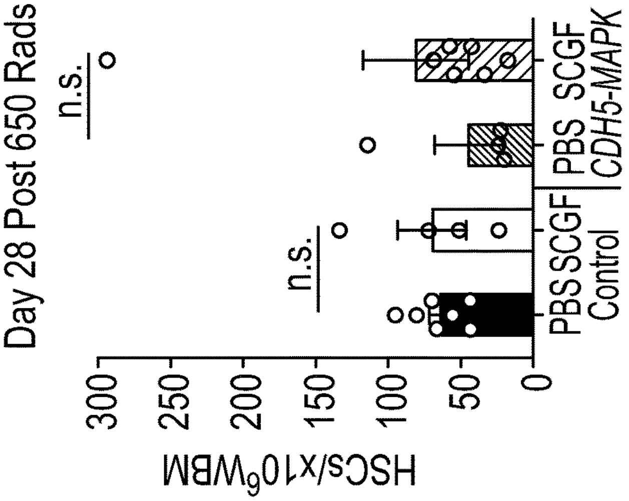

Since SCGF has been shown to promote osteogenesis, it is likely that the decrease in plasma SCGF levels along with the BM inflammation observed in CDH5-MAPK mice could result in osteopenia. CDH5-MAPK mice indeed displayed an overall decrease in trabecular bone volume, trabecular numbers and thickness demonstrating that endothelial MAPK activation has a deleterious impact on bone health (SUPP. FIG. 9A, SUPP. FIG. 9B, SUPP. FIG. 9C and SUPP. FIG. 9D). The ability of SCGF to restore bone formation in CDH5-MAPK mice was then studied. Similar to its effects on hematopoiesis, SCGF did not affect bone formation in control mice (SUPP. FIG. 9A, SUPP. FIG. 9B, SUPP. FIG. 9C and FIG. 9D). However, infusion of SCGF caused a significant increase in trabecular bone volume and trabecular numbers and thickness in CDH5-MAPK mice, confirming its role in promoting osteogenesis (SUPP. FIG. 9A, SUPP. FIG. 9B, SUPP. FIG. 9C and SUPP. FIG. 9D). Notably, SCGF expression was absent in hematopoietic cells and BMECs, and was primarily expressed in BM stromal cells including BM Lepr+ and osteoblastic stromal subsets (SUPP. FIG. 9E). Analysis of SCGF expression in total stromal cells, Lepr+ cells and osteoblasts from BM of Tie2-IkB-SS, CDH5-MAPK, and CDH5-MAPK::IkB mice, however, revealed no significant changes in mRNA expression (SUPP. FIG. 9F) indicating that decreased plasma SCGF in CDH5-MAPK mice is not due to transcriptional alterations.

It is known that cytokines mediating inflammatory responses can be regulated at the translational level and a recent report demonstrated that I11b regulates the secretory response of chondrocytes by regulating translation. (Mazumder, B., Li, X. & Barik, S. Translation control: a multifaceted regulator of inflammatory response. J Immunol (2010) 184, 3311-3319, doi:10.4049/jimmunol.0903778; McDermott, B. T., Peffers, M. J., McDonagh, B. & Tew, S. R. Translational regulation contributes to the secretory response of chondrocytic cells following exposure to Interleukin,1beta. J Biol Chem (2019) doi:10.1074/jbc.RA118.006865). Given that SCGF is a secreted protein and appears to regulate inflammatory responses, it is likely that it might be subject to translational regulation. However, the most likely explanation for decreased plasma SCGF in CDH5-MAPK mice appears to be due to the overall decrease in BM stromal cell numbers (the cells producing plasma SCGF) in CDH5-MAPK mice due to their apoptosis. (FIG. 7H, FIG. 7K). Collectively, these data indicate that SCGF infusion restores hematopoietic defects observed in CDH5-MAPK mice by restoring vascular integrity, resolving BM inflammation and improving bone health, thus suggesting that SCGF might play key roles in mediating hematopoietic recovery under stress situations.

SCGF enhances hematopoietic regeneration following myelosuppressive injury. Myelosuppressive insults have been shown to adversely impact the endothelial niche resulting in a loss of vascular integrity and delayed hematopoietic recovery. (Hooper, A. T. et al. Engraftment and reconstitution of hematopoiesis is dependent on VEGFR2-¬ mediated regeneration of sinusoidal endothelial cells. Cell stem cell (2009) 4, 263-274, doi:10.1016/j.stem.2009.01.006; Li, X. M., Hu, Z., Jorgenson, M. L., Wingard, J. R. & Slayton, W. B. Bone marrow sinusoidal endothelial cells undergo nonapoptotic cell death and are replaced by proliferating sinusoidal cells in situ to maintain the vascular niche following lethal irradiation. Exp Hematol (2008) 36, 1143,10661156, doi:10.1016/j.exphem.2008.06.009). In particular, ionizing radiation is known to activate NF-kB signaling within the endothelium leading to inflammation and endothelial dysfunction. (Baselet, B., Sonveaux, P., Baatout, S. & Aerts, A. Pathological effects of ionizing radiation: endothelial activation and dysfunction. Cell Mol Life Sci (2019) 76, 699-728, doi:10.1007/s00018-018, 2956-z).

Figure 9G:
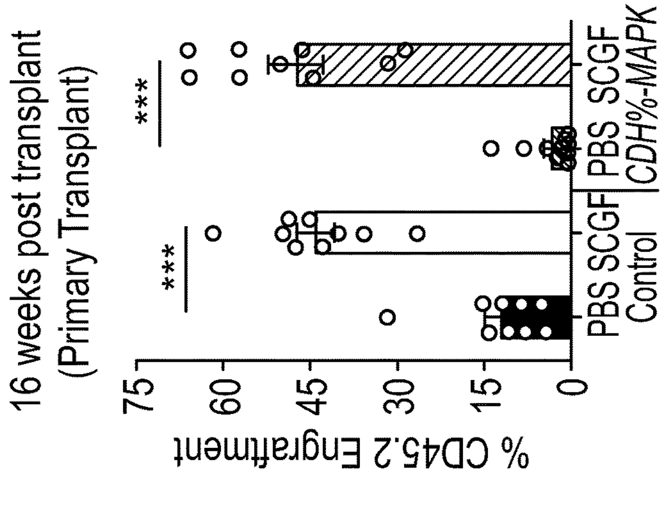
Figure 9H:
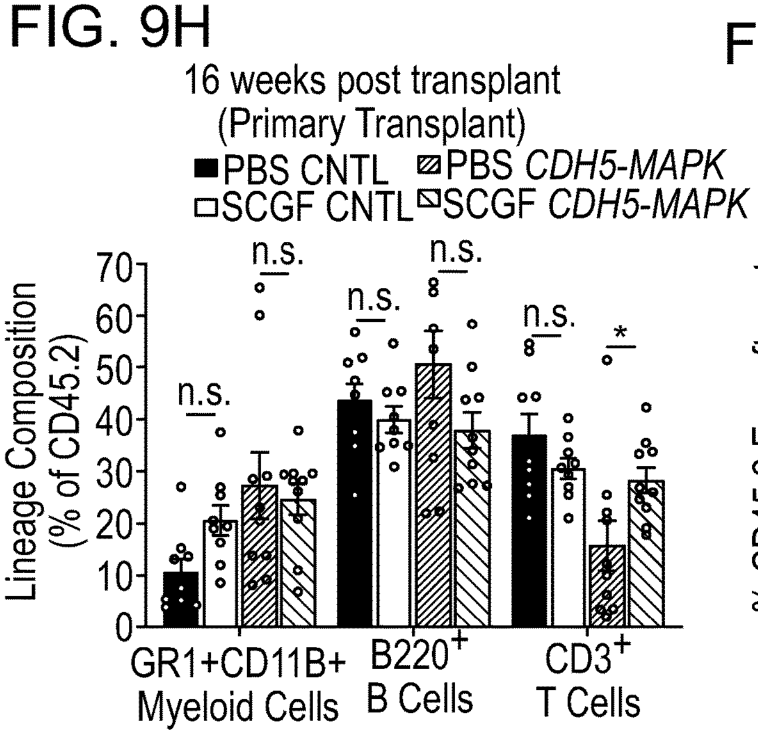
Figure 9I:
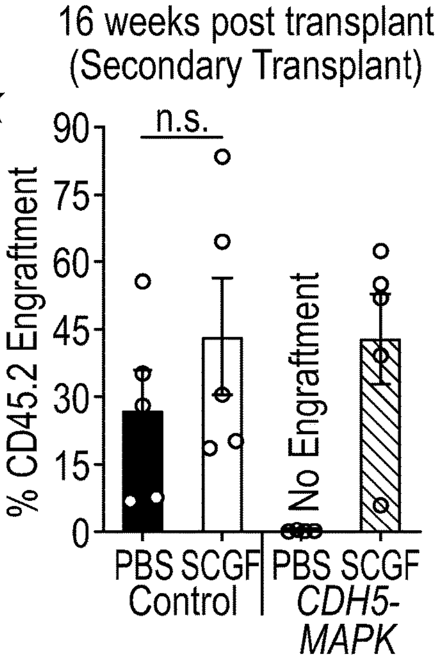
Figure 9J:
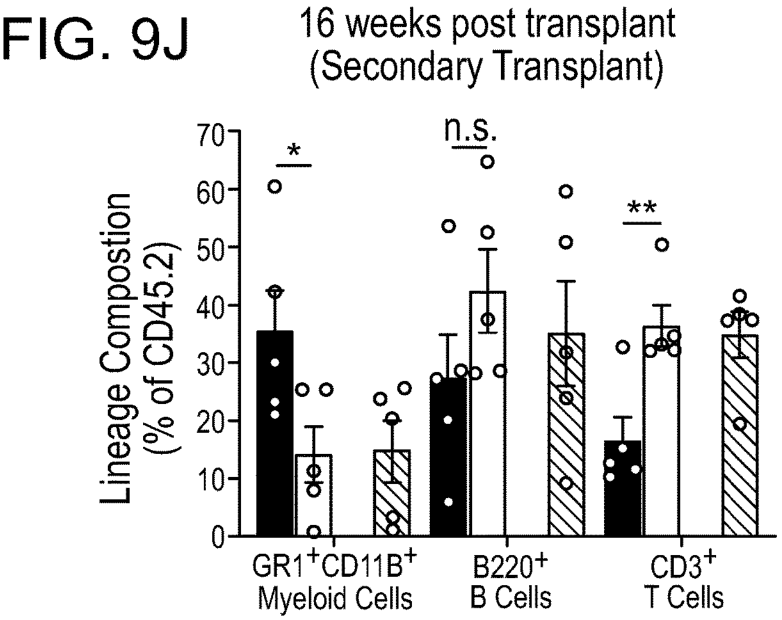

Given that SCGF infusion resolves vascular and hematopoietic defects in CDH5-MAPK mice, it was studied whether SCGF could enhance hematopoietic recovery following myelosuppressive stress Wild type mice were given a myelosuppressive dose of irradiation (650 Rads) and infused every other day with either 0.5 μg, 1 μg, or 2 μg of SCGF for a total of 7 injections starting at Day +1 post-irradiation and hematopoietic recovery was assessed for 21 days (Supp. FIG. 10*a*). The dose-response experiment indicated that infusion of 2 μg of SCGF resulted in a significantly enhanced recovery of white blood cells, red blood cells, and platelets, confirming that SCGF enhances hematopoietic recovery following myelosuppressive stress (SUPP. FIG. 10A). Utilizing this strategy, it was tested whether SCGF can improve hematopoietic recovery and preserve HSPC activity in both control and CDH5-MAPK mice (SUPP. FIG. 10B). We found that infusion of SCGF improved hematopoietic recovery following 650 Rads of myelosuppressive irradiation in both control and CDH5, MAPK mice (FIG. 9A, FIG. 9B). Immunofluorescence analysis of femoral BM sections at Day 28 post irradiation revealed that SCGF infusion resulted in preservation of vascular integrity in both control as well as CDH5-MAPK mice (FIG. 9C, FIG. 9D). Evaluation of BM cellularity and HSC frequency after 28 days following myelosuppressive injury revealed that there was a significant increase in BM cellularity in both control and CDH5-MAPK mice treated with SCGF (FIG. 9E), while no significant changes were observed in phenotypic HSC frequency (FIG. 9F). Given that HSC frequency has been shown to poorly correlate with engraftment potential under conditions of inflammatory stress, the ability of SCGF infusion being able to enhance HSC functionality following myelosuppression was studied. (Zhang, H. et al. Sepsis Induces Hematopoietic Stem Cell Exhaustion and Myelosuppression through Distinct Contributions of TRIF and MYD88. Stem Cell Reports (2016) 6, 940-956, doi:10.1016/j.stemcr.2016.05.002). To this end, a competitive BM transplant on day 28 post-irradiation was performed, wherein $2.5\times10^6$ donor WBM cells from CDH5¬ MAPK mice or littermate controls (treated with PBS or SCGF) were transplanted along with $5\times10^5$ CD45.1 competitor WBM cells into lethally irradiated (950 Rads) CD45.1 mice (FIG. 9G, FIG. 9H). Analysis of CD45.2 cell engraftment 4 months post-transplant revealed that infusion of SCGF significantly enhanced long-term engraftment potential and multi-lineage reconstitution abilities for hematopoietic cells derived from both control and CDH5-MAPK mice (FIG. 9G, FIG. 9H). Notably, SCGF infusion was able to maintain the serial repopulation ability of hematopoietic cells derived from CDH5-MAPK mice during secondary transplantation assays (FIG. 9G, FIG. 9H), demonstrating that SCGF preserves HSC functionality in CDH5-MAPK mice both at steady-state (FIG. 8D, FIG. 8E, FIG. 8F, and FIG. 8G), as well as following myelosuppressive injury (FIG. 9G, FIG. 9H, FIG. I and FIG. 9J ). More importantly, although SCGF infusion did not impact steady state hematopoiesis in control mice (FIG. 8), these data show that SCGF preserves HSC function in control mice following myelosuppressive injury (FIG. 9G, FIG. 9H), thereby defining a novel role for SCGF during hematopoietic stress. Collectively, these findings demonstrate that SCGF has potent therapeutic properties that not only enhances vascular and hematopoietic recovery under an inflammatory stress, but also significantly improves the functionality of the HSC following myelosuppressive insult to the hematopoietic system.

DISCUSSION

Figure 10:
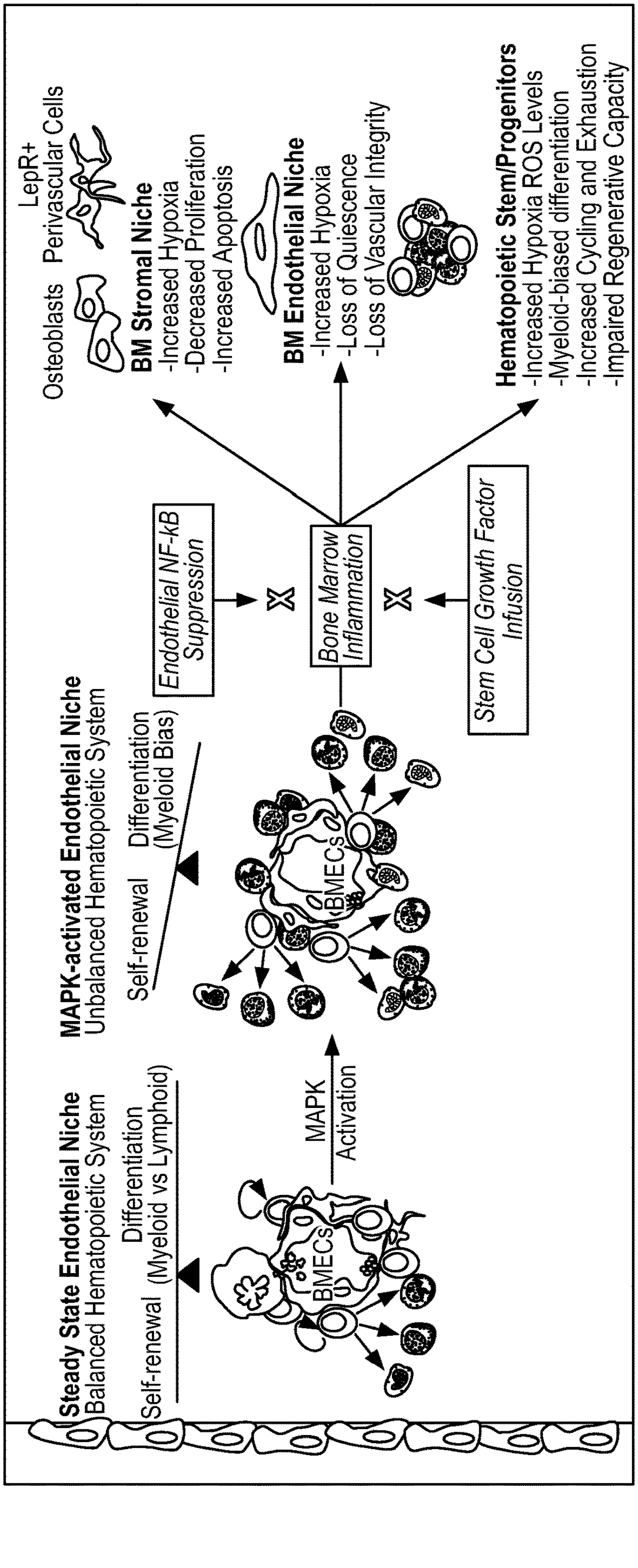
FIG. 10 is a schematic describing the impact of inflammation on BM niche cells and HSPCs. Endothelial MAPK activation drives an NF-kB dependent inflammatory stress response within the bone marrow leading to functional defects in the vascular niche and HSPCs. Suppression of inflammation by inhibition of endothelial NF-kB or infusion of SCGF restores vascular integrity, resolves HSPC and niche defects, and augments post-myelosuppressive hematopoietic recovery.

The direct effects of specific inflammatory cytokines on HSC function have been extensively investigated. (Mirantes, C., Passegue, E. & Pietras, E. M. Pro-inflammatory cytokines: emerging players regulating HSC function in normal and diseased hematopoiesis. Experimental cell research (2014) 329, 248-254, doi:10.1016/j.yexcr.2014.08.017). However, the impact of chronic inflammation on HSC-supportive niche cells within the BM microenvironment remains poorly understood due to the paucity of model systems that recapitulate microenvironment-derived inflammation. In this study, it was demonstrated that sustained inflammation within the BM endothelial niche adversely impacts HSC function resulting from altered oxygenation status, ROS levels and pro-inflammatory cytokine milieu within the BM microenvironment. Activation of MAPK signaling selectively within the endothelium of adult mice drives an NF-kB dependent inflammatory stress response within the BM microenvironment including HSPCs and multiple niche cells, highlighting the essential role of endothelium during chronic inflammation (FIG. 10). Moreover, inflammatory stress resulting from endothelial MAPK activation caused a significant impairment in hematopoietic recovery and HSC functionality following myelosuppressive injury. Importantly, resolution of inflammation by genetic (suppression of endothelial NF-kB) or pharmacological (SCGF infusion) means was able to resolve all of the hematopoietic and HSC defects observed due to endothelial MAPK activation, indicating that stem cell dysfunction induced by inflammation within tissue-specific microenvironments is reversible.

The NF-kB and MAPK pathways are intimately involved in modulating the response to infections, recovery from myelosuppressive injuries, and inflammation. Although the cell-intrinsic roles of these pathways in HSC maintenance, hematopoiesis and immune cell function have been exhaustively investigated, it is becoming increasingly clear that these pathways play essential roles in modulating inflammatory responses within the microvascular endothelium. (Pober, J. S. & Sessa, W. C. Evolving functions of endothelial cells in inflammation. Nature reviews. Immunology (2007) 7, 803-815, doi:10.1038/nri2171; Bottero, V., Withoff, S. & Verma, I. M. NF-kappaB and the regulation of hematopoiesis. Cell death and differentiation (2006) 13, 785-797, doi:10.1038/sj.cdd.4401888; Geest, C. R. & Coffer, P. J. MAPK signaling pathways in the regulation of hematopoiesis. Journal of leukocyte biology (2009) 86, 237-250, doi:10.1189/jlb.0209097).

Within endothelial cells, NF-κB serves as a master regulator of a vast repertoire of pro-inflammatory cytokines. (Xiao, L., Liu, Y. & Wang, N. New paradigms in inflammatory signaling in vascular endothelial cells. Am. J Physiology. Heart and circulatory physiology (2014)306, H317-325, doi:10.1152/ajpheart.00182.2013). In addition to the established roles of endothelial NF-kB signaling in launching immune responses against invading pathogens, it is also activated following injuries such as irradiation, leading to chronic vascular inflammation, tissue damage and organ dysfunction. (Baselet, B., Sonveaux, P., Baatout, S. & Aerts, A. Pathological effects of ionizing radiation: endothelial activation and dysfunction. Cell Mol Life Sci (2019) 76, 699-728, doi:10.1007/s00018-018¬ 2956-z; Korpela, E. & Liu, S. K. Endothelial perturbations and therapeutic strategies in normal tissue radiation damage. Radiation oncology (London, England) (2014) 9, 266, doi:10.1186/s13014-014-0266-1083 7).

Interestingly, NF-kB signaling within blood vessels remains activated for several years following radiation therapy, leading to sustained expression of pro-inflammatory cytokines. (Halle, M. et al. Sustained inflammation due to nuclear factor-kappa B activation in irradiated human arteries. J. Am. Coll. Cardiol. 5(2010) 5, 1227-1236, doi: 10.1016/j.jacc.2009.10.047). Studies have suggested that inhibiting NF-κB may be beneficial in protecting against myeloablative therapy, graft rejection, and graft-versus-host disease by decreasing the quantity of cytokines secreted by the graft. (Bottero, V., Withoff, S. & Verma, I. M. NF-kappaB and the regulation of hematopoiesis. Cell death and differentiation (2006) 13, 785-797, doi:10.1038/sj.cdd.4401888).

Indeed, this study demonstrated that inhibition of the canonical NF-κB signaling pathway specifically in endothelial cells has a profound impact on enhancing both steady state hematopoiesis as well as regeneration following irradiation induced myelosuppression, in part by decreasing pro-inflammatory cytokines. (Poulos, M. G. et al. Endothelial-specific inhibition of NF-kappaB enhances functional haematopoiesis. Nat Commun (2016) 7, 13829, doi: 10.1038/ncomms13829). Recent studies have begun to illuminate the role of MAPK signaling during regeneration of the hematopoietic system, in particular when patients are exposed to moderate to high doses of total-body irradiation. (Munshi, A. & Ramesh, R. Mitogen-activated protein kinases and their role in radiation response. Genes Cancer (2013) 4, 401-408, doi:10.1177/1947601913485414). The delay in hematopoietic recovery following radiation injury has been attributed to increased MAPK signaling. (Wang, Y., Liu, L. & Zhou, D. Inhibition of p38 MAPK attenuates ionizing radiation-induced hematopoietic cell senescence and residual bone marrow injury. Radiat Res (2011) 176, 743-752). Chronic endothelial MAPK activation has been shown to cause increased vascular permeability, a hallmark of vascular dysfunction particularly following inflammation-induced injury. (Dong, F. et al. Cadmium induces vascular permeability via activation of the p38 MAPK pathway. Biochem Biophys Res Commun (2014) 450, 447-452, doi:10.1016/j.bbrc.2014.05.140; Li, L. et al. P38/MAPK contributes to endothelial barrier dysfunction via MAP4 phosphorylation-dependent microtubule disassembly in inflammation-induced acute lung injury. Sci Rep (2015) 5, 8895, doi:10.1038/srep08895). Growing evidence suggests that MAPK activation in endothelial cells results in increased vascular inflammation and endothelial dysfunction. (Roth Flach, R. J. et al. Endothelial protein kinase MAP4K4 promotes vascular inflammation and atherosclerosis. Nat Commun (2015) 6, 8995, doi:10.1038/ncomms9995). Collectively, these studies indicate that chronic inflammation within the endothelium might involve the interplay between both MAPK and NF-kB signaling pathways.

The present study demonstrates that cross-talk between ERK-MAPK and NF-kB pathways regulate the outcomes of chronic endothelial inflammation within the BM and its resultant impact on niche activity and HSC function. The myeloid-biased output of HSCs observed in CDH5-MAPK mice illustrates the impact of chronic vascular inflammation on HSC function and highlights the potential of sustained niche-driven inflammation to influence aging-associated HSC phenotypes including predisposition towards myeloid neoplasms. Importantly, the complete rescue of hematopoietic defects observed in CDH5-MAPK mice upon endothelial NF-kB inhibition allows the opportunity to utilize these genetic models to derive testable hypotheses for interrogating stem-cell niche interactions during chronic inflammation and to identify novel factors like SCGF that resolve inflammation-associated HSC and niche defects. SCGF/Clec11a is a member of the C-type lectin proteins belonging to the Tetranectin family. (Brown, G. D., Willment, J. A. & Whitehead, L. C-type lectins in immunity and homeostasis. Nature reviews. Immunology (2018) 18, 374-389, doi:10.1038/s41577-018-0004-8). Recent studies have highlighted the significant roles played by C-type lectins in the context of immunity, inflammation and a wide array of physiological processes. (See id.) Although SCGF did not impact steady state hematopoiesis in control mice, infusion of SCGF into CDH5-MAPK mice had tremendous benefits to the phenotypic and functional hematopoietic attributes indicating that SCGF might play key roles in mediating hematopoietic recovery under stress situations. The ability of SCGF to enhance post¬myelosuppressive hematopoietic recovery in both control as well as CDH5-MAPK mice confirms its role as a rejuvenation factor during stress hematopoiesis. Considering the impact of SCGF in suppressing BM inflammation, restoring vascular integrity, promoting myelosuppressive recovery as well as its osteogenic properties, the identification of its gene regulatory mechanisms, cognate receptor/s and downstream signaling pathways are exciting future directions. These studies will become important to understand the precise molecular mechanisms by which SCGF enhances hematopoietic regeneration and to develop treatment strategies directed towards protecting the hematopoietic system and the BM endothelial niche following myelosuppressive therapies.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

REFERENCES

1. Wagers, A. J. The stem cell niche in regenerative medicine. Cell stem cell 10, 362-369, doi:10.1016/j.stem.2012.02.018 (2012).
2. Lane, S. W., Williams, D. A. & Watt, F. M. Modulating the stem cell niche for tissue regeneration. Nature biotechnology 32, 795-803, doi:10.1038/nbt.2978 (2014).
3. Schepers, K., Campbell, T. B. & Passegue, E. Normal and leukemic stem cell niches: insights and therapeutic opportunities. Cell stem cell 16, 254-267, doi:10.1016/j.stem.2015.02.014 911 (2015).
4. Baldridge, M. T., King, K. Y. & Goodell, M. A. Inflammatory signals regulate hematopoietic stem cells. Trends in immunology 32, 57-65, doi:10.1016/j.it.2010.12.003 (2011).
5. Zhao, J. L. & Baltimore, D. Regulation of stress-induced hematopoiesis. Current opinion in 915 hematology 22, 286-292, doi:10.1097/moh.0000000000000149 (2015).
6. Boettcher, S. & Manz, M. G. Regulation of Inflammation- and Infection-Driven Hematopoiesis. Trends in immunology 38, 345-357, doi:10.1016/j.it.2017.01.004 (2017)
7. Espin-Palazon, R., Weijts, B., Mulero, V. & Traver, D. Proinflammatory Signals as Fuel for the Fire of Hematopoietic Stem Cell Emergence. Trends in cell biology 28, 58-66, doi:10.1016/j.tcb.2017.08.003 (2018).
8. Bowers, E. et al. Granulocyte-derived TNFalpha promotes vascular and hematopoietic regeneration in the bone marrow. Nature medicine 24, 95-102, doi:10.1038/nm.4448 (2018).
9. Kovtonyuk, L. V., Fritsch, K., Feng, X., Manz, M. G. & Takizawa, H. Inflamm-Aging of Hematopoiesis, Hematopoietic Stem Cells, and the Bone Marrow Microenvironment. Frontiers in immunology 7, 502, doi:10.3389/fimmu.2016.00502 (2016).
10. Pietras, E. M. et al. Chronic interleukin-1 exposure drives haematopoietic stem cells towards precocious myeloid differentiation at the expense of self-renewal. Nature cell biology 18, 607 ¬-618, doi:10.1038/ncb3346 (2016).
11. Lussana, F. & Rambaldi, A. Inflammation and myeloproliferative neoplasms. Journal of autoimmunity 85, 58-63, doi:10.1016/j.jaut.2017.06.010 (2017).
12. Pietras, E. M. Inflammation: a key regulator of hematopoietic stem cell fate in health and disease. Blood 130, 1693-1698, doi:10.1182/blood-2017-06-780882 (2017).
13. 13 Hooper, A. T. et al. Engraftment and reconstitution of hematopoiesis is dependent on VEGFR2-¬mediated regeneration of sinusoidal endothelial cells. Cell stem cell 4, 263-274, doi:10.1016/j.stem.2009.01.006 (2009).
14. 14 Butler, J. M. et al. Endothelial cells are essential for the self-renewal and repopulation of Notch¬dependent hematopoietic stem cells. Cell stem cell 6, 251-264, doi:10.1016/j.stem.2010.02.001 (2010).
15. Kobayashi, H. et al. Angiocrine factors from Akt-activated endothelial cells balance self-renewal and differentiation of haematopoietic stem cells. Nature cell biology 12, 1046-1056, doi:10.1038/ncb2108 (2010).
16. Winkler, I. G. et al. Vascular niche E-selectin regulates hematopoietic stem cell dormancy, self renewal and chemoresistance. Nature medicine 18, 1651-1657, doi:10.1038/nm.2969 (2012).
17. Ding, L., Saunders, T. L., Enikolopov, G. & Morrison, S. J. Endothelial and perivascular cells maintain haematopoietic stem cells. Nature 481, 457-462, doi:10.1038/nature10783 (2012).
18. Poulos, M. G. et al. Endothelial jagged-1 is necessary for homeostatic and regenerative 947 hematopoiesis. Cell reports 4, 1022-1034, doi:10.1016/j.celrep.2013.07.048 (2013).
19. Greenbaum, A. et al. CXCL12 in early mesenchymal progenitors is required for haematopoietic stem-cell maintenance. Nature 495, 227-230, doi:10.1038/nature11926 (2013).

20. Doan, P. L. et al. Epidermal growth factor regulates hematopoietic regeneration after radiation injury. Nature medicine 19, 295-304, doi:10.1038/nm.3070 (2013).
21. Poulos, M. G. et al. Endothelial-specific inhibition of NF-kappaB enhances functional haematopoiesis. Nat Commun 7, 13829, doi:10.1038/ncomms13829 (2016).
22. Kusumbe, A. P. et al. Age-dependent modulation of vascular niches for haematopoietic stem cells. Nature 532, 380-384, doi:10.1038/nature17638 (2016).
23. Morrison, S. J. & Scadden, D. T. The bone marrow niche for haematopoietic stem cells. Nature 505, 327-334, doi:10.1038/nature12984 (2014).
24. Rafii, S., Butler, J. M. & Ding, B. S. Angiocrine functions of organ-specific endothelial cells. Nature 529, 316-325, doi:10.1038/nature17040 (2016).
25. Pober, J. S. & Sessa, W. C. Evolving functions of endothelial cells in inflammation. Nature reviews. Immunology 7, 803-815, doi:10.1038/nri2171 (2007).
26. Boettcher, S. et al. Endothelial cells translate pathogen signals into G-CSF-driven emergency granulopoiesis. Blood 124, 1393-1403, doi:10.1182/blood-2014-04-570762 (2014).
27. Wang, L. et al. Notch-dependent repression of miR-155 in the bone marrow niche regulates hematopoiesis in an NF-kappaB-dependent manner. Cell stem cell 15, 51-65, doi:10.1016/j.stem.2014.04.021 (2014).
28. Sanchez, A. et al. Map3k8 controls granulocyte colony-stimulating factor production and neutrophil precursor proliferation in lipopolysaccharide-induced emergency granulopoiesis. Sci Rep 7, 5010, doi:10.1038/s41598-017-04538-3 (2017).
29. Roth Flach, R. J. et al. Endothelial protein kinase MAP4K4 promotes vascular inflammation and atherosclerosis. Nat Commun 6, 8995, doi:10.1038/ncomms9995 (2015).
30. Vandoorne, K. et al. Imaging the Vascular Bone Marrow Niche During Inflammatory Stress. Circ Res 123, 415-427, doi:10.1161/circresaha.118.313302 (2018).
31. Baker, R. G., Hayden, M. S. & Ghosh, S. NF-kappaB, inflammation, and metabolic disease. Cell metabolism 13, 11-22, doi:10.1016/j.cmet.2010.12.008 (2011).
32. Bottero, V., Withoff, S. & Verma, I. M. NF-kappaB and the regulation of hematopoiesis. Cell death and differentiation 13, 785-797, doi:10.1038/sj.cdd.4401888 (2006).
33. Brown, K., Park, S., Kanno, T., Franzoso, G. & Siebenlist, U. Mutual regulation of the transcriptional activator NF-kappa B and its inhibitor, I kappa B-alpha. Proc Natl Acad Sci USA 90, 2532-2536, doi:10.1073/pnas.90.6.2532 (1993).
34. Wu, C. & Ghosh, S. Differential phosphorylation of the signal-responsive domain of I kappa B alpha and I kappa B beta by I kappa B kinases. J Biol Chem 278, 31980-31987, 983 doi:10.1074/jbc.M304278200 (2003).
35. Yang, F., Tang, E., Guan, K. & Wang, C. Y. IKK beta plays an essential role in the phosphorylation of Re1A/p65 on serine 536 induced by lipopolysaccharide. J Immunol 170, 5630-5635, doi:10.4049/jimmunol.170.11.5630 (2003).
36. Wessel, A. W. & Hanson, E. P. A method for the quantitative analysis of stimulation-induced 988 nuclear translocation of the p65 subunit of NF-kappaB from patient-derived dermal fibroblasts. 989 Methods Mol Biol 1280, 413-426, doi:10.1007/978-1-4939-2422-6_25 (2015). 990
37. Boehm, J. S. et al. Integrative genomic approaches identify IKBKE as a breast cancer oncogene. 991 Cell 129, 1065-1079, doi:10.1016/j.cell.2007.03.052 (2007).
38. Brown, K., Gerstberger, S., Carlson, L., Franzoso, G. & Siebenlist, U. Control of I kappa B¬alpha proteolysis by site-specific, signal-induced phosphorylation. Science 267, 1485-1488, doi:10.1126/science.7878466 (1995).
39. Kisseleva, T. et al. NF-kappaB regulation of endothelial cell function during LPS-induced toxemia and cancer. J Clin Invest 116, 2955-2963, doi:10.1172/jci27392 (2006).
40. Wei, Q. & Frenette, P. S. Niches for Hematopoietic Stem Cells and Their Progeny. Immunity 48, 632-648, doi:10.1016/j.immuni.2018.03.024 (2018).
41. Crane, G. M., Jeffery, E. & Morrison, S. J. Adult haematopoietic stem cell niches. Nature reviews. Immunology 17, 573-590, doi:10.1038/nri.2017.53 (2017).
42. Comazzetto, S. et al. Restricted Hematopoietic Progenitors and Erythropoiesis Require SCF from Leptin Receptor+ Niche Cells in the Bone Marrow. Cell stem cell 24, 477-486.e476, doi:10.1016/j.stem.2018.11.022 (2019).
43. Inra, C. N. et al. A perisinusoidal niche for extramedullary haematopoiesis in the spleen. Nature 527, 466-471, doi:10.1038/nature15530 (2015).
44. Sorensen, I., Adams, R. H. & Gossler, A. DLL1-mediated Notch activation regulates endothelial identity in mouse fetal arteries. Blood 113, 5680-5688, doi:10.1182/blood-2008-08-174508 (2009).
45. Langen, U. H. et al. Cell-matrix signals specify bone endothelial cells during developmental osteogenesis. Nature cell biology 19, 189-201, doi:10.1038/ncb3476 (2017). 46 Payne, S., De Val, S. & Neal, A. Endothelial-Specific Cre Mouse Models. Arterioscler Thromb Vase Biol 38, 2550-2561, doi:10.1161/atvbaha.118.309669 (2018).
47. Kilani, B. et al. Comparison of endothelial promoter efficiency and specificity in mice reveals a subset of Pdgfb-positive hematopoietic cells. J Thromb Haemost 17, 827-840, doi:10.1111/jth.14417 (2019).
48. Forde, A., Constien, R., Grone, H. J., Hammerling, G. & Arnold, B. Temporal Cre-mediated recombination exclusively in endothelial cells using Tie2 regulatory elements. Genesis 33, 191 ¬-197, doi:10.1002/gene.10117 (2002).
49. Tang, Y., Harrington, A., Yang, X., Friesel, R. E. & Liaw, L. The contribution of the Tie2+ lineage to primitive and definitive hematopoietic cells. Genesis 48, 563-567, doi:10.1002/dvg.20654 (2010).
50 Gareus, R. et al. Endothelial cell-specific NF-kappaB inhibition protects mice from atherosclerosis. Cell metabolism 8, 372-383, doi:10.1016/j.cmet.2008.08.016 (2008).
51. Korhonen, H. et al. Anaphylactic shock depends on endothelial Gq/G11. J Exp Med 206, 411 ¬-420, doi:10.1084/jem.20082150 (2009).
52. Poulos, M. G. et al. Endothelial-specific inhibition of NF-kappaB enhances functional haematopoiesis. Nat Commun 7, 13829, doi:10.1038/ncomms13829 (2016).
53. Bartels, K., Grenz, A. & Eltzschig, H. K. Hypoxia and inflammation are two sides of the same coin. Proc Natl Acad Sci USA 110, 18351-18352, doi:10.1073/pnas.1318345110 (2013).
54. Karhausen, J., Haase, V. H. & Colgan, S. P. Inflammatory hypoxia: role of hypoxia-inducible factor. Cell Cycle 4, 256-258 (2005).
55. Eltzschig, H. K. & Carmeliet, P. Hypoxia and inflammation. N Engl J Med 364, 656-665, doi:10.1056/NEJMra0910283 (2011).
56. Mittal, M., Siddiqui, M. R., Tran, K., Reddy, S. P. & Malik, A. B. Reactive oxygen species in 1035 inflammation and tissue injury. Antioxid Redox Signal 20, 1126-1167, doi:10.1089/ars.2012.5149 (2014).

57. Bigarella, C. L., Liang, R. & Ghaffari, S. Stem cells and the impact of ROS signaling. Development 141, 4206-4218, doi:10.1242/dev.107086 (2014).

58. Takubo, K. et al. Regulation of the HIF-1alpha level is essential for hematopoietic stem cells. Cell stem cell 7, 391-402, doi:10.1016/j.stem.2010.06.020 (2010).

59. Ludin, A. et al. Reactive oxygen species regulate hematopoietic stem cell self-renewal, migration and development, as well as their bone marrow microenvironment. Antioxid Redox Signal 21, 1605-1619, doi:10.1089/ars.2014.5941 (2014).

60. Zhou, B. O., Yue, R., Murphy, M. M., Peyer, J. G. & Morrison, S. J. Leptin-receptor-expressing mesenchymal stromal cells represent the main source of bone formed by adult bone marrow. Cell stem cell 15, 154-168, doi:10.1016/j.stem.2014.06.008 (2014).

61. Ding, L. & Morrison, S. J. Haematopoietic stem cells and early lymphoid progenitors occupy distinctbone marrow niches. Nature 495, 231-235, doi:10.1038/nature11885 (2013).

62 Mossadegh-Keller, N. et al. M-CSF instructs myeloid lineage fate in single haematopoietic stem cells. Nature 497, 239-243, doi:10.1038/nature12026 (2013).

63. Yue, R., Shen, B. & Morrison, S. J. Clec11a/osteolectin is an osteogenic growth factor that promotes the maintenance of the adult skeleton. Elife 5, doi:10.7554/eLife.18782 (2016).

64 Keller, C. C. et al. Suppression of a novel hematopoietic mediator in children with severe malarial anemia. Infect Immun 77, 3864-3871, doi:10.1128/IAI.00342-09 (2009).

65. Ito, C. et al. Serum stem cell growth factor for monitoring hematopoietic recovery following stem cell transplantation. Bone Marrow Transplant 32, 391-398, doi:10.1038/sj.bmt.1704152 (2003).

66. Mazumder, B., Li, X. & Barik, S. Translation control: a multifaceted regulator of inflammatory response. J Immunol 184, 3311-3319, doi:10.4049/jimmunol.0903778 (2010).

67. McDermott, B. T., Peffers, M. J., McDonagh, B. & Tew, S. R. Translational regulation contributes to the secretory response of chondrocytic cells following exposure to Interleukin¬1beta. J Biol Chem, doi:10.1074/jbc.RA118.006865 (2019).

68. Li, X. M., Hu, Z., Jorgenson, M. L., Wingard, J. R. & Slayton, W. B. Bone marrow sinusoidal endothelial cells undergo nonapoptotic cell death and are replaced by proliferating sinusoidal cells in situ to maintain the vascular niche following lethal irradiation. Exp Hematol 36, 1143¬1066 1156, doi:10.1016/j.exphem.2008.06.009 (2008).

69. Baselet, B., Sonveaux, P., Baatout, S. & Aerts, A. Pathological effects of ionizing radiation: endothelial activation and dysfunction. Cell Mol Life Sci 76, 699-728, doi:10.1007/s00018-018¬2956-z (2019).

70. Zhang, H. et al. Sepsis Induces Hematopoietic Stem Cell Exhaustion and Myelosuppression through Distinct Contributions of TRIF and MYD88. Stem Cell Reports 6, 940-956, doi:10.1016/j.stemcr.2016.05.002 (2016).

71. Mirantes, C., Passegue, E. & Pietras, E. M. Pro-inflammatory cytokines: emerging players regulating HSC function in normal and diseased hematopoiesis. Experimental cell research 329, 248-254, doi:10.1016/j.yexcr.2014.08.017 (2014).

72. Geest, C. R. & Coffer, P. J. MAPK signaling pathways in the regulation of hematopoiesis. Journal of leukocyte biology 86, 237-250, doi:10.1189/jlb.0209097 (2009).

73. Xiao, L., Liu, Y. & Wang, N. New paradigms in inflammatory signaling in vascular endothelial cells. American journal of physiology. Heart and circulatory physiology 306, H317-325, doi:10.1152/ajpheart.00182.2013 (2014).

74. Korpela, E. & Liu, S. K. Endothelial perturbations and therapeutic strategies in normal tissue radiation damage. Radiation oncology (London, England) 9, 266, doi:10.1186/s13014-014-0266¬1083 7 (2014).

75. Halle, M. et al. Sustained inflammation due to nuclear factor-kappa B activation in irradiated human arteries. Journal of the American College of Cardiology 55, 1227-1236, doi:10.1016/j.jacc.2009.10.047 (2010).

76. Munshi, A. & Ramesh, R. Mitogen-activated protein kinases and their role in radiation response. Genes Cancer 4, 401-408, doi:10.1177/1947601913485414 (2013).

77. Wang, Y., Liu, L. & Zhou, D. Inhibition of p38 MAPK attenuates ionizing radiation-induced hematopoietic cell senescence and residual bone marrow injury. Radiat Res 176, 743-752 (2011).

78. Dong, F. et al. Cadmium induces vascular permeability via activation of the p38 MAPK pathway. Biochem Biophys Res Commun 450, 447-452, doi:10.1016/j.bbrc.2014.05.140 (2014).

79. Li, L. et al. P38/MAPK contributes to endothelial barrier dysfunction via MAP4 phosphorylation-dependent microtubule disassembly in inflammation-induced acute lung injury. Sci Rep 5, 8895, doi:10.1038/srep08895 (2015).

80. Brown, G. D., Willment, J. A. & Whitehead, L. C-type lectins in immunity and homeostasis. Nature reviews. Immunology 18, 374-389, doi:10.1038/s41577-018-0004-8 (2018).

81. Srinivasan, L. et al. P13 kinase signals BCR-dependent mature B cell survival. Cell 139, 573¬-586, doi:10.1016/j.cell.2009.08.041 (2009).

82. Benedito, R. et al. The notch ligands D114 and Jagged1 have opposing effects on angiogenesis. Cell 137, 1124-1135, doi:10.1016/j.cell.2009.03.025 (2009).

83. DeFalco, J. et al. Virus-assisted mapping of neural inputs to a feeding center in the hypothalamus. Science 291, 2608-2613, doi:10.1126/science.1056602 (2001).

84. Hu, Y. & Smyth, G. K. ELDA: extreme limiting dilution analysis for comparing depleted and enriched populations in stem cell and other assays. J Immunol Methods 347, 70-78, doi:10.1016/j.jim.2009.06.008 (2009).

85. Poulos, M. G. et al. Endothelial transplantation rejuvenates aged hematopoietic stem cell function. J Clin Invest 127, 4163-4178, doi:10.1172/jci93940 (2017).

86. Gold, L. et al. Aptamer-based multiplexed proteomic technology for biomarker discovery. PloS one 5, e15004, doi:10.1371/journal.pone.0015004 (2010).

What is claimed is:

1. A method for improving hematopoietic homing, engraftment, reconstitution, and regeneration of bone marrow (BM) after a myelosuppressive insult in a subject in need thereof, the method comprising:

(a) administering to the subject a pharmaceutical composition comprising a recombinant or synthetic angiocrine factor and a pharmaceutically acceptable carrier, wherein the angiocrine factor is one or more recombinant or synthetic protein selected from the group consisting of c-type lectin domain family 11 member A (Clec11a)/stem cell growth factor (SCGF), hyaluronan and proteoglycan link protein 1 (Hapln1), heat shock protein family D member 1 (Hspd1), insulin-like growth factor-binding protein 1 (Igfbp1), biglycan (Bgn), wnt family member 7A (Wnt7a), secreted protein acidic and rich in cysteine (Sparc), ribosomal protein S3 (Rps3), bone morphogenetic protein receptor type 1A (Bmpr1a), immunoglobulin heavy chain constant mu (Ighm), thrombospondin 4 (Thbs4), calcium/calmodulin dependent protein kinase II delta (Camk2d), sirtuin 2 (Sirt2), calcium/calmodulin dependent protein kinase II beta (Camk2b), SLIT and NTRK like family member 5 (Slitrk5), dCTP pyrophosphatase (Dctpp1), heterogenous nuclear ribonucleoprotein A2/B1 (Hnrnpa2b), and endoplasmic reticulum aminopeptidase 1 (Erap1);

(b) administering a stem cell co-therapy comprising transplantation of a therapeutic amount of multipotent, self-renewing hematopoietic stem cells (HSCs) effective to regenerate a blood system and promote hematopoietic reconstitution of the BM; and (c) administering a vascular endothelial cell co-therapy comprising transplantation of a therapeutic amount of bone marrow endothelial cells (BMECs) effective to regenerate the blood system and promote hematopoietic reconstitution of the BM, wherein the myelosuppressive insult reduces BMEC activity in the bone marrow and leads to defects in steady state hematopoiesis and HSC function; and wherein the method enhances hematopoietic recovery in a hematopoietic bone marrow microenvironment comprising bone marrow endothelial cells (BMECs), hematopoietic stem cells (HSCs), and bone marrow stromal cells following the myelosuppressive insult by one or more of:

(i) reducing inflammation in the hematopoietic bone marrow microenvironment, wherein the inflammation in the hematopoietic bone marrow microenvironment comprises vascular inflammation;

(ii) preserving vascular integrity by suppressing vascular leakiness within the hematopoietic bone marrow microenvironment; and (iii) increasing frequency and cell types in the hematopoietic bone marrow microenvironment comprising one or more of hematopoietic stem cells (HSCs), hematopoietic stem and progenitor cells (HSPCs), multipotent progenitor cells (MPPs), and hematopoietic progenitor cell subsets to effect multi-lineage reconstitution.

2. The method according to claim 1, wherein the angiocrine factor is a recombinant or synthetic Clec11a/SCGF.

3. The method according to claim 1, wherein the stem cell co-therapy comprises a) isolating a population of mononuclear cells from a tissue source, b) enriching a population of hematopoietic stem cells from the isolated population of mononuclear cells by positive or negative selection, and c) administering the enriched population of hematopoietic stem cells to the subject.

4. The method according to claim 3, a) wherein the tissue source is autologous; or b) wherein the tissue source is allogeneic.

5. The method according to claim 1, wherein the vascular endothelial cell co-therapy comprises a) isolating endothelial cells from human umbilical cord, b) enriching a population of vascular endothelial cells from the isolated population of endothelial cells by positive or negative selection, and c) administering the enriched population of vascular endothelial cells to the subject.

6. The method according to claim 1, wherein the pharmaceutical composition is administered before, after, or contemporaneously with the administration of the stem cell co-therapy.

7. The method according to claim 1, wherein the myelosuppressive insult comprises exposure to radiation, chemotherapy, or both.

8. The method according to claim 7, a) wherein the radiation is sublethal radiation, total body irradiation, or total lymphoid irradiation; or b) wherein the myelosuppressive insult is chemotherapy; or c) wherein the myelosuppressive insult is myeloablative.

9. The method according to claim 1, wherein the defects in HSC function include impaired HSC quiescence and increased HSC apoptosis.

10. The method according to claim 1, wherein the hematopoietic bone marrow microenvironment comprises BMECs, BM stromal cells, BM Lepr+ cells, and BM osteoblasts.

11. The method according to claim 10, a) wherein the BMECs are sinusoidal and arteriole BMECs; or b) wherein the immunophenotype of BMECs is CD45−Ter119−CD31+VEcadherin+; or c) wherein the immunophenotype of BM stromal cells is CD45−Ter119−CD31−VEcadherin−; or d) wherein the immunophenotype of BM Lepr+ cells within the BM stromal population is CD45−Ter119−CD31−Lepr+; or e) wherein the immunophenotype of murine HSCs comprises lin−Ter119−CD11b−GR1−B220−CD3−CD41−ckit+SCA1+CD48−CD150+; or f) wherein the immunophenotype of human HSCs comprises CD45RA−CD38−CD34+CD90+.

12. The method according to claim 1, wherein the reduced vascular inflammation includes suppressed NFκB signaling, downregulated NFκB target genes, or both in the endothelial cells in the bone marrow.

13. The method according to claim 1, wherein the method enhances long term stable engraftment of the bone marrow, reduced myeloid bias in the peripheral blood, or both.

* * * * *